United States Patent
Lee et al.

(10) Patent No.: US 10,522,766 B2
(45) Date of Patent: Dec. 31, 2019

(54) ORGANIC OPTOELECTRONIC DEVICE AND DISPLAY DEVICE

(71) Applicant: SAMSUNG SDI CO., LTD., Yongin-si, Gyeonggi-do (KR)

(72) Inventors: Han-Ill Lee, Suwon-si (KR); Chang-Woo Kim, Suwon-si (KR); Dong-Wan Ryu, Suwon-si (KR); Young-Sung Park, Suwon-si (KR); Chang-Ju Shin, Suwon-si (KR); Eun-Sun Yu, Suwon-si (KR); Sung-Hyun Jung, Suwon-si (KR); Su-Jin Han, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 363 days.

(21) Appl. No.: 15/328,180

(22) PCT Filed: Dec. 11, 2014

(86) PCT No.: PCT/KR2014/012217
§ 371 (c)(1),
(2) Date: Jan. 23, 2017

(87) PCT Pub. No.: WO2016/024675
PCT Pub. Date: Feb. 18, 2016

(65) Prior Publication Data
US 2017/0213985 A1    Jul. 27, 2017

(30) Foreign Application Priority Data
Aug. 13, 2014 (KR) .................. 10-2014-0105353

(51) Int. Cl.
| | |
|---|---|
| H01L 51/50 | (2006.01) |
| H01L 51/00 | (2006.01) |
| C09K 11/06 | (2006.01) |
| C07D 209/86 | (2006.01) |

(Continued)

(52) U.S. Cl.
CPC ........ H01L 51/0072 (2013.01); C07D 209/86 (2013.01); C07D 405/12 (2013.01);
(Continued)

(58) Field of Classification Search
None
See application file for complete search history.

(56) References Cited

U.S. PATENT DOCUMENTS

2013/0001528 A1* 1/2013 Chang ................. H01L 51/0051
257/40
2013/0082591 A1  4/2013 Seo et al.
(Continued)

FOREIGN PATENT DOCUMENTS

| CN | 101445422 A | 6/2009 |
| CN | 101952250 A | 1/2011 |

(Continued)

OTHER PUBLICATIONS

Chinese Search Report dated May 17, 2018, which was attached to the Office Action dated May 30, 2018, of the corresponding Chinese Patent Application No. 201480081069.X.

Primary Examiner — Gregory D Clark
(74) Attorney, Agent, or Firm — Lee & Morse, P.C.

(57) ABSTRACT

The present invention relates to an organic photoelectronic device and a display device comprising the organic photoelectronic device, the organic photoelectronic device comprising: an anode; a cathode facing the anode; a light-emitting layer interposed between the anode and cathode; a hole transport layer interposed between the anode and the light-emitting layer; and an auxiliary hole transport layer interposed between the hole transport layer and the light-emitting layer, wherein the hole transport layer comprises a compound represented by Chemical formula I, and the auxiliary hole transport layer comprises a compound repre-
(Continued)

sented by Chemical formula II. Chemical formulas I and II are the same as set forth in the description.

19 Claims, 1 Drawing Sheet

(51) Int. Cl.
    *C07D 405/12*       (2006.01)
    *C09K 11/02*       (2006.01)

(52) U.S. Cl.
    CPC ............ *C09K 11/025* (2013.01); *C09K 11/06* (2013.01); *H01L 51/006* (2013.01); *H01L 51/0059* (2013.01); *H01L 51/0061* (2013.01); *H01L 51/0073* (2013.01); *C09K 2211/1011* (2013.01); *H01L 51/0052* (2013.01); *H01L 51/0081* (2013.01); *H01L 51/5064* (2013.01); *H01L 2251/552* (2013.01)

(56) References Cited

U.S. PATENT DOCUMENTS

| | | |
|---|---|---|
| 2013/0241401 A1 | 9/2013 | Kwong et al. |
| 2014/0001446 A1 | 1/2014 | Mizuki et al. |
| 2014/0155601 A1 | 6/2014 | Jin |
| 2016/0163995 A1* | 6/2016 | Kang .................. H01L 51/0067 257/40 |

FOREIGN PATENT DOCUMENTS

| | | |
|---|---|---|
| CN | 103797604 A | 5/2014 |
| CN | 103887444 A | 6/2014 |
| CN | 104045595 A | 9/2014 |
| JP | 2000-286056 | 10/2000 |
| JP | 2002-308837 | 10/2002 |
| JP | 2004-217557 | 8/2004 |
| JP | 2004-273128 | 9/2004 |
| JP | 2006-352045 | 12/2006 |
| JP | 4103492 B2 | 6/2008 |
| JP | 4103493 B2 | 6/2008 |
| JP | 2009-057307 | 3/2009 |
| JP | 4305046 B2 | 7/2009 |
| JP | 2013-183047 | 9/2013 |
| KR | 10-2012-0034648 | 4/2012 |
| KR | 10-2013-0009972 | 1/2013 |
| KR | 10-2014-0049227 A | 4/2014 |
| KR | 10-2014-0070365 | 6/2014 |
| KR | 10-2014-0087803 | 7/2014 |
| WO | WO 2009/072587 A1 | 6/2009 |
| WO | WO 2012/153780 A1 | 11/2012 |
| WO | WO 2013/069242 A1 | 5/2013 |
| WO | WO 2013/115340 A1 | 8/2013 |
| WO | WO 2013/146942 A1 | 10/2013 |
| WO | WO 2013/147205 A1 | 10/2013 |

* cited by examiner

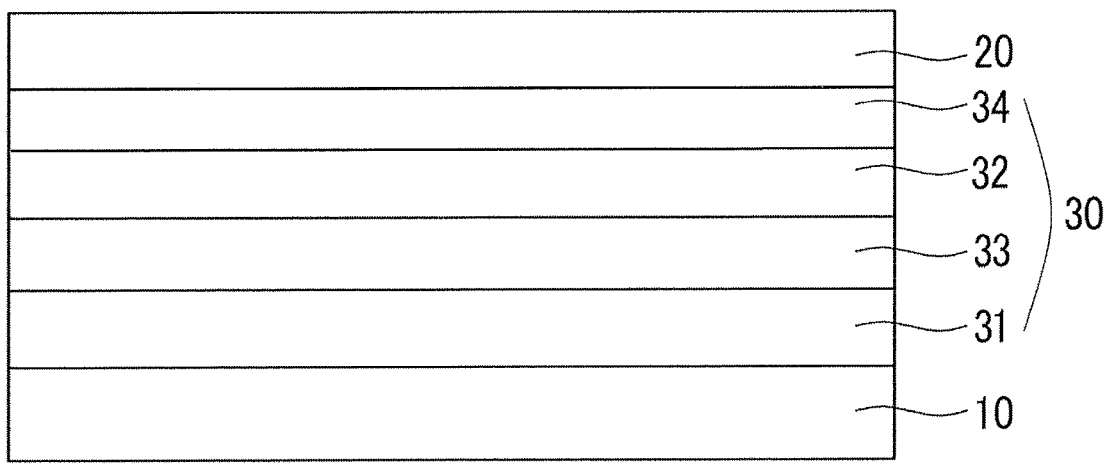

ORGANIC OPTOELECTRONIC DEVICE AND DISPLAY DEVICE

CROSS REFERENCE TO RELATED APPLICATIONS

This is the U.S. national phase application based on PCT Application No. PCT/KR2014/012217, filed Dec. 11, 2014, which is based on Korean Patent Application No. 10-2014-0105353, filed Aug. 13, 2014, the entire contents of all of which are hereby incorporated by reference.

TECHNICAL FIELD

An organic optoelectric device and a display device are disclosed.

BACKGROUND ART

An organic optoelectric device is a device that converts electrical energy into photoenergy, and vice versa. An organic optoelectric device may be classified as follows in accordance with its driving principles. One is a photoelectric diode where excitons are generated by photoenergy, separated into electrons and holes, and are transferred to different electrodes to generate electrical energy, and the other is a light emitting device where a voltage or a current is supplied to an electrode to generate photoenergy from electrical energy. Examples of the organic optoelectric device may be an organic photoelectric device, an organic light emitting diode, an organic solar cell, and an organic photo conductor drum. Of these, an organic light emitting diode (OLED) has recently drawn attention due to an increase in demand for flat panel displays. The organic light emitting diode converts electrical energy into light by applying current to an organic light emitting material and has a structure in which an organic layer is disposed between an anode and a cathode.

DISCLOSURE

Technical Problem

An embodiment provides an organic optoelectric device capable of realizing a long life-span and high efficiency characteristics.

Another embodiment provides a display device including the organic optoelectric device.

Technical Solution

According to one embodiment, an organic optoelectric device includes an anode and a cathode facing each other, a light-emitting layer disposed between the anode and cathode, a hole transport layer disposed between the anode and the light-emitting layer and an auxiliary hole transport layer disposed between the hole transport layer and the light-emitting layer, the hole transport layer includes a compound represented by Chemical Formula I and, the hole transport auxiliary layer includes a compound represented by Chemical Formula II.

[Chemical Formula I]

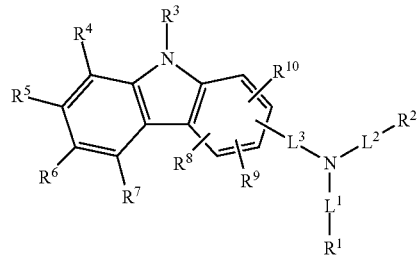

In Chemical Formula I,
$R^1$ to $R^3$ are independently a substituted or unsubstituted C6 to C30 aryl group, a substituted or unsubstituted C2 to C30 heterocyclic group, or a combination thereof,
$R^4$ to $R^{10}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof,
adjacent two of $R^4$ to $R^{10}$ are fused to provide a ring, and
$L^1$ to $L^3$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 heteroarylene group, a substituted or unsubstituted C6 to C30 aryleneamine group, a substituted or unsubstituted C1 to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof,
wherein "substituted" refers to replacement of at least one hydrogen by deuterium, a halogen, a hydroxy group, an amino group, a C1 to 030 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group,

[Chemical Formula II]

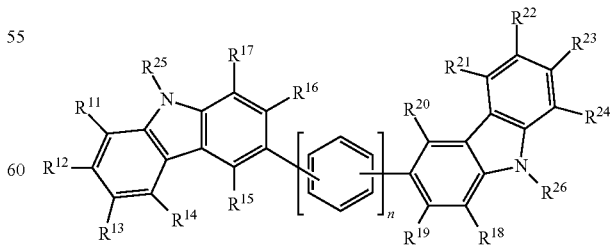

wherein, in Chemical Formula II,
$R^{11}$ to $R^{24}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, adjacent two of $R^{11}$ to $R^{17}$ and $R^{18}$ to $R^{24}$ are fused to provide a ring, $R^{25}$ and $R^{26}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, and n is an integer ranging from 1 to 4, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

According to another embodiment, a display device including the organic optoelectric device is provided.

Advantageous Effects

An organic optoelectric device having a long life-span and high efficiency may be realized.

DESCRIPTION OF THE DRAWINGS

FIG. 1 is a schematic cross-sectional view showing an organic optoelectric device according to an embodiment.

| <Description of Symbols> | |
|---|---|
| 10: anode | 20: cathode |
| 30: organic layer | 31: hole transport layer |
| 32: light-emitting layer | 33: hole transport auxiliary layer |
| 34: electron transport layer (ETL) | |

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to one substituted with deuterium, a halogen, a hydroxy group, an amino group, a substituted or unsubstituted C1 to C30 amine group, a nitro group, a substituted or unsubstituted C1 to C40 silyl group, C1 to C30 alkyl group, C1 to C10 alkylsilyl group, C3 to C30 cycloalkyl group, C2 to C30 heterocycloalkyl group, C6 to C30 aryl group, C2 to C30 heteroaryl group, C1 to C20 alkoxy group, a fluoro group, a C1 to C10 trifluoroalkyl group such as a trifluoromethyl group, and the like, or a cyano group, instead of at least one hydrogen of a substituent or a compound.

In addition, two adjacent substituents of the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C2 to C30 heterocycloalkyl group, C6 to C30 aryl group, C2 to C30 heteroaryl group, C1 to C20 alkoxy group, fluoro group, C1 to C10 trifluoroalkyl group such as trifluoromethyl group and the like, or cyano group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including at least one hetero atom selected from the group consisting of N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a substituent including all element of the cycle having p-orbitals which form conjugation, and may be monocyclic, polycyclic or fused ring polycyclic (i.e., rings sharing adjacent pairs of carbon atoms) functional group.

In the present specification, "heterocyclic group" may include at least one hetero atom selected from N, O, S, P, and Si in a cyclic compound such as an aryl group, a cycloalkyl group, a fused ring thereof, or a combination thereof, and remaining carbons. When the heterocyclic group is a fused ring, the entire ring or each ring of the heterocyclic group may include one or more heteroatoms. Accordingly, the heterocyclic group is a general concept of a heteroaryl group.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrylene group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, a substituted or unsubstituted dibenzothiophenyl group, a substituted or unsubstituted carbazole group, a combination thereof, or a fused form of combinations thereof, but are not limited thereto.

In the present specification, a single bond refers to a direct bond not by carbon or a hetero atom except carbon, and specifically the meaning that L is a single bond means that a substituent linked to L directly bonds with a central core. That is, in the present specification, the single bond does not refer to methylene that is bonded via carbon.

In the specification, hole characteristics refer to an ability to donate an electron to form a hole when an electric field is applied and that a hole formed in the anode may be easily injected into the light-emitting layer, and a hole formed in a light-emitting layer may be easily transported into an anode and transported in the light-emitting layer due to conductive characteristics according to a highest occupied molecular orbital (HOMO) level.

In addition, electron characteristics refer to an ability to accept an electron when an electric field is applied and that an electron formed in a cathode may be easily injected into the light-emitting layer, and an electron formed in a light-emitting layer may be easily transported into a cathode and transported in the light-emitting layer due to conductive characteristics according to a lowest unoccupied molecular orbital (LUMO) level.

Hereinafter, an organic optoelectric device according to an embodiment is described.

The organic optoelectric device may be any device to convert electrical energy into photoenergy and vice versa without particular limitation, and may be, for example an organic photoelectric device, an organic light emitting diode, an organic solar cell, and an organic photo-conductor drum.

Herein, an organic light emitting diode as one example of an organic optoelectric device is described, but the present invention can be applied to other organic optoelectric devices in the same way.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

FIG. 1 is a schematic cross-sectional view showing organic optoelectric devices according to one embodiment.

Referring to FIG. 1, an organic optoelectric device according to one embodiment includes an anode 10 and a cathode 20 facing each other and an organic layer 30 between the anode 10 and the cathode 20.

The anode 10 may be made of a conductor having a large work function to help hole injection, and may be for example metal, metal oxide and/or a conductive polymer. The anode 10 may be, for example a metal such as nickel, platinum, vanadium, chromium, copper, zinc, and gold or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 20 may be made of a conductor having a small work function to help electron injection, and may be for example metal, metal oxide and/or a conductive polymer. The cathode 20 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 30 includes a hole transport layer 31, a light-emitting layer 32, and a hole transport auxiliary layer 33 between the hole transport layer 31 and the light-emitting layer 32.

The hole transport layer 31 facilitates hole transport from the anode 10 to the light-emitting layer 32 and the hole transport layer according to an embodiment includes a compound represented by Chemical Formula I.

[Chemical Formula I]

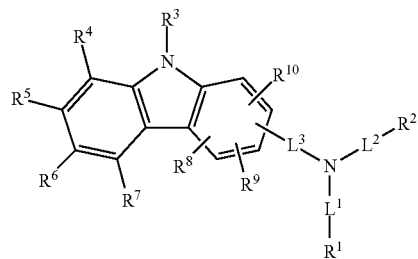

In Chemical Formula I, $R^1$ to $R^3$ are independently a substituted or unsubstituted C6 to C30 aryl group, a substituted or unsubstituted C2 to C30 heterocyclic group, or a combination thereof, $R^4$ to $R^{10}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, and adjacent two of $R^4$ to $R^{10}$ are fused to provide a ring, and $L^1$ to $L^3$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 heteroarylene group, a substituted or unsubstituted C6 to C30 aryleneamine group, a substituted or unsubstituted C1 to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

The compound represented by Chemical Formula I simultaneously includes a carbazole group and an amine group and thereby has a HOMO energy level adjusted in a range of −4.5 eV to −5.0 eV.

The compound having a HOMO energy level within the range may have excellent hole characteristics and thus efficiently transfer holes in a hole transport layer.

In addition, the compound represented by Chemical Formula II includes two carbazole groups and thus may have a HOMO energy level adjusted in a range of −4.9 eV to −5.5 eV.

The compound represented by Chemical Formula I may be represented by one of Chemical Formula I-1 to Chemical Formula I-5 in accordance with that a substituent of a carbazole group is present or not and a substituent of a carbazole is fused or not.

[Chemical Formula I-1]

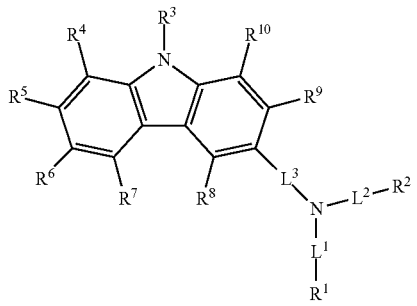

[Chemical Formula I-2]

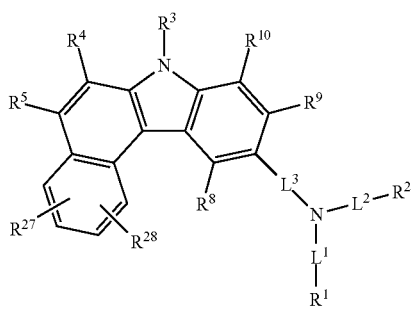

[Chemical Formula I-3]

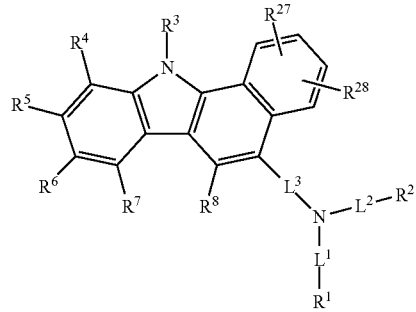

[Chemical Formula I-4]

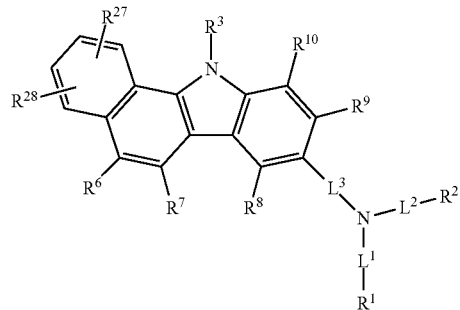

[Chemical Formula I-5]

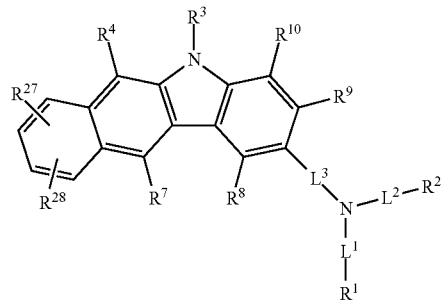

In Chemical Formula I-1 to Chemical Formula I-5, $R^1$ to $R^{10}$ and to $L^3$ are the same as defined as above, and $R^{27}$ and $R^{28}$ are independently hydrogen, deuterium, a substituted or unsubstituted C1 to C30 alkyl group, a substituted or unsubstituted C6 to C30 aryl group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

The $L^1$ to $L^3$ of Chemical Formula I may independently be a single bond or selected from substituted or unsubstituted groups of Group I.

[Group I]

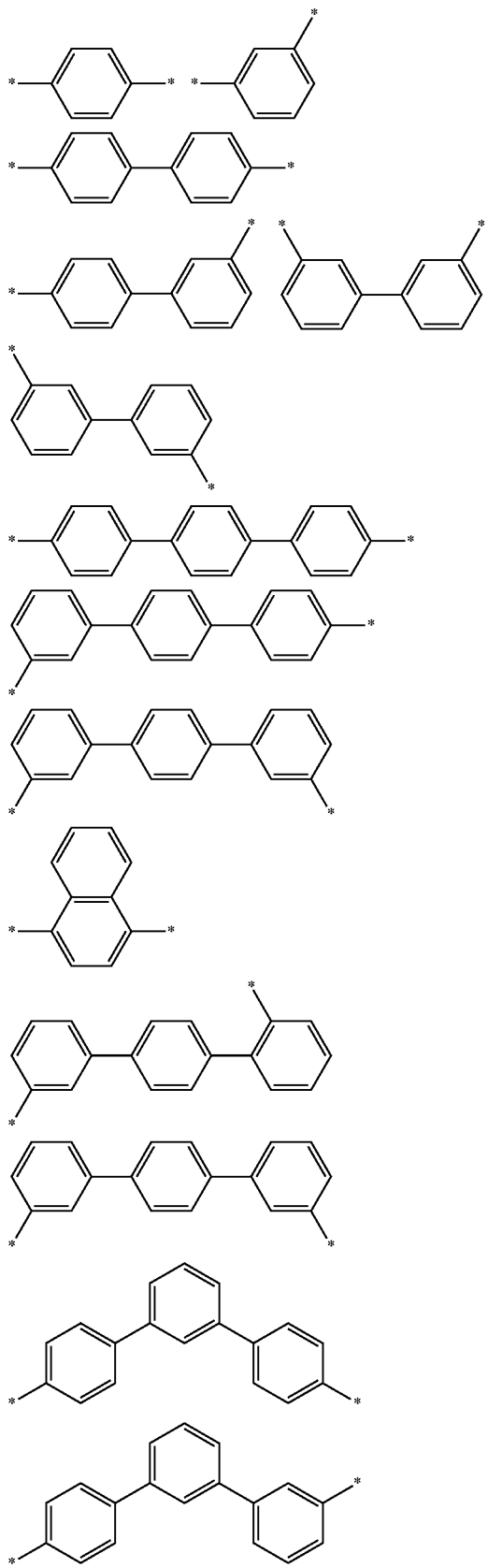
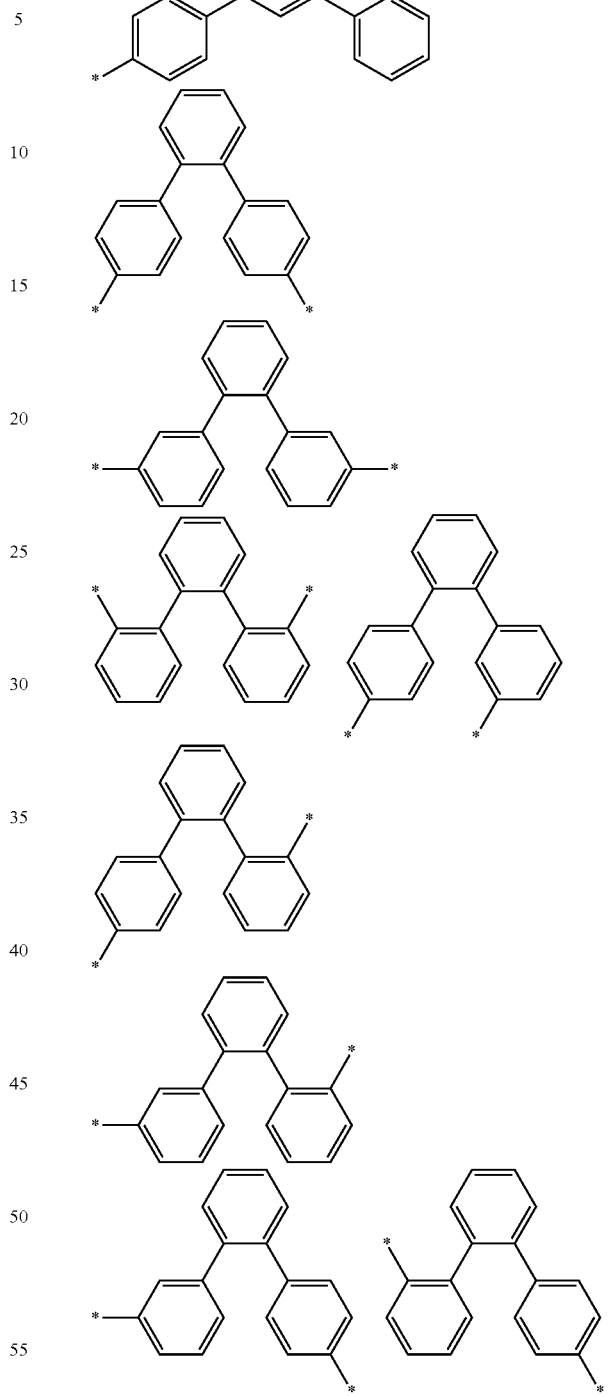

In Group I, * is a linking point,

"substituted" refers to replacement of at least one hydrogen with deuterium, halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

In addition, the compound represented by Chemical Formula I may be represented by Chemical Formula I-6 or I-7 when the most specific $L^3$ selected from Group I is applied thereto.

[Chemical Formula I-6]

[Chemical Formula I-7]

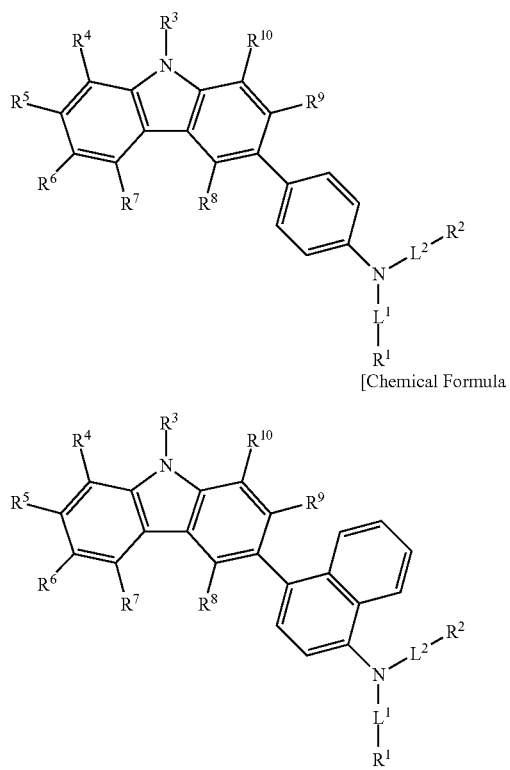

[Group II]

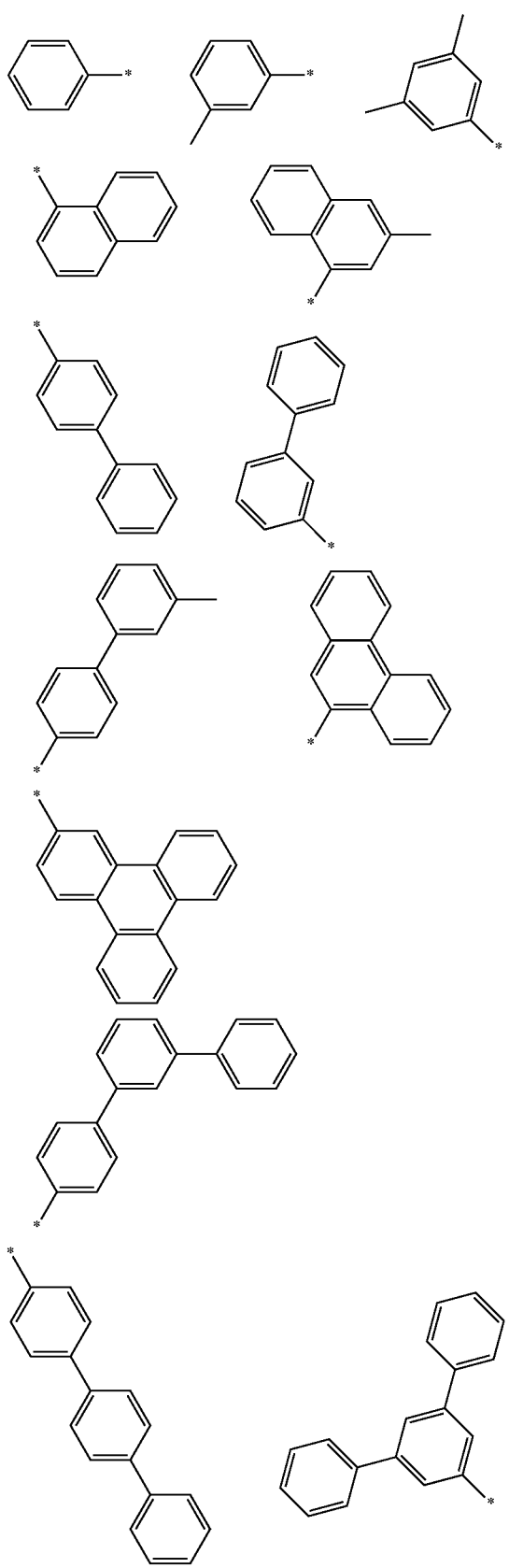

$R^1$ to $R^{10}$, $L^1$, and $L^2$ are the same as described above.

Specifically, the $R^4$ to $R^{10}$ of Chemical Formula I may independently be hydrogen, deuterium, a substituted or unsubstituted C1 to C30 alkyl group, or a substituted or unsubstituted C6 to C30 aryl group.

As specific examples, $R^1$ to $R^3$ of Chemical Formula I may independently be a substituted or unsubstituted C6 to C30 aryl group, a substituted or unsubstituted C2 to C30 heterocyclic group, or a combination thereof, for example, the substituted or unsubstituted C6 to C30 aryl group may be a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted fluorenyl group, a substituted or unsubstituted triphenylene group, combination thereof, or a fused form thereof, and the substituted or unsubstituted C2 to C30 heterocyclic group may be a substituted or unsubstituted carbazolyl group, a substituted or unsubstituted benzofuranyl group, a substituted or unsubstituted benzothiophenyl group, a substituted or unsubstituted dibenzofuranyl group, a substituted or unsubstituted dibenzothiophenyl group, or a combination thereof.

On the other hand, as more specific examples, the substituted or unsubstituted C6 to C30 aryl group and the substituted or unsubstituted C2 to C30 heterocyclic group may be selected from substituted or unsubstituted groups of Group II.

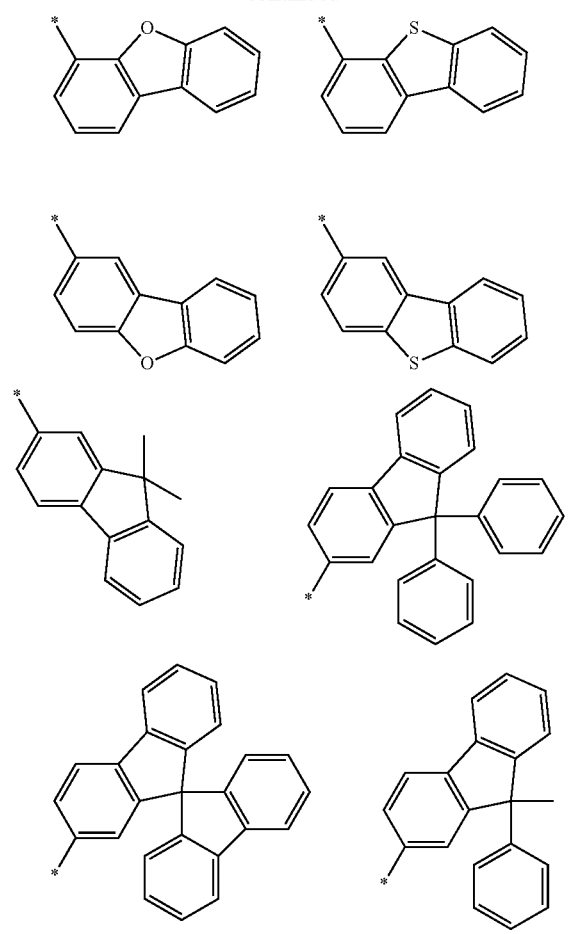

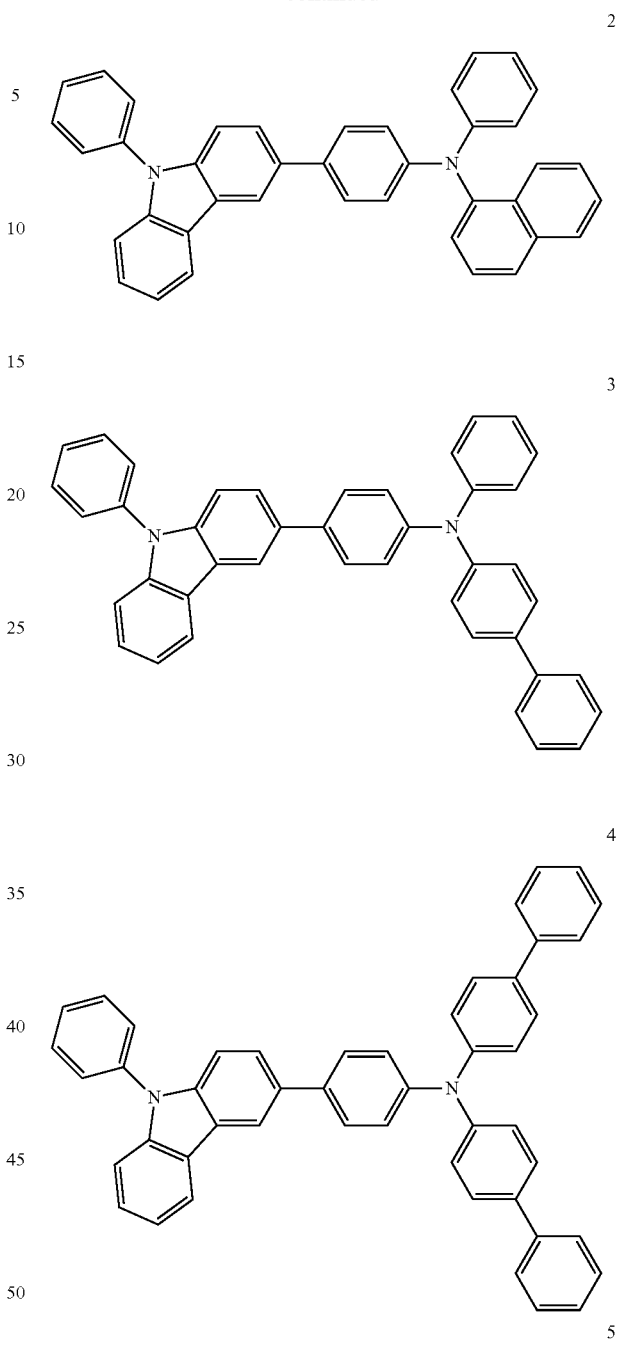

In Group II, * is a linking point, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

The compound represented by Chemical Formula I may be selected from compounds of Group III, but is not limited thereto.

[Group III]

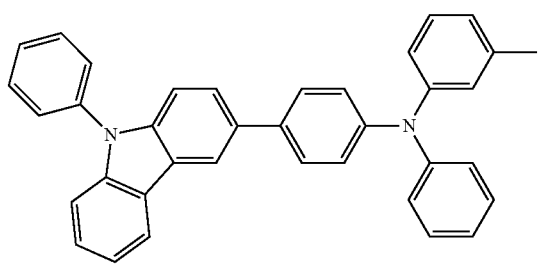

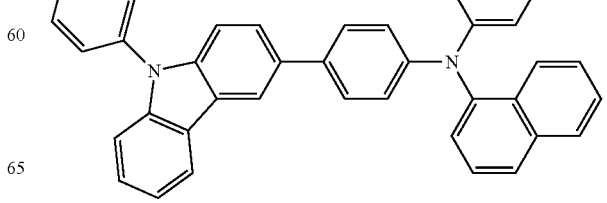

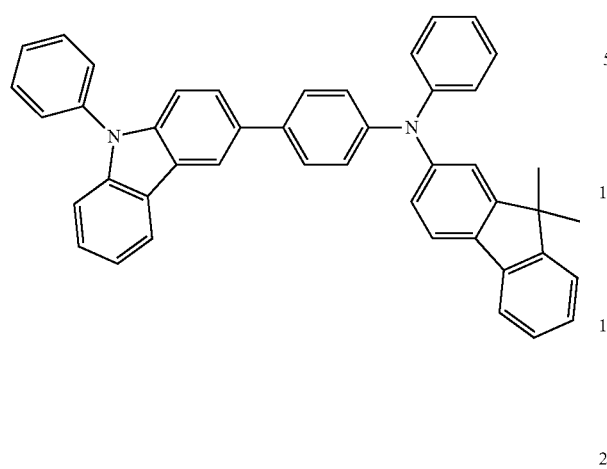
6
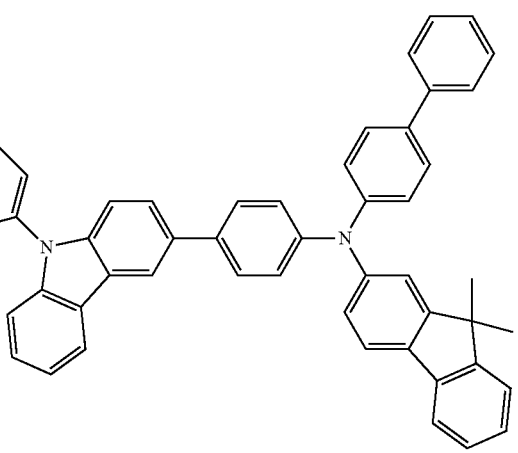
9
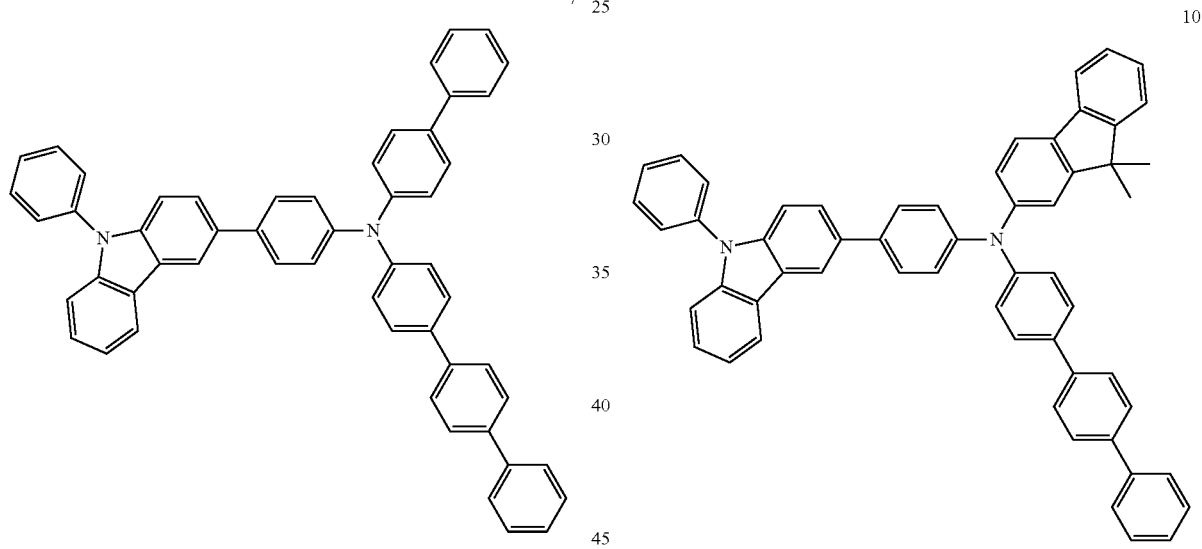
7
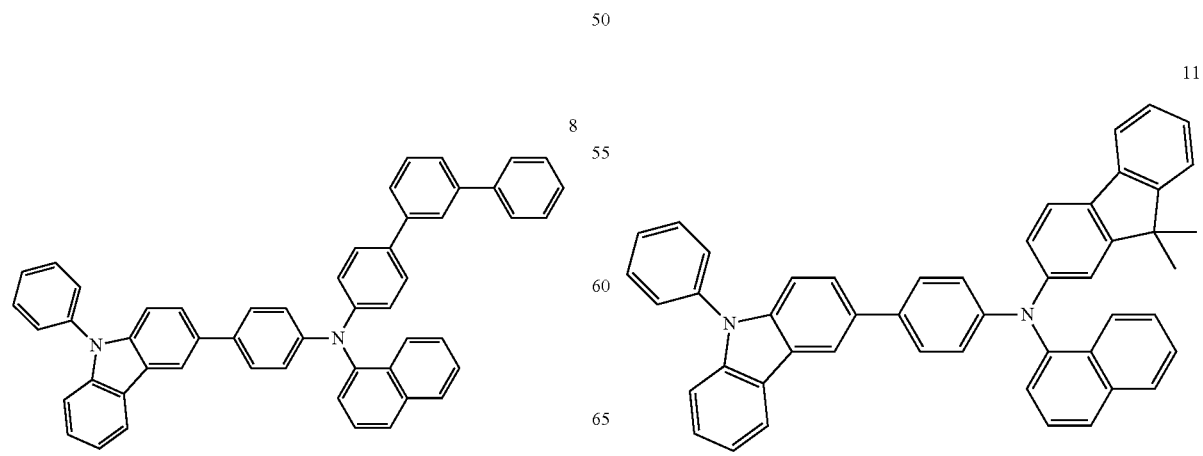
8

12
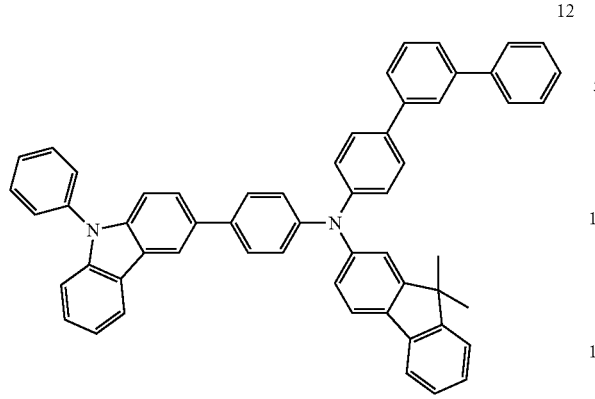
13
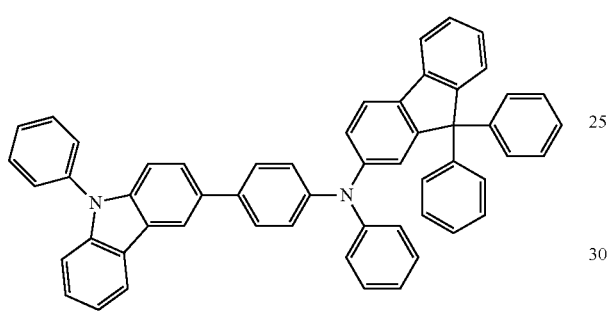
14
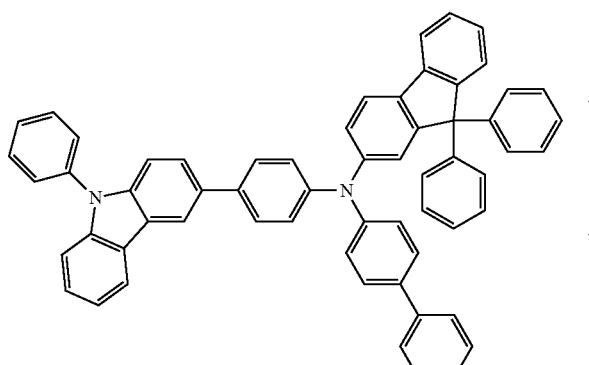
15
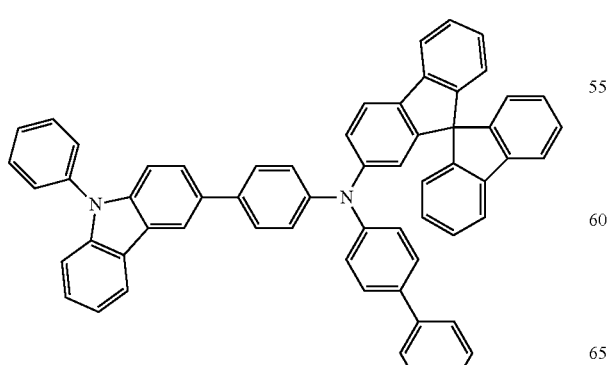
16
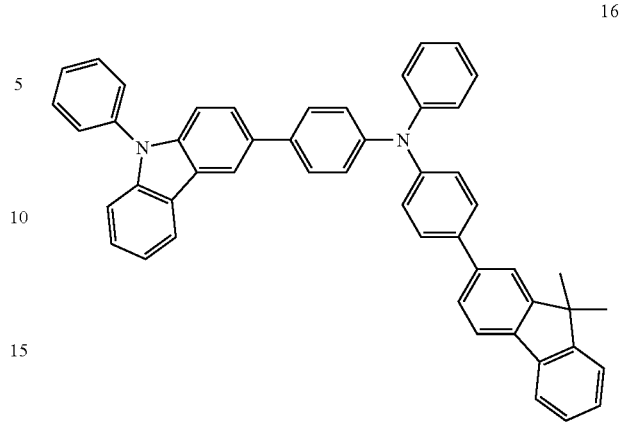
17
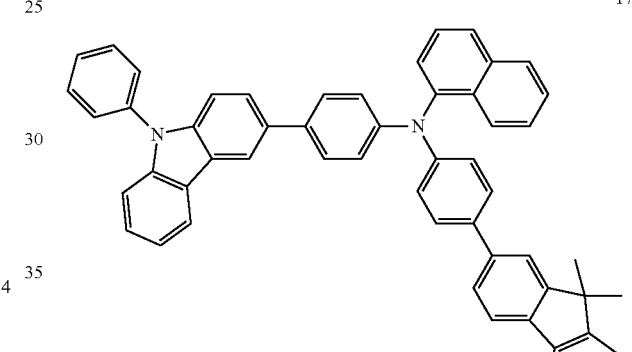
18

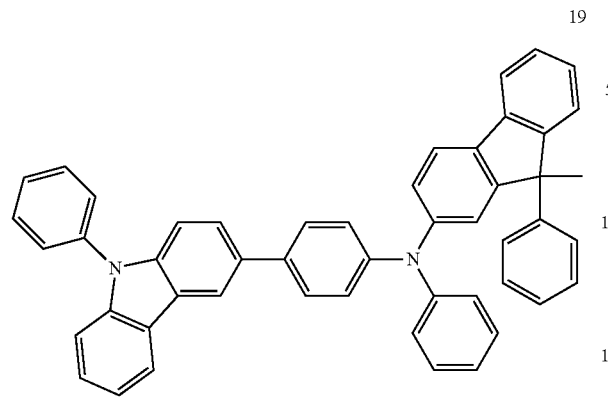
19
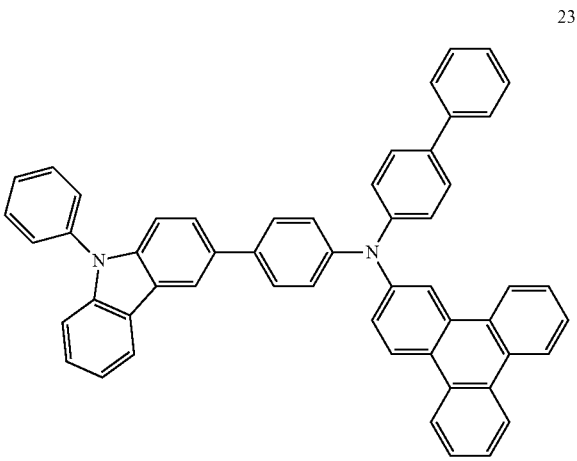
23
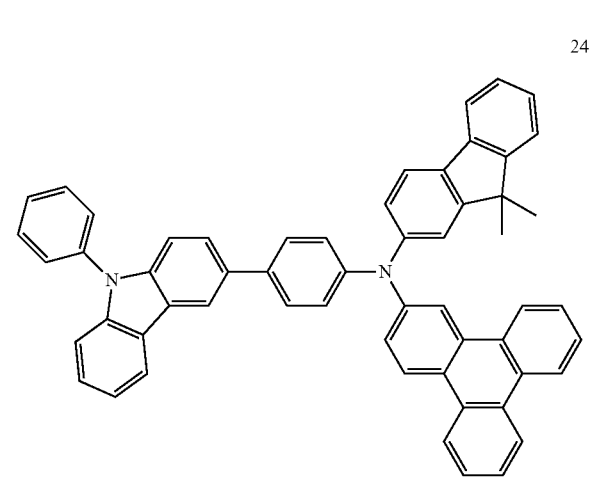
24
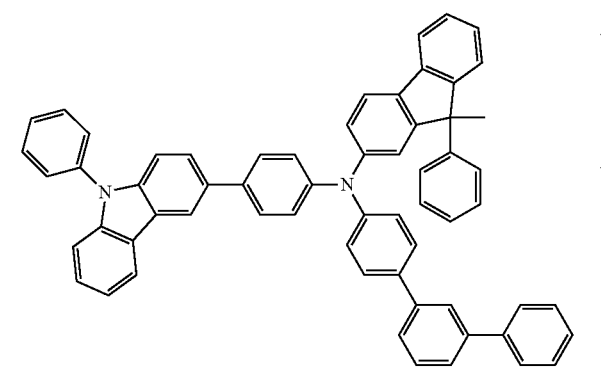
21
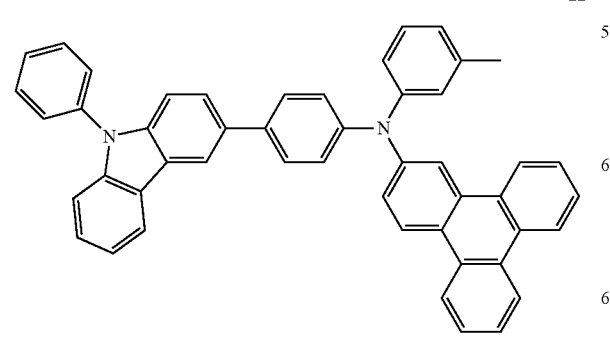
22
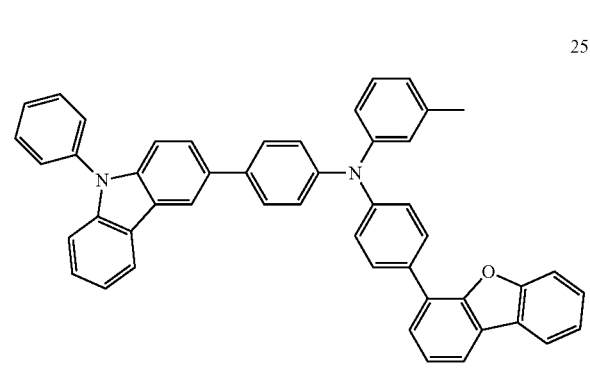
25
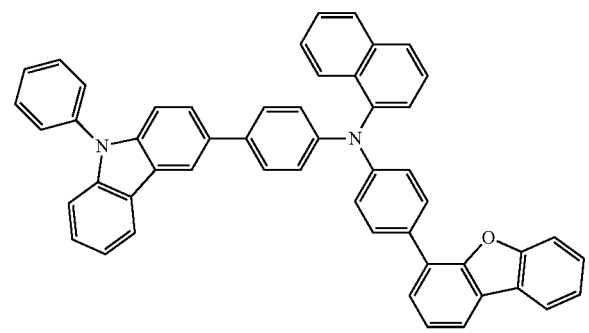
26

27
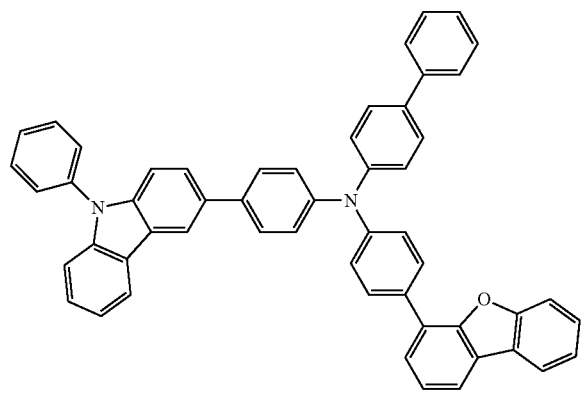
28
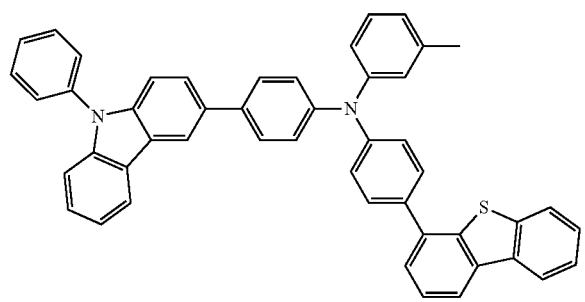
29
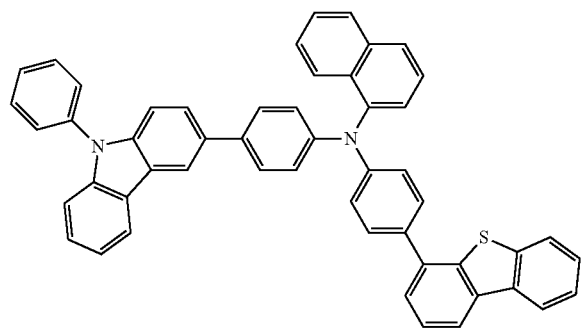
30
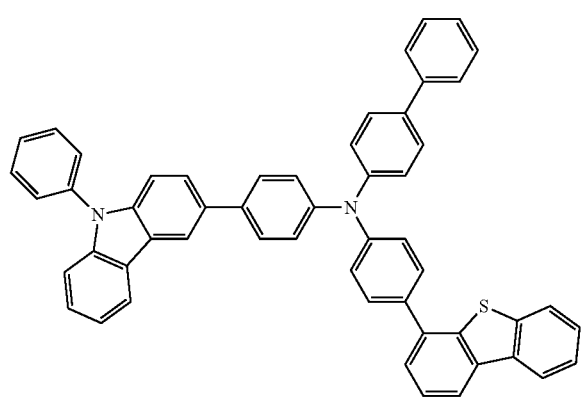
31

32
33
34
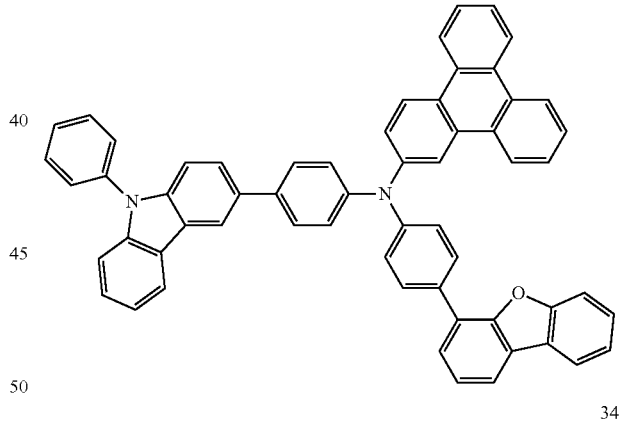

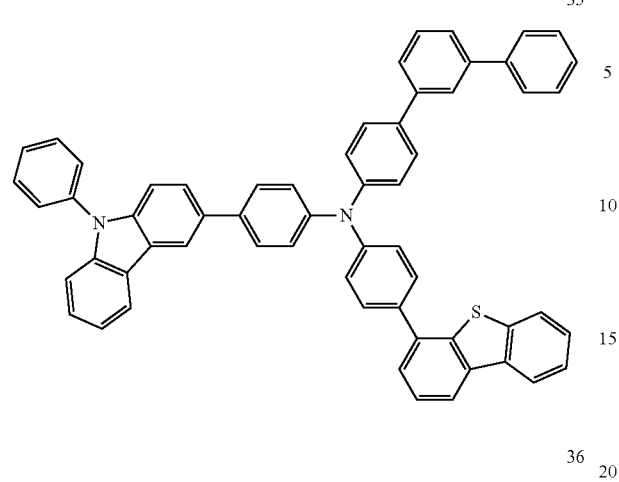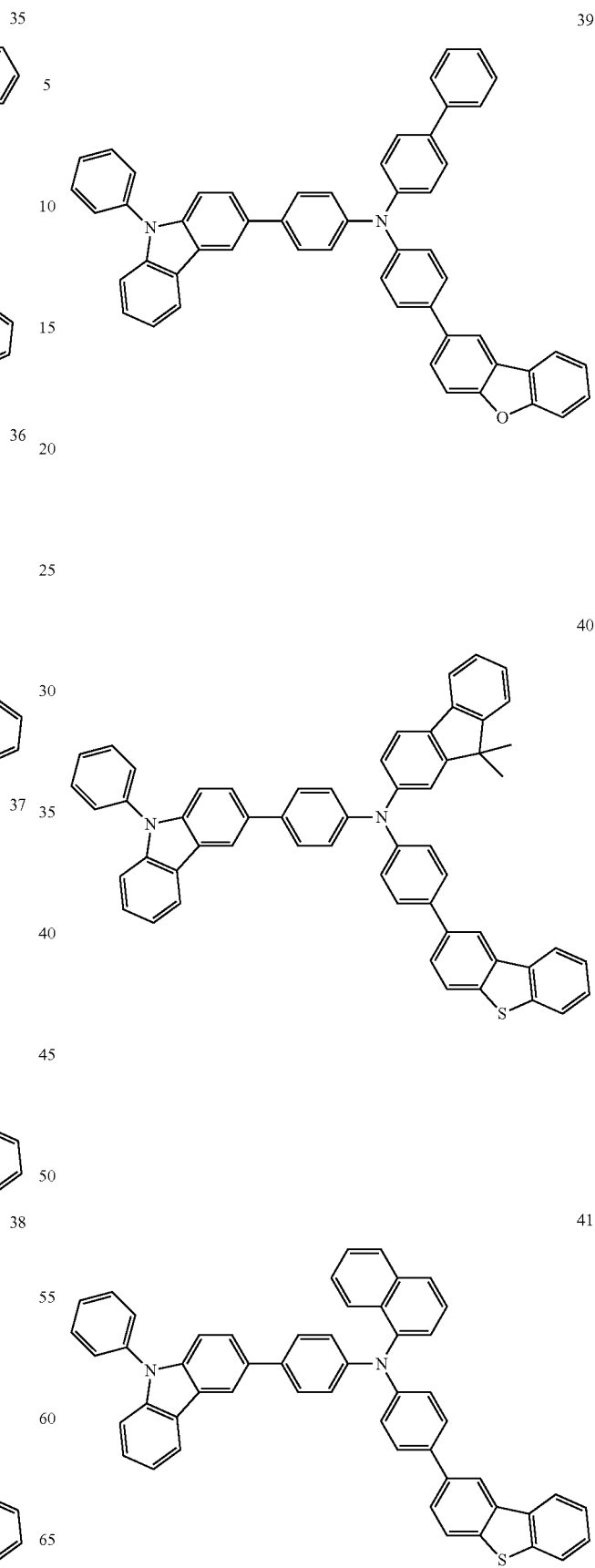

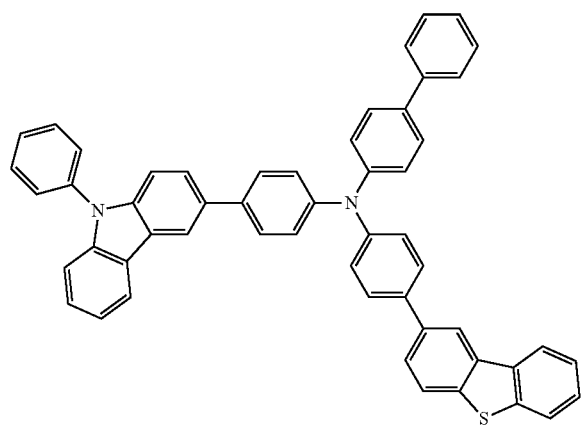
42
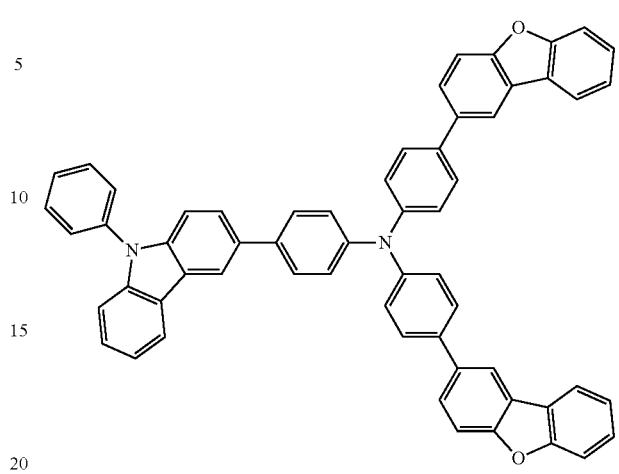
45
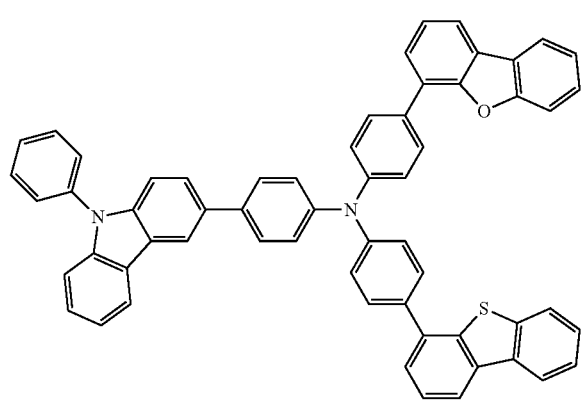
43
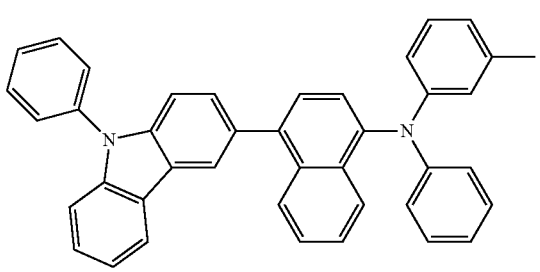
46
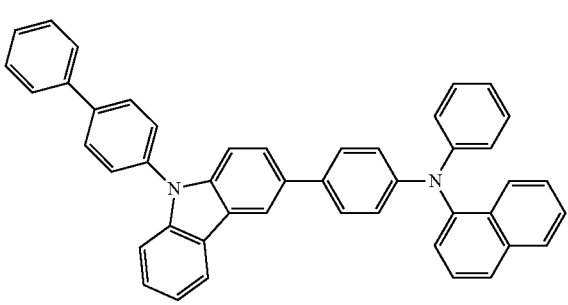
47
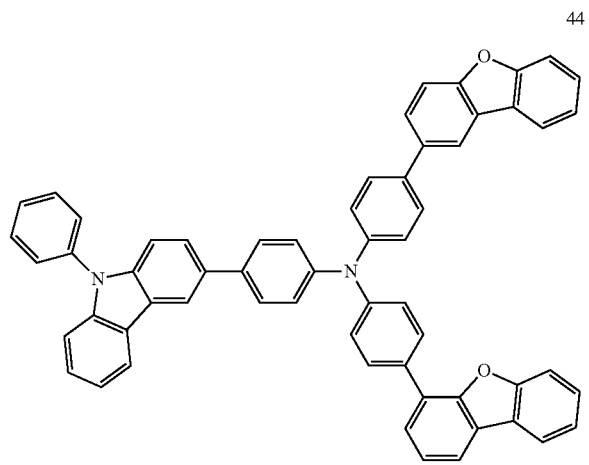
44
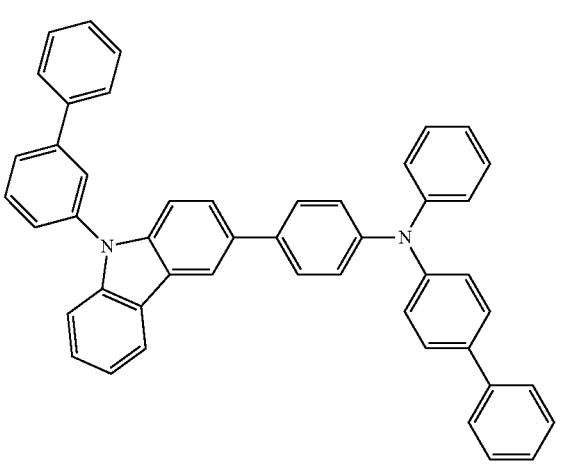
48

49
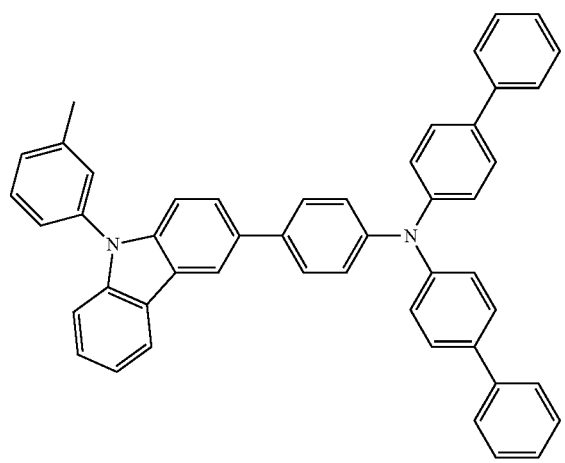
50
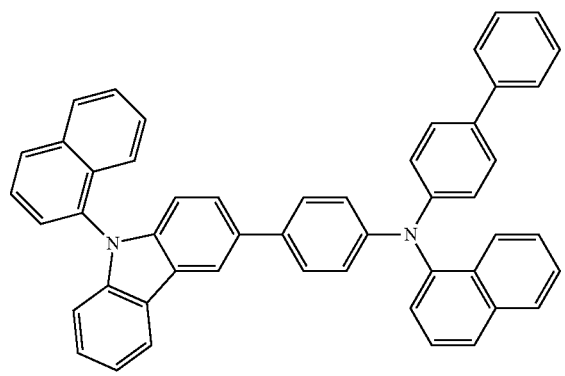
51
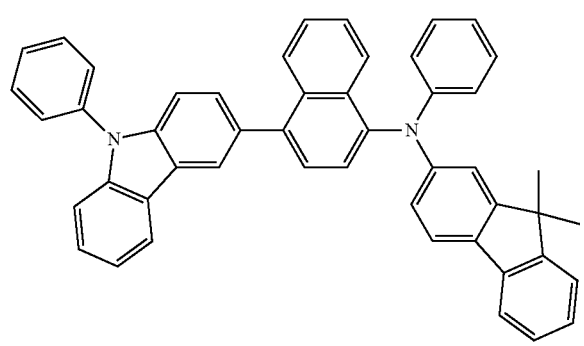
52
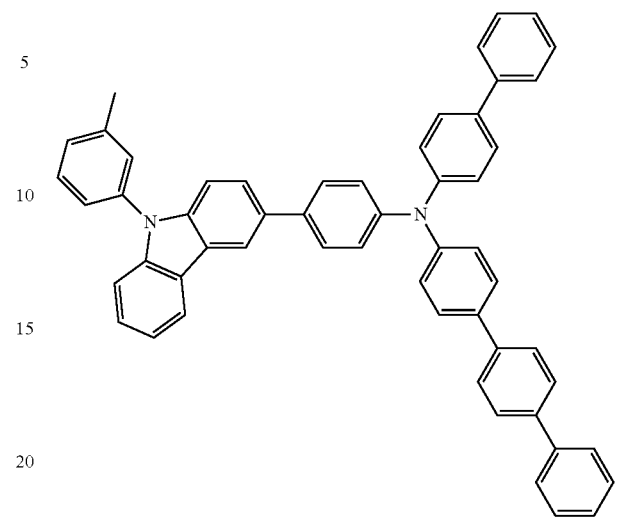
53
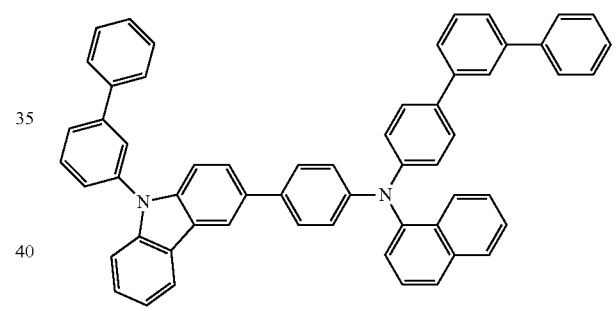
54
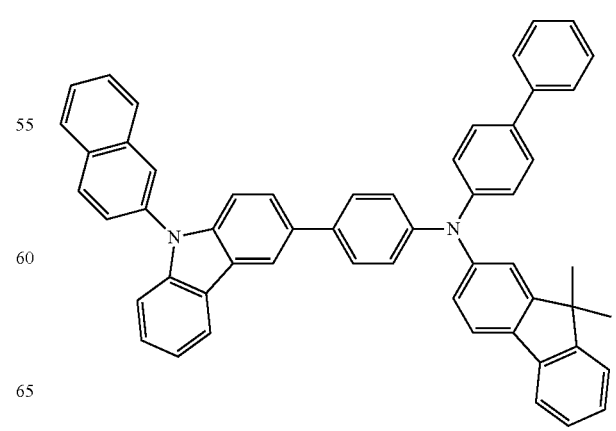

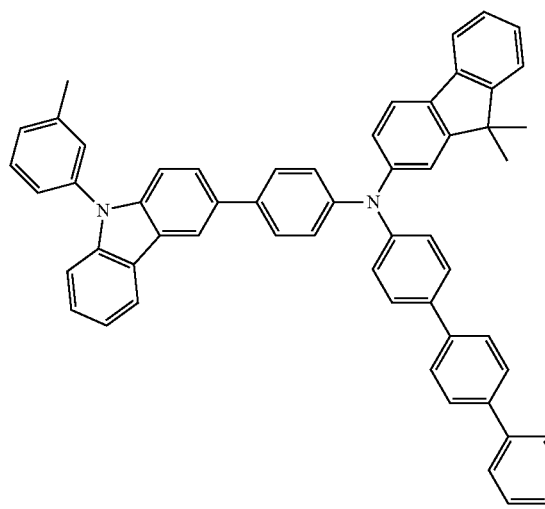
55
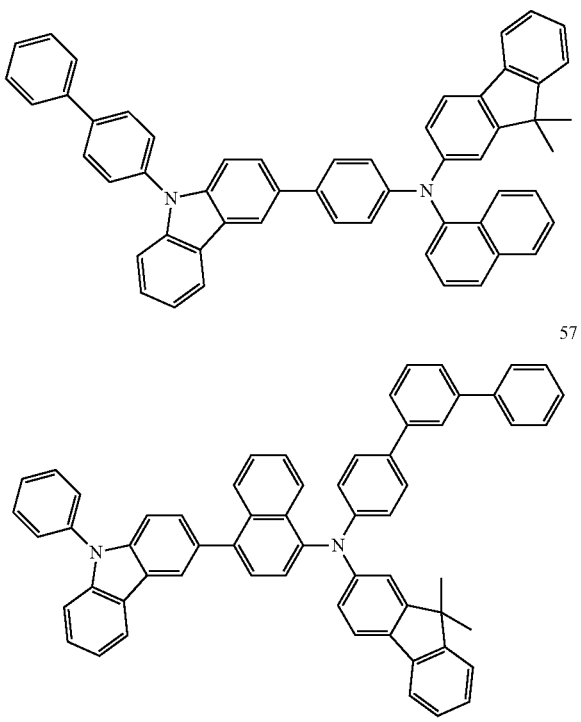
56
57
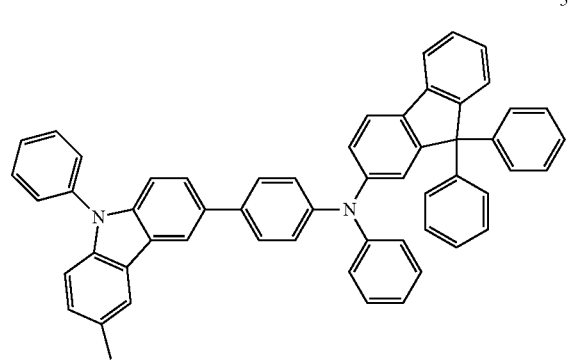
58
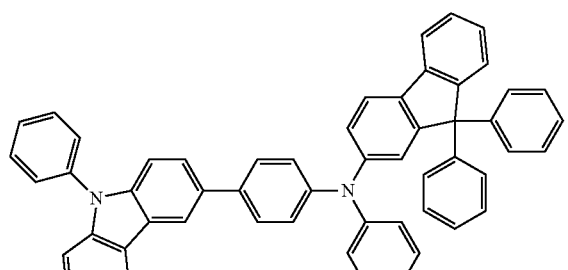
59
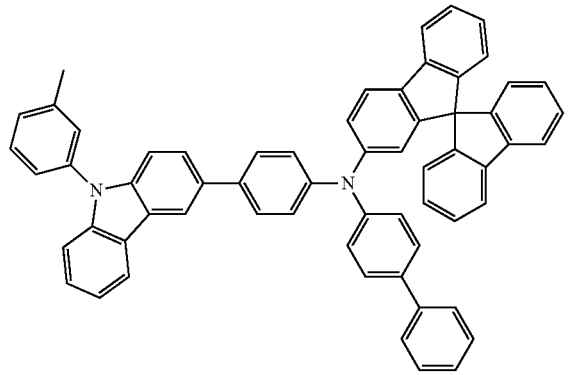
60
61

62
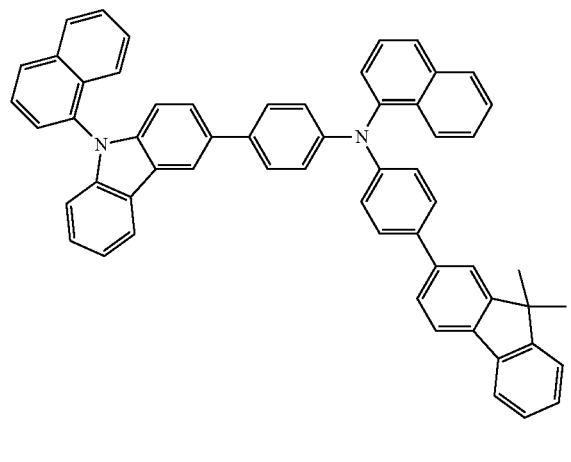
63
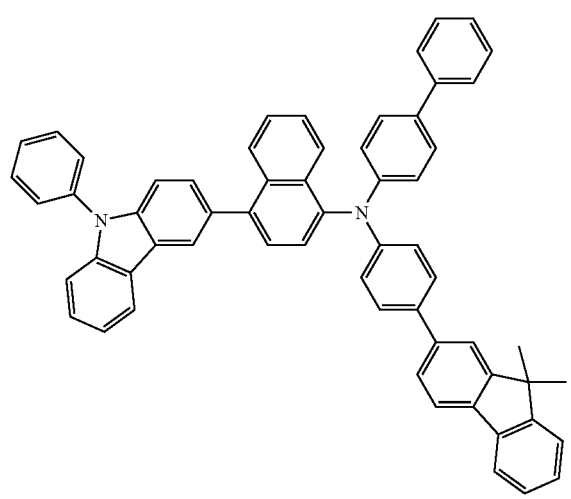
64
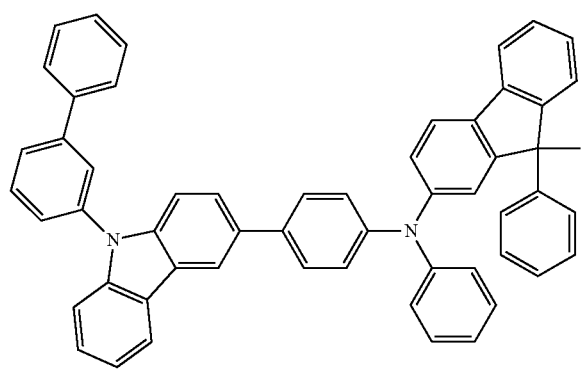
65
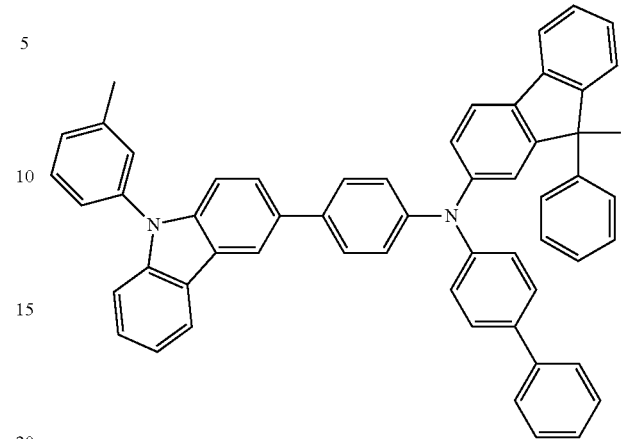
66
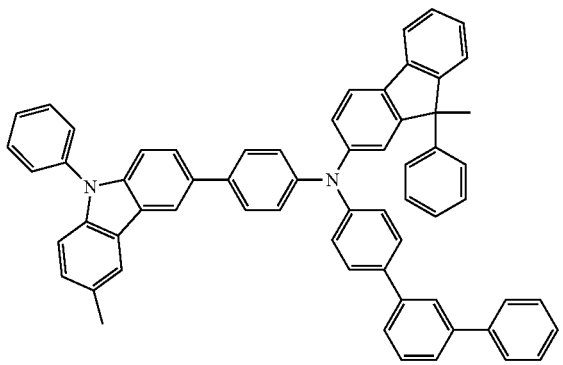
67
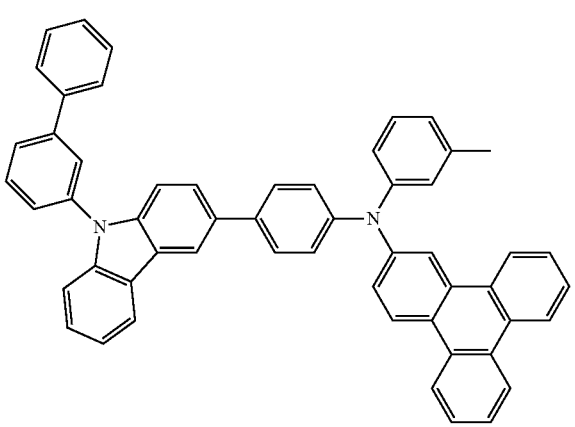

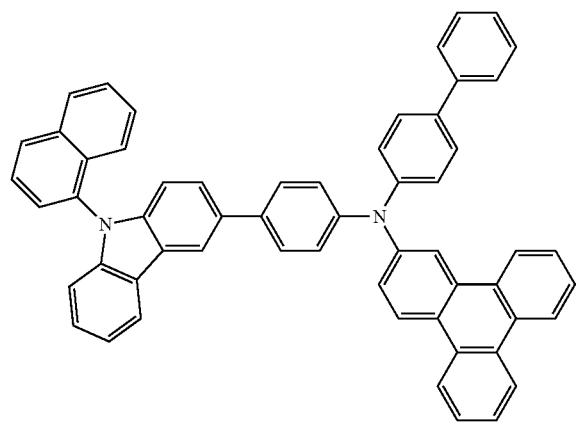
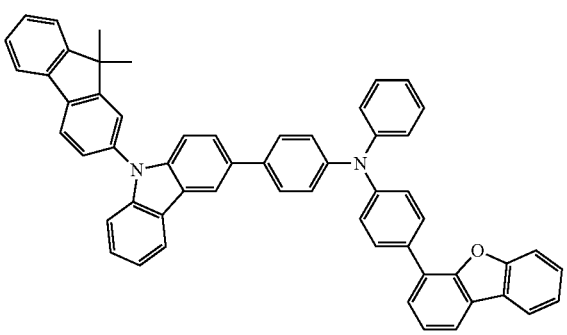
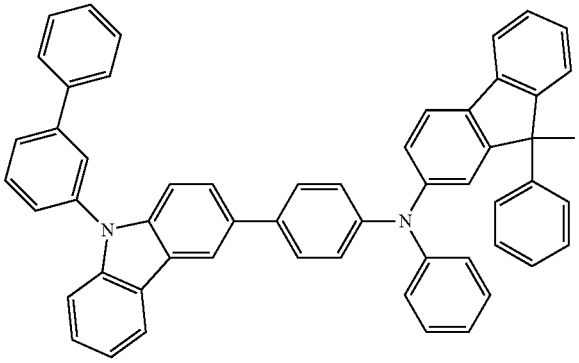
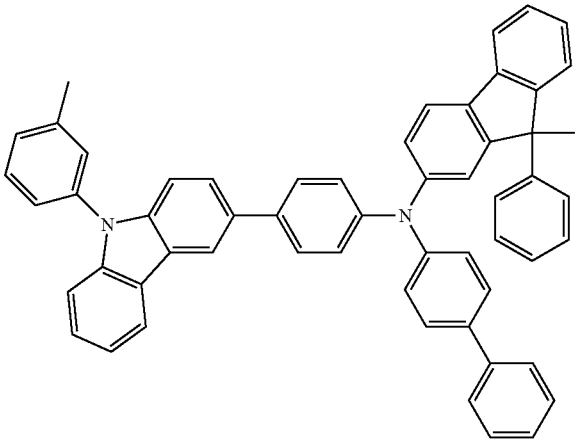
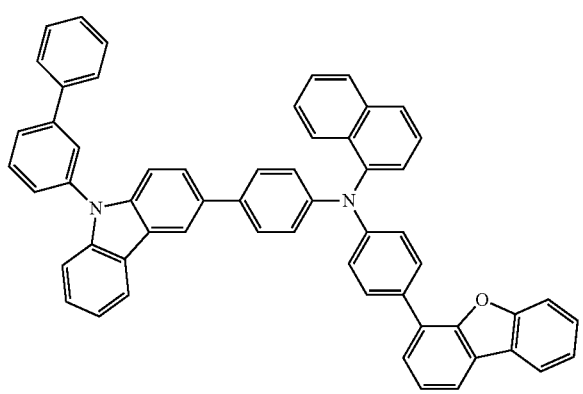

76
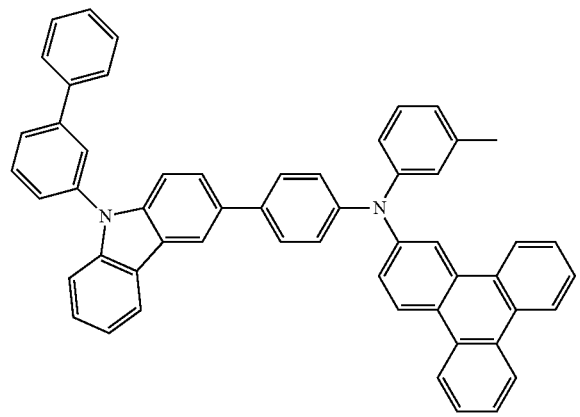
77
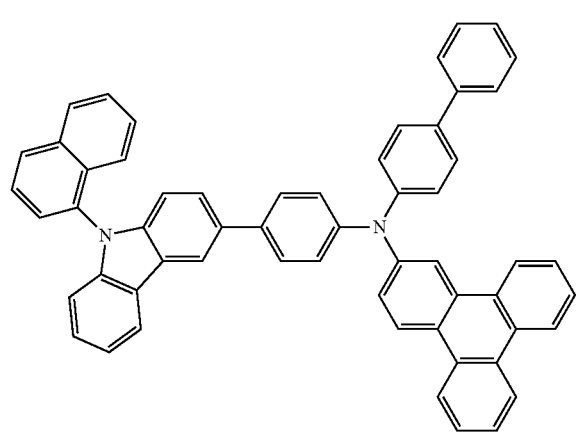
78
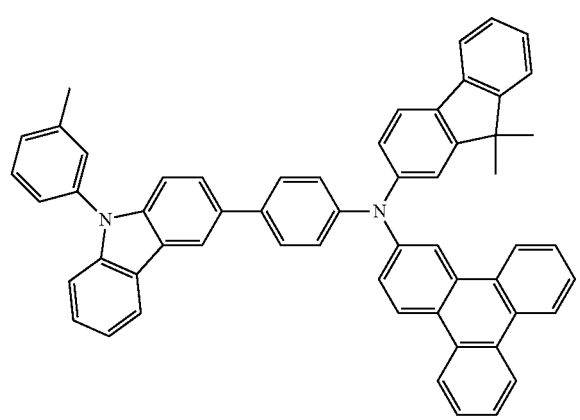
79
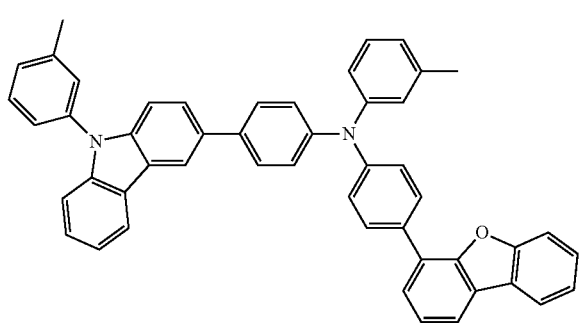
80
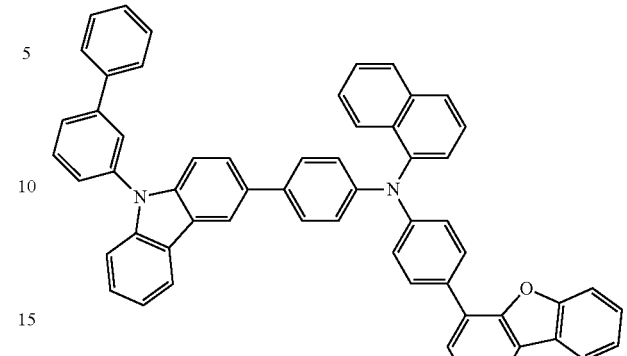
81
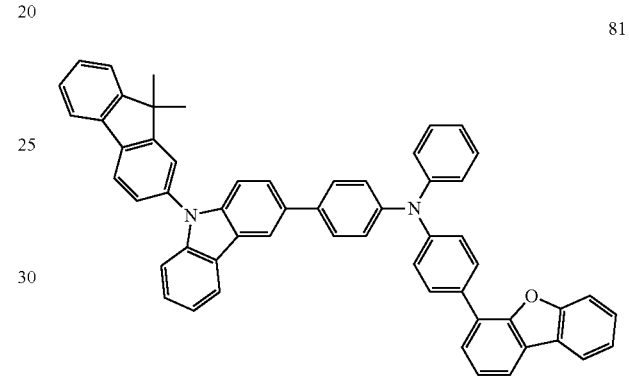
82
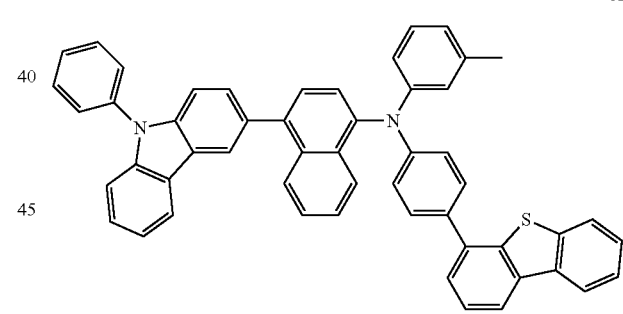
83
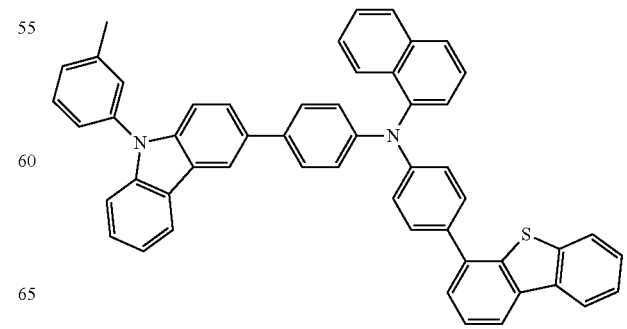

84
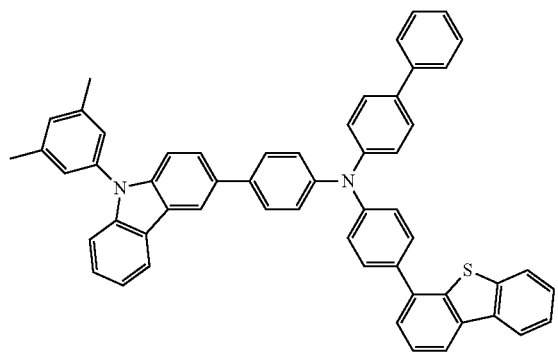
85
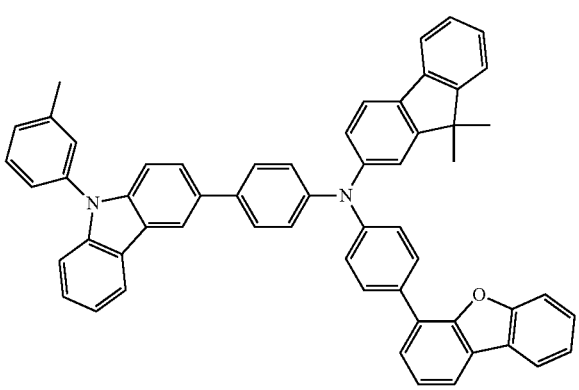
86
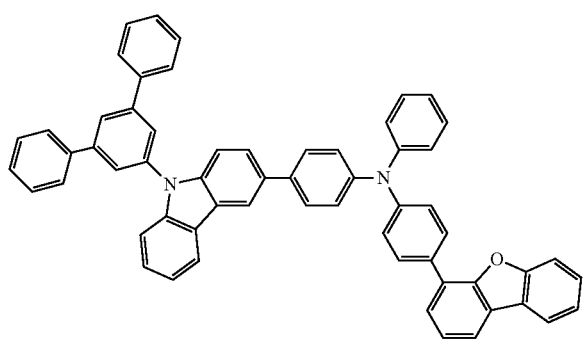
87
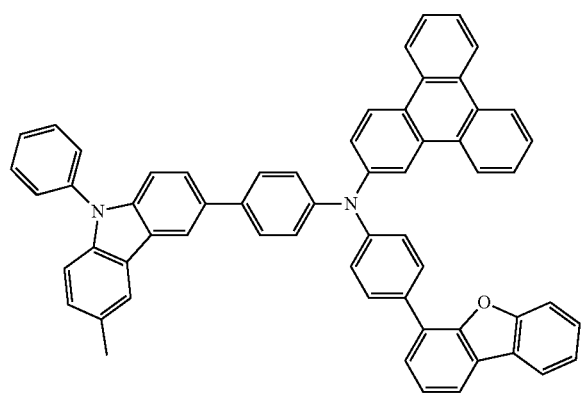
88
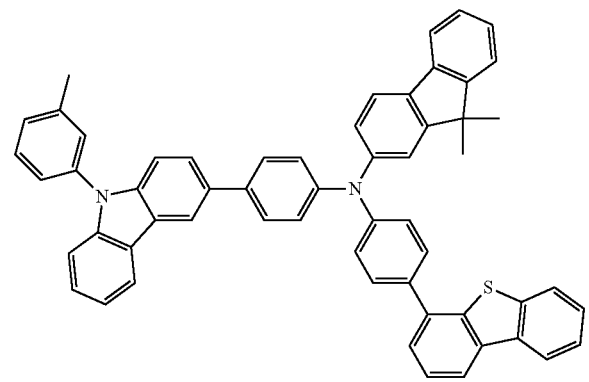
89
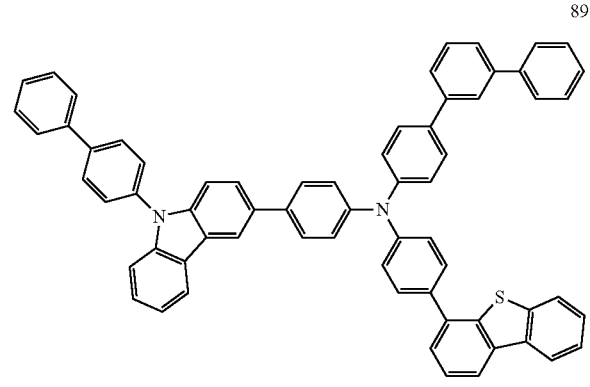
90
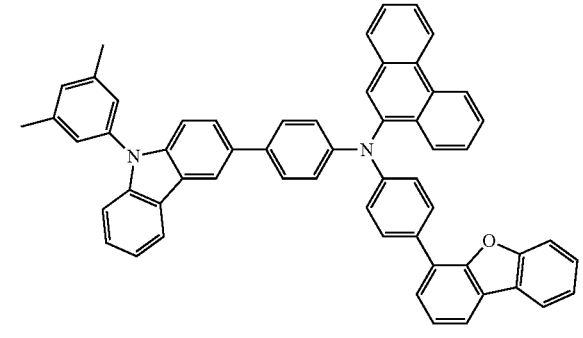
91
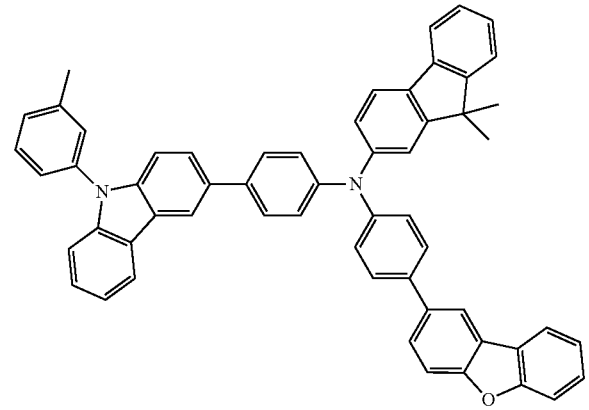

92
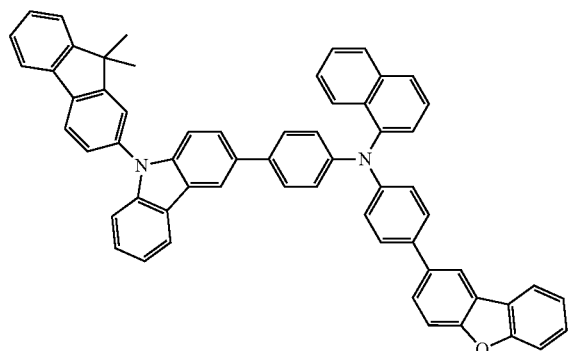
93
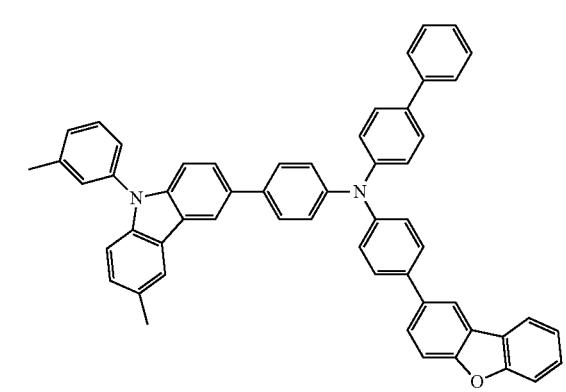
94
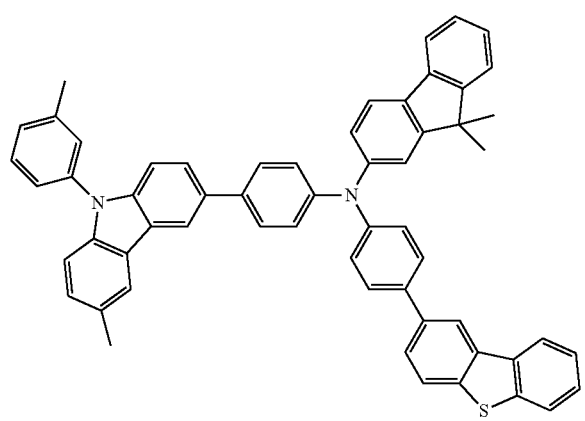
95
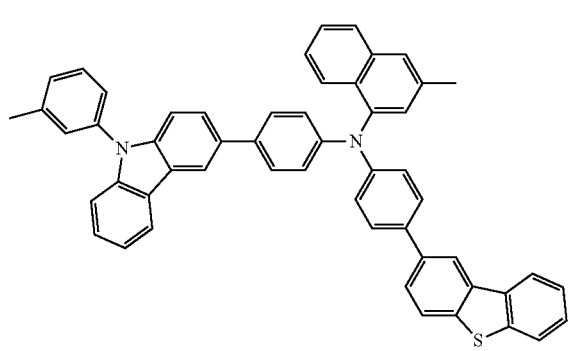
96
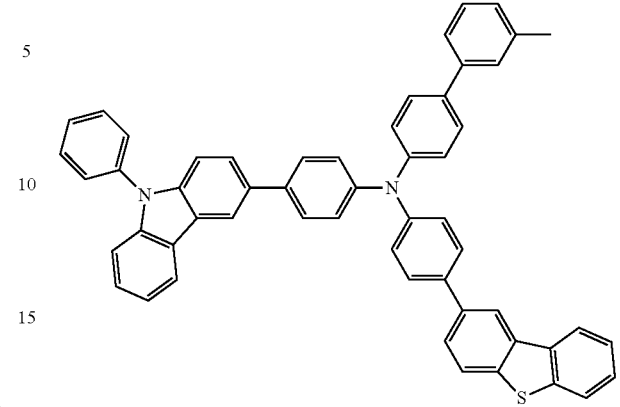
97
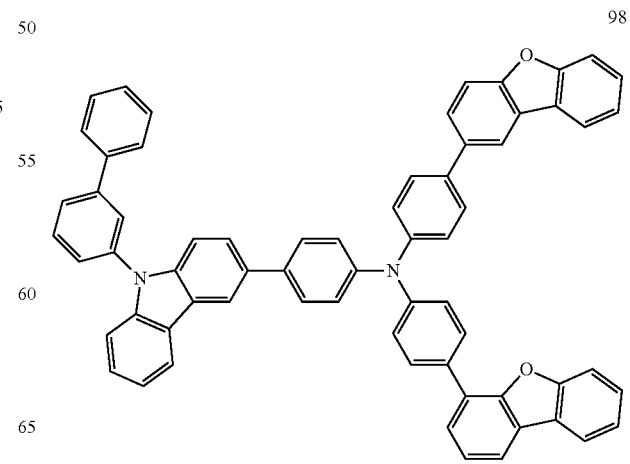
98

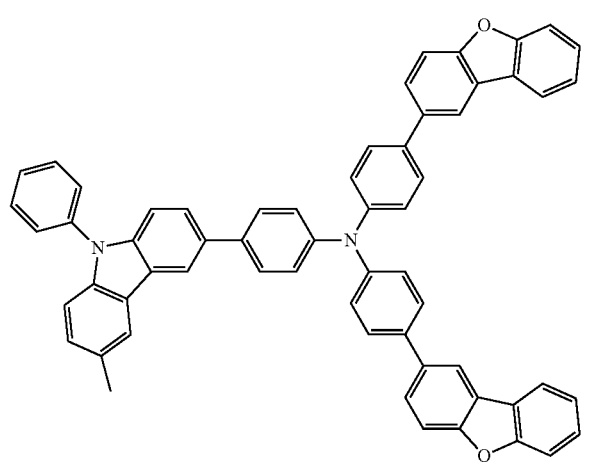
99
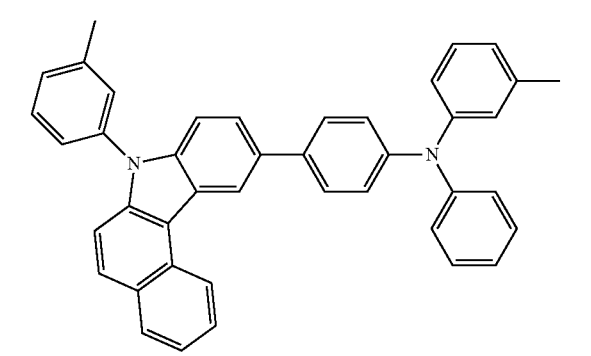
100
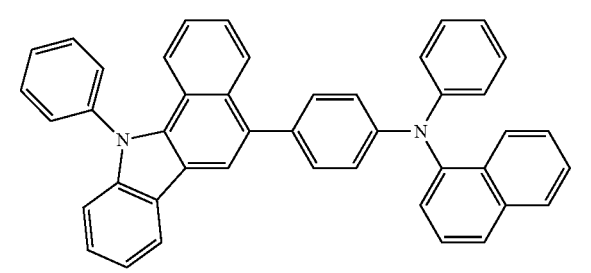
101
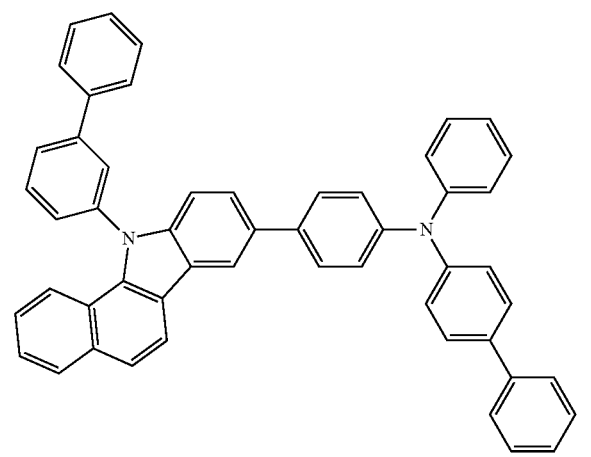
102
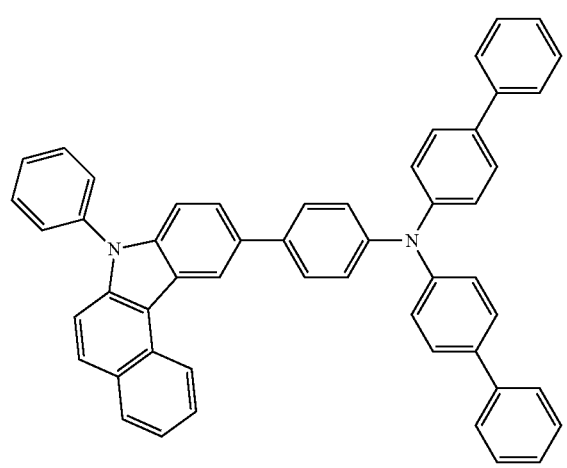
103
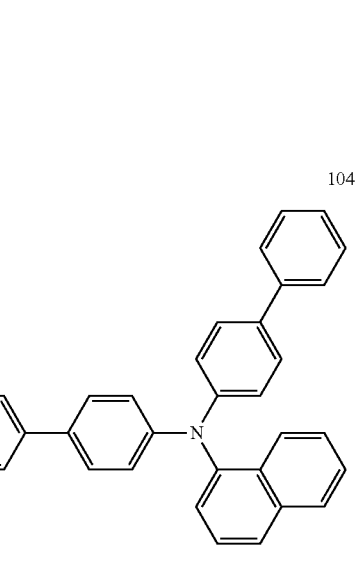
104
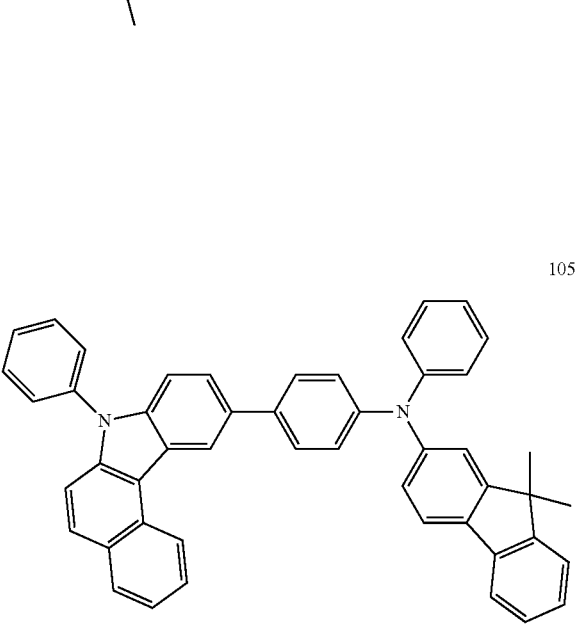
105

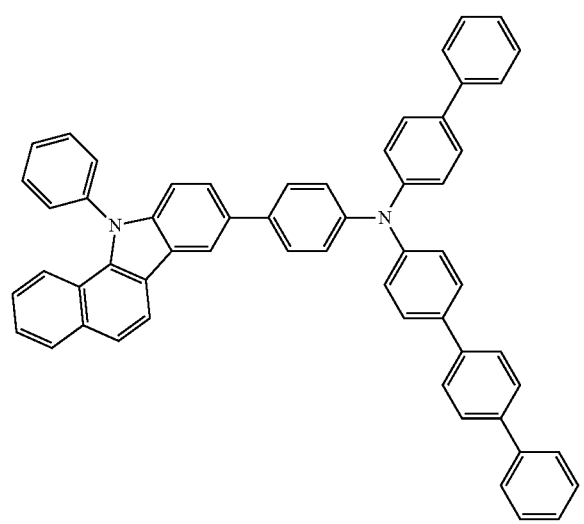
106
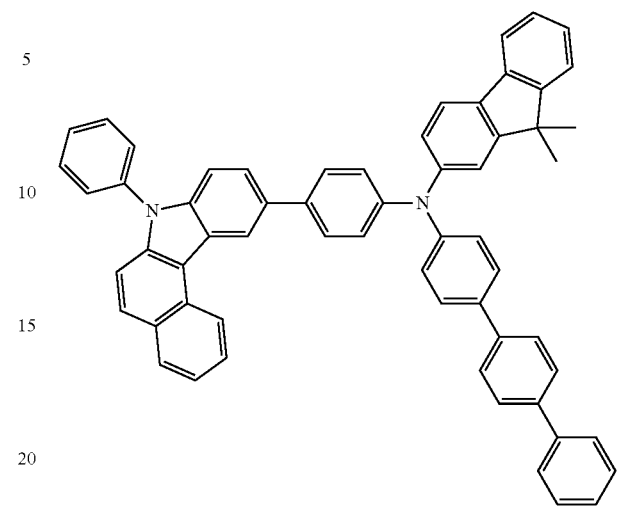
109
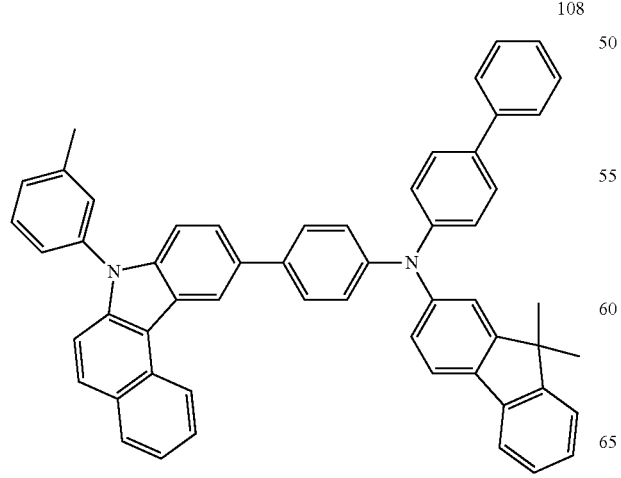
107
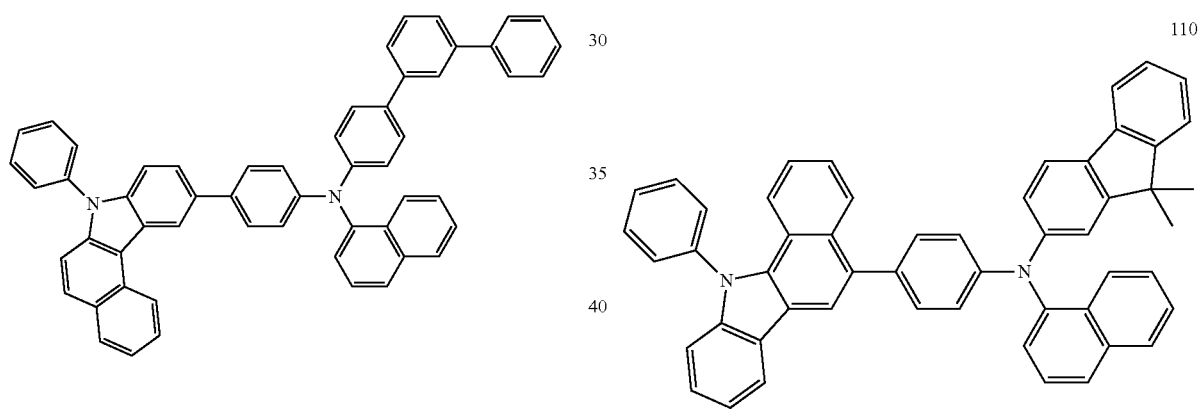
110
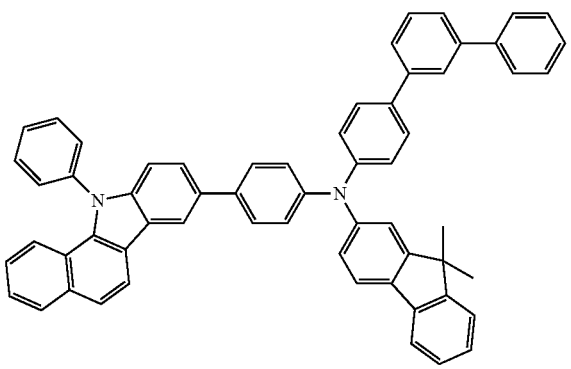
108
111

112
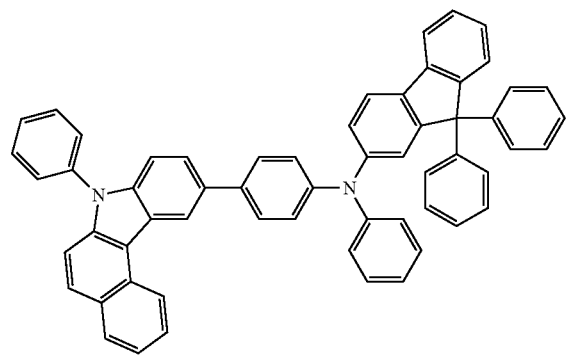
113
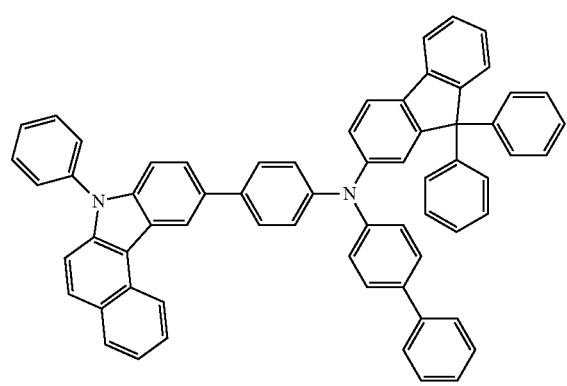
114
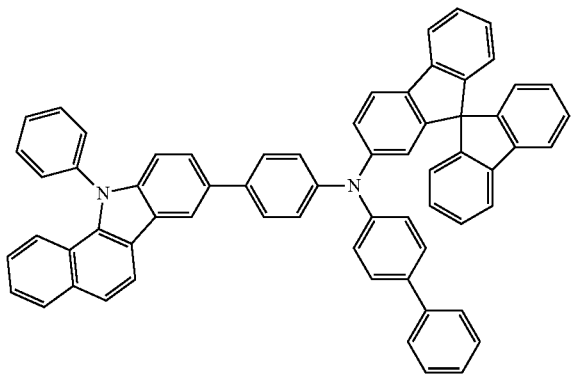
115
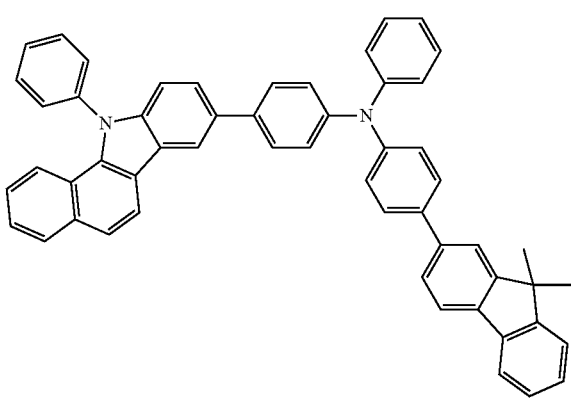
116
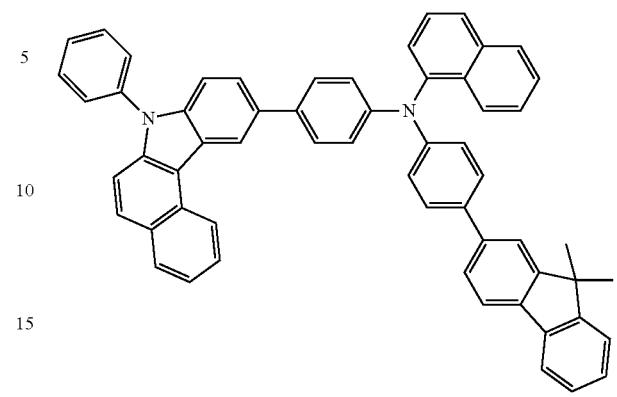
117
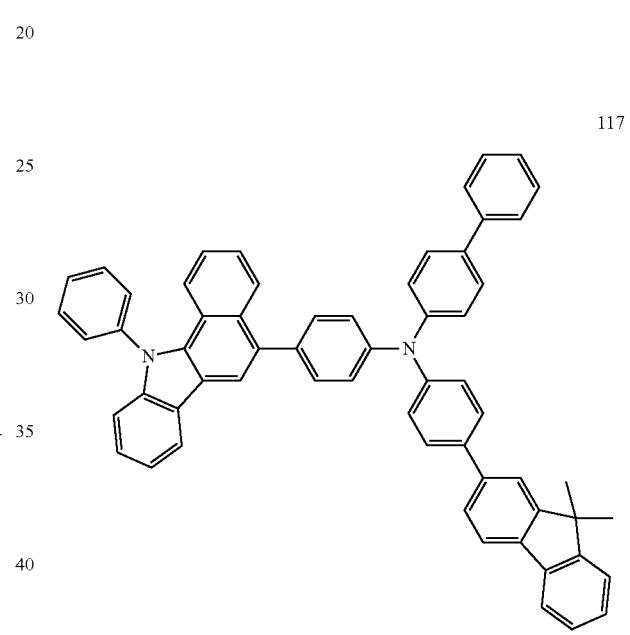
118
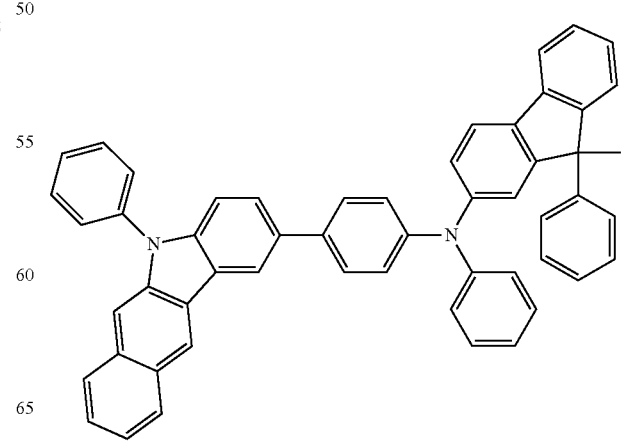

119
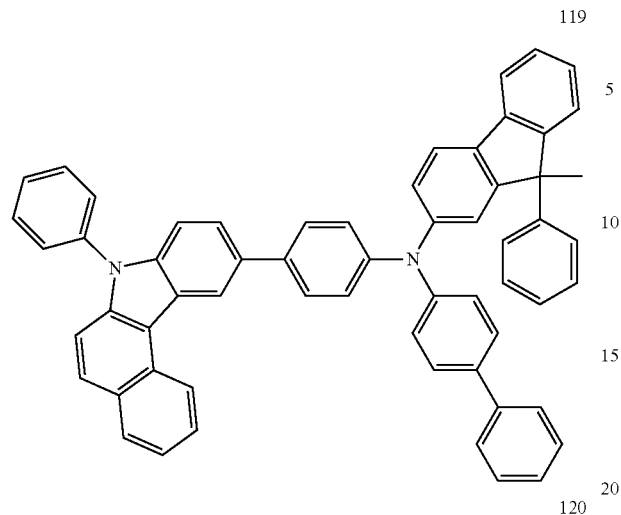
120
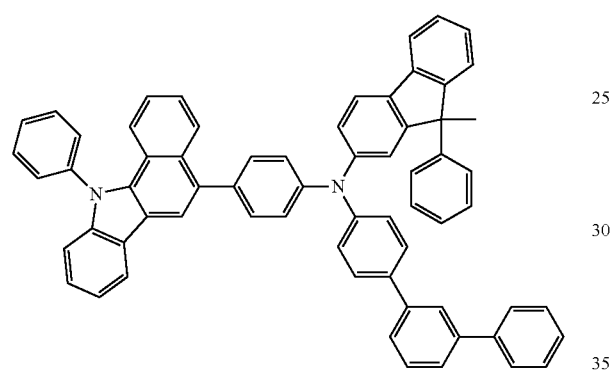
121
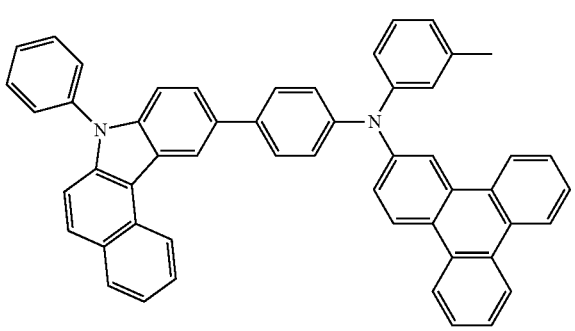
122
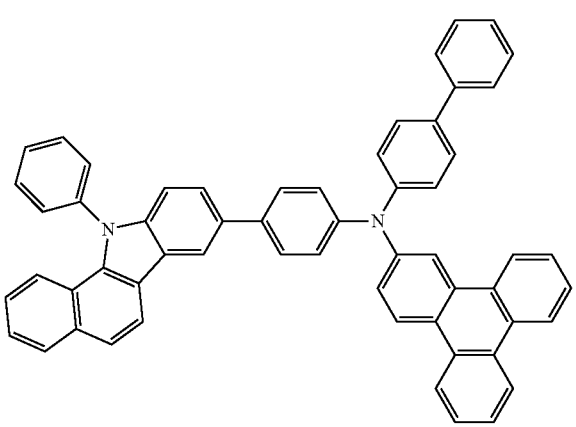
123
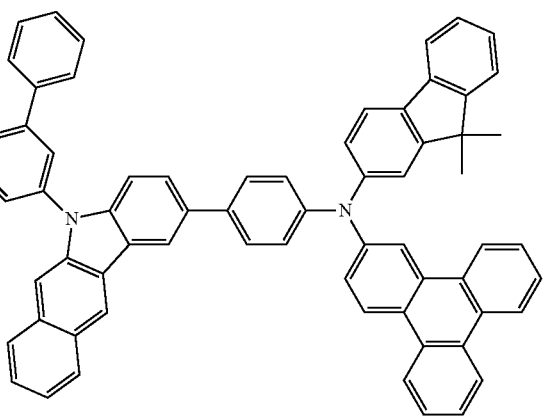
124
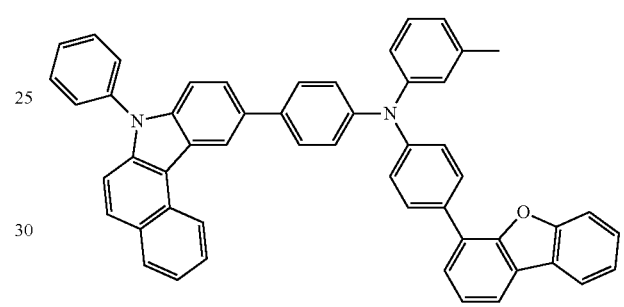
125
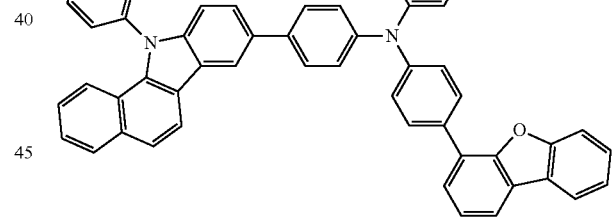
126
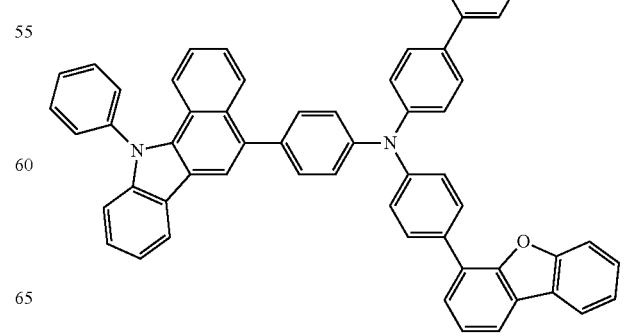

127
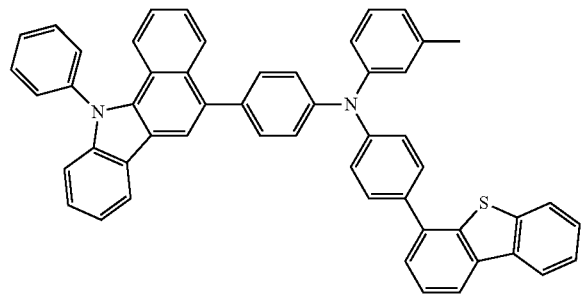
128
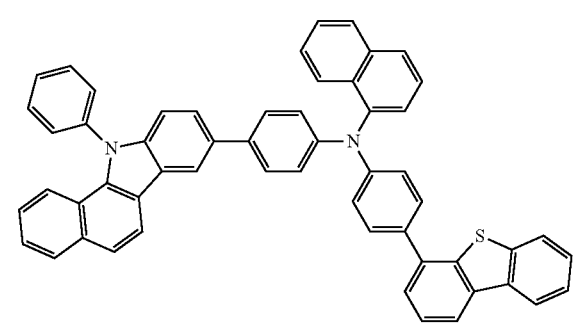
129
130
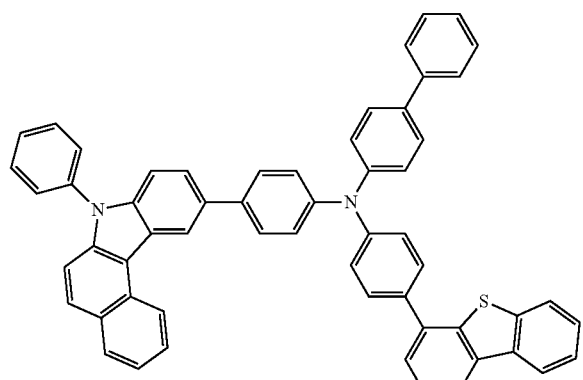
131
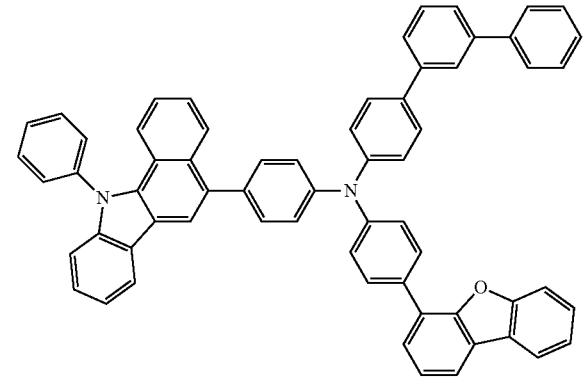
132
133
134
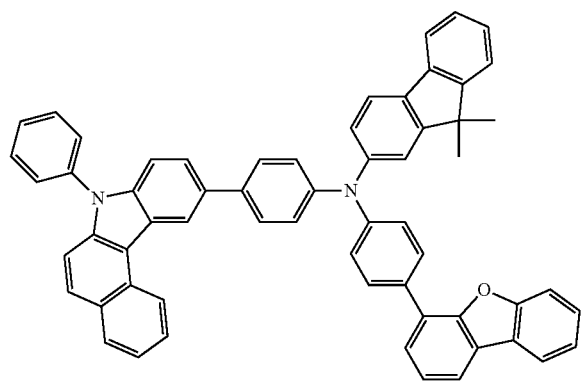

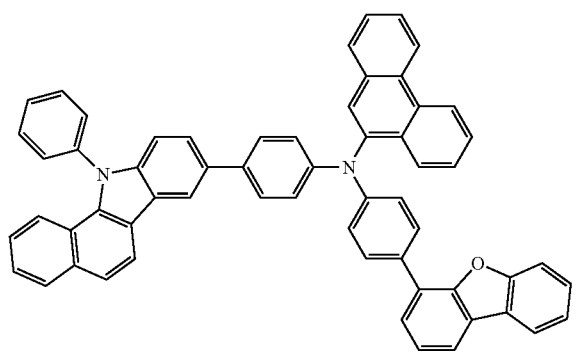
135
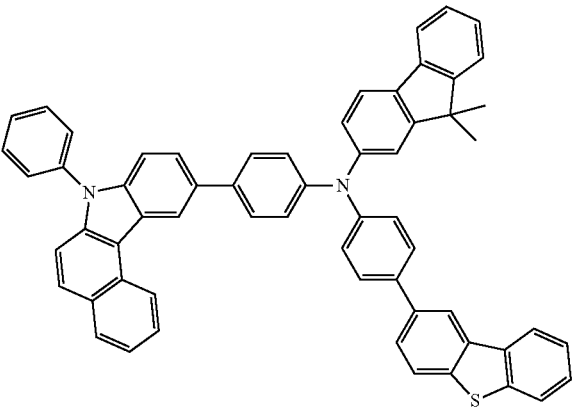
139
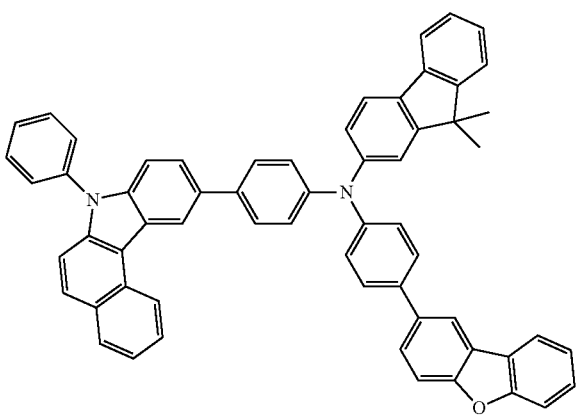
136
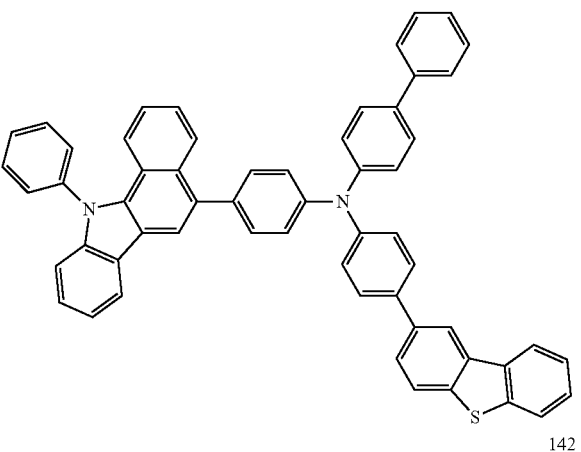
140
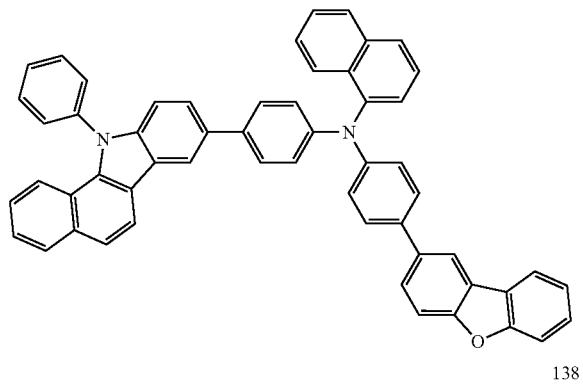
137
141
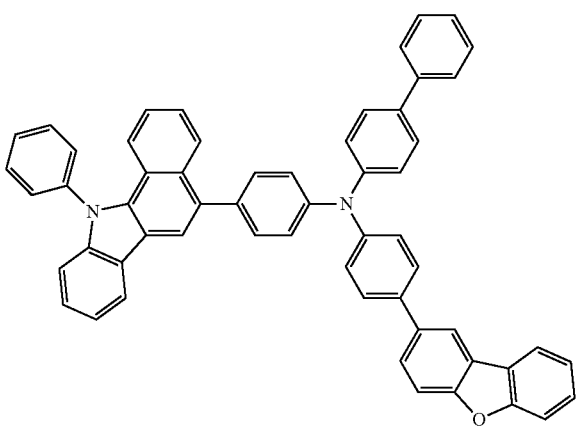
138
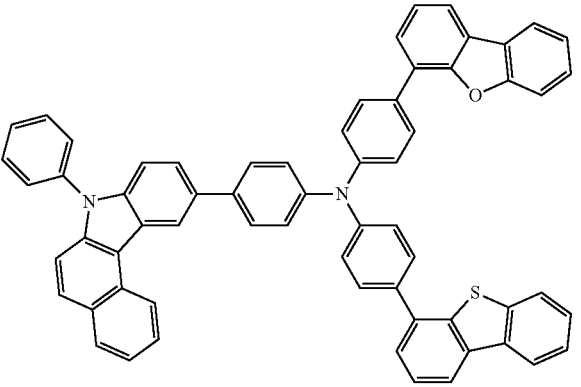
142

-continued

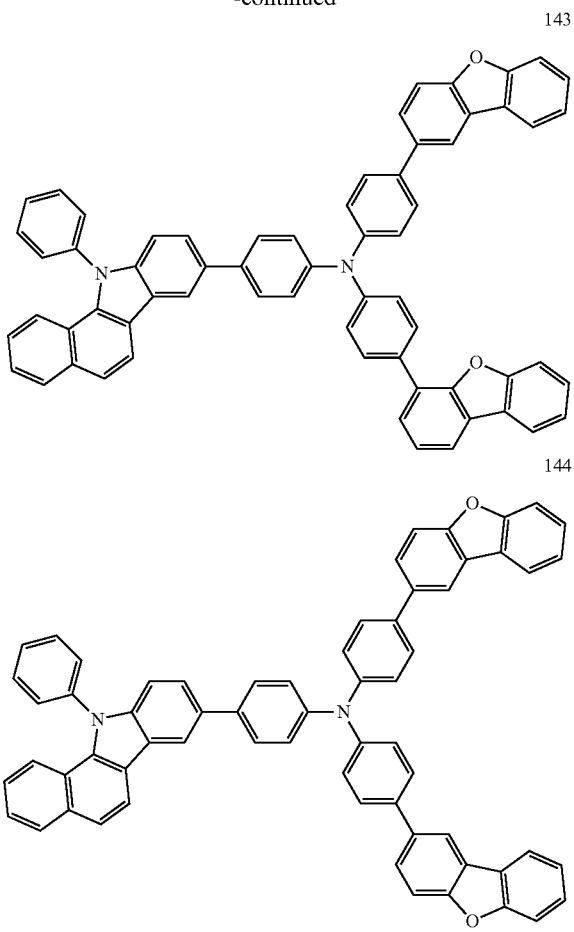

143

144

The hole transport auxiliary layer 33 may include a compound represented by Chemical Formula II.

[Chemical Formula II]

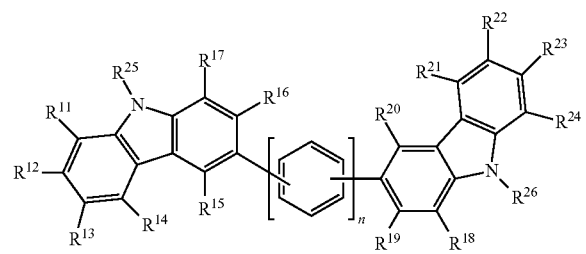

In Chemical Formula II, $R^{11}$ to $R^{24}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, adjacent two of $R^{11}$ to $R^{17}$ and $R^{18}$ to $R^{24}$ are fused to provide a ring, $R^{25}$ and $R^{26}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, and n is an integer ranging from 1 to 4, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

The compound represented by Chemical Formula II includes a linking group connected with one to four phenylenes and thus may have a flexible molecule structure compared with bicarbazole directly connected with no linking group, wherein this flexible molecule structure may effectively prevent stacking of the compound and thus improve thin film characteristics and resultantly increase process stability and simultaneously lower a deposition temperature.

However, the compound represented by Chemical Formula II has a HOMO energy level ranging from about −4.9 eV to −5.5 eV due to bicarbazole characteristics and thus may have deep energy compared with a known hole transport material.

The compound having the HOMO energy level may have remarkably deteriorated hole mobility compared with the known hole transport material, and accordingly when the compound represented by Chemical Formula II alone is used for a hole transport layer, holes are difficult to transfer from a hole injection layer (HIL).

Accordingly, the compound represented by Chemical Formula II for a hole transport auxiliary layer and the compound represented by Chemical Formula1 for the hole transport layer may be used to supplement hole characteristics and thus realize an organic optoelectric device having high efficiency and a long life-span.

The compound represented by Chemical Formula II may be represented by one of Chemical Formulas II-1 to II-16 according to a kind of an intermediate linking group.

[Chemical Formula II-1]
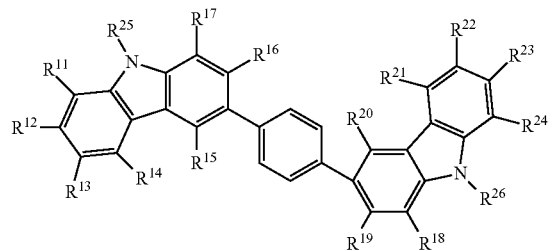
[Chemical Formula II-2]
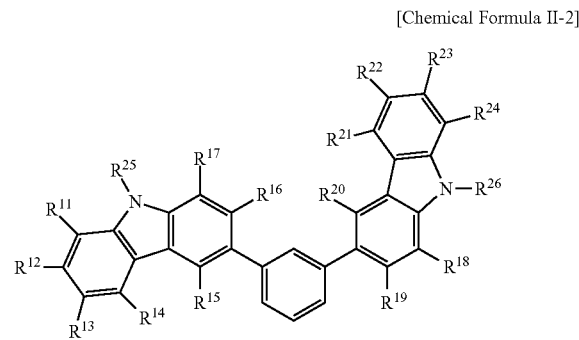
[Chemical Formula II-3]
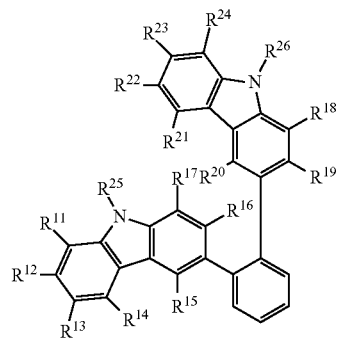
[Chemical Formula II-4]
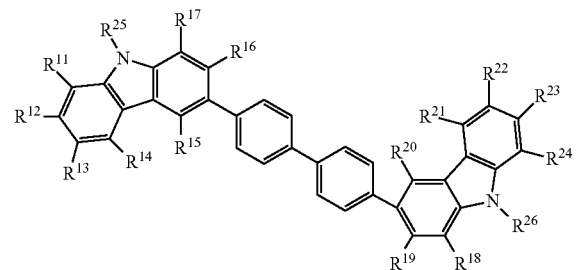
[Chemical Formula II-5]
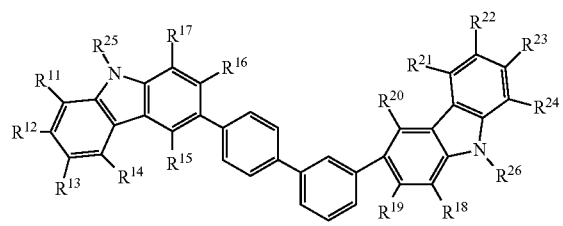
[Chemical Formula II-6]
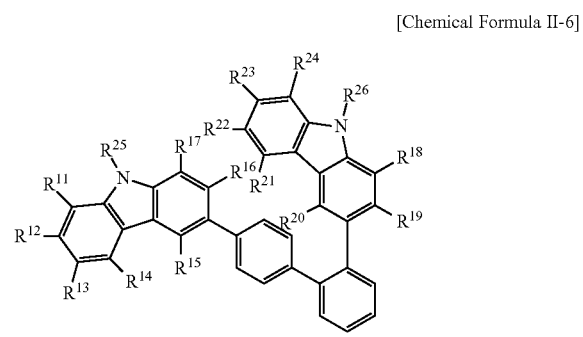
[Chemical Formula II-7]
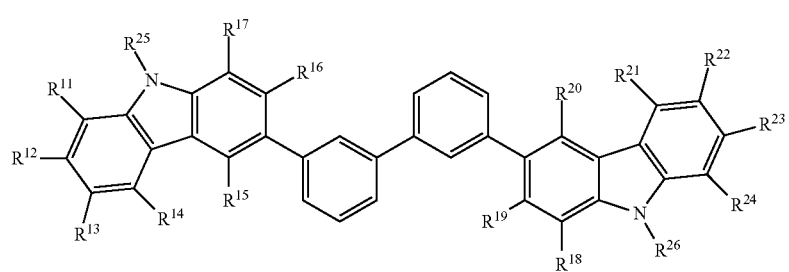

-continued
[Chemical Formula II-8]
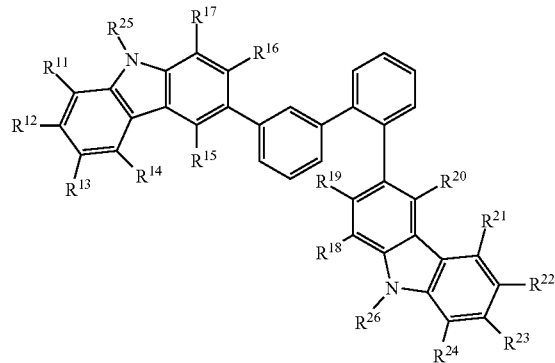
[Chemical Formula II-9]
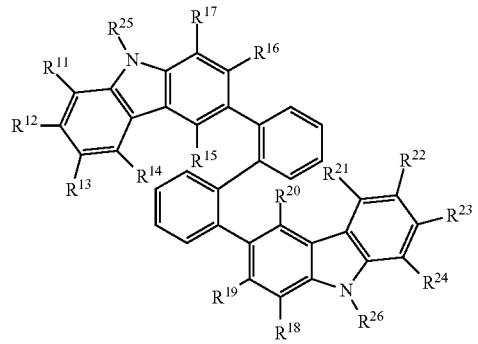
[Chemical Formula II-10]
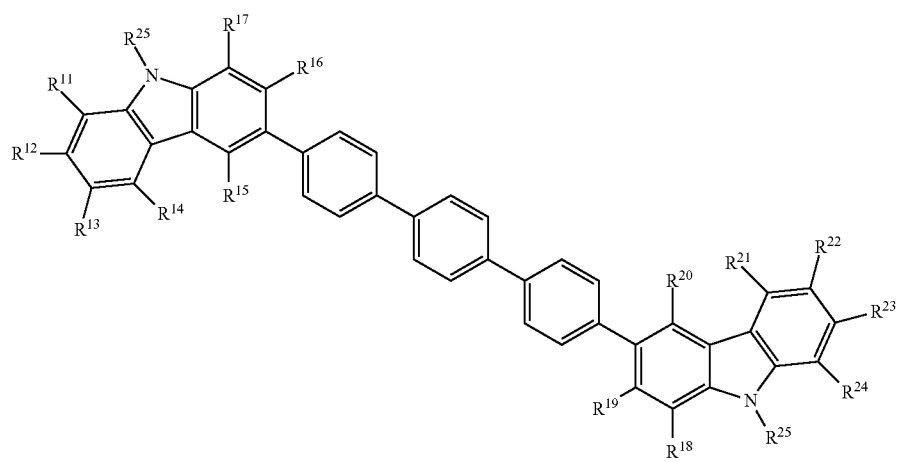
[Chemical Formula II-11]
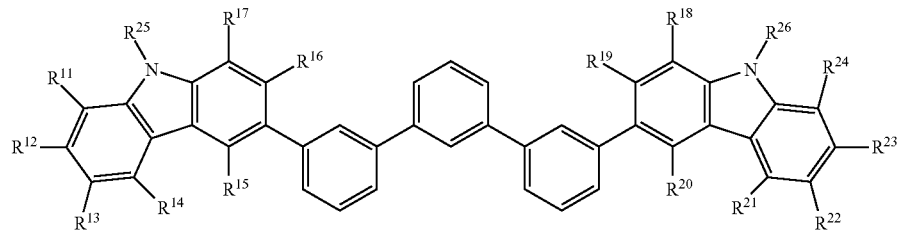
[Chemical Formula II-12]
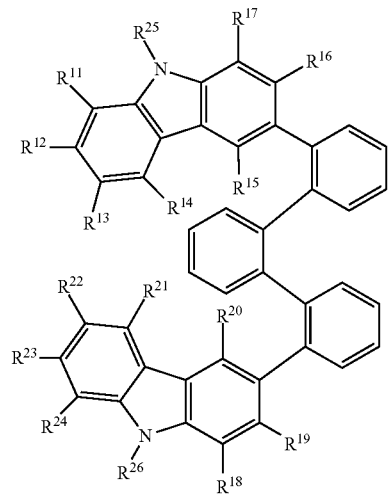

[Chemical Formula II-13]
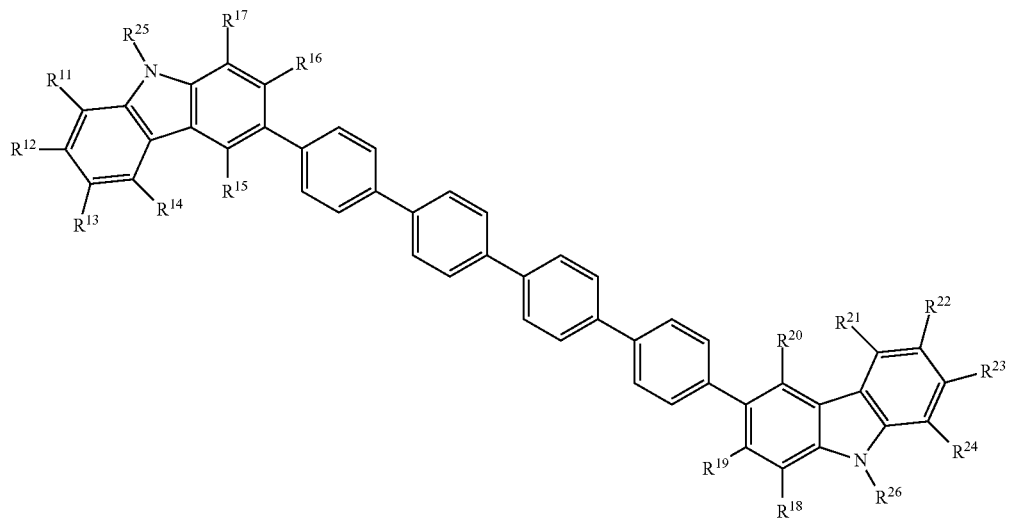
[Chemical Formula II-14]
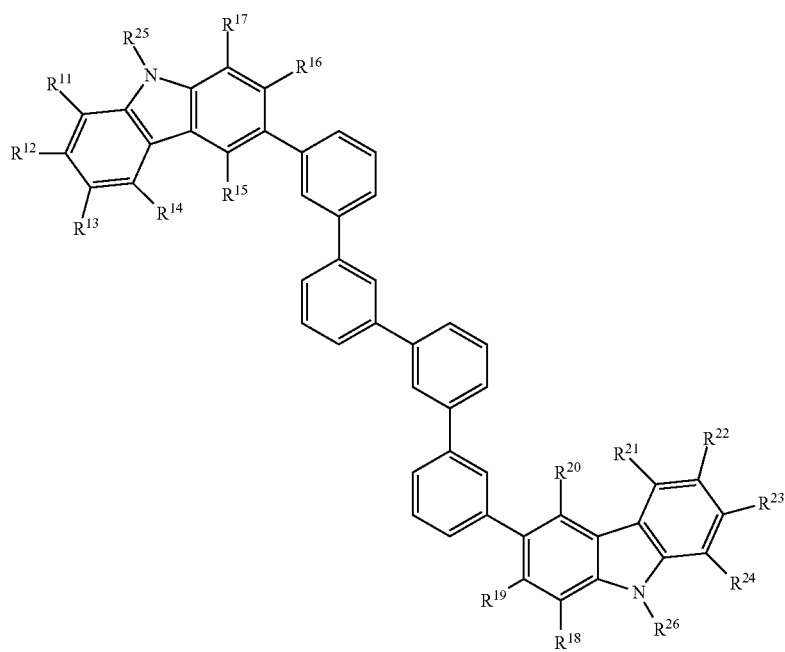

[Chemical Formula II-15]

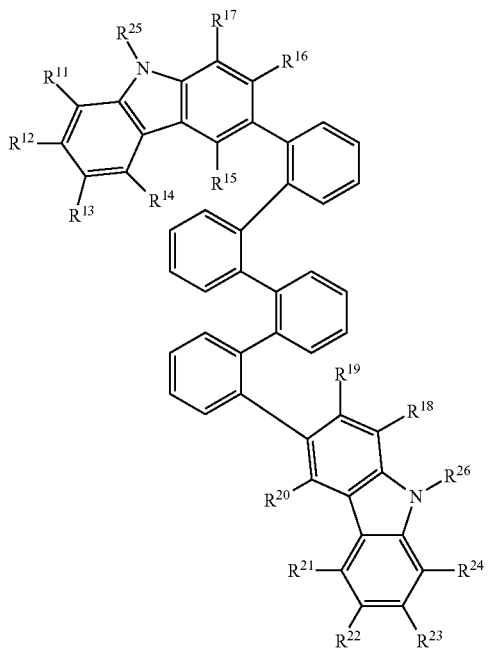

[Chemical Formula II-16]

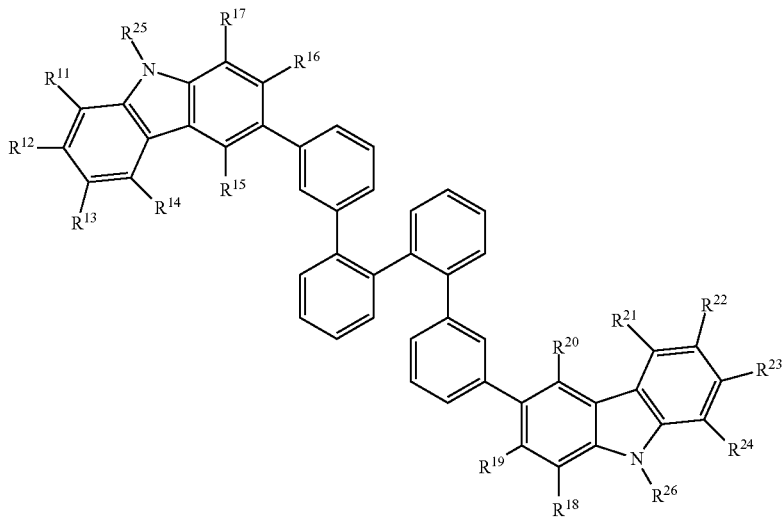

In Chemical Formula II-1 to Chemical Formula II-16, $R^{11}$ to $R^{26}$ are the same as described above.

The compounds represented by Chemical Formulas II-1 to II-16 includes a linking group connected with one to four phenylenes and thus has a flexible molecule structure, which may effectively prevent stacking of the compound and promote its deposition.

The $R^{25}$ and $R^{26}$ may independently be hydrogen, deuterium, a substituted or unsubstituted C6 to C30 aryl group, or a substituted or unsubstituted C2 to C30 heteroaryl group, and more specifically, the substituted or unsubstituted C6 to C30 aryl group may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted fluorenyl group, a substituted or unsubstituted triphenylene group, or a combination thereof, the substituted or unsubstituted C2 to C30 heteroaryl group, a substituted or unsubstituted pyridyl group, a substituted or unsubstituted pyrimidinyl group, a substituted or unsubstituted triazinyl group, or a combination thereof.

In addition, in the compound represented by Chemical Formula II, at least one hydrogen of $R^{25}$ and $R^{26}$ may be replaced or unreplaced by a phenyl group, a biphenyl group, a naphthyl group, a pyridyl group, a pyrimidinyl group, or a triazinyl group.

The $R^{11}$ to $R^{24}$ of Chemical Formula II may independently be hydrogen, deuterium, or a substituted or unsubstituted C6 to C30 aryl group.

Specifically, the substituted or unsubstituted C6 to C30 aryl group may be a substituted or unsubstituted phenyl group, a substituted or unsubstituted biphenyl group, a substituted or unsubstituted o-terphenyl group, a substituted or unsubstituted p-terphenyl group, a substituted or unsubstituted m-terphenyl group, a substituted or unsubstituted naphthyl group, or a combination thereof, but is not limited thereto.
The compound represented by Chemical Formula II may be, for example selected from compounds of Group IV, but is not limited thereto.
[Group IV]
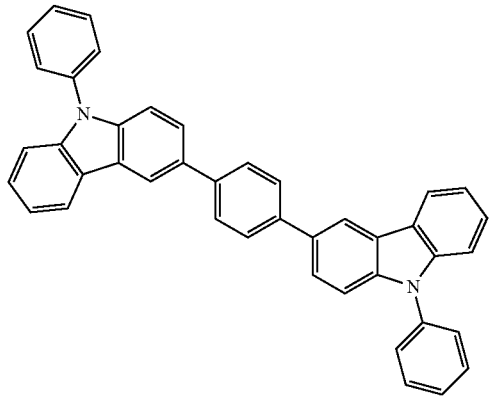
1
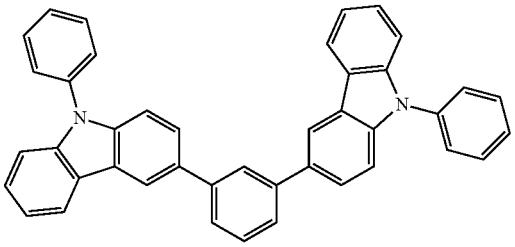
2
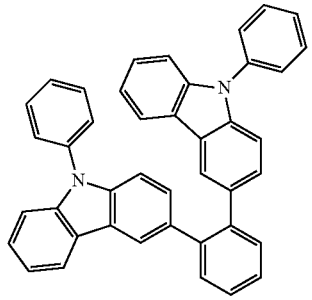
3
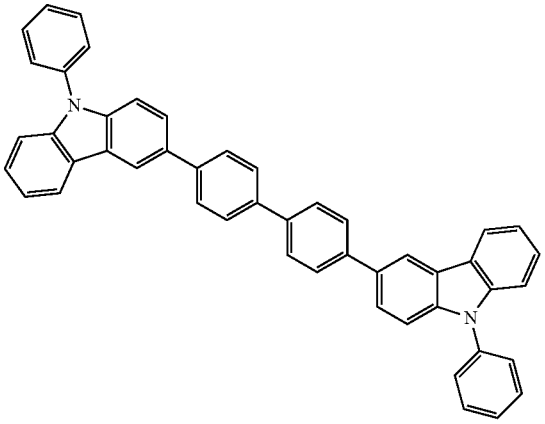
4
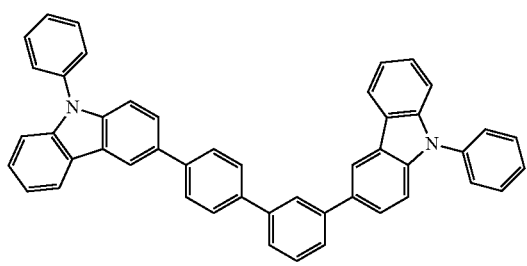
5
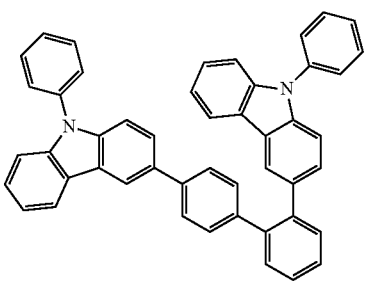
6

7
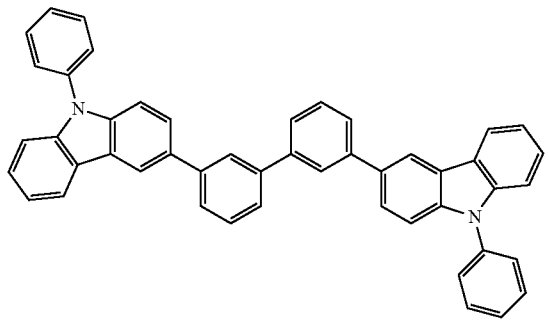
8
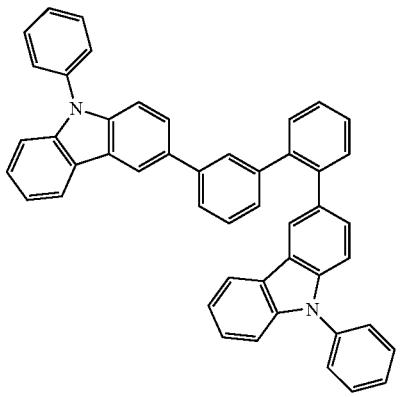
9
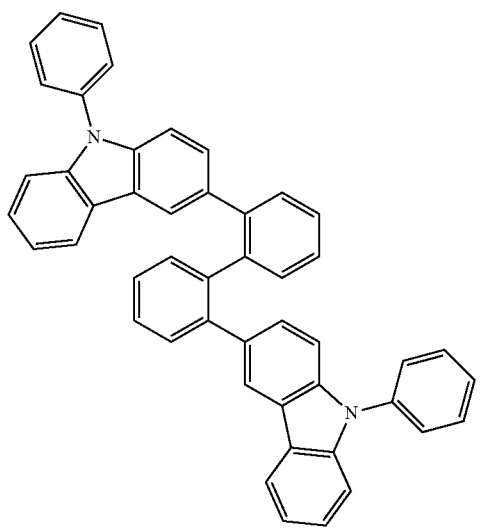
10
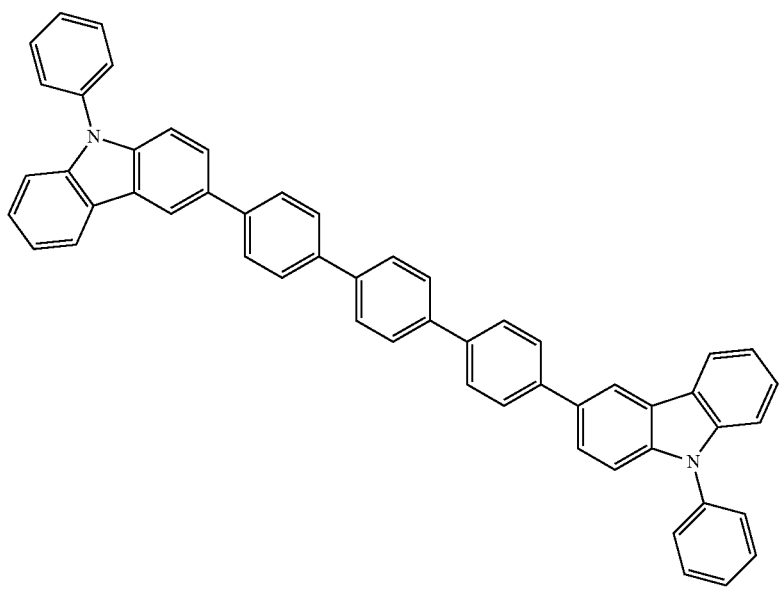

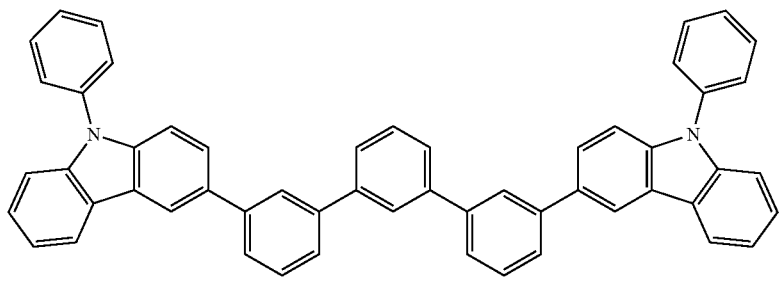
11
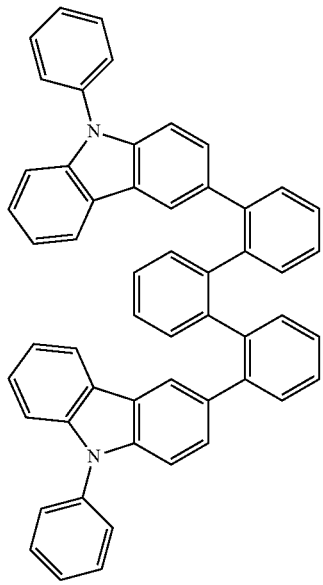
12
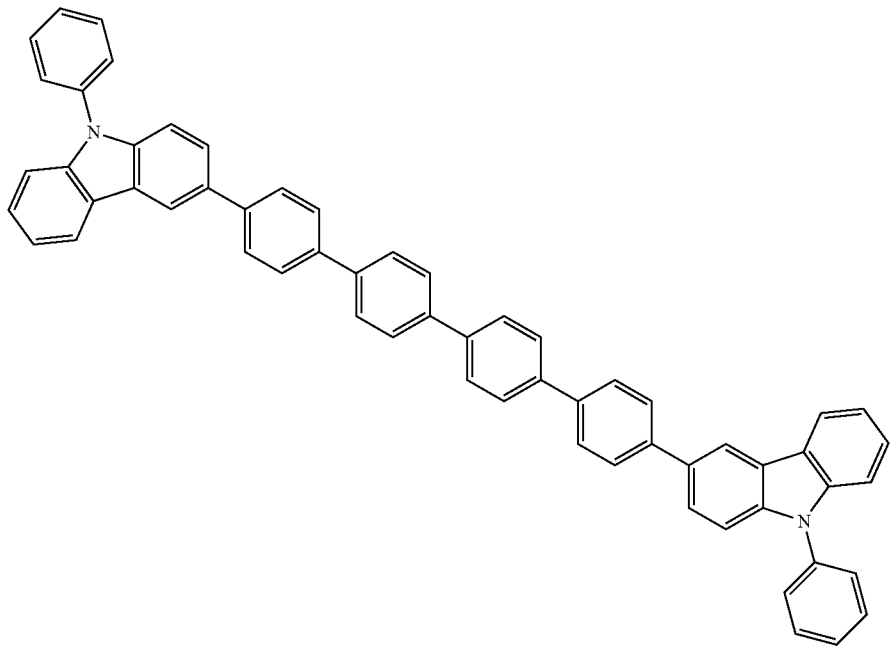
13

-continued
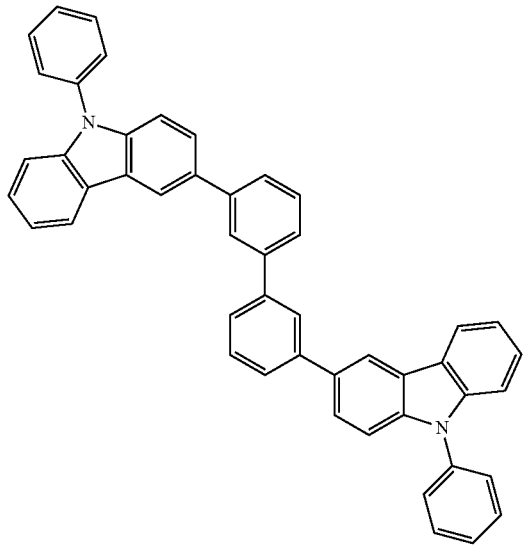
14
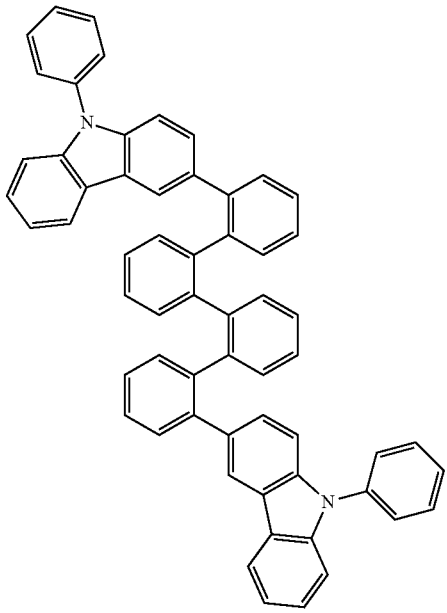
15
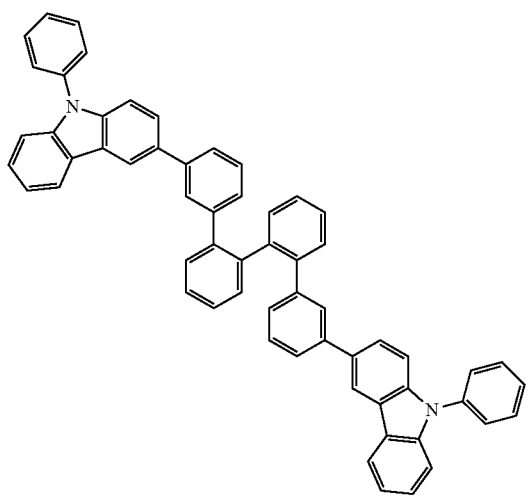
16
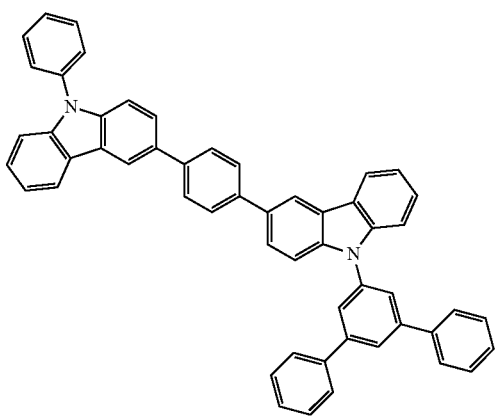
17
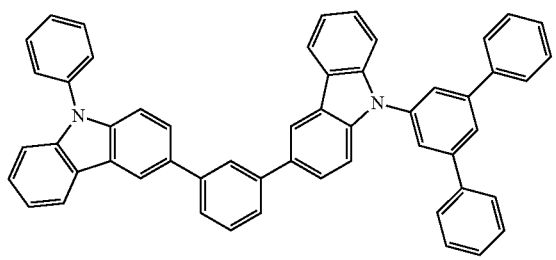
18
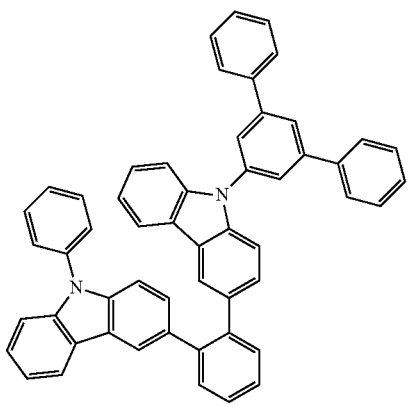
19

20
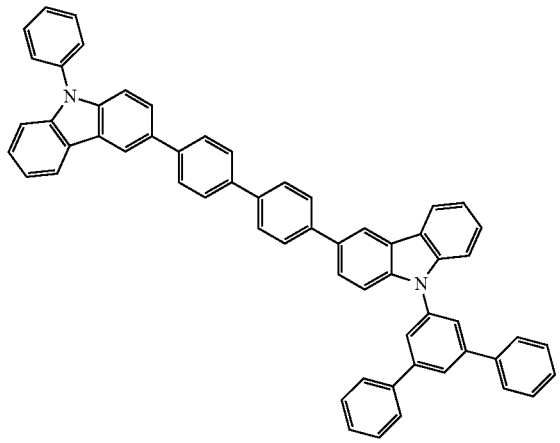
21
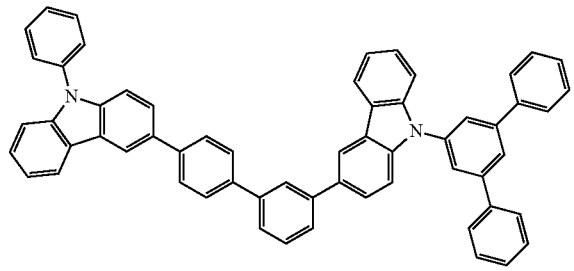
22
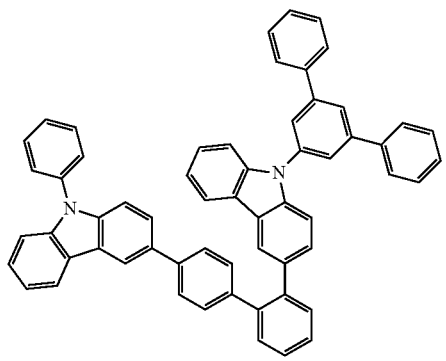
23
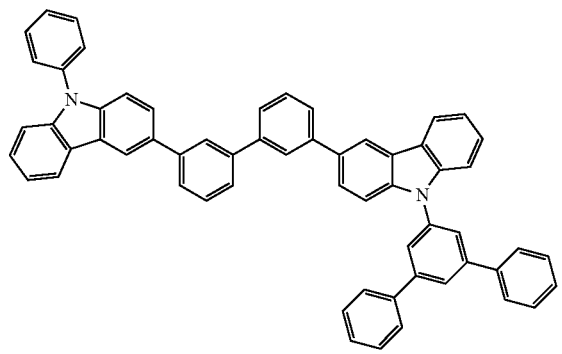
24
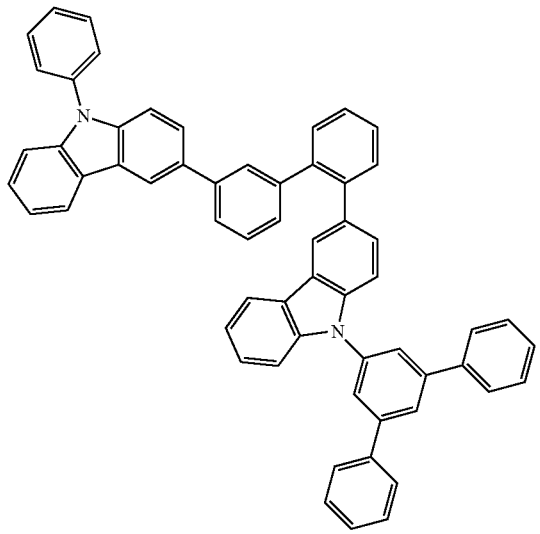
25
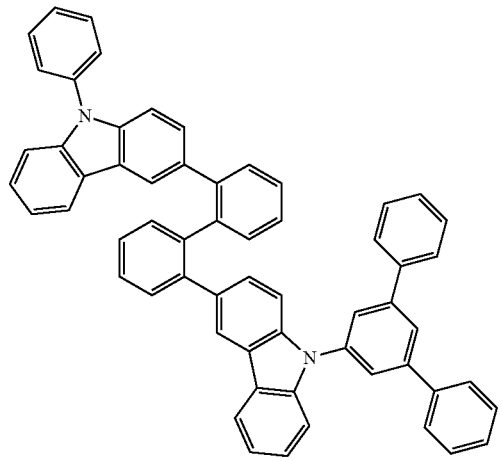

-continued
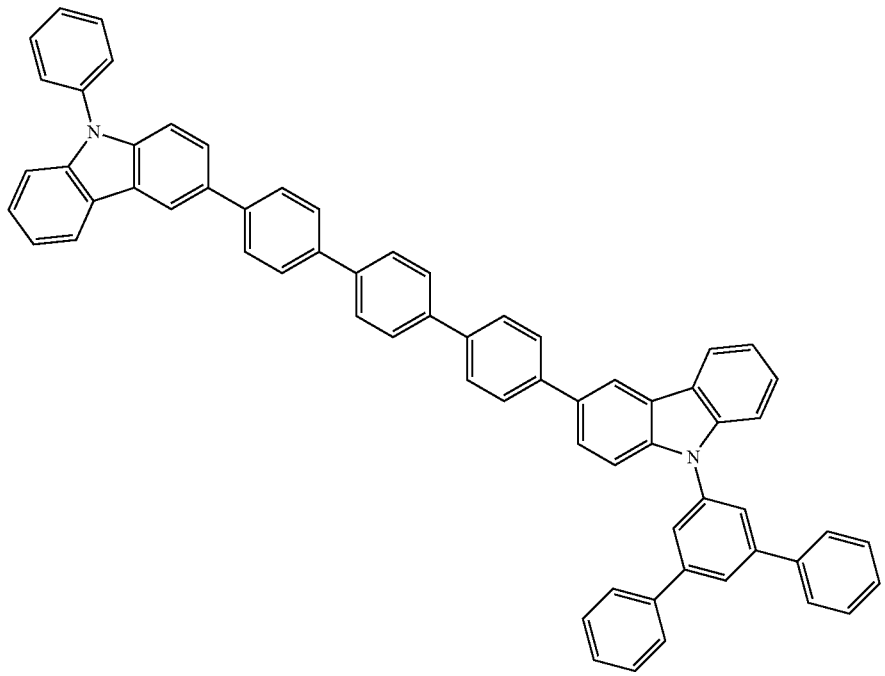
26
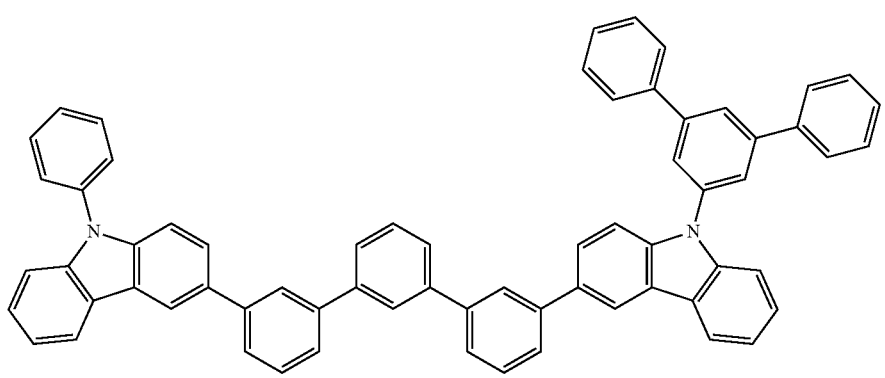
27

28
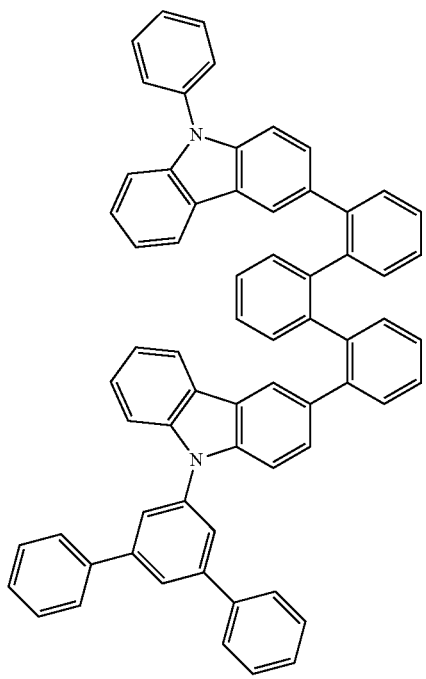
29
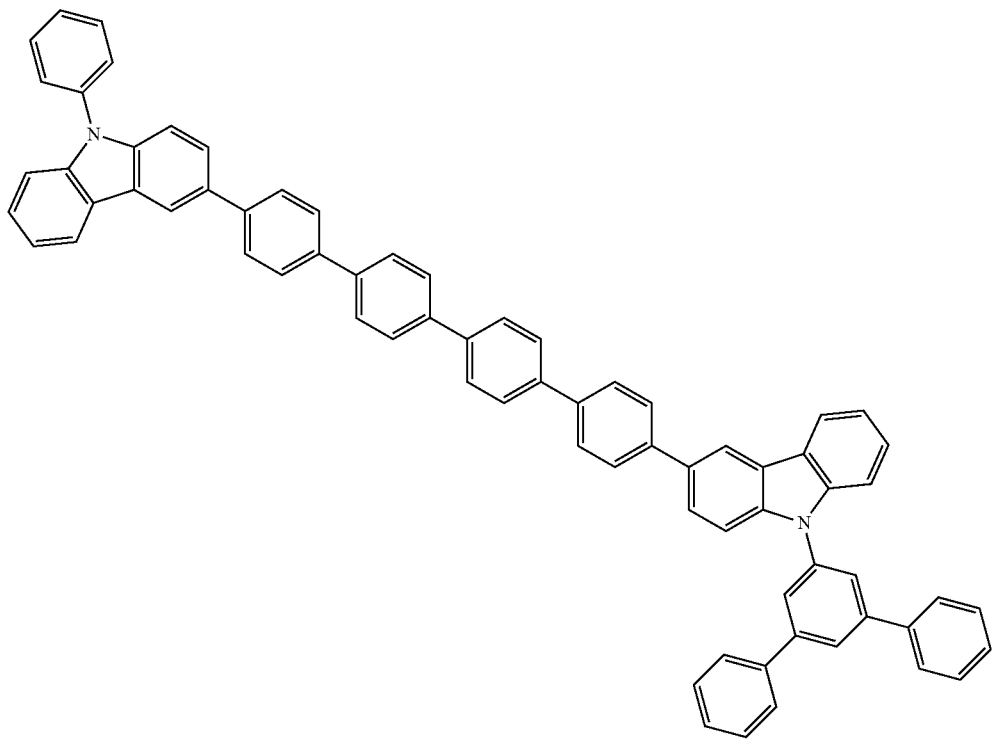

-continued
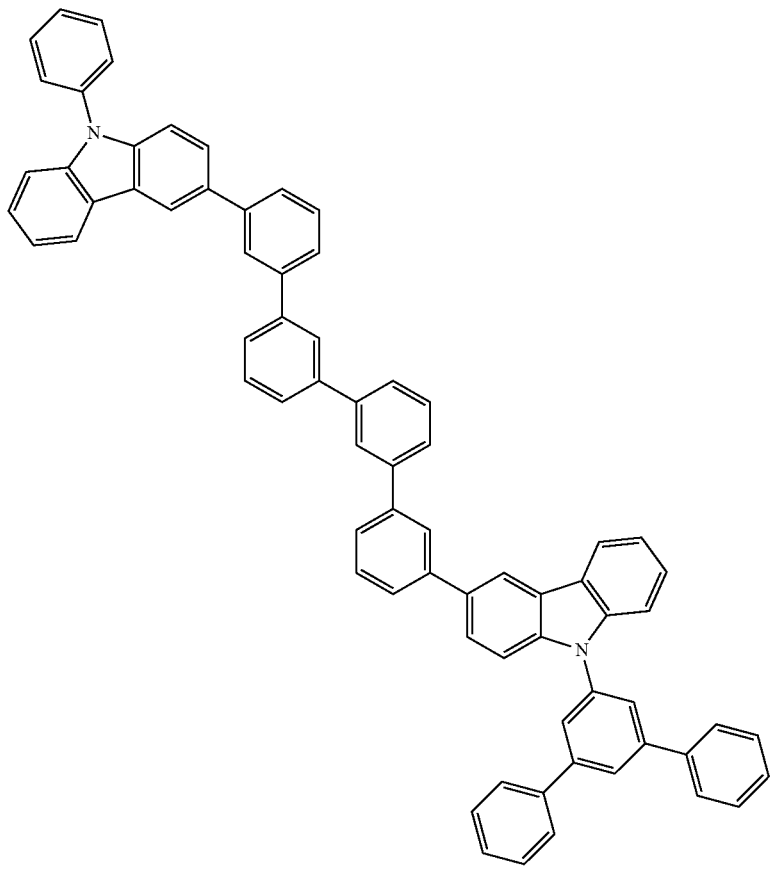
30
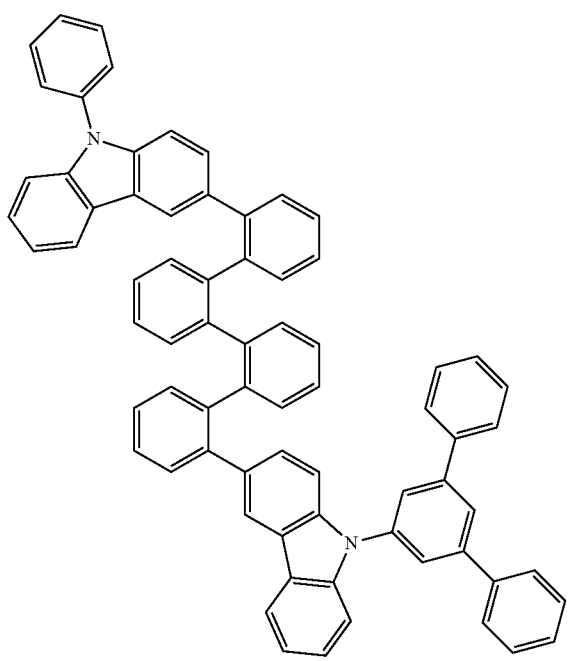
31

-continued
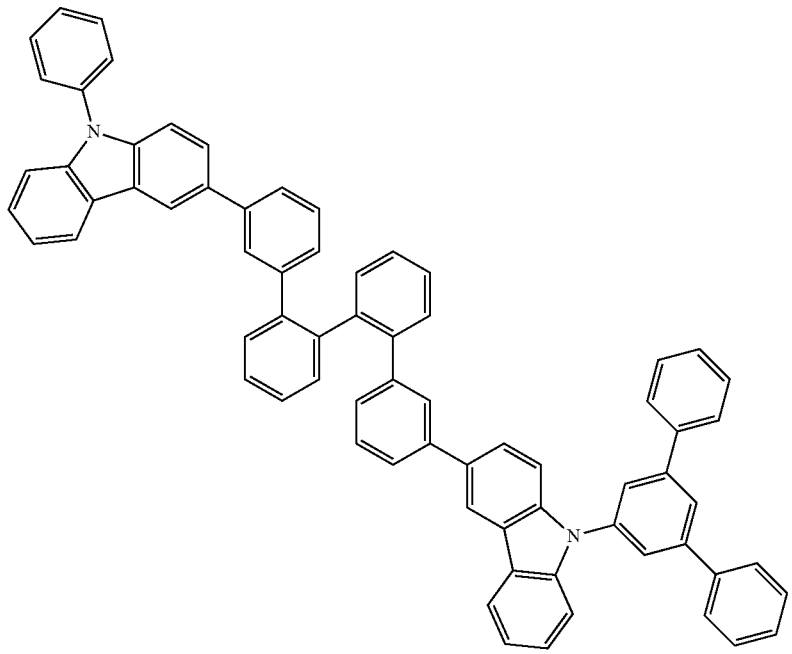
32
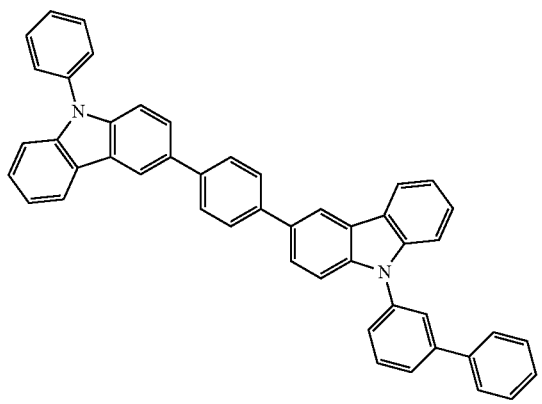
33
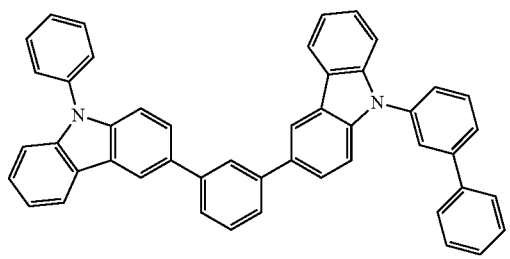
34
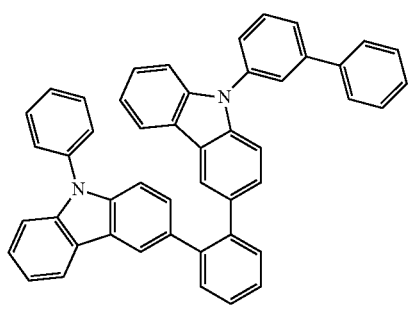
35
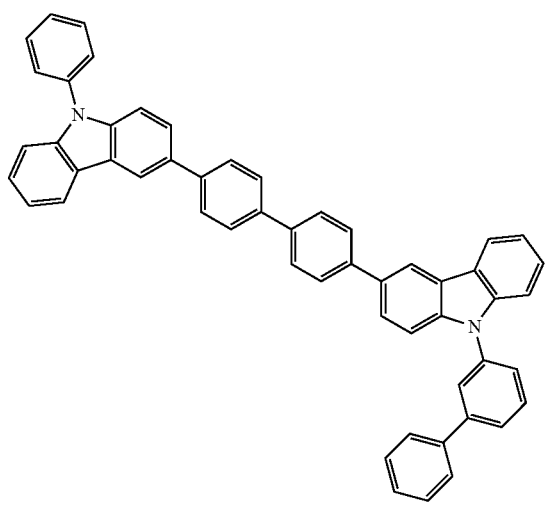
36

-continued
37
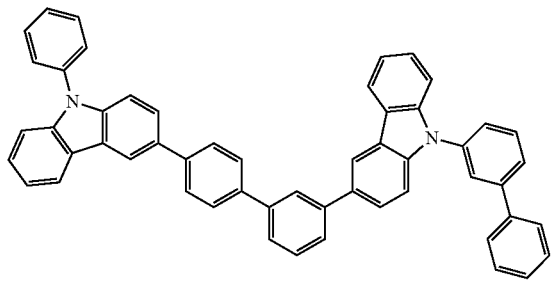
38
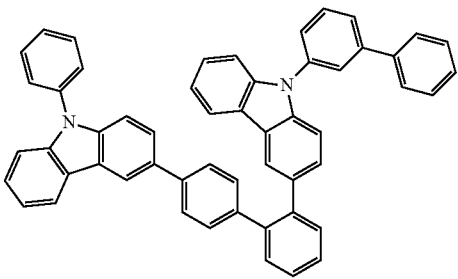
39
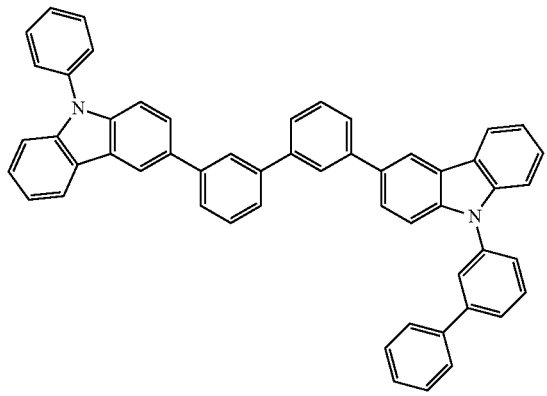
40
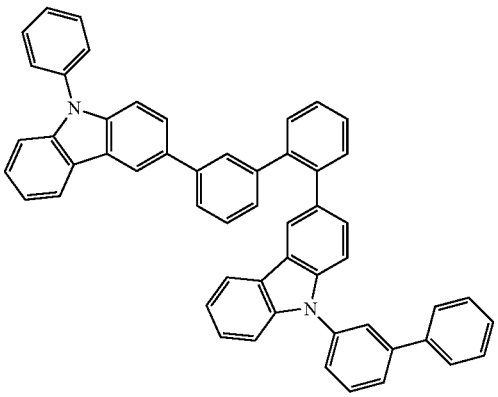
41
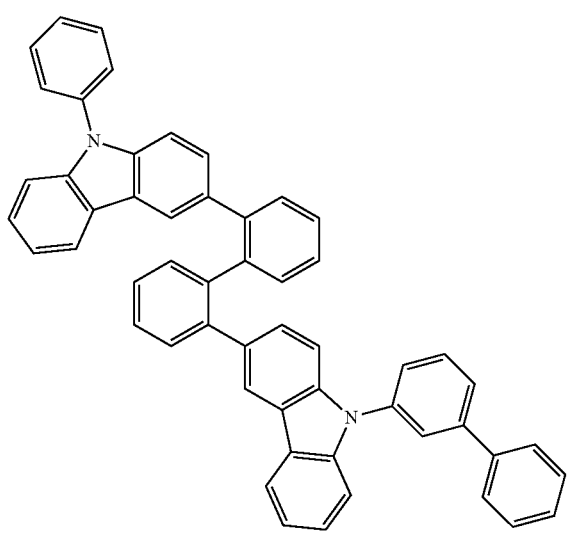

42
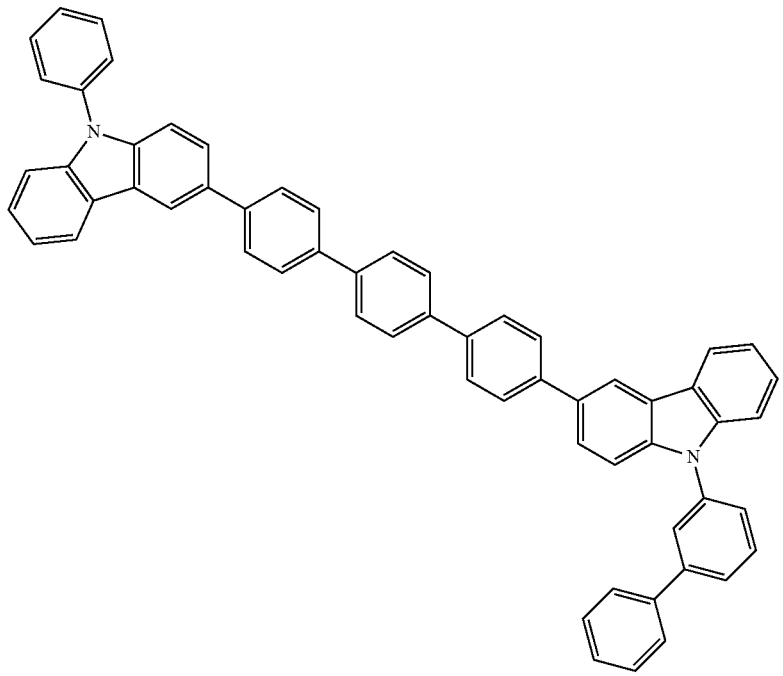
43
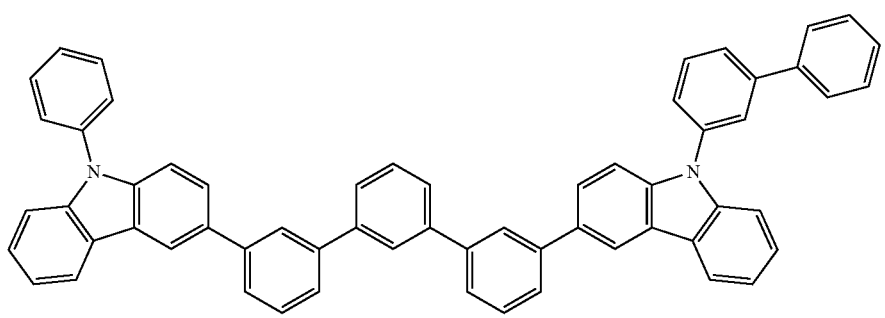
44
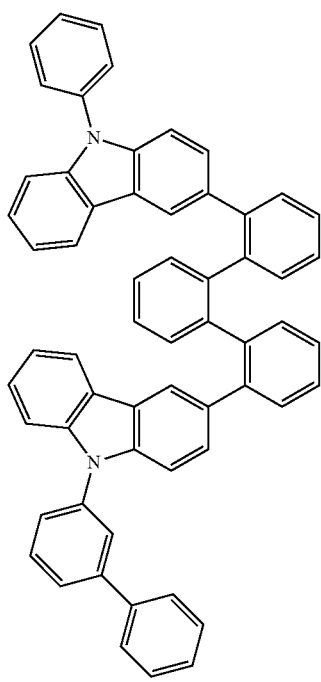

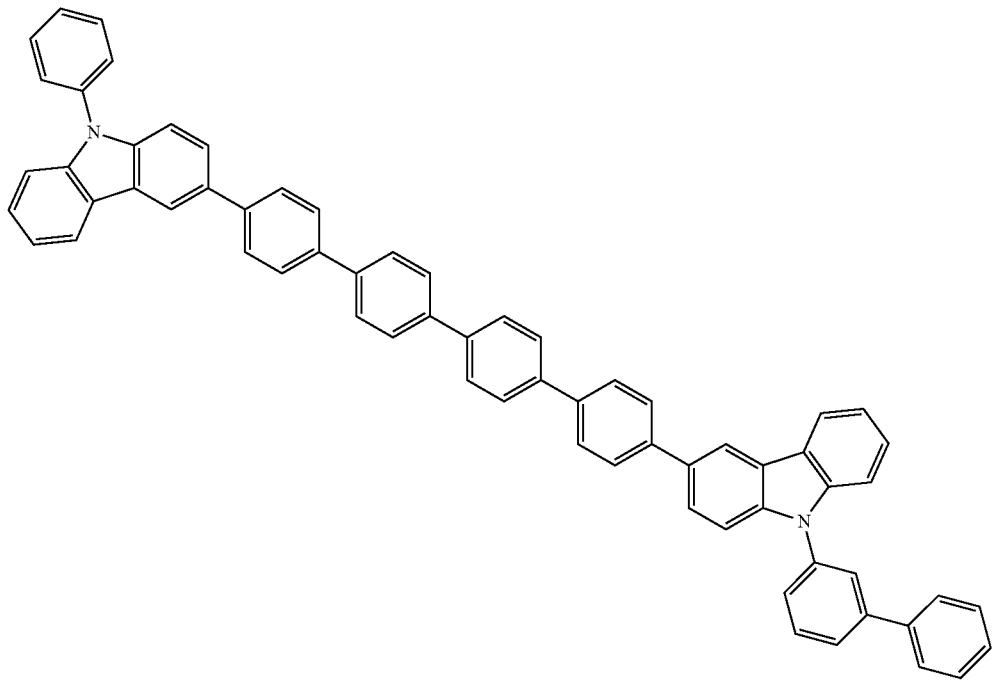
45
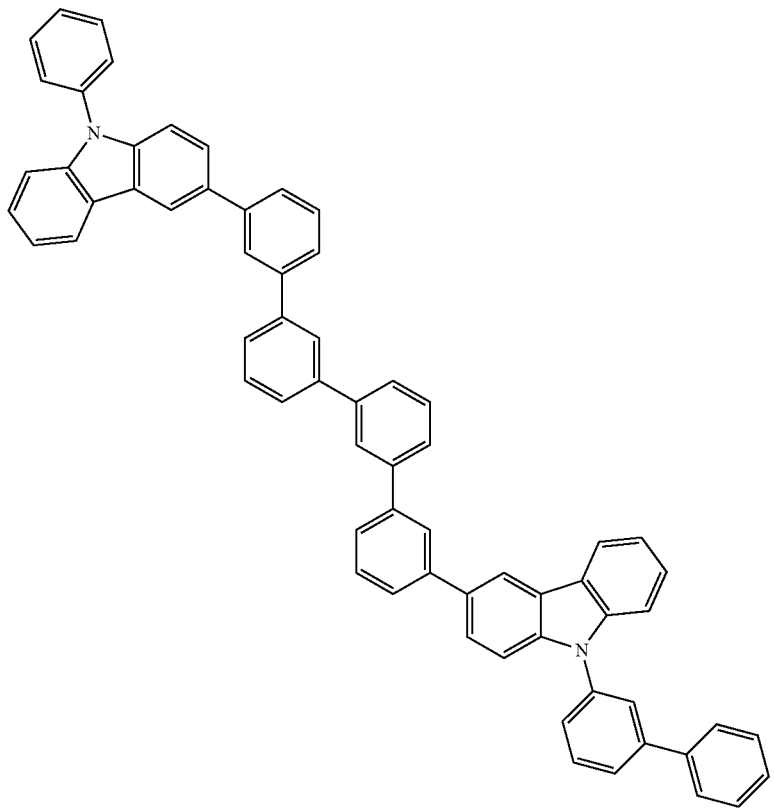
46

47
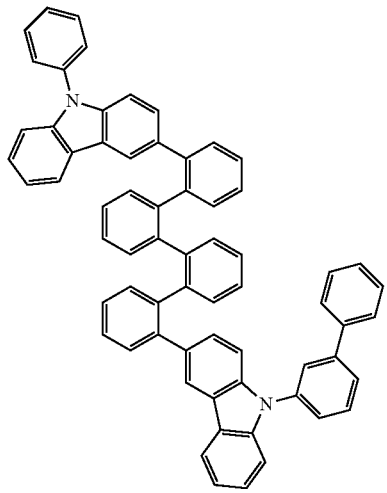
48
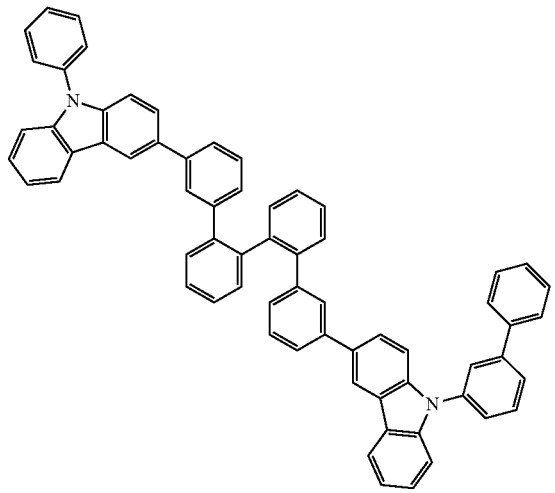
49
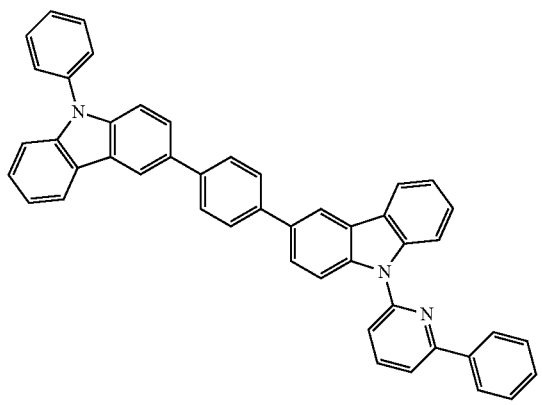
50
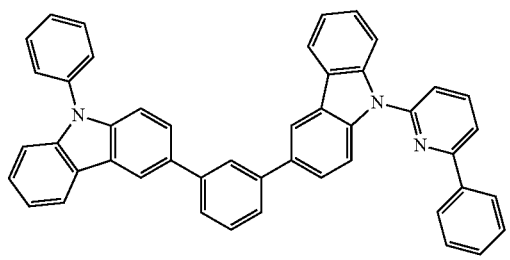
51
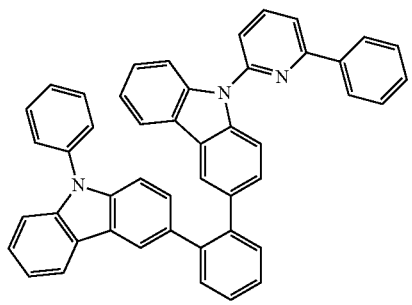
52
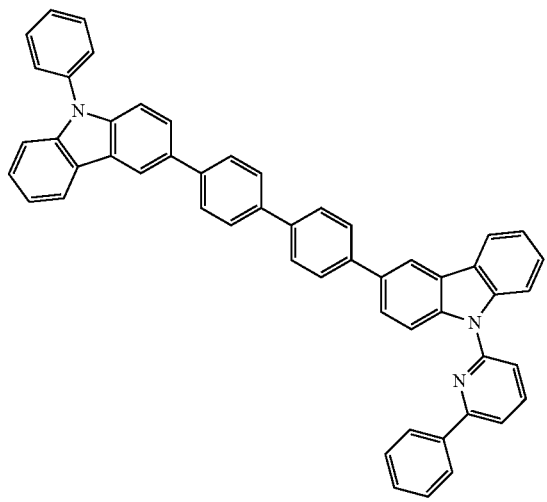

53
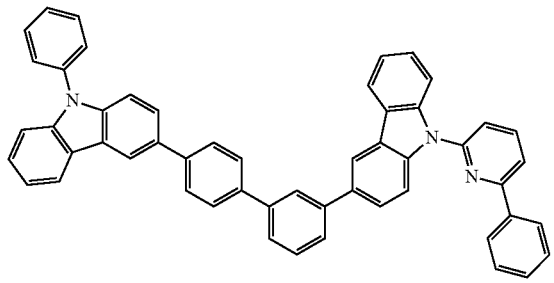
54
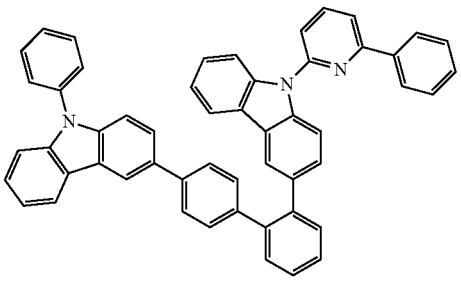
55
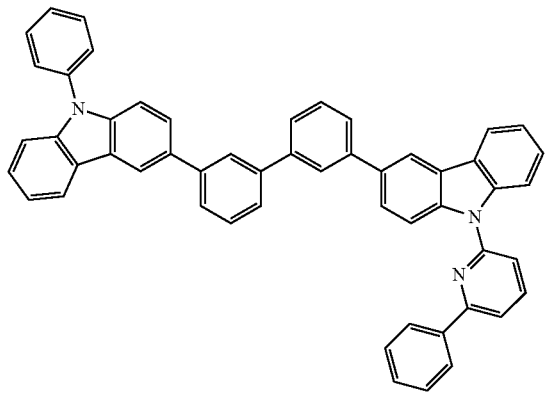
56
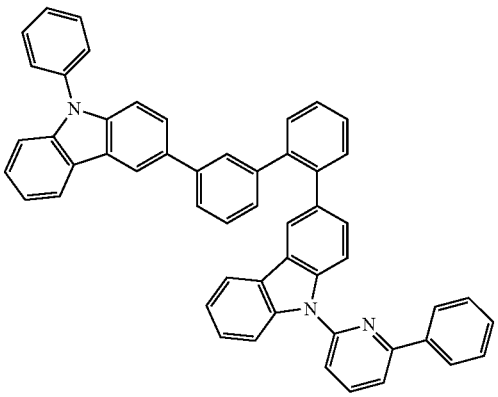
57
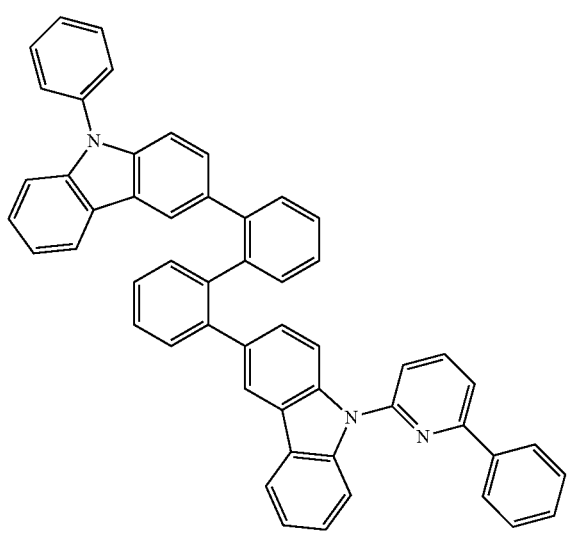

58
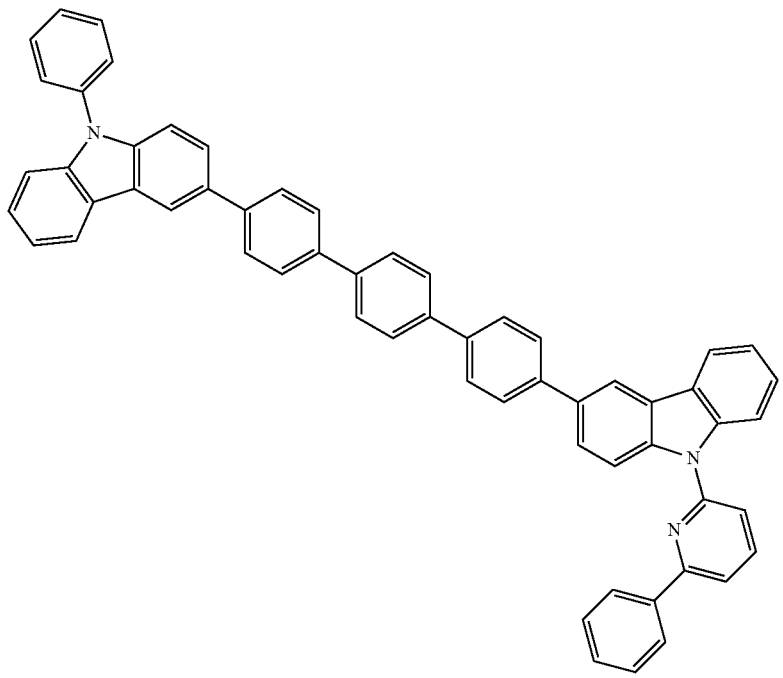
59
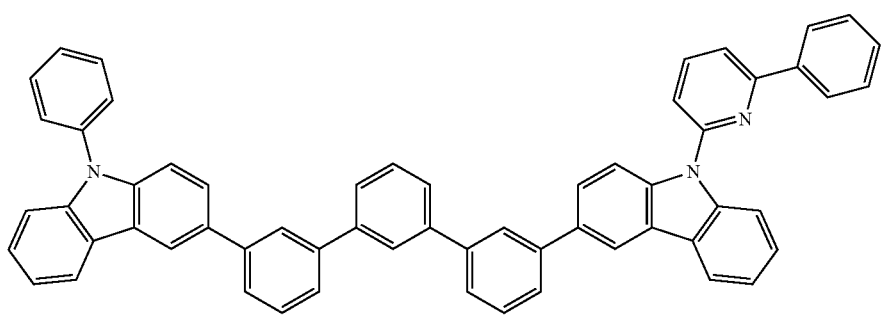
60
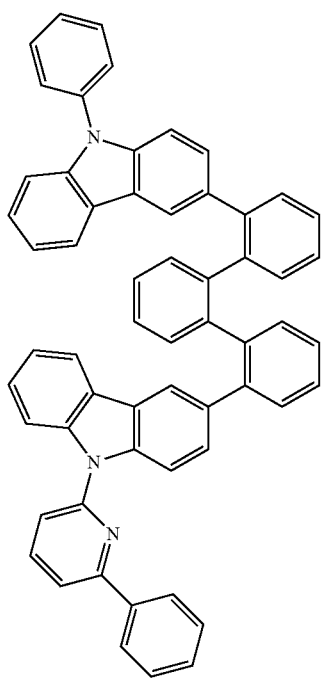

61
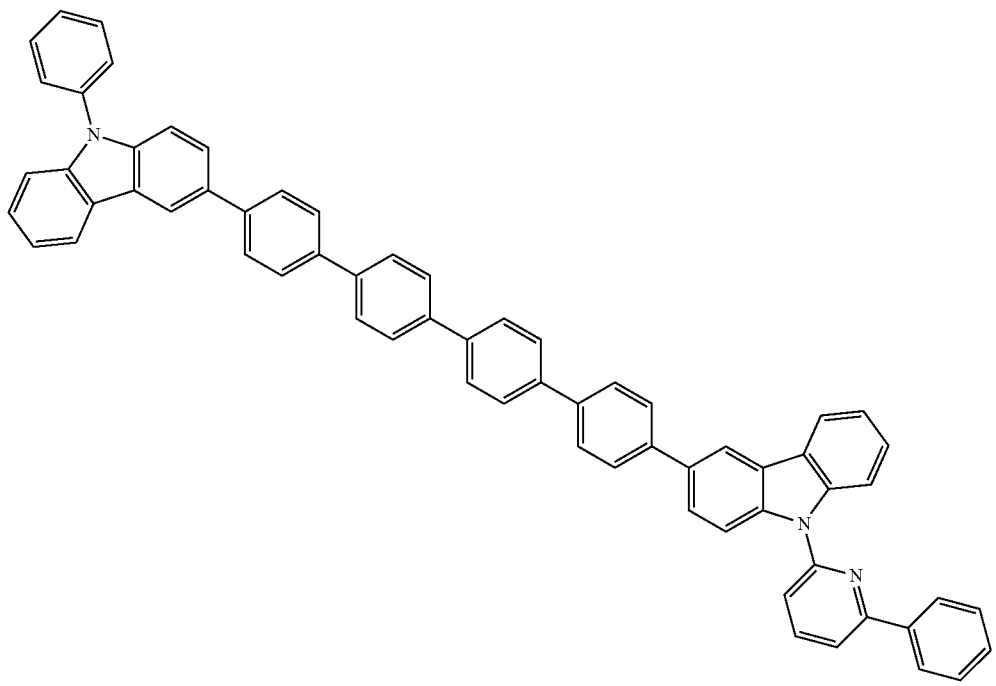
62
63
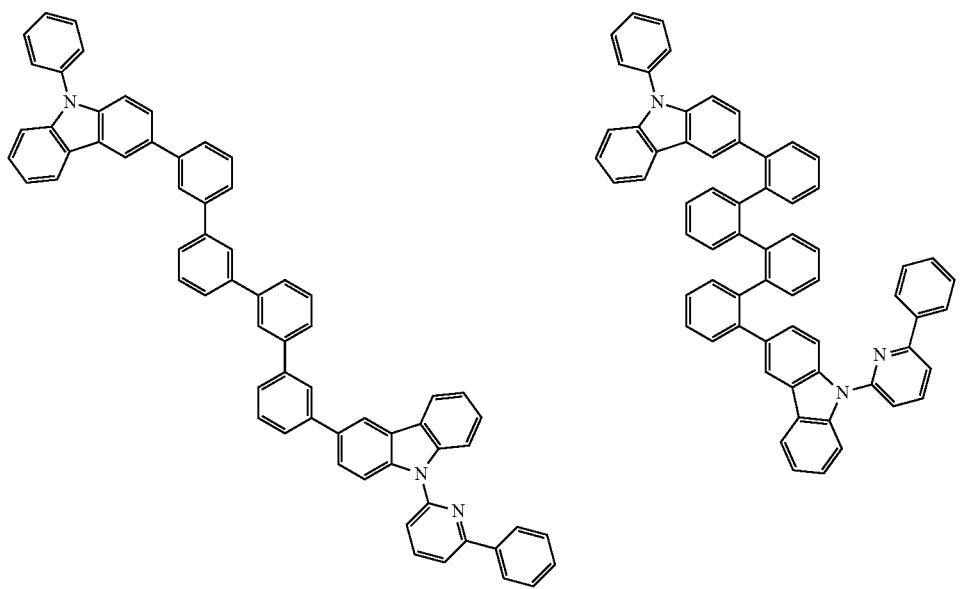

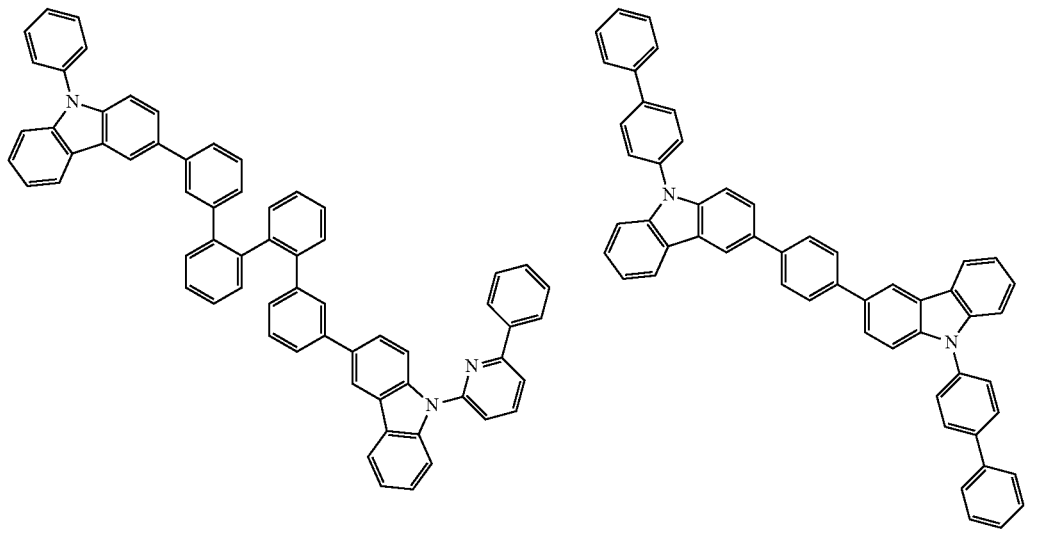
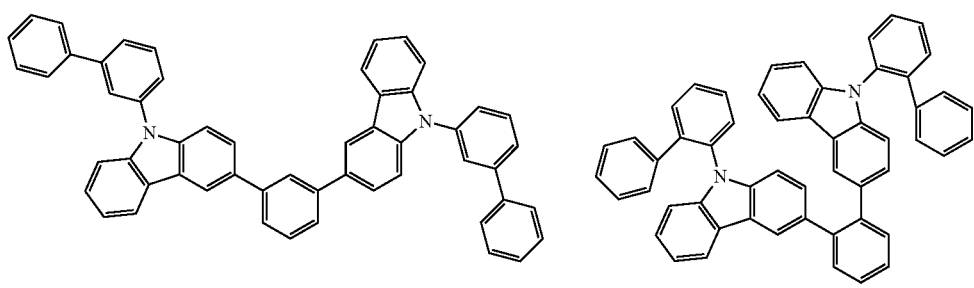
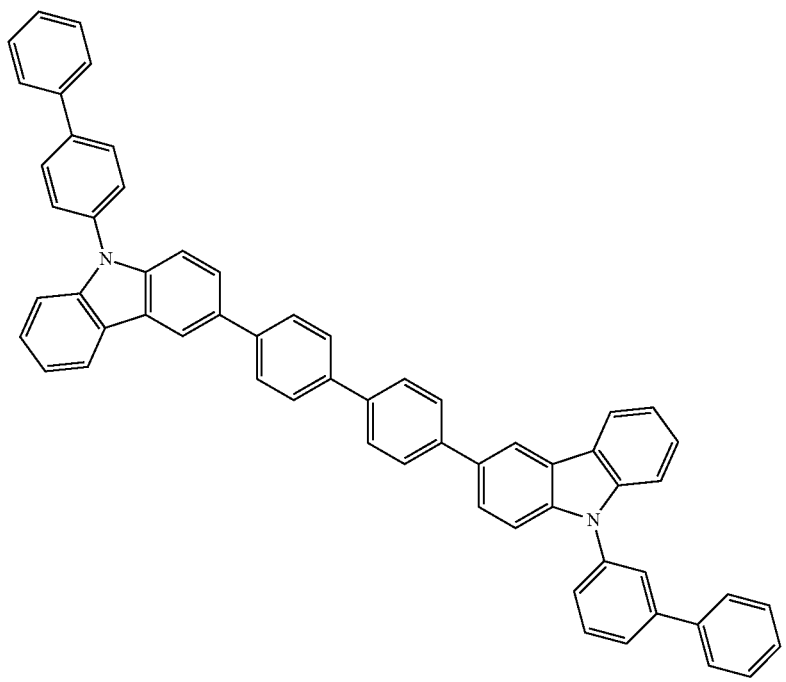

-continued
69
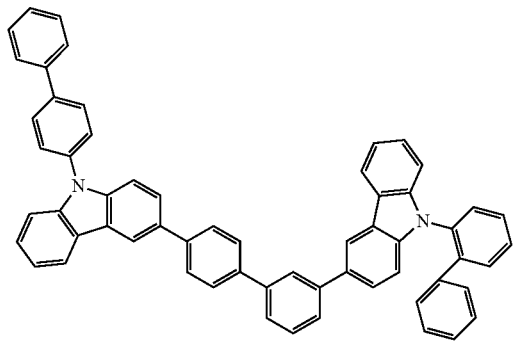
70
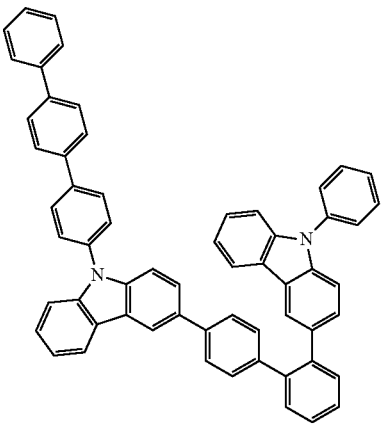
71
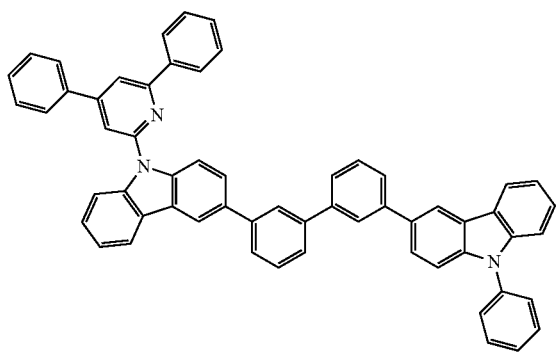
72
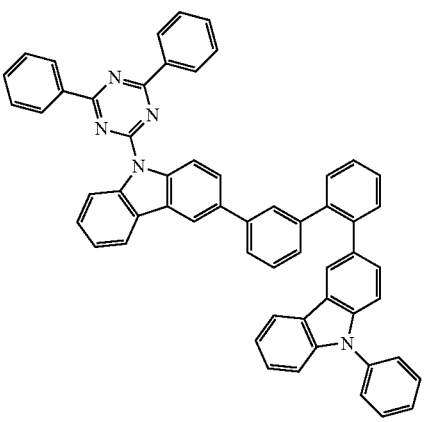
73
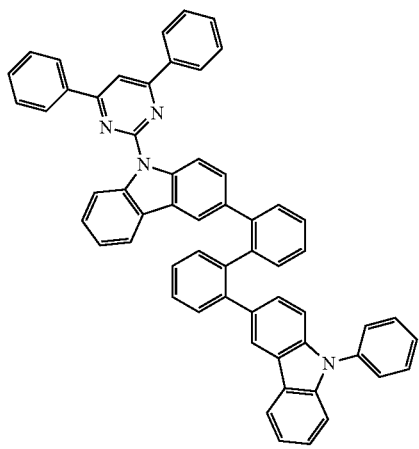
74
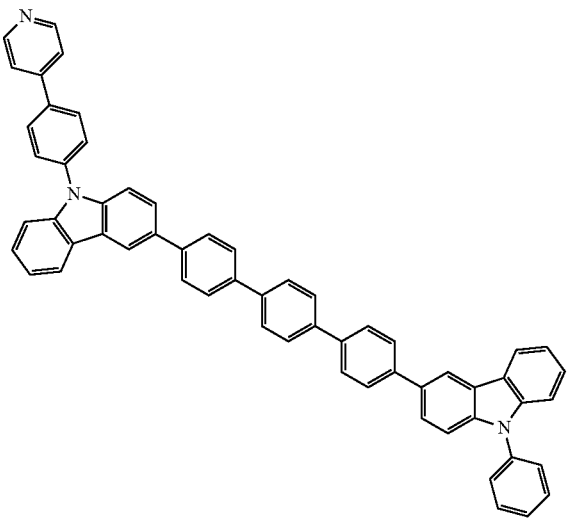

75
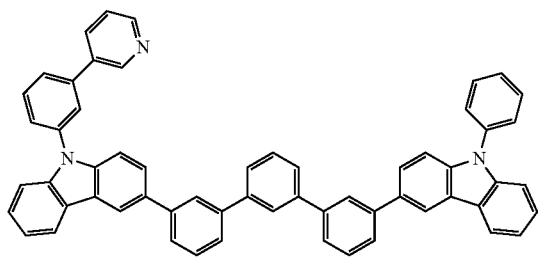
76
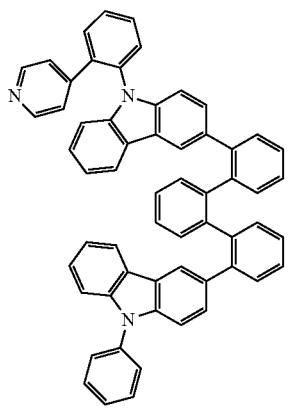
77
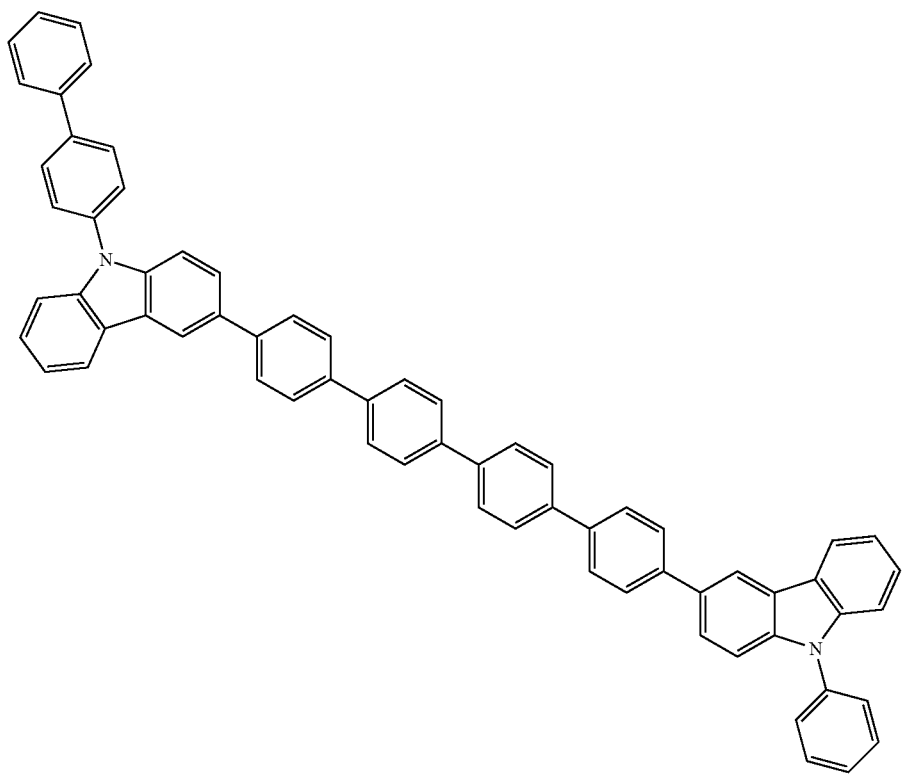

-continued
78
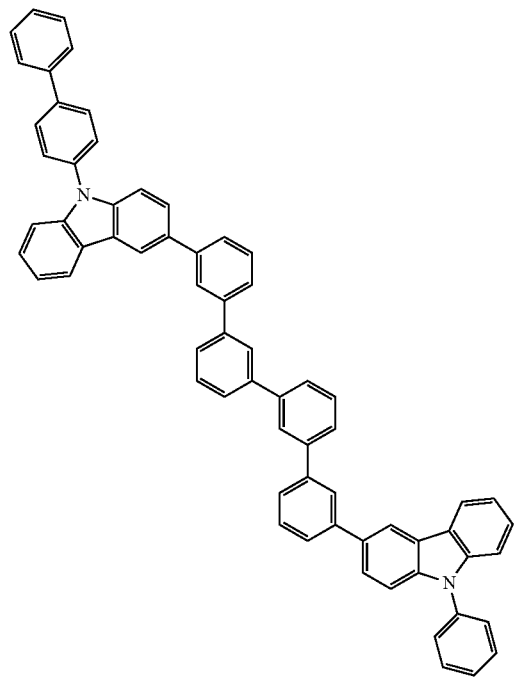
79
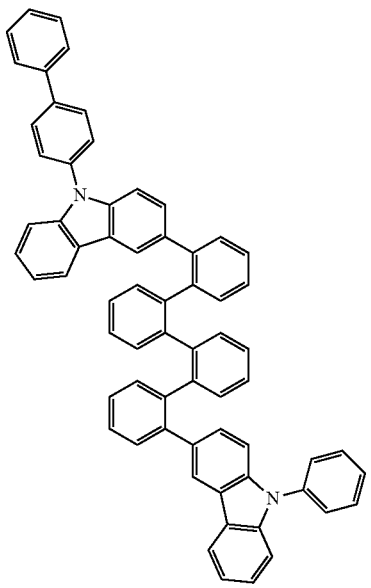
80
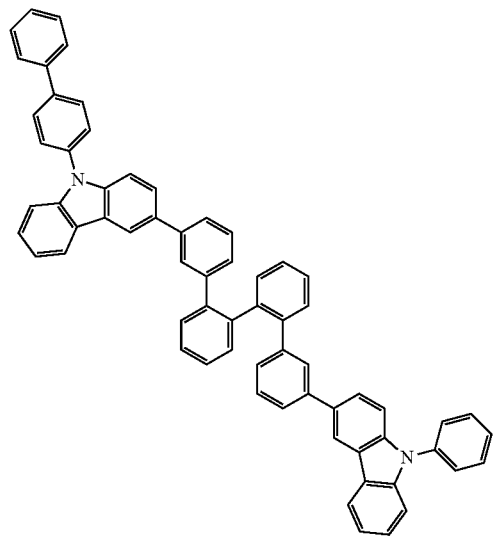
81
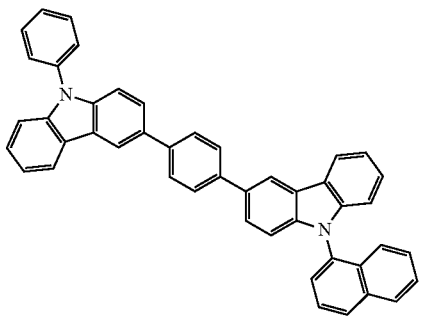
82
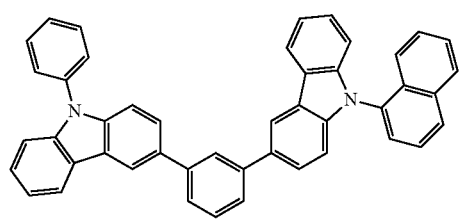
83
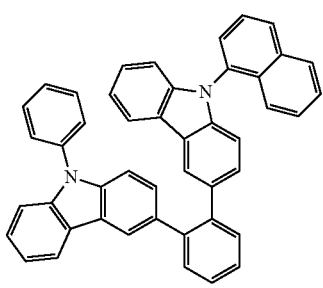

-continued
84
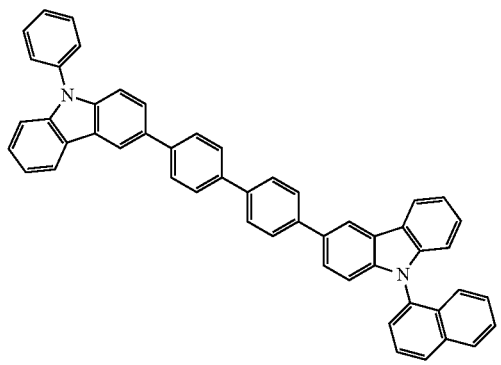
85
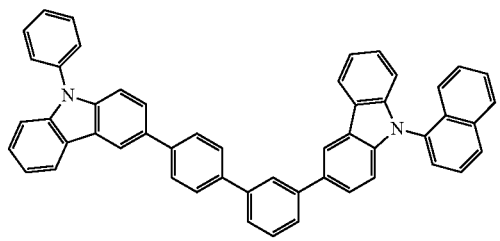
86
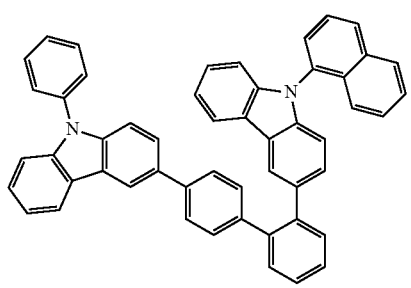
87
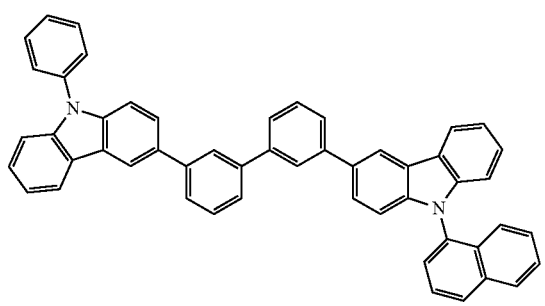
88
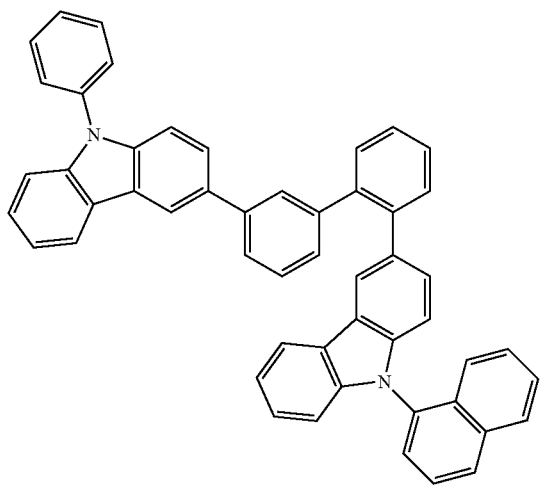
89
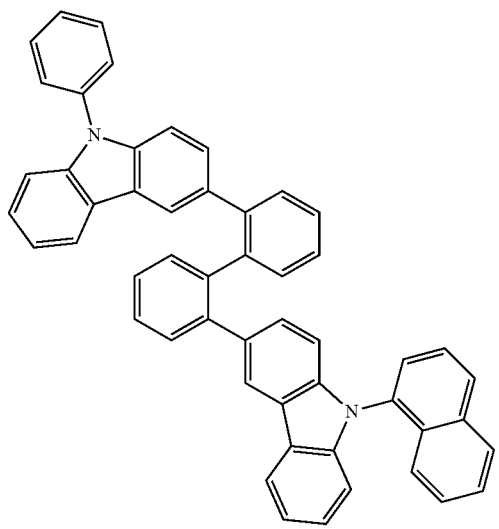

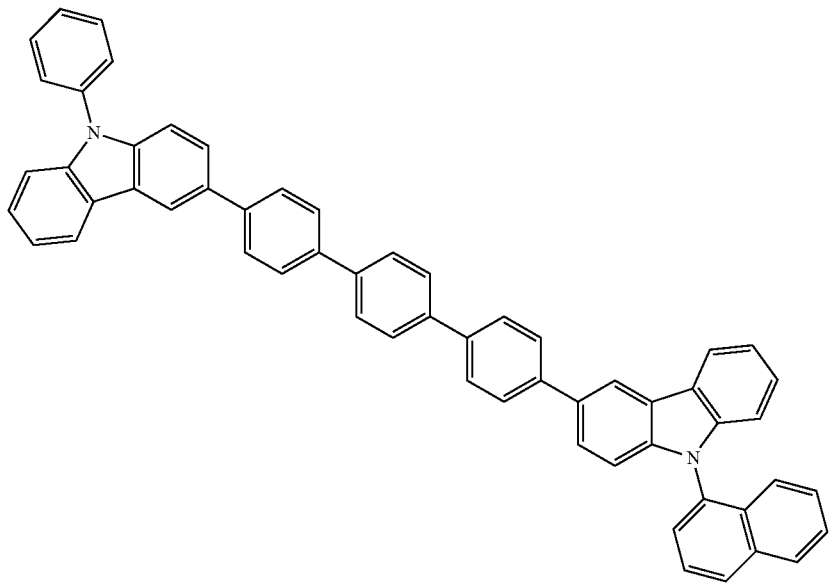
90
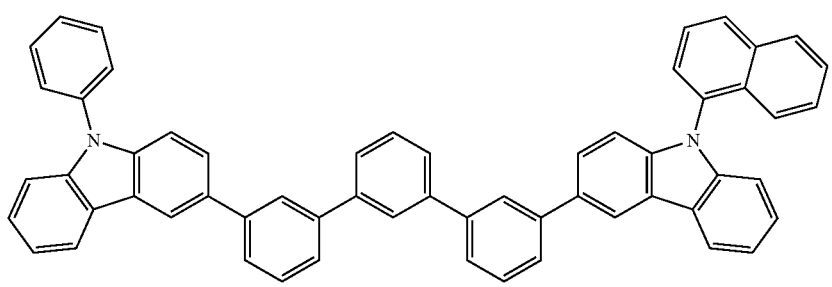
91
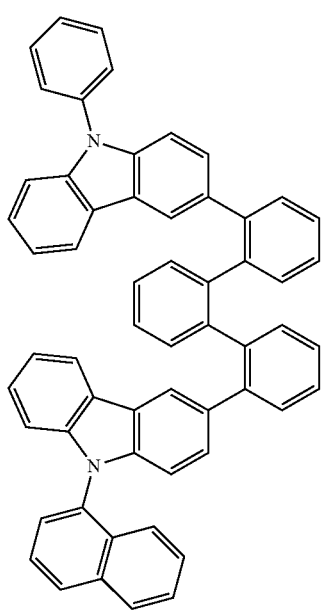
92

-continued
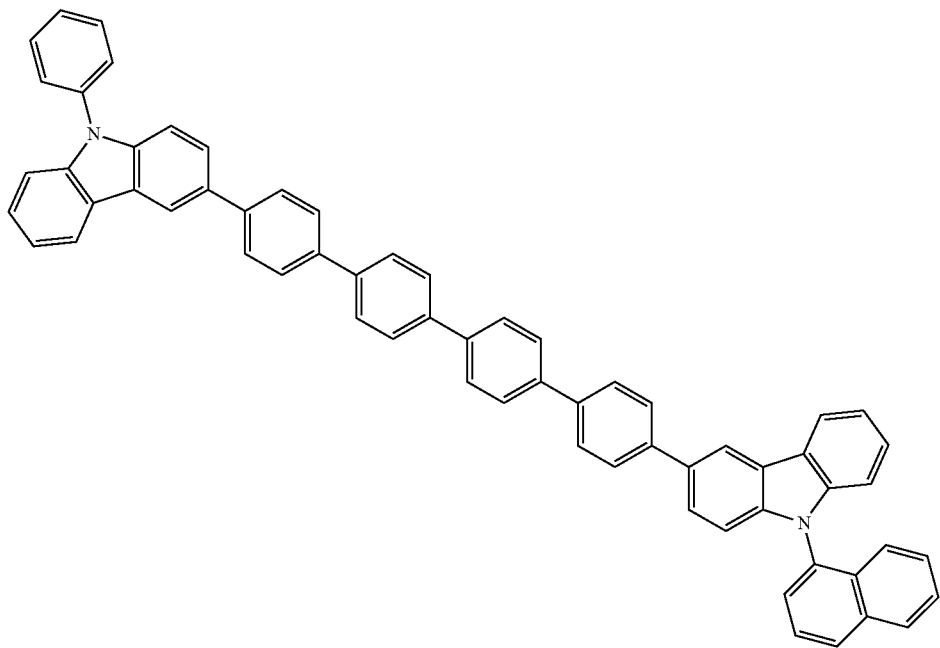
93
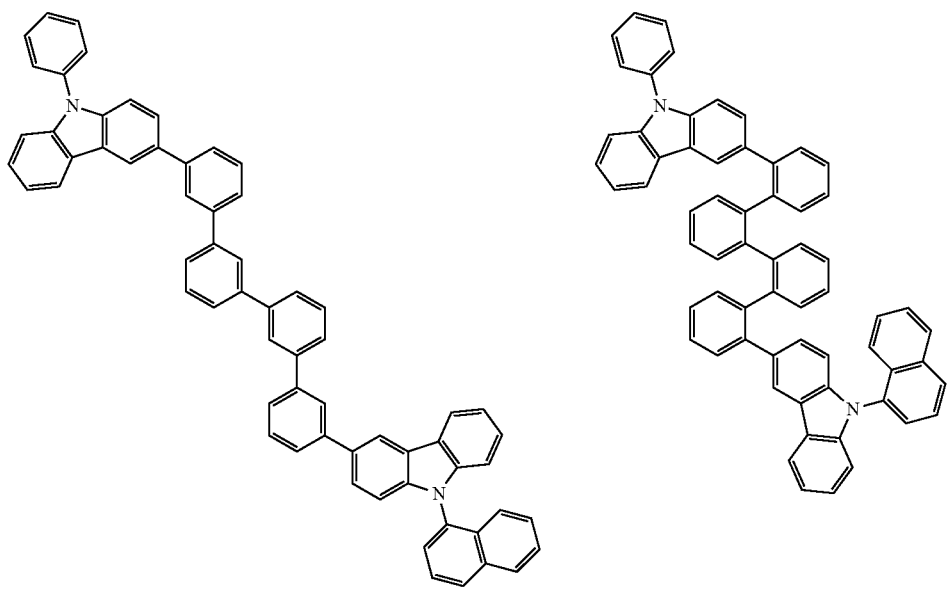
94
95

-continued
96
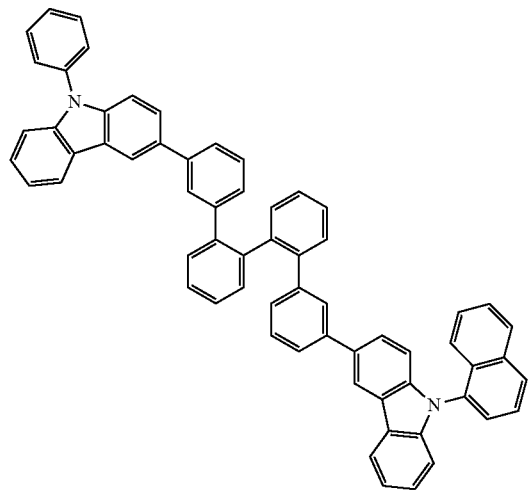
97
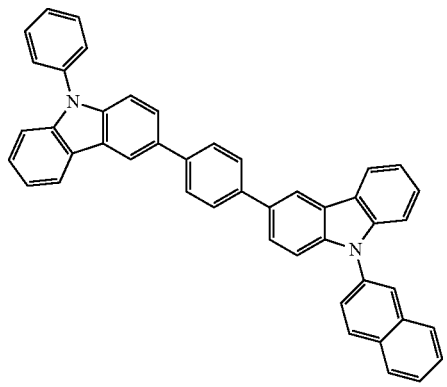
98
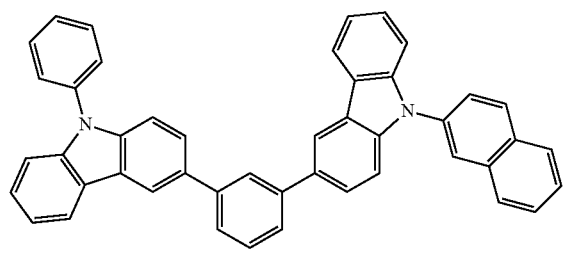
99
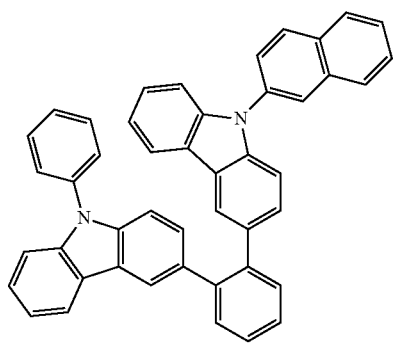
100
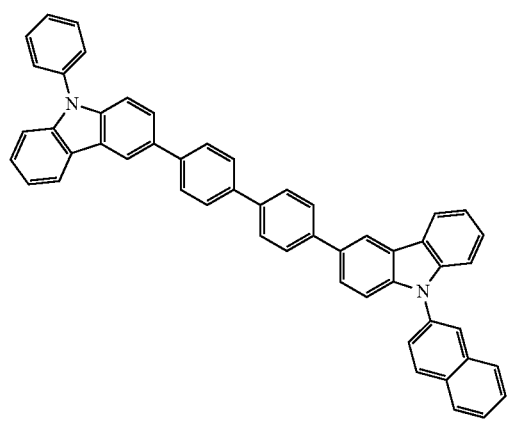
101
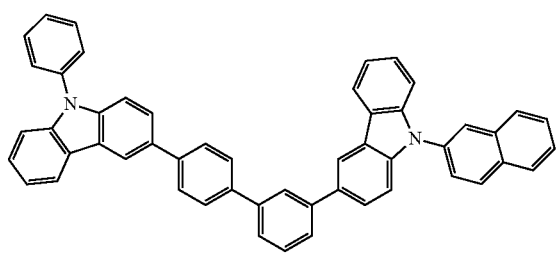

-continued
102
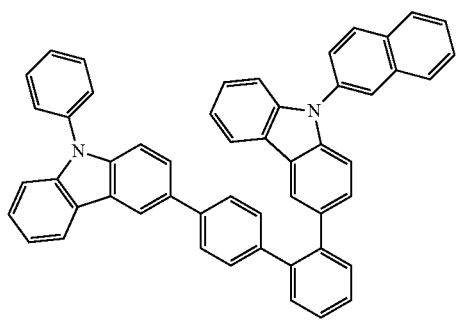
103
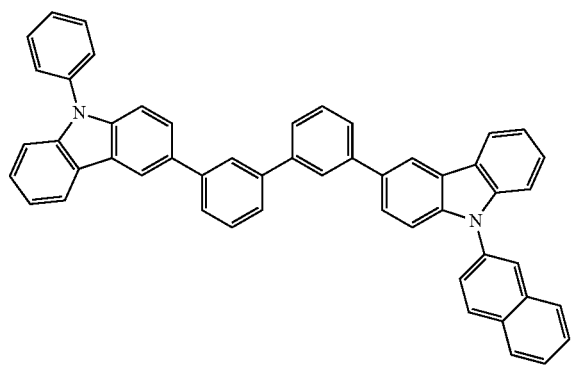
104
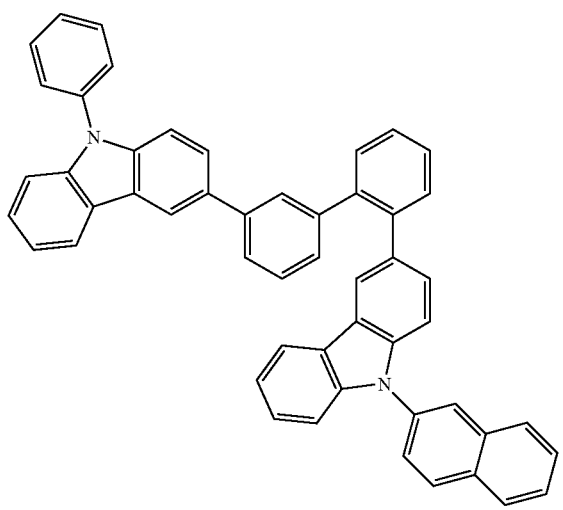
105
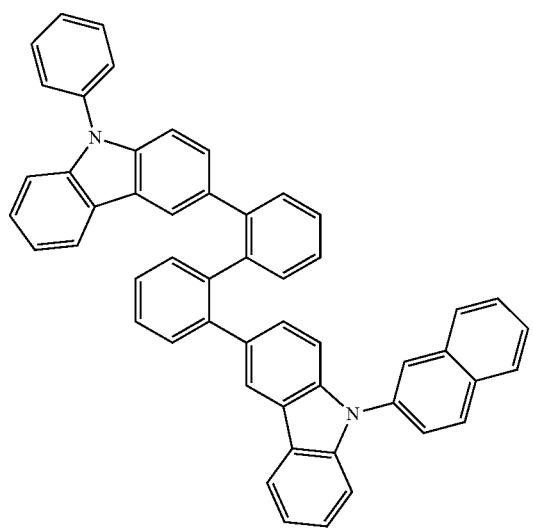
106
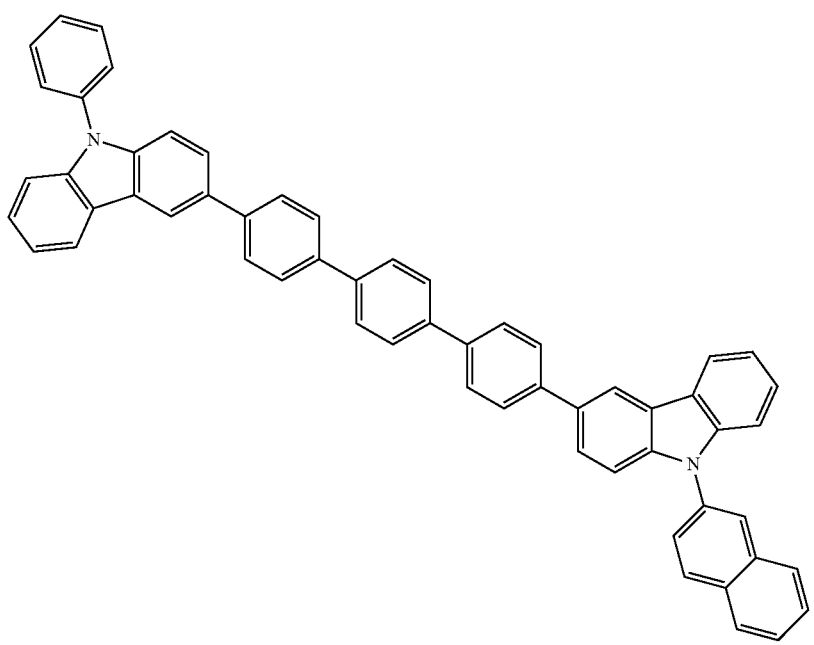

-continued
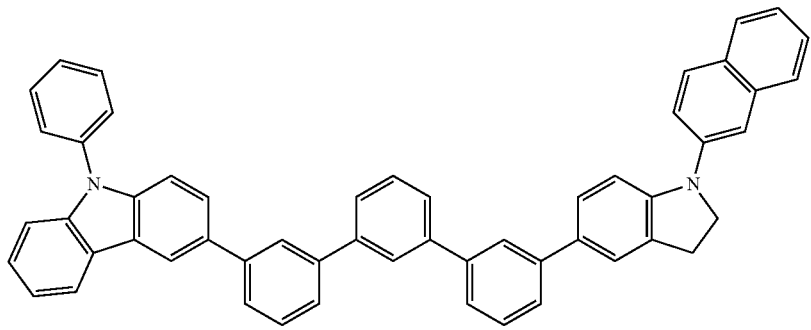
107
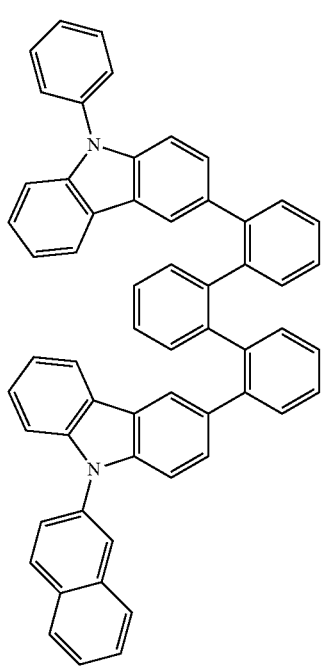
108

-continued
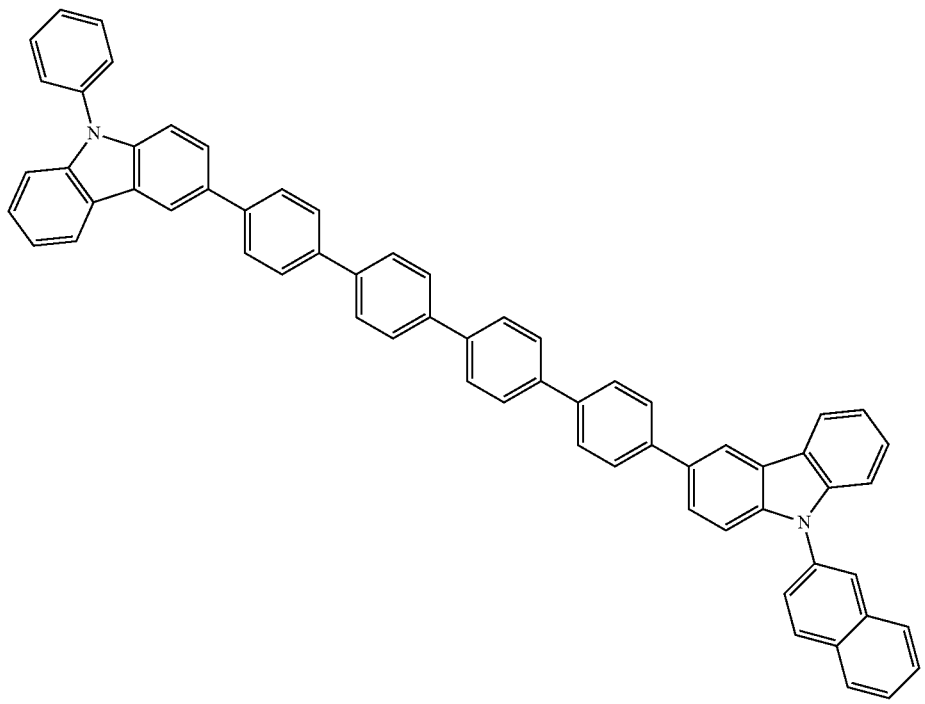
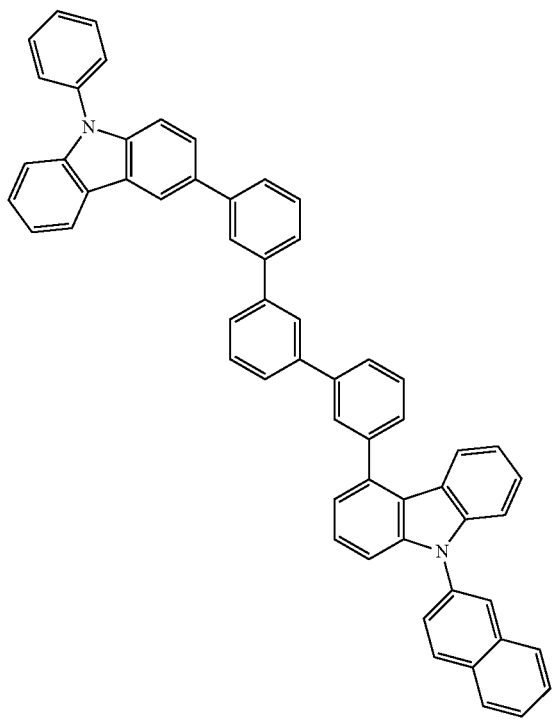
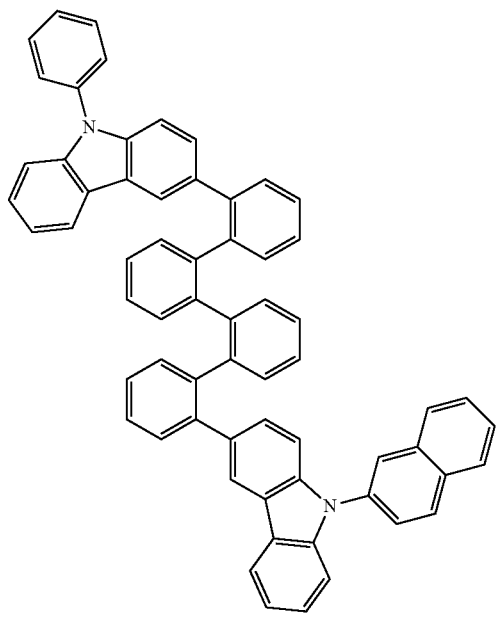

-continued
112 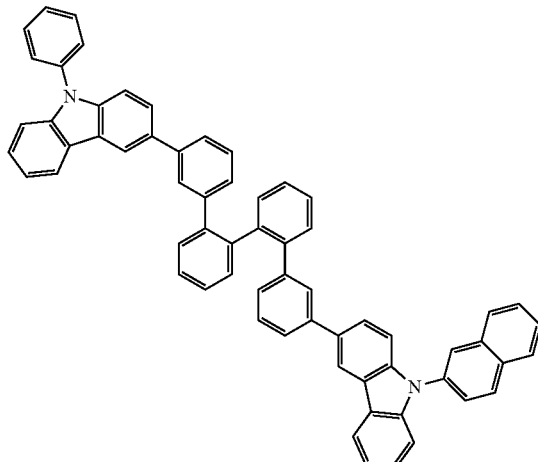
113 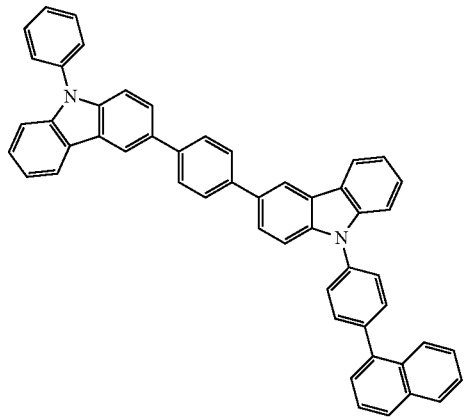
114 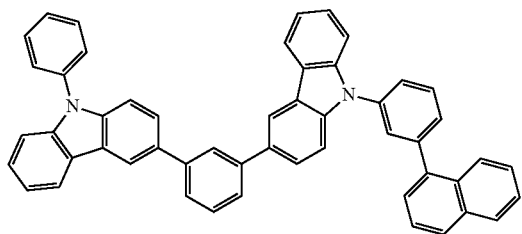
115 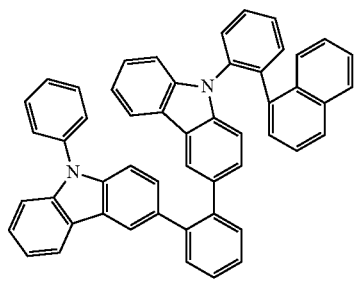
116 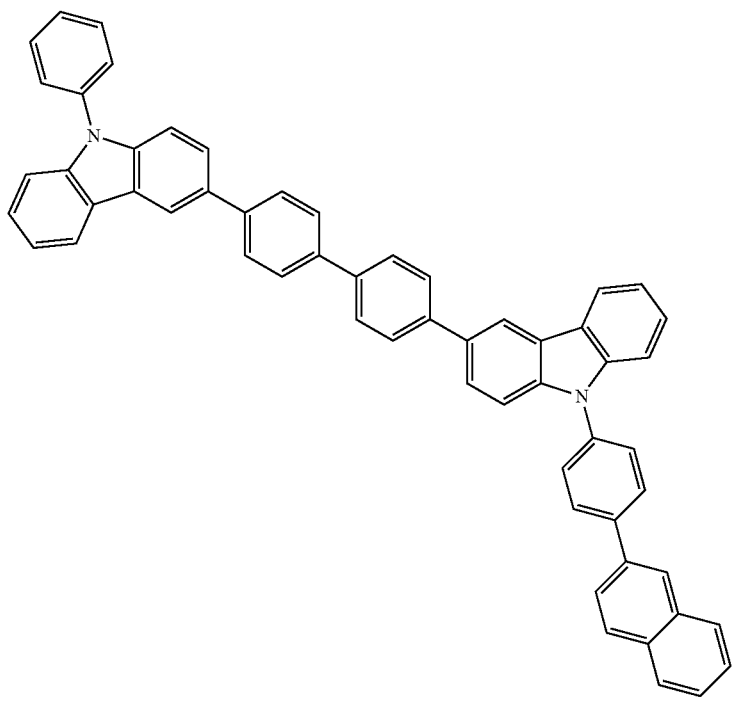

117
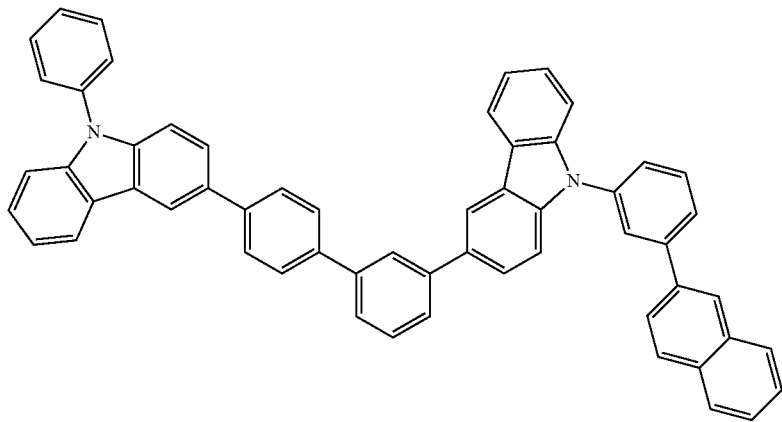
118
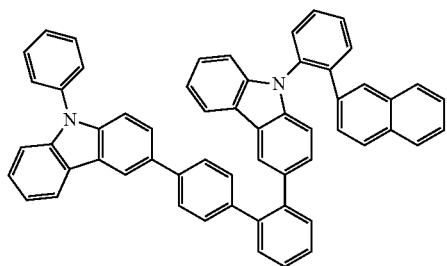
119
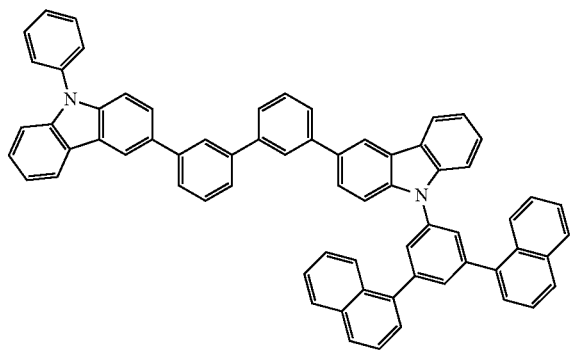
120
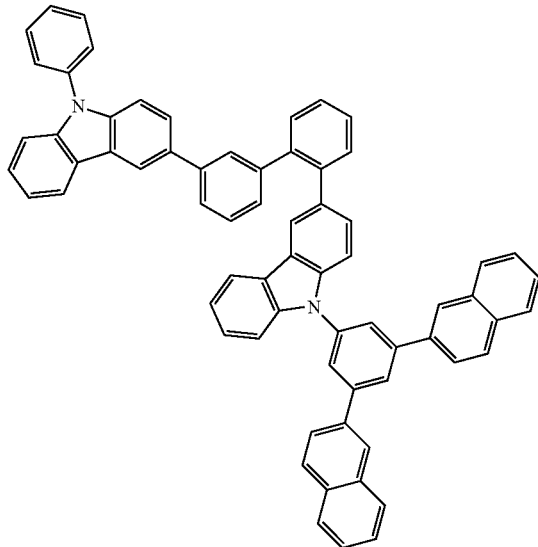
121
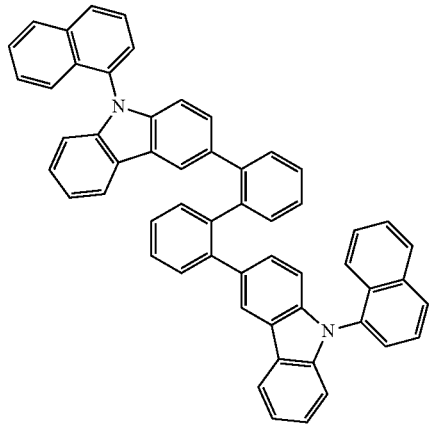

-continued
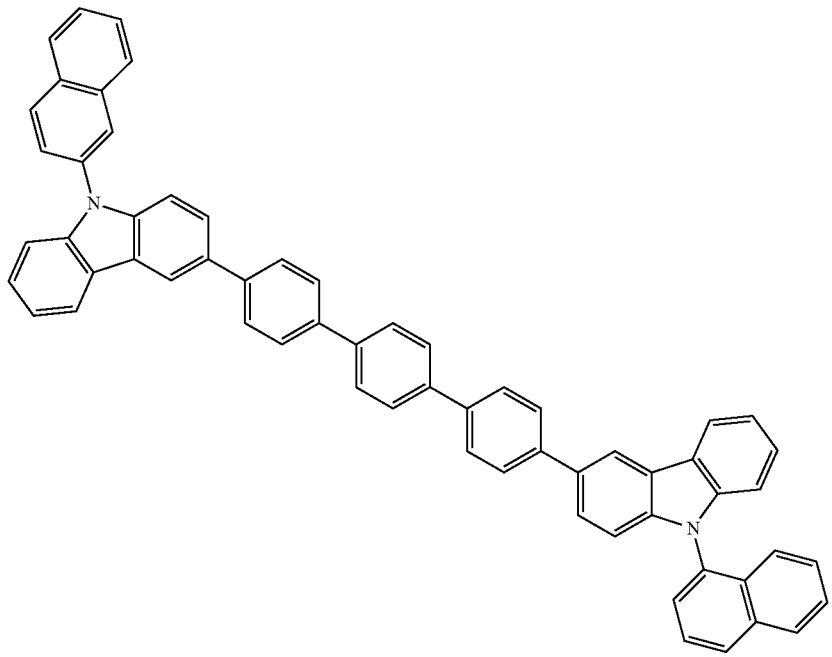
122
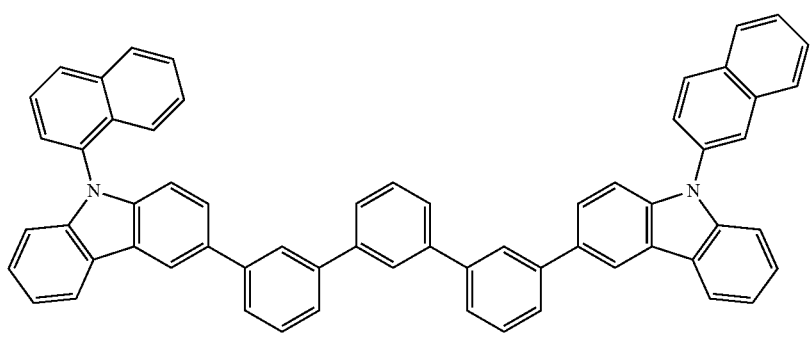
123

-continued
124
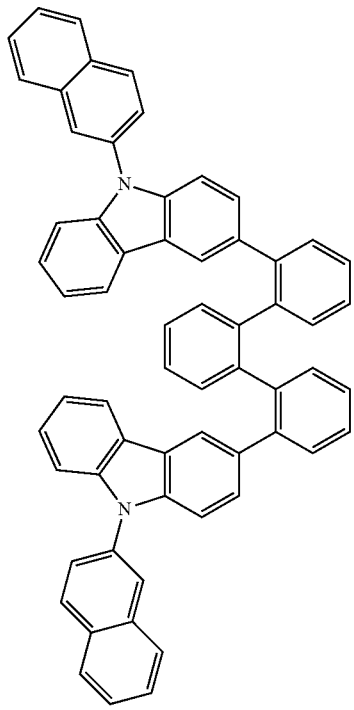
125
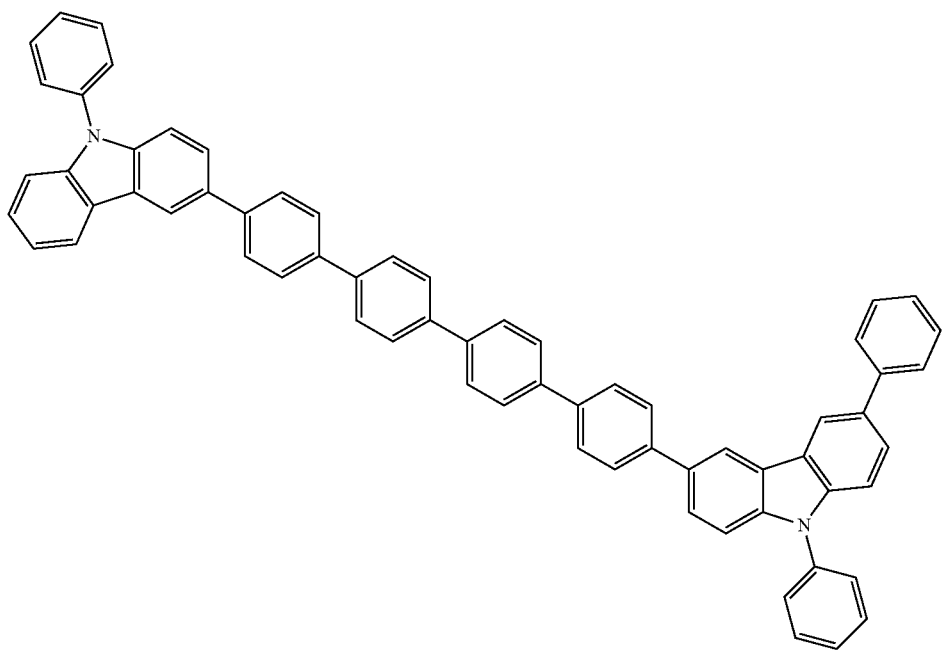

-continued
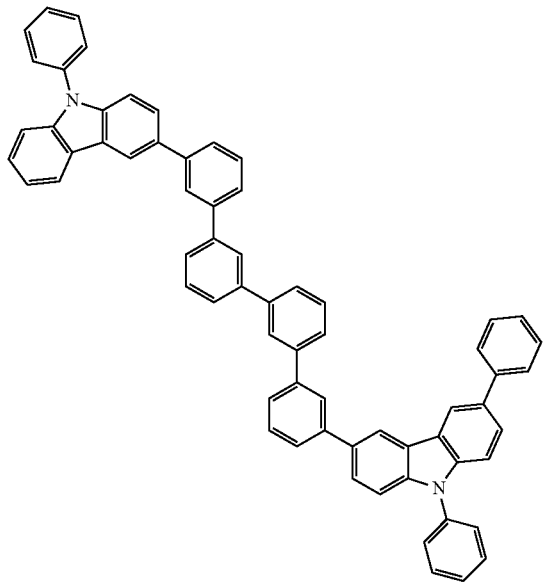
126
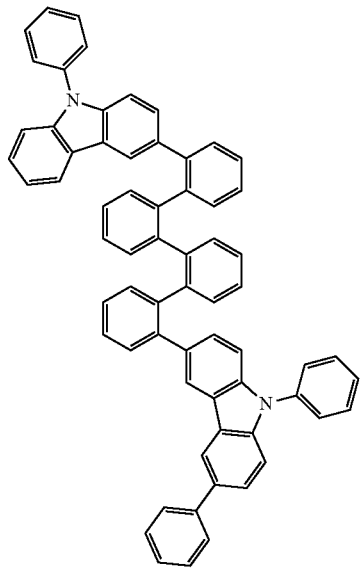
127
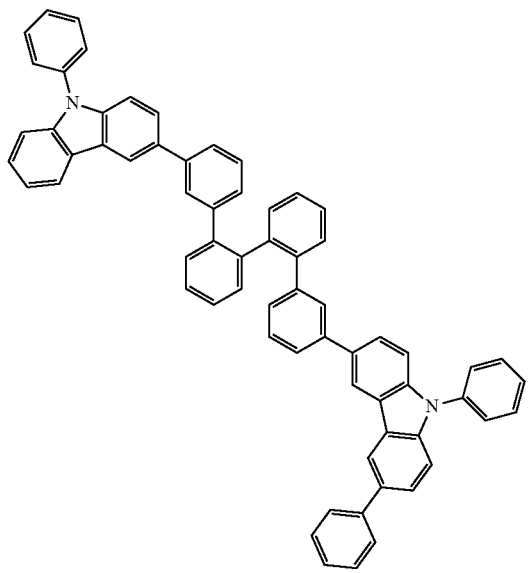
128
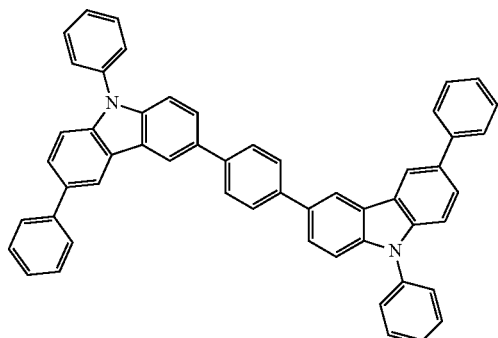
129
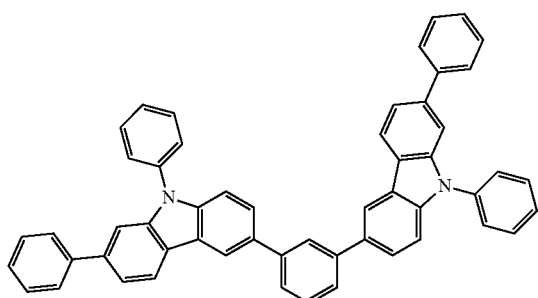
130
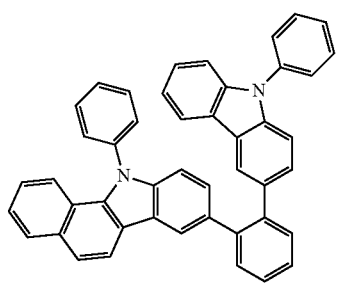
131

-continued
132
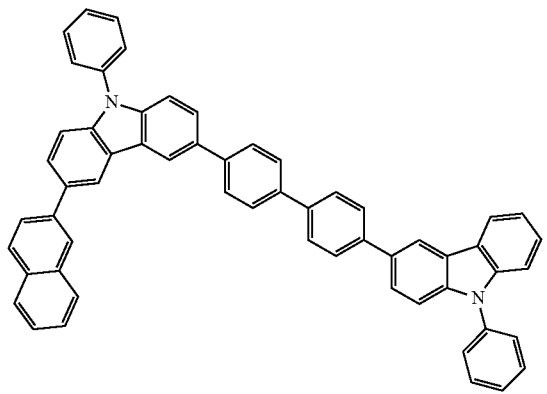
133
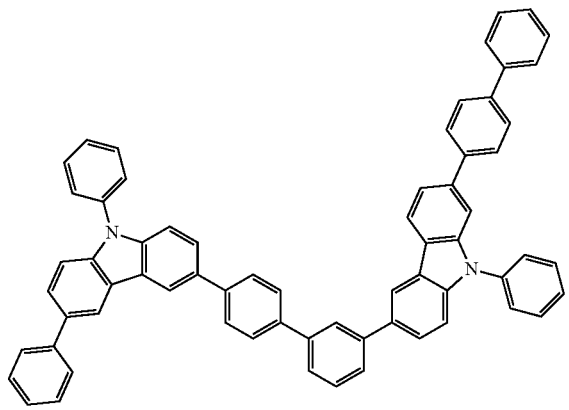
134
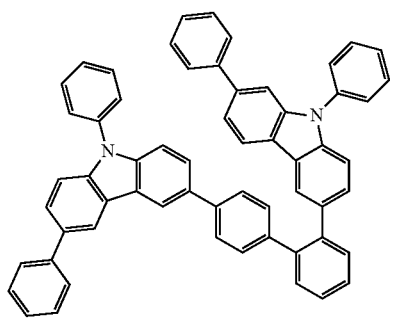
135
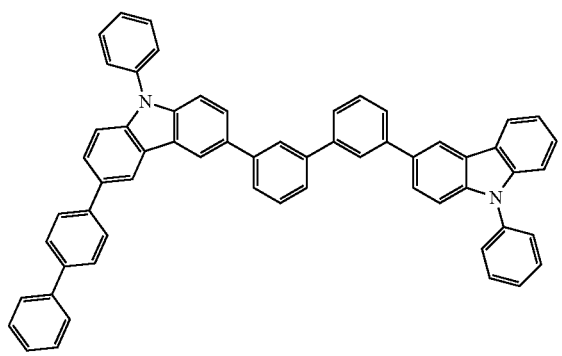
136
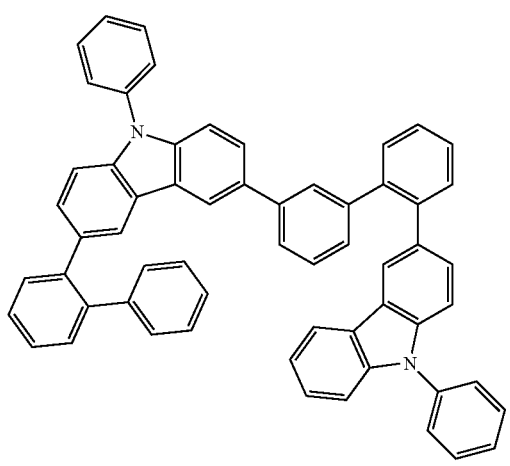
137
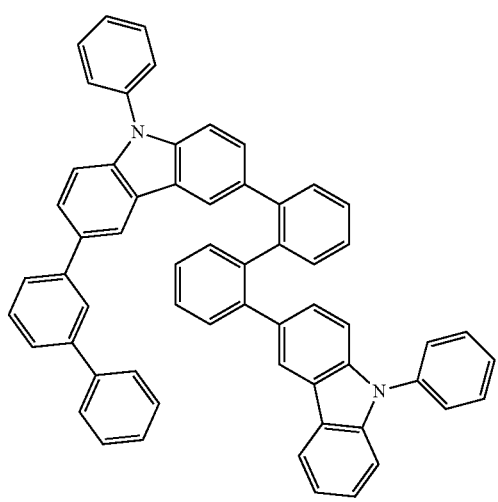

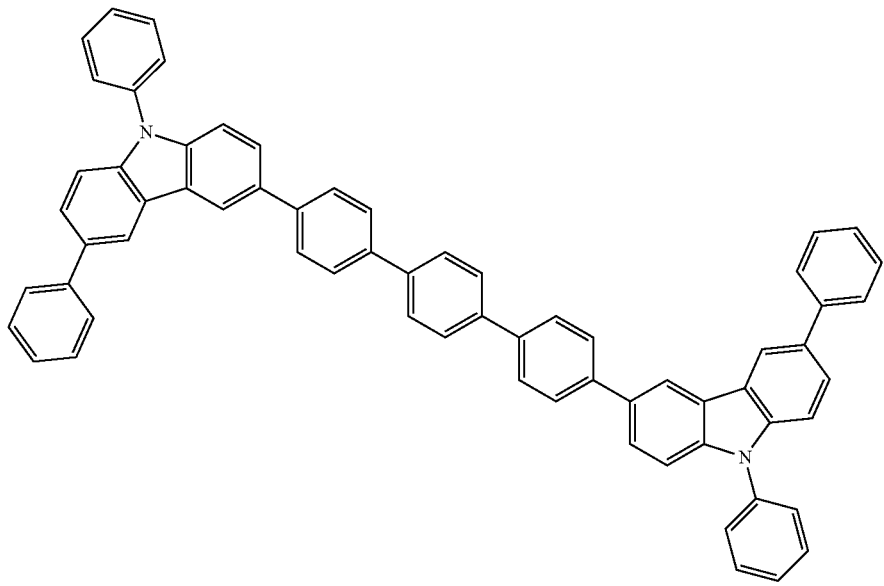
138
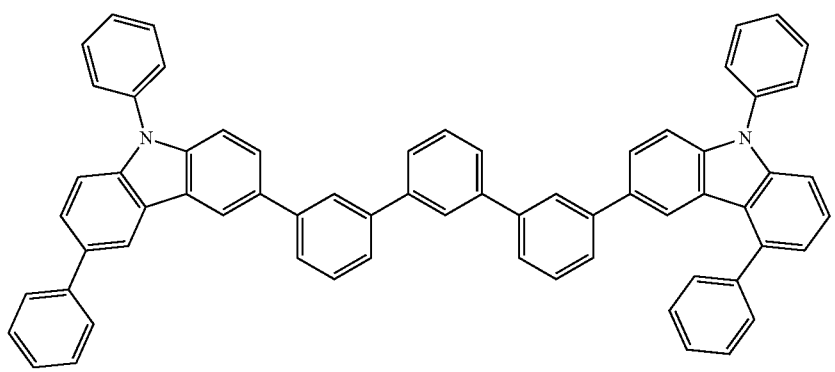
139
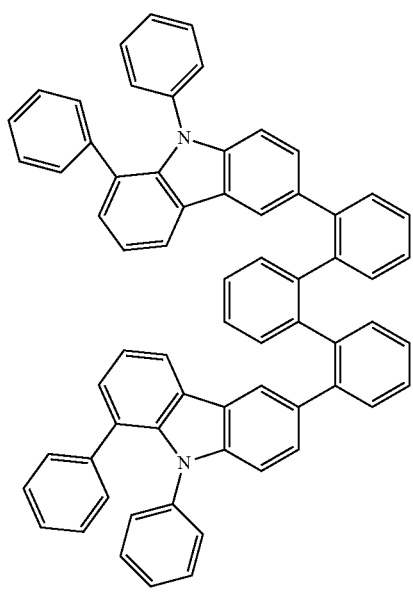
140

As described above, the compound represented by Chemical Formula II which is advantageous for a deposition may be used for a hole transport auxiliary layer, while the compound represented by Chemical Formula I and having improved hole mobility is used for a hole transport layer, processibility and a life-span and efficiency of a device may be remarkably improved.

The compound represented by Chemical Formula I and the compound represented by Chemical Formula II may be applied in various combinations in each of the hole transport layer and the hole transport auxiliary layer.

The light-emitting layer 32 includes a host and a dopant.

The host is a matrix material having low self light emitting capability but high film forming capability and high light emitting capability.

The material used as a host may have electrons or holes injection property, a satisfactory film-formation, high heat resistance, a high exciton energy level, and excellent charge mobility, wherein a light emitting spectrum is overlapped with a dopant absorption spectrum, and a energy gap between Homo and Lumo should be wide.

A compound satisfying these properties may be an aromatic monocyclic compound, an aromatic condensed cyclic compound, a hetero monocyclic compound, a hetero condensed cyclic compound, a metal complex, a phi conjugated polymer compound, a sigma conjugated polymer compound, a metal complex, an amine derivative, a stilbene-based compound, a hydrazone-based compound, and the like.

In the present invention, known host materials may be used. For example, the host material may be selected from CBP (carbazole biphenyl), mCP (1,3-bis(carbazol-9-yl), 4,4'-bis(9-carbazo-lyl)-2,2'-dimethyl-biphenyl (CDBP), 4,4',4''-tri(N-carbazolyl)triphenylamine (TCTA), 2,9-dimethyl-4,7-diphenyl-phenanthroline (BCP), 9,10-bis(4-(N-carbazolyl)phenyl)anthracene (BCPA), 3-(biphenyl-4-yl)-4-phenyl-5-(4-tert-butylphenyl)-1,2,4-triazole (TAZ), 1,1-bis (4-bis (4-methylphenyl)-aminophenyl)-cyclohexane (TAPC), tris-(8-hydroxyquinolone)aluminum ($Alq_3$), metal phthalocyanine, 4-biphenyloxolato aluminum(III)bis (2-methyl-8-quinolinato)4-phenylphenolate (BAlq), N,N'-Bis (3-methylphenyl)-N,N'-diphenylbenzidine (TPD), 4,4'-bis{N-(1-naphthyl)-N-phenyl-amino}biphenyl (α-NPD), N-(4-(1E-2-(10-(4-(diphenylamino)styryl)anthracene-9-yl) vinyl)phenyl)-N-phenylbenzeneamine (BSA-2), 4,4'-bis (2,2'diphenylvinyl)-1,1'-biphenyl (DPVBi), 2-tert-butylphenyl-5-biphenyl-1,3,4-oxadiazole (PBD), poly(vinylcarbazole) (PVK) and derivatives thereof, carbazole substituted polyacetylenes (PAC), poly(p-phenylene vinylene) (PPV) and derivatives thereof, poly[2-methoxy-5-(2'-ethylhexyloxy)-1,4-phenylenevinylene-co-4,4'-bisphenylenevinylene] (MEH-BP-PPV), poly(thiophene) (PAT) and derivatives thereof, poly (9,9'-dialkylfluorene) (PDAF) and derivatives thereof, poly(p-phenylene) (PPP), and derivatives thereof, poly(1,4-naphthalene vinylene) (PNV), and derivatives thereof, polystyrene(PS) and derivatives thereof, polysilane and derivatives thereof, poly (arylenevinylene) (PAV) and derivatives thereof, but is not limited thereto.

The dopant is mixed with a host in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be a red, green, or blue dopant, for example a phosphorescent dopant. The phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd, or a combination thereof, and the L and X may be, for example a bidendate ligand.

The light-emitting layer 32 may include a material that emits red, green, and blue and white light, and for example, when the light-emitting layer 32 emits red light, it includes a host material of CBP (carbazole biphenyl) or mCP (1,3-bis(carbazol-9-yl), and a phosphorescent material including a dopant including one or more selected from PlQIr(acac) (bis(1-phenylisoquinoline)acetylacetonate iridium), PQIr(acac) (bis(1-phenylquinoline)acetylacetonate iridium), PQIr (tris(1-phenylquinoline)iridium) and PtOEP (octaethylporphyrin platinum), or a fluorescent material including PBD: $Eu(DBM)_3$ (Phen), or perylene, but is not limited thereto. When the light-emitting layer 32 emits green light, it includes a host material including CBP or mCP, and a phosphorescent material including a dopant including $Ir(ppy)_3$(fac tris(2-phenylpyridine)iridium), or a fluorescent material including $Alq_3$(tris(8-hydroxyquinolino)aluminum), but is not limited thereto. When the light-emitting layer 32 emits blue light, it includes a host material including CBP or mCP and a phosphorescent material including a dopant including $(4,6-F_2ppy)_2Irpic$. On the contrary, the light-emitting layer 32 may be made of a fluorescent material including any one selected from spiro-DPVBi, spiro-6P, distyryl benzene (DSB), distyryl arylene (DSA), a PFO-based polymer, and a PPV-based polymer, but is not limited thereto.

Particularly, when the hole transport layer 31 and the hole transport auxiliary layer 33 are used with a blue light emitting material, a driving voltage may be lowered and long life-span characteristics may be further maximized.

On the other hand, the hole transport auxiliary layer 33 may contact the hole transport layer 31 and the light-emitting layer 32.

The organic layer 30 may further include an electron transport layer 34. The electron transport layer 34 is a layer to help electron transfer from the cathode 20 and to the light-emitting layer 32, and may be omitted as needed.

The organic layer 30 may further optionally include a hole injection layer (not shown) between the anode 10 and the hole transport layer 31 and/or an electron injection layer (not shown) between the cathode 20 and the electron transport layer 34.

The organic light emitting diode may be applied to an organic light emitting display device.

BEST MODE

Hereinafter, the embodiments are illustrated in more detail with reference to examples. These examples, however, are not in any sense to be interpreted as limiting the scope of the invention.

Hole Transport Layer: Synthesis of Compounds Represent by Chemical Formula I

Synthesis Example 1: Synthesis of Intermediate I-1

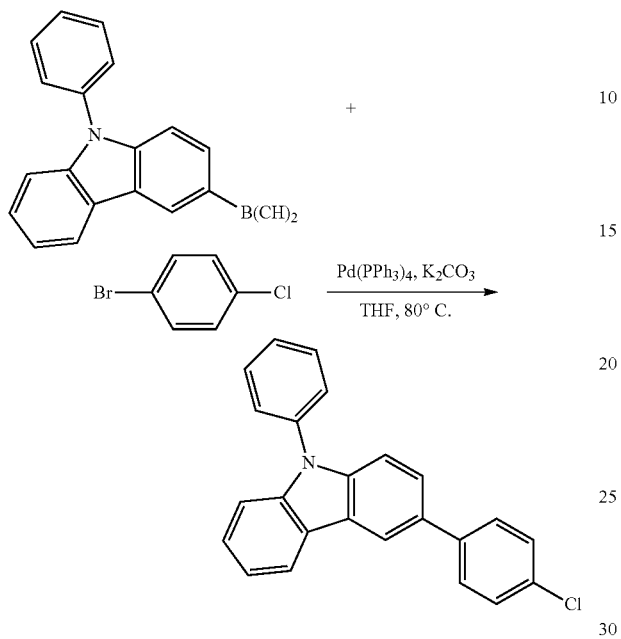

9-phenyl-9H-carbazol-3-ylboronic acid (100 g, 348 mmol) was dissolved in 0.9 L of tetrahydrofuran (THF) under a nitrogen environment, 1-bromo-4-chlorobenzene (73.3 g, 383 mmol) and tetrakis(triphenylphosphine)palladium (4.02 g, 3.48 mmol) were added thereto, and the mixture was stirred. Potassium carbonate (128 g, 870 mmol) saturated in water was added thereto, and the obtained mixture was heated and refluxed at 80° C. for 8 hours. When the reaction was completed, water was added to the reaction solution, dichloromethane (DCM) was used for an extraction, and an extract therefrom was filtered after removing moisture with anhydrous MgSO₄ and then, concentrated under a reduced pressure. The obtained residue was separated and purified through flash column chromatography to obtain an intermediate I-1 (119 g, 97%).

HRMS (70 eV, El+): m/z calcd for C24H16ClN: 353.0971, found: 353.

Elemental Analysis: C, 81%; H, 5%

Synthesis Example 2: Synthesis of Compound 4 of Chemical Formula I

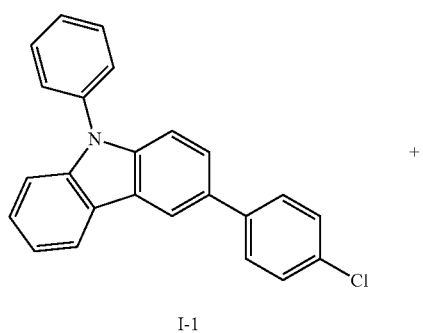

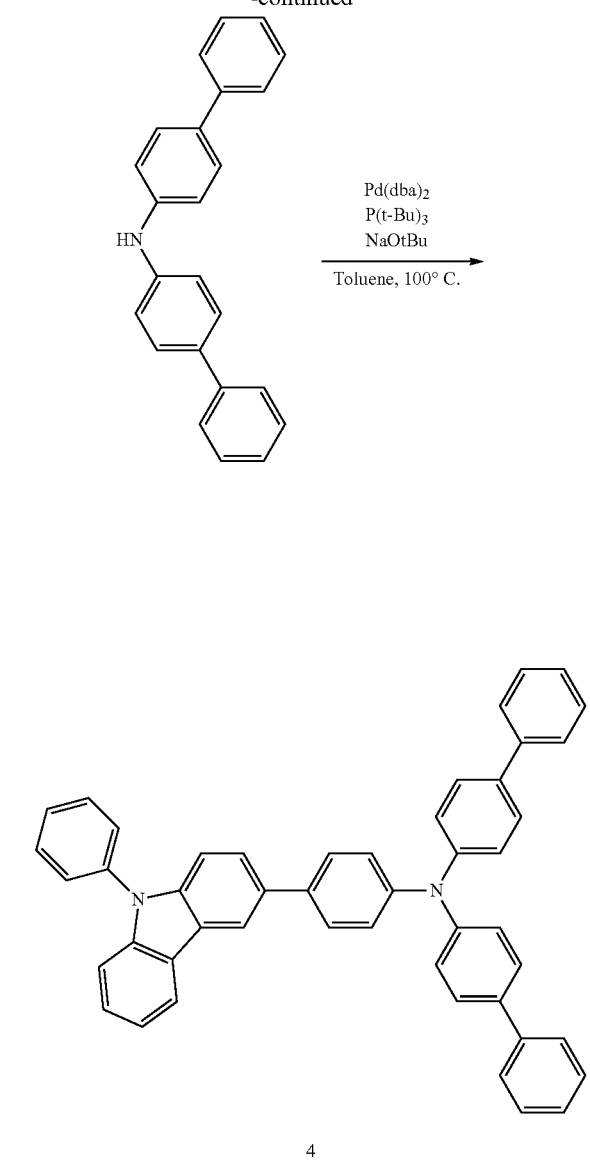

The intermediate I-1 (20 g, 56.5 mmol) was dissolved in 0.2 L of toluene under a nitrogen environment, dibiphenyl-4-ylamine made by Shenzhen Gre-syn Chemical Technology Co., Ltd. (http://www.gre-syn.com/) (18.2 g, 56.5 mmol), bis(dibenzylideneacetone)palladium (0) (0.33 g, 0.57 mmol), tris-tert butylphosphine (0.58 g, 2.83 mmol), and sodium tert-butoxide (6.52 g, 67.8 mmol) were sequentially added thereto, and the mixture was heated and refluxed at 100° C. for 15 hours. When the reaction was completed, water was added to the reaction solution, dichloromethane (DCM) was used for an extraction, and an extract therefrom was filtered after removing moisture with anhydrous MgSO₄ and then, concentrated under a reduced pressure. This obtained residue was separated and purified through flash column chromatography to obtain Compound 4 (32.5 g, 90%) of Chemical Formula I.

HRMS (70 eV, El+): m/z calcd for C48H34N2: 638.2722, found: 638.

Elemental Analysis: C, 90%; H, 5%

Synthesis Example 3: Synthesis of Compound 9 of Chemical Formula I

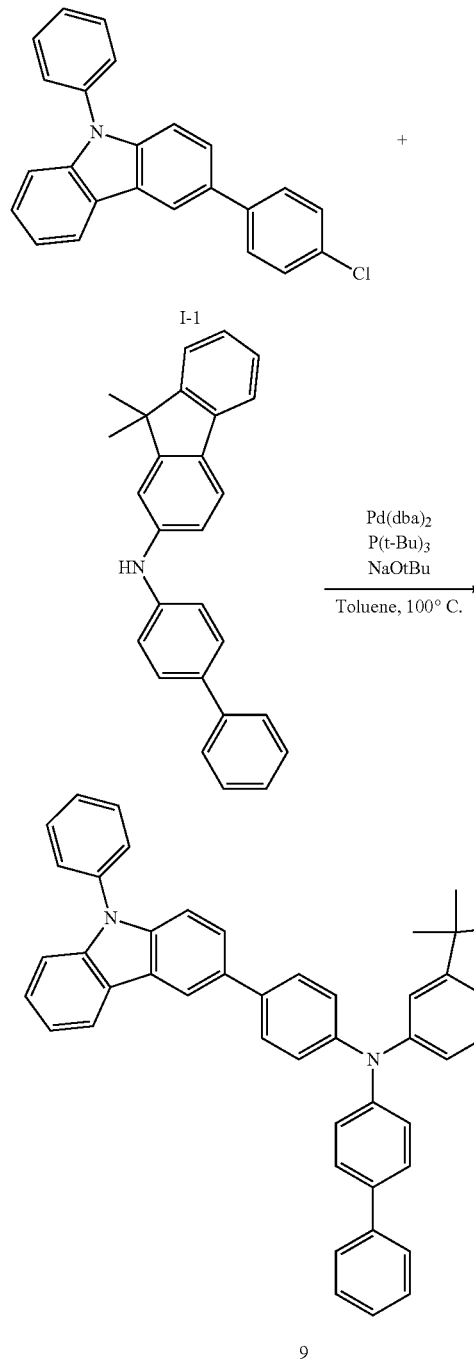

The intermediate I-1 (20 g, 56.5 mmol) was dissolved in 0.2 L of toluene under a nitrogen environment, N-(biphenyl-4-yl)-9,9-dimethyl-9H-fluoren-2-amine made by Shenzhen Gre-syn Chemical Technology Co., Ltd. (http://www.gre-syn.com/) (20.4 g, 56.5 mmol), bis(dibenzylideneacetone) palladium (0) (0.33 g, 0.57 mmol), tris-tert butylphosphine (0.58 g, 2.83 mmol), and sodium tert-butoxide (6.52 g, 67.8 mmol) were sequentially added thereto, and the mixture was heated and refluxed at 100° C. for 13 hours. When the reaction was completed, water was added to the reaction solution, dichloromethane (DCM) was used for an extraction, and an extract therefrom was filtered after removing moisture with anhydrous $MgSO_4$ and then, concentrated under a reduced pressure. The obtained residue was separated and purified through flash column chromatography to obtain Compound 9 (33.8 g, 88%) of Chemical Formula I.

HRMS (70 eV, El+): m/z calcd for C48H34N2: 678.3045, found: 678.

Elemental Analysis: C, 90%; H, 6%

Synthesis Example 4: Synthesis of Compound 27 of Chemical Formula I

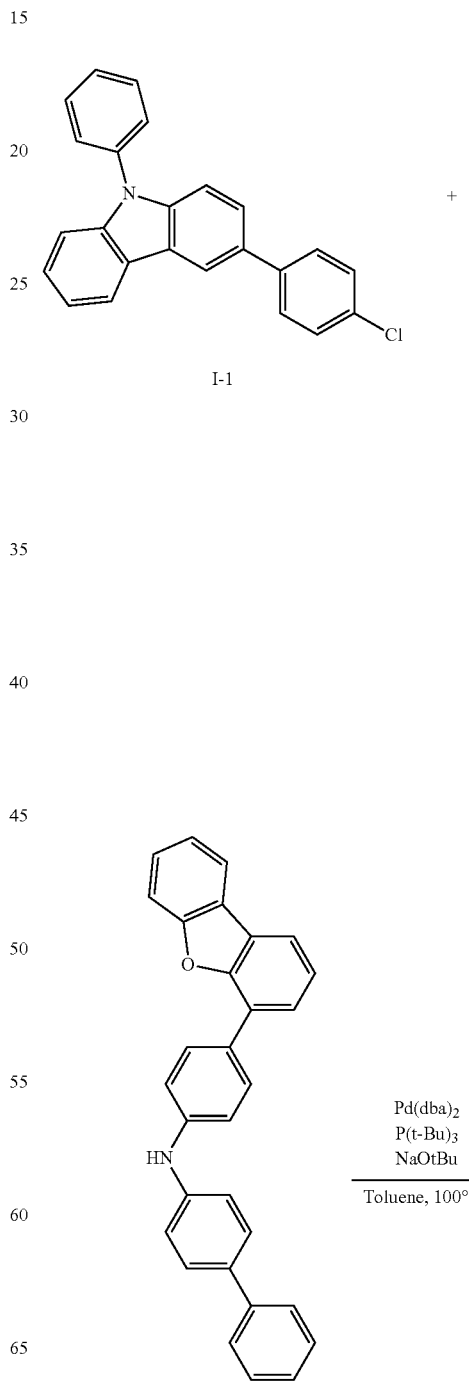

-continued

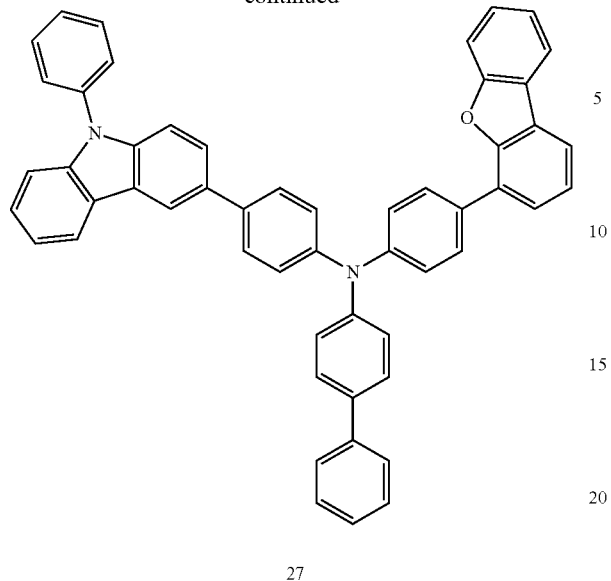

27

The intermediate I-1 (20 g, 56.5 mmol) was dissolved in 0.2 L of toluene under a nitrogen environment, N-(4-(dibenzo[b,d]furan-4-yl)phenyl)biphenyl-4-amine made by Shenzhen Gre-syn Chemical Technology (http://www.gre-syn.com/) (23.2 g, 56.5 mmol), bis(dibenzylideneacetone) palladium (0) (0.33 g, 0.57 mmol), tris-tert butylphosphine (0.58 g, 2.83 mmol), and sodium tert-butoxide (6.52 g, 67.8 mmol) were sequentially added thereto, and the mixture was heated and refluxed at 100° C. for 18 hours. When the reaction was completed, water was added to the reaction solution, dichloromethane (DCM) was used for an extraction, and an extract therefrom was filtered after removing moisture with anhydrous MgSO₄ and then, concentrated under a reduced pressure. The obtained residue was separated and purified through flash column chromatography to obtain Compound 27 (37.5 g, 91%) of Chemical Formula I.

HRMS (70 eV, EI+): m/z calcd for C54H36N2O: 728.2828, found: 728.

Elemental Analysis: C, 89%; H, 5%

Hole Transport Auxiliary Layer: Synthesis of Compounds Represented by Chemical Formula II Synthesis Example 5: Synthesis of Intermediate I-2

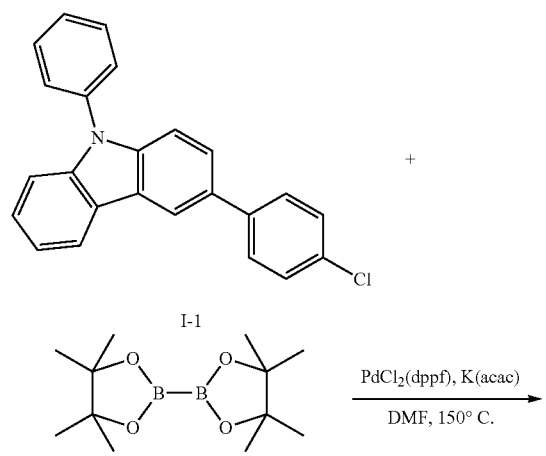

-continued

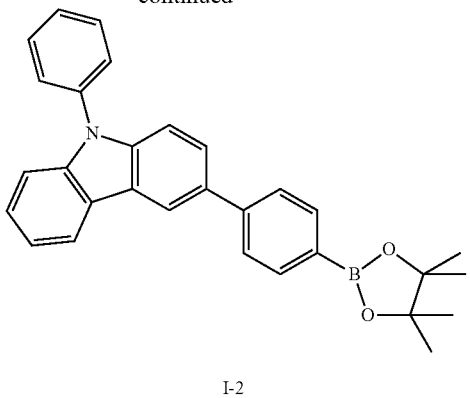

I-2

The intermediate I-1 (90 g, 254 mmol) was dissolved in 0.8 L of dimethylforamide (DMF) under a nitrogen environment, bis(pinacolato)diboron (77.5 g, 305 mmol), (1,1'-bis(diphenylphosphine)ferrocene)dichloropalladium (II) (2.70 g, 2.54 mmol), and potassium acetate (74.8 g, 762 mmol) were added thereto, and the mixture was heated and refluxed at 150° C. for 20 hours. When the reaction was complete, water was added to the reaction solution, and the mixture was filtered and dried in a vacuum oven. The obtained residue was separated and purified through flash column chromatography to obtain an intermediate I-2 (75.8 g, 67%).

HRMS (70 eV, EI+): m/z calcd for C30H28BNO2: 445.2213, found: 445.

Elemental Analysis: C, 81%; H, 6%

Synthesis Example 6: Synthesis of Intermediate I-3

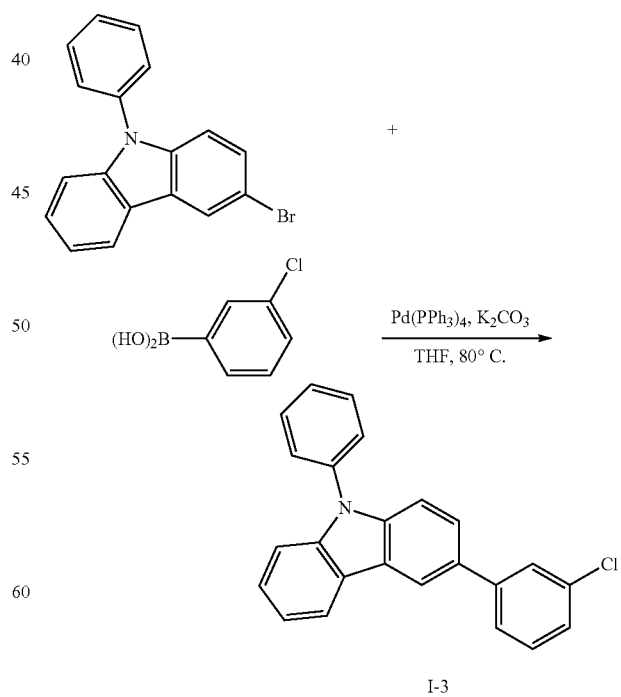

3-bromo-9-phenyl-9H-carbazole (100 g, 310 mmol) was dissolved in 0.8 L of tetrahydrofuran (THF) under a nitrogen environment, 3-chlorophenylboronic acid (53.4 g, 341 mmol) and tetrakis(triphenylphosphine)palladium (3.58 g, 3.10 mmol) were added thereto, and the mixture was stirred. Potassium carbonate (114 g, 775 mmol) saturated in water was added thereto, and the obtained mixture was heated and refluxed at 80° C. for 16 hours. When the reaction was completed, water was added to the reaction solution, dichloromethane (DCM) was used for an extraction, and an extract therefrom was filtered after removing moisture with anhydrous MgSO$_4$ and then, concentrated under a reduced pressure. The obtained residue was separated and purified through flash column chromatography to obtain an intermediate I-3 (91.0 g, 83%).

HRMS (70 eV, El+): m/z calcd for C24H16ClN: 353.0971, found: 353.

Elemental Analysis: C, 81%; H, 5%

Synthesis Example 7: Synthesis of Intermediate I-4

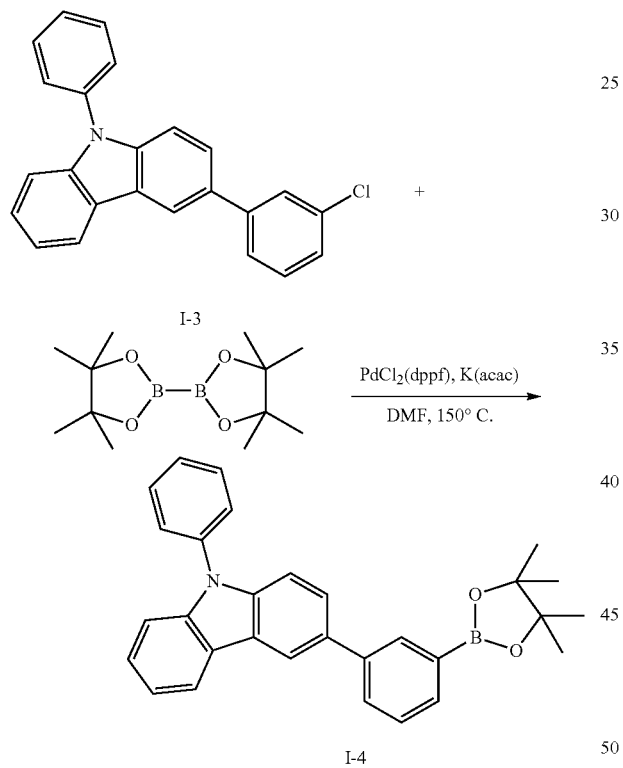

The intermediate I-3 (90 g, 254 mmol) was dissolved in 0.8 L of dimethylforamide (DMF) under a nitrogen environment, bis(pinacolato)diboron (77.5 g, 305 mmol), (1,1'-bis(diphenylphosphine)ferrocene)dichloropalladium (II) (2.70 g, 2.54 mmol), and potassium acetate (74.8 g, 762 mmol) were added thereto, and the mixture was heated and refluxed at 150° C. for 25 hours. When the reaction was complete, water was added to the reaction solution, and obtained mixture was filtered and dried in a vacuum oven. This obtained residue was separated and purified through flash column chromatography to obtain an intermediate I-4 (67.9 g, 60%).

HRMS (70 eV, El+): m/z calcd for C30H28BNO2: 445.2213, found: 445.

Elemental Analysis: C, 81%; H, 6%

Synthesis Example 8: Synthesis of Intermediate I-5

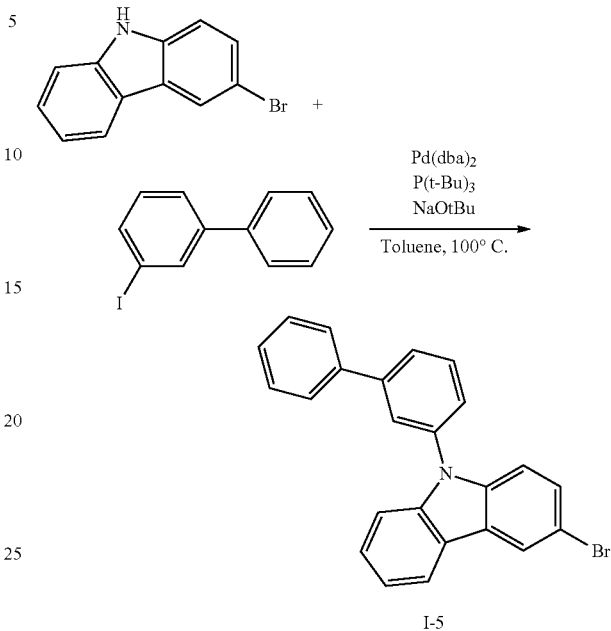

3-bromo-9H-carbazole (100 g, 406 mmol) was dissolved in 1.2 L of toluene under a nitrogen environment, 3-iodobiphenyl (137 g, 488 mmol), bis(dibenzylideneacetone)palladium (0) (2.33 g, 4.06 mmol), tris-tert butylphosphine (4.11 g, 20.3 mmol), and sodium tert-butoxide (46.8 g, 487 mmol) were sequentially added thereto, and the mixture was heated and refluxed at 100° C. for 10 hours. When the reaction was completed, water was added to the reaction solution, dichloromethane (DCM) was used for an extraction, and an extract therefrom was filtered after removing moisture with anhydrous MgSO$_4$ and then, concentrated under a reduced pressure. This obtained residue was separated and purified through flash column chromatography to obtain an intermediate I-5 (82.5 g, 51%).

HRMS (70 eV, El+): m/z calcd for C24H16BrN: 397.0466, found: 397.

Elemental Analysis: C, 72%; H, 4%

Synthesis Example 9: Synthesis of Compound 1 of Chemical Formula II

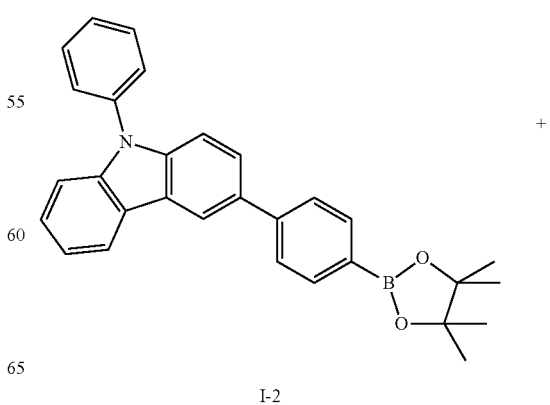

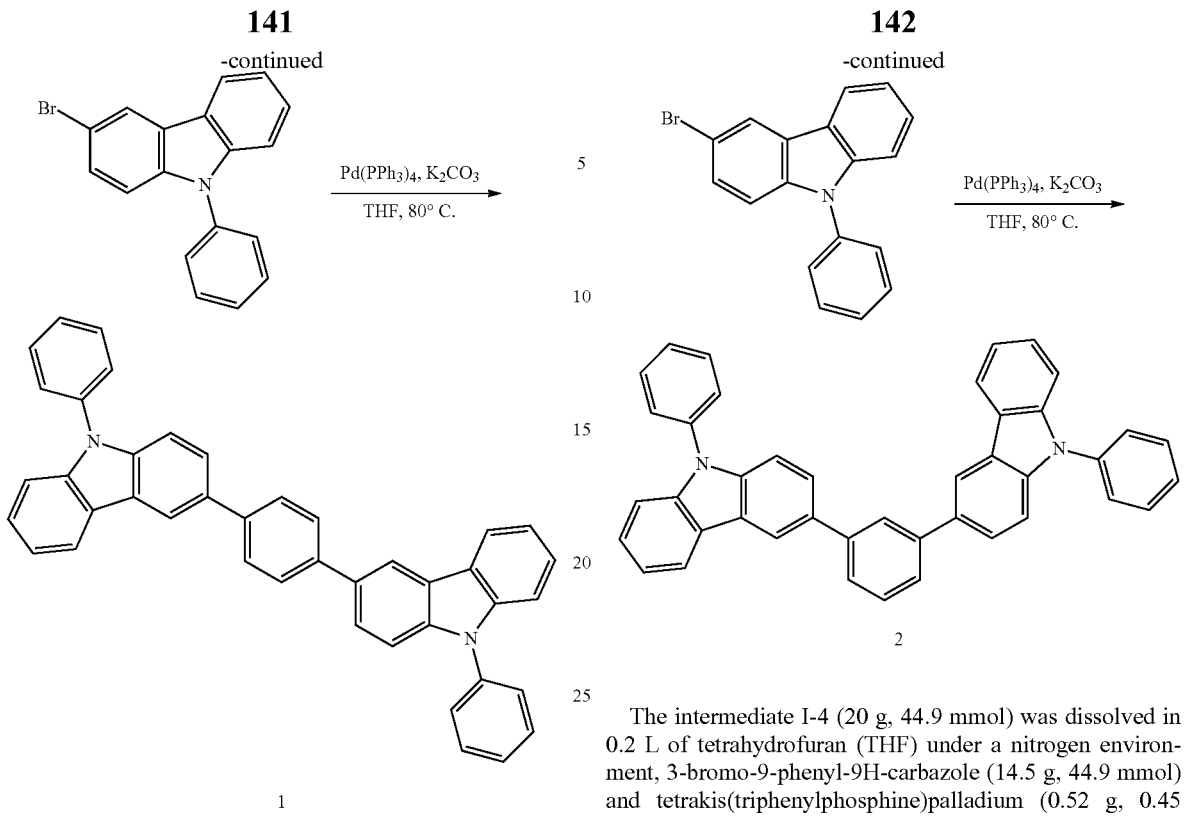

The intermediate I-2 (20 g, 44.9 mmol) was dissolved in 0.2 L of tetrahydrofuran (THF) under a nitrogen environment, 3-bromo-9-phenyl-9H-carbazole (14.5 g, 44.9 mmol) and tetrakis(triphenylphosphine)palladium (0.52 g, 0.45 mmol) were added thereto, and the mixture was stirred. Potassium carbonate (16.5 g, 112 mmol) saturated in water was added thereto, and the obtained mixture was heated and refluxed at 80° C. for 15 hours. When the reaction was completed, water was added to the reaction solution, dichloromethane (DCM) was used for an extraction, and an extract therefrom was filtered after removing moisture with anhydrous $MgSO_4$ and then, concentrated under a reduced pressure. The obtained residue was separated and purified through flash column chromatography to obtain Compound 1 (22.7 g, 90%) of Chemical Formula II.

HRMS (70 eV, EI+): m/z calcd for C42H28N2: 560.2252, found: 560.

Elemental Analysis: C, 90%; H, 5%

Synthesis Example 10: Synthesis of Compound 2 of Chemical Formula II

The intermediate I-4 (20 g, 44.9 mmol) was dissolved in 0.2 L of tetrahydrofuran (THF) under a nitrogen environment, 3-bromo-9-phenyl-9H-carbazole (14.5 g, 44.9 mmol) and tetrakis(triphenylphosphine)palladium (0.52 g, 0.45 mmol) were added thereto, and the mixture was stirred. Potassium carbonate (16.5 g, 112 mmol) saturated in water was added thereto, and the obtained mixture was heated and refluxed at 80° C. for 17 hours. When the reaction was completed, water was added to the reaction solution, dichloromethane (DCM) was used for an extraction, and an extract therefrom was filtered after removing moisture with anhydrous $MgSO_4$ and then, concentrated under a reduced pressure. This obtained residue was separated and purified through flash column chromatography to obtain Compound 2 (21.4 g, 85%) of Chemical Formula II.

HRMS (70 eV, EI+): m/z calcd for C42H28N2: 560.2252, found: 560.

Elemental Analysis: C, 90%; H, 5%

Synthesis Example 11: Synthesis of Compound II-33 of Chemical Formula II

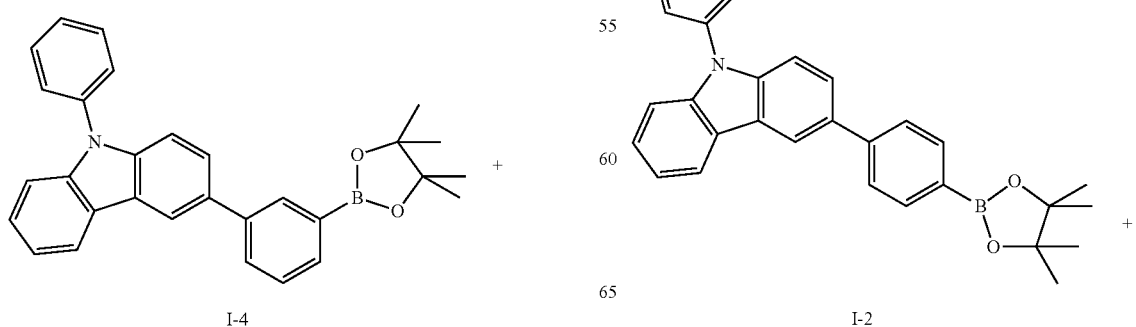

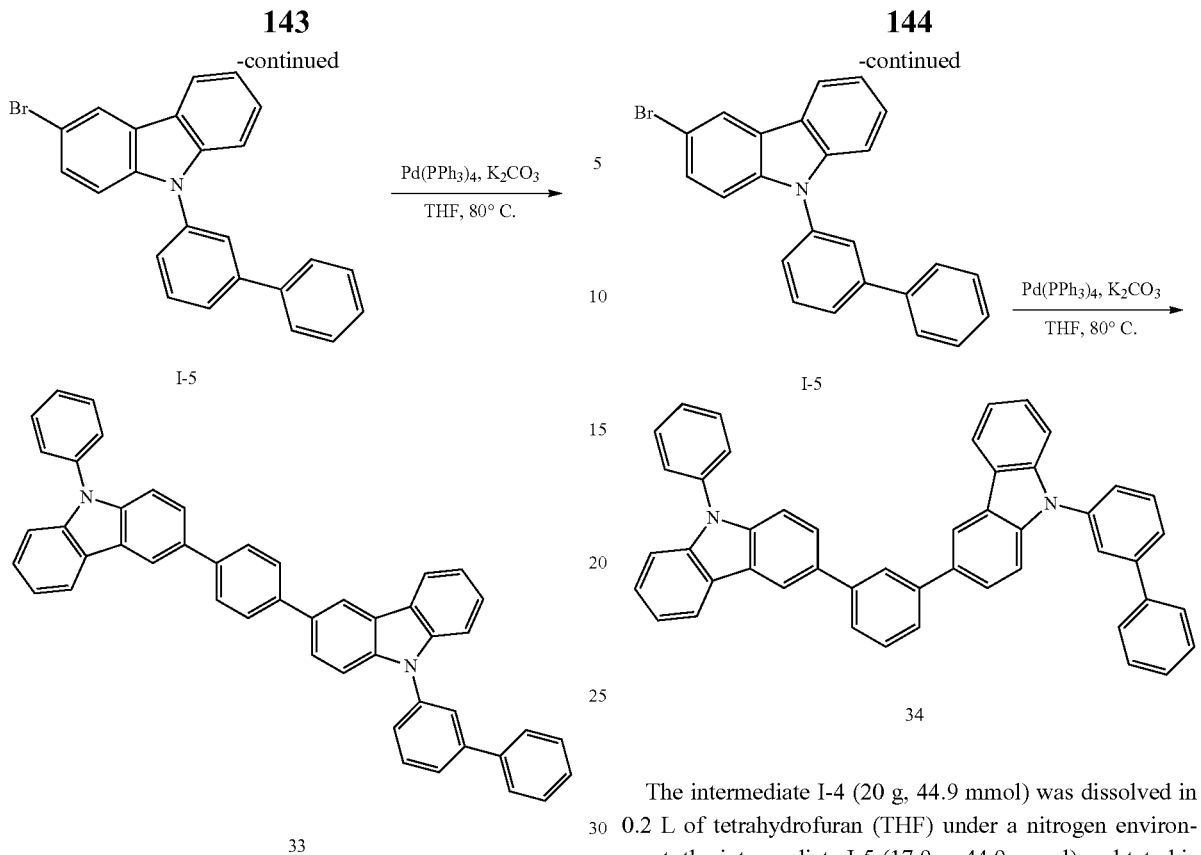

The intermediate I-2 (20 g, 44.9 mmol) was dissolved in 0.2 L of tetrahydrofuran (THF) under a nitrogen environment, the intermediate I-5 (17.9 g, 44.9 mmol) and tetrakis (triphenylphosphine)palladium (0.52 g, 0.45 mmol) were added thereto, and the mixture was stirred. Potassium carbonate (16.5 g, 112 mmol) saturated in water was added thereto, and the obtained mixture was heated and refluxed at 80° C. for 18 hours. When the reaction was completed, water was added to the reaction solution, dichloromethane (DCM) was used for an extraction, and an extract therefrom was filtered after removing moisture with anhydrous MgSO₄ and then, concentrated under a reduced pressure. The obtained residue was separated and purified through flash column chromatography to obtain Compound II-33 (24.6 g, 86%) of Chemical Formula II.

HRMS (70 eV, El+): m/z calcd for C48H32N2: 636.2565, found: 636.

Elemental Analysis: C, 91%; H, 5%

Synthesis Example 12: Synthesis of Compound 34 of Chemical Formula II

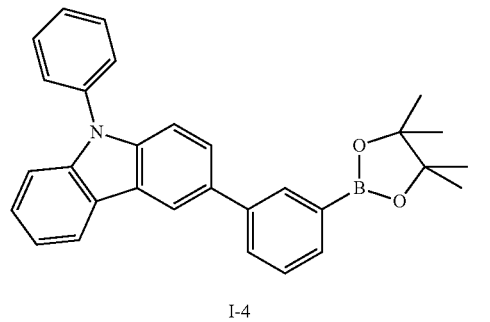

The intermediate I-4 (20 g, 44.9 mmol) was dissolved in 0.2 L of tetrahydrofuran (THF) under a nitrogen environment, the intermediate I-5 (17.9 g, 44.9 mmol) and tetrakis (triphenylphosphine)palladium (0.52 g, 0.45 mmol) were added thereto, and the mixture was stirred. Potassium carbonate (16.5 g, 112 mmol) saturated in water was added thereto, and the mixture was heated and refluxed at 80° C. for 18 hours. When the reaction was completed, water was added to the reaction solution, dichloromethane (DCM) was used for an extraction, and an extract therefrom was filtered after removing moisture with anhydrous MgSO₄ and then, concentrated under a reduced pressure. The obtained residue was separated and purified through flash column chromatography to obtain Compound 34 (25.7 g, 90%) of Chemical Formula II.

HRMS (70 eV, El+): m/z calcd for C42H32N2: 636.2565, found: 636.

Elemental Analysis: C, 91%; H, 5%

Synthesis Example 13: Synthesis of Compound HT-1 of Chemical Formula II

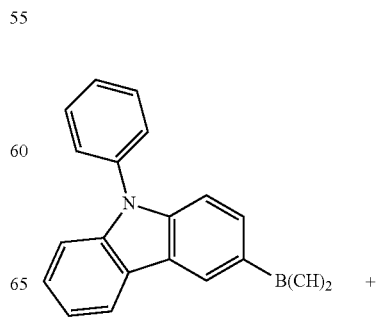

-continued

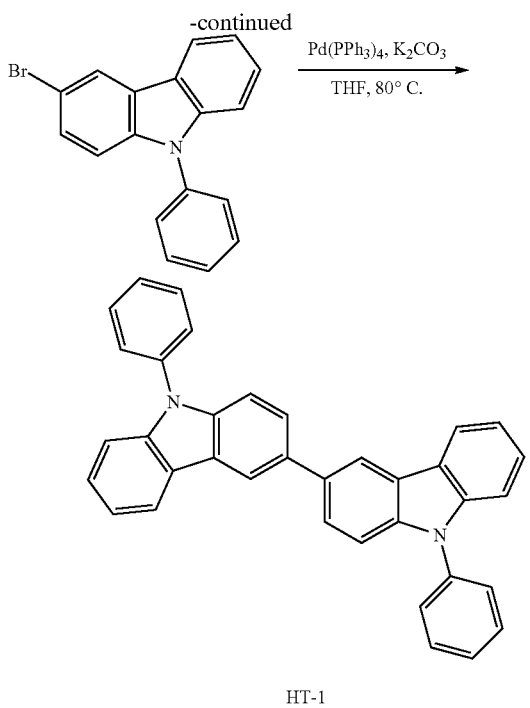

HT-1

9-phenyl-9H-carbazol-3-ylboronic acid (20 g, 69.7 mmol) was dissolved in 0.2 L of tetrahydrofuran (THF), 3-bromo-9-phenyl-9H-carbazole (22.4 g, 69.7 mmol) and tetrakis(triphenylphosphine)palladium (0.81 g, 0.70 mmol) were added thereto, and the mixture was stirred. Potassium carbonate (25.7 g, 174 mmol) saturated in water was added thereto, and the obtained mixture was heated and refluxed at 80° C. for 16 hours. When the reaction was completed, water was added to the reaction solution, dichloromethane (DCM) was used for an extraction, and an extract therefrom was filtered after removing moisture with anhydrous $MgSO_4$ and then, concentrated under a reduced pressure. The obtained residue was separated and purified through flash column chromatography to obtain Compound HT-1 (28.7 g, 85%) of Chemical Formula II.

HRMS (70 eV, El+): m/z calcd for $C_{36}H_{24}N_2$: 484.1939, found: 484.

Elemental Analysis: C, 89%; H, 5%

(Energy Level Using Gaussian Tool)

An energy level of each material was measured in a B3LYP/6-31G** method by using a program Gaussian 09 with a super computer, GAIA (IBM power 6), and the results are shown in Table 1.

TABLE 1

| Material | HOMO (eV) | LUMO (eV) |
|---|---|---|
| Compound I-4 | −4.77 | −0.87 |
| Compound I-9 | −4.70 | −0.91 |
| Compound I-27 | −4.75 | −1.10 |
| Compound II-1 | −5.04 | −0.77 |
| Compound II-2 | −5.17 | −0.73 |
| Compound II-33 | −5.04 | −0.98 |
| Compound II-34 | −5.17 | −0.97 |

According to the results, Compound II-1, Compounds II-2, II-33, and II-34 had a lower HOMO energy level than Compounds I-4, I-9, and I-27. Thereby, hole injection and flow are made more easily to realize a device having a lower driving voltage, high efficiency, and a long life-span.

(Manufacture of Organic Light Emitting Diode)

Example 1: Manufacture of Organic Light Emitting Diode (Blue Auxiliary Layer)

ITO (indium tin oxide) was coated to be 1500 Å thick on a glass substrate, and the coated glass was ultrasonic wave-washed with a distilled water. Subsequently, the glass substrate was ultrasonic wave-washed with a solvent such as isopropyl alcohol, acetone, methanol, and the like, moved to a plasma cleaner, cleaned by using oxygen plasma for 5 minutes, and then, moved to a vacuum depositor. This ITO transparent electrode was used as an anode, a 600 Å-thick hole injection layer was formed thereon by vacuum-depositing 4,4'-bis[N-[4-{N,N-bis(3-methylphenyl)amino}-phenyl]-N-phenylamino]biphenyl (DNTPD). Subsequently, Compound 4 of Chemical Formula I synthesized in Synthesis Example 2 was vacuum-deposited to form a hole transport layer having a 250 Å thickness. Compound 1 of Chemical Formula II synthesized in Synthesis Example 9 was vacuum-deposited to form an auxiliary layer having a 50 Å thickness of a hole transport layer. On the hole transport layer, a 250 Å-thick light-emitting layer was formed by vacuum-depositing 9,10-di-(2-naphthyl)anthracene (ADN) as a host and 3 wt % of 2,5,8,11-tetra(tert-butyl)perylene (TBPe) as a dopant. On the light-emitting layer, Alq3 was vacuum-deposited to form an electron transport layer having a thickness of 250 Å. A cathode was formed by sequentially vacuum-depositing Liq to be 10 Å thick and Al to be 1000 Å thick on the electron transport layer to manufacture an organic light emitting diode.

The organic light emitting diode had a five-layered organic thin film structure and specifically, Al (1000 Å)/LiF (10 Å)/Alq3 (250 Å)/EML [ADN:TBPe=97:3] (250 Å)/hole transport auxiliary layer (50 Å)/hole transport layer (250 Å)/DNTPD (600 Å)/ITO (1500 Å).

Example 2

An organic light emitting diode was manufactured according to the same method as Example 1 except for using Compound 2 of Chemical Formula II synthesized in Synthesis Example 10 instead of Compound 1 synthesized in Synthesis Example 9 for the hole transport auxiliary layer.

Example 3

An organic light emitting diode was manufactured according to the same method as Example 1 except for using Compound 33 of Chemical Formula II synthesized in Synthesis Example 11 instead of Compound 1 synthesized in Synthesis Example 9 for the hole transport auxiliary layer.

Example 4

An organic light emitting diode was manufactured according to the same method as Example 1 except for using Compound 34 of Chemical Formula II synthesized in Synthesis Example 12 instead of Compound 1 synthesized in Synthesis Example 9 for the hole transport auxiliary layer.

Example 5

An organic light emitting diode was manufactured according to the same method as Example 3 except for using Compound 9 of Chemical Formula I synthesized in Synthesis Example 3 instead of Compound 4 synthesized in Synthesis Example 2 for the hole transport layer.

Example 6

An organic light emitting diode was manufactured according to the same method as Example 3 except for using Compound 27 of Chemical Formula I synthesized in Synthesis Example 4 instead of Compound 4 synthesized in Synthesis Example 2 for the hole transport layer.

Comparative Example 1

An organic light emitting diode was manufactured according to the same method as Example 1 except for using Compound HT-1 of Chemical Formula II synthesized in Synthesis Example 13 instead of Compound 1 synthesized in Synthesis Example 9 for the hole transport auxiliary layer.

Comparative Example 2

An organic light emitting diode was manufactured according to the same method as Comparative Example 1 except for using Compound 9 of Chemical Formula I synthesized in Synthesis Example 3 instead of Compound 4 synthesized in Synthesis Example 2 for the hole transport layer.

Comparative Example 3

An organic light emitting diode was manufactured according to the same method as Comparative Example 1 except for using Compound 27 of Chemical Formula I synthesized in Synthesis Example 4 instead of Compound 4 synthesized in Synthesis Example 2 for the hole transport layer.

Comparative Example 4

An organic light emitting diode was manufactured according to the same method as Example 1 except for using Compound 4 of Chemical Formula I synthesized in Synthesis Example 2 instead of Compound 1 of Chemical Formula II synthesized in Synthesis Example 9 for the hole transport auxiliary layer.

Comparative Example 5

An organic light emitting diode was manufactured according to the same method as Example 5 except for using Compound 9 of Chemical Formula I synthesized in Synthesis Example 3 instead of Compound 33 of Chemical Formula II synthesized in Synthesis Example 11 for the hole transport auxiliary layer.

Comparative Example 6

An organic light emitting diode was manufactured according to the same method as Example 6 except for using Compound 27 of Chemical Formula I synthesized in Synthesis Example 4 instead of Compound 33 of Chemical Formula II synthesized in Synthesis Example 11 for the hole transport auxiliary layer.

Comparative Example 7

An organic light emitting diode was manufactured according to the same method as Example 1 except for using Compound 1 of Chemical Formula II synthesized in Synthesis Example 9 instead of Compound 4 of Chemical Formula I synthesized in Synthesis Example 2 for the hole transport layer.

Comparative Example 8

An organic light emitting diode was manufactured according to the same method as Example 2 except for using Compound 2 of Chemical Formula II synthesized in Synthesis Example 10 instead of Compound 4 of Chemical Formula I synthesized in Synthesis Example 2 for the hole transport layer.

Comparative Example 9

An organic light emitting diode was manufactured according to the same method as Example 3 except for using Compound 33 of Chemical Formula II synthesized in Synthesis Example 11 instead of Compound 4 of Chemical Formula I synthesized in Synthesis Example 2 for the hole transport layer.

Comparative Example 10

An organic light emitting diode was manufactured according to the same method as Example 4 except for using Compound 34 of Chemical Formula II synthesized in Synthesis Example 12 instead of Compound 4 of Chemical Formula I synthesized in Synthesis Example 2 for the hole transport layer.

DNTPD, ADN, NPB, and TBPe used to manufacture the organic light emitting diode have the following structures.

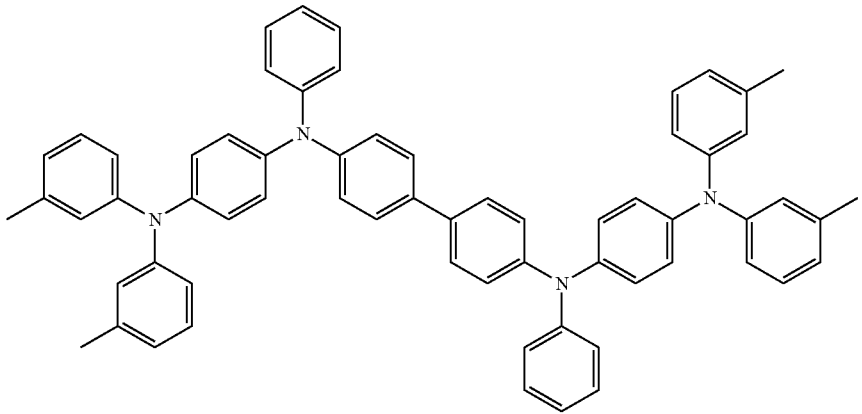

[DNTPD]

-continued

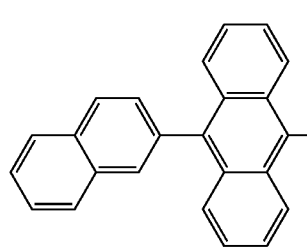
[ADN]

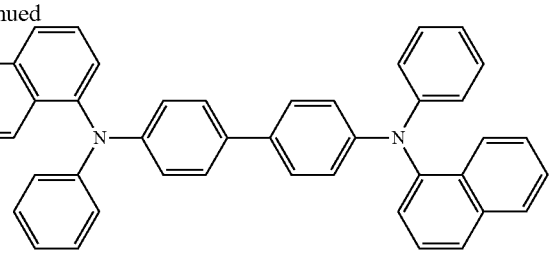
[NPB]

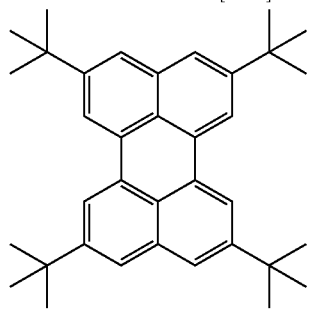
[TBPe]

(Performance Measurement of Organic Light Emitting Diode)

Current density and luminance changes depending on a voltage and luminous efficiency of each organic light emitting diode according to Examples 1 to 6 and Comparative Examples 1 to 10 were measured. The measurements were specifically performed in the following methods, and the results are shown in Table 2.

(1) Measurement of Current Density Change Depending on Voltage Change

Current values flowing in the unit devices of the obtained organic light emitting diodes were measured by using a current-voltage meter (Keithley 2400), while the voltage was increased from 0 V to 10 V, and the measured current value was divided by area to provide results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltage from the items (1) and (2).

(4) Measurement of Life-Span

A life-span was obtained by using 1000 cd/m$^2$ of initial luminance of an organic light emitting diode, measuring its luminance decrease as time goes, and measuring a time taken until the luminance decreased by 50% relative to the initial luminance.

TABLE 2

| Devices | Compounds used in hole transport layer | Compound used in hole transport auxiliary layer | Voltage (V) | Color (EL color) | Efficiency (cd/A) | 50% life-span (h) at 1000 cd/m$^2$ |
|---|---|---|---|---|---|---|
| Example 1 | Compound 4 of Chemical Formula I | Compound 1 of Chemical Formula II | 6.3 | Blue | 7.1 | 1,400 |
| Example 2 | Compound 4 of Chemical Formula I | Compound 2 of Chemical Formula II | 6.5 | Blue | 7.6 | 1,380 |
| Example 3 | Compound 4 of Chemical Formula I | Compound 33 of Chemical Formula II | 6.4 | Blue | 7.3 | 1,490 |
| Example 4 | Compound 4 of Chemical Formula I | Compound 34 of Chemical Formula II | 6.6 | Blue | 7.7 | 1,450 |
| Example 5 | Compound 9 of Chemical Formula I | Compound 33 of Chemical Formula II | 6.2 | Blue | 7.5 | 1,500 |

TABLE 2-continued

| Devices | Compounds used in hole transport layer | Compound used in hole transport auxiliary layer | Voltage (V) | Color (EL color) | Efficiency (cd/A) | 50% life-span (h) at 1000 cd/m² |
|---|---|---|---|---|---|---|
| Example 6 | Compound 27 of Chemical Formula I | Compound 33 of Chemical Formula II | 6.5 | Blue | 7.6 | 1,650 |
| Comparative Example 1 | Compound 4 of Chemical Formula I | HT-1 | 7.0 | Blue | 6.3 | 710 |
| Comparative Example 2 | Compound 9 of Chemical Formula I | HT-1 | 6.8 | Blue | 6.5 | 690 |
| Comparative Example 3 | Compound 27 of Chemical Formula I | HT-1 | 6.8 | Blue | 6.5 | 850 |
| Comparative Example 4 | Compound 4 of Chemical Formula I | Compound 4 of Chemical FormulaI | 6.6 | Blue | 5.7 | 1,340 |
| Comparative Example 5 | Compound 9 of Chemical Formula I | Compound 9 of Chemical FormulaI | 6.3 | Blue | 6.1 | 1,450 |
| Comparative Example 6 | Compound 27 of Chemical Formula I | Compound 27 of Chemical FormulaI | 6.5 | Blue | 6.0 | 1,500 |
| Comparative Example 7 | Compound 1 of Chemical Formula II | Compound 1 of Chemical Formula II | 6.9 | Blue | 6.7 | 910 |
| Comparative Example 8 | Compound 2 of Chemical Formula II | Compound 2 of Chemical Formula II | 7.1 | Blue | 7.1 | 900 |
| Comparative Example 9 | Compound 33 of Chemical Formula II | Compound 33 of Chemical Formula II | 6.7 | Blue | 6.9 | 1,010 |
| Comparative Example 10 | Compound 34 of Chemical Formula II | Compound 34 of Chemical Formula II | 6.9 | Blue | 7.2 | 980 |

Referring to the results of Table 2, Examples 1 to 6 realized a lower driving voltage, higher efficiency, and a longer life-span than Comparative Examples 1 to 10. Specifically, Comparative Examples 4, 5, and 6 using both a hole transport layer and a hole transport auxiliary layer only formed of Compound I realized a long life-span but greater than or equal to 20% lower efficiency than Examples 1 to 6.

Examples 1 to 6 realized relatively very high efficiency, considering that it is difficult to greater than or equal to 10% of increase efficiency of a blue fluorescent device. In addition, Comparative Examples 1, 2, and 3 using a hole transport auxiliary layer using bicarbazole having no phenyl linker among themselves realized high efficiency but a very low life-span. The reason is that the bicarbazole had an inherent problem of being rigid and not uniformly deposited, but Comparative Examples 7 to 10 used a hole transport layer and a hole transport auxiliary layer formed of a material having no above problem and thus realized a high life-span compared with Comparative Examples 1 to 3. Furthermore, this material (used in Comparative Examples 7 to 10) was used with Compound represented by Chemical Formula I having a high life-span and thus effectively realized a low driving voltage, high efficiency, and a long life-span like Examples 1 to 6.

Accordingly, an organic light emitting diode having a low voltage, high efficiency, high luminance, and a long life-span based on excellent hole injection and hole transfer capability may be provided.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:
1. An organic optoelectric device, comprising
an anode and a cathode facing each other,
a light-emitting layer disposed between the anode and cathode,
a hole transport layer disposed between the anode and the light-emitting layer, and an auxiliary hole transport layer disposed between the hole transport layer and the light-emitting layer, wherein the hole transport layer includes a compound represented by Chemical Formula I, and the hole transport auxiliary layer includes a compound represented by Chemical Formula II:

[Chemical Formula I]

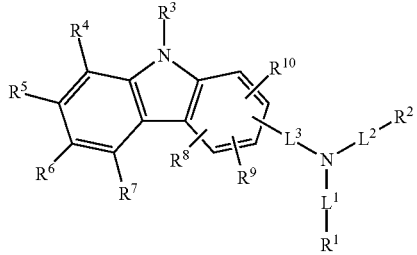

wherein, in Chemical Formula 1, $R^1$ to $R^3$ are independently a substituted or unsubstituted C6 to C30 aryl group, a substituted or unsubstituted C2 to C30 heterocyclic group, or a combination thereof, $R^4$ to $R^{10}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, adjacent two of $R^4$ to $R^{10}$ are fused to provide a ring, and $L^1$ to $L^3$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 heteroarylene group, a substituted or unsubstituted C2 to C30 alkenylene group, a substituted or unsubstituted C2 to C30 alkynylene group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group,

[Chemical Formula II]

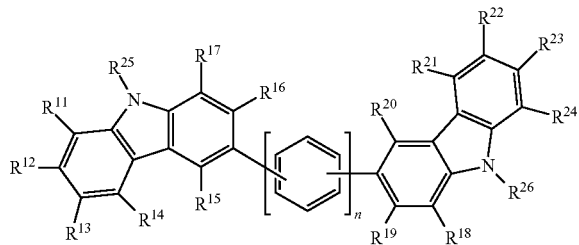

wherein, in Chemical Formula II, $R^{11}$ to $R^{24}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, adjacent two of $R^{11}$ to $R^{17}$ and $R^{18}$ to $R^{24}$ are fused to provide a ring, $R^{25}$ and $R^{26}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, and n is an integer ranging from 1 to 4, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

2. The organic optoelectric device of claim 1, wherein the compound represented by Chemical Formula I is represented by one of Chemical Formula I-1 to Chemical Formula I-5:

[Chemical Formula I-1]

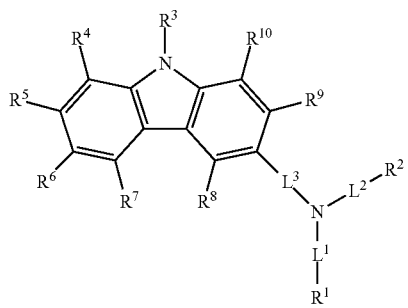

-continued

[Chemical Formula I-2]

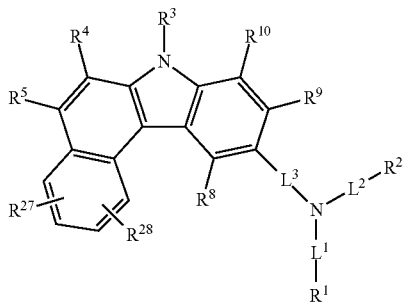

[Chemical Formula I-3]

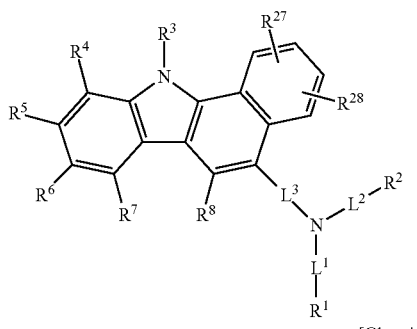

[Chemical Formula I-4]

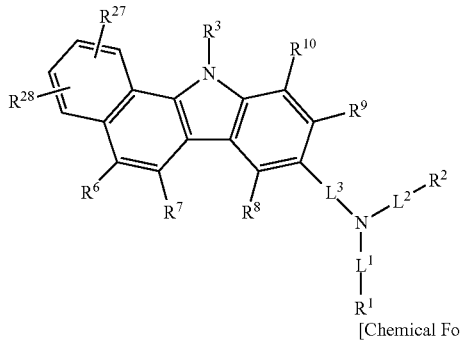

[Chemical Formula I-5]

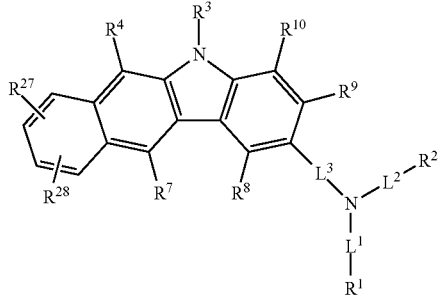

wherein, in Chemical Formula I-1 to Chemical Formula I-5, $R^1$ to $R^3$ are independently a substituted or unsubstituted C6 to C30 aryl group, a substituted or unsubstituted C2 to C30 heterocyclic group, or a combination thereof, $R^4$ to $R^0$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, $L^1$ to $L^3$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 heteroarylene group, a substituted or unsubstituted C6 to C30 aryleneamine group, a substituted or unsubstituted C1 to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof, and $R^{27}$ and $R^{28}$ are independently hydrogen, deuterium, a substituted or unsubstituted C1 to C30 alkyl group, a substituted or unsubstituted C6 to C30 aryl group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

3. The organic optoelectric device of claim 1, wherein the $L^1$ to $L^3$ of Chemical Formula I are independently a single bond or selected from substituted or unsubstituted groups of Group I:

[Group I]

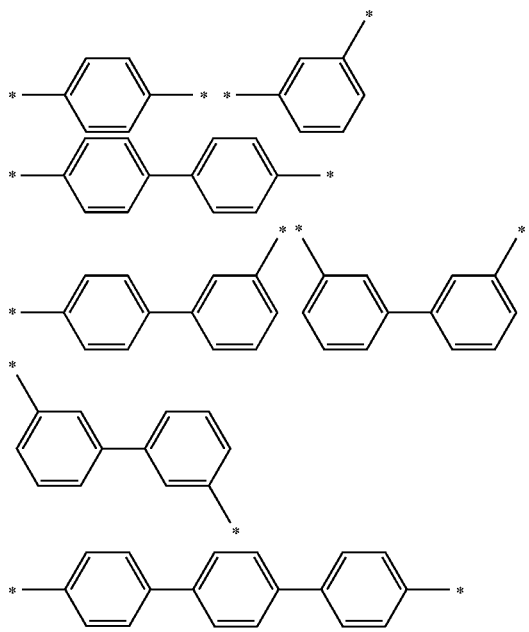

-continued

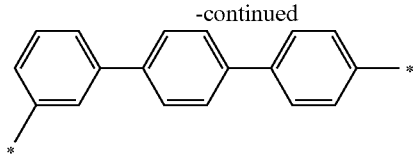
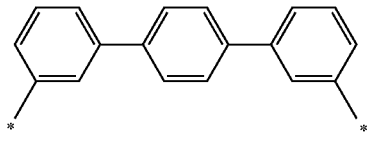
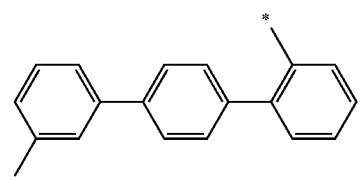
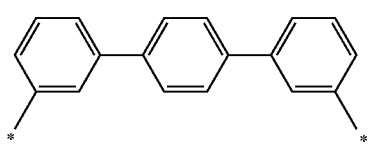
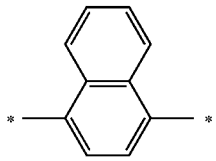
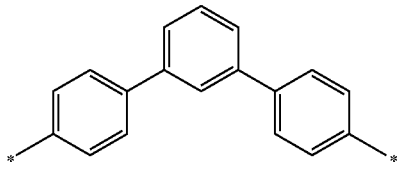
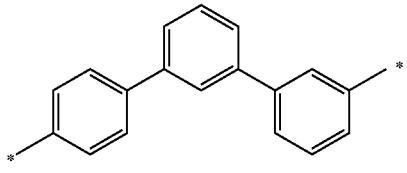
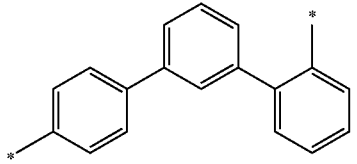
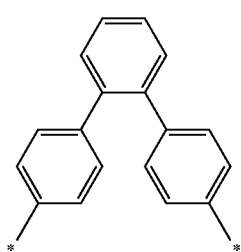

-continued

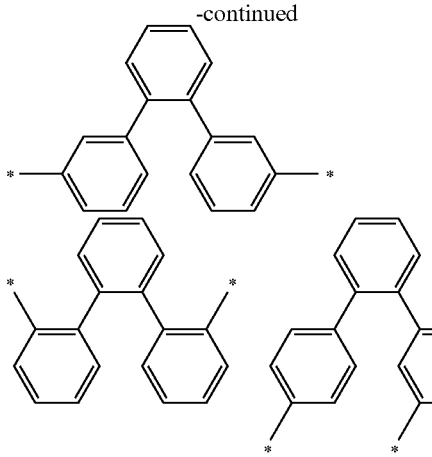
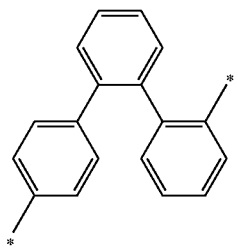
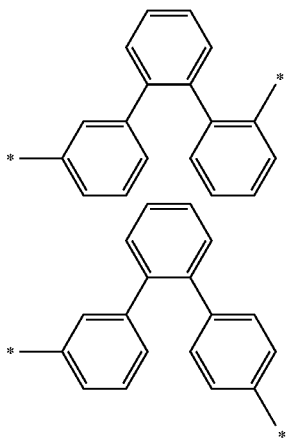
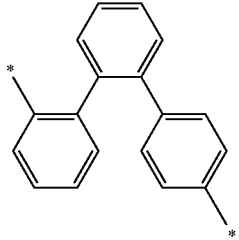

wherein, in Group I,
is a linking point,
wherein "substituted" refers to replacement of at least one hydrogen by deuterium, a halogen, hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

4. The organic optoelectric device of claim 1, wherein the compound represented by Chemical Formula I is represented by Chemical Formula I-6 or Chemical Formula I-7:

[Chemical Formula I-6]

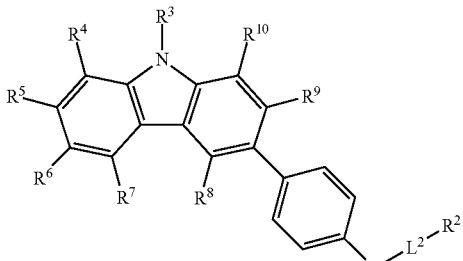

[Chemical Formula I-7]

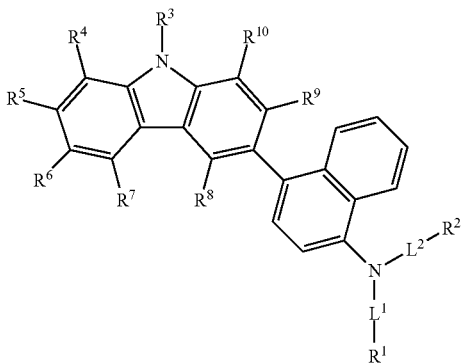

$R^1$ to $R^3$ are independently a substituted or unsubstituted C6 to C30 aryl group, a substituted or unsubstituted C2 to C30 heterocyclic group, or a combination thereof, $R^4$ to $R^{10}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, adjacent two of $R^4$ to $R^{10}$ are fused to provide a ring, and $L^1$ and $L^2$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 heteroarylene group, a substituted or unsubstituted C6 to C30 aryleneamine group, a substituted or unsubstituted C1 to C30 alkoxylene group, a substituted or unsubstituted C1 to C30 aryloxylene group, a substituted or unsubstituted C2 to C30 alkenylene group, a substituted or unsubstituted C2 to C30 alkynylene group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

5. The organic optoelectric device of claim 1, wherein the $R^4$ to $R^{10}$ of Chemical Formula I are independently hydrogen, deuterium, a substituted or unsubstituted C1 to C30 alkyl group, or a substituted or unsubstituted C6 to C30 aryl group.

6. The organic optoelectric device of claim 1, wherein the $R^1$ to $R^3$ of Chemical Formula I are independently a substituted or unsubstituted C6 to C30 aryl group, or a substituted or unsubstituted C2 to C30 heterocyclic group, the substituted or unsubstituted C6 to C30 aryl group, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted fluorenyl group, a substituted or unsubstituted spiro fluorenyl group, a substituted or unsubstituted triphenylene group, a combination thereof, or a fused form thereof, and the substituted or unsubstituted C2 to C30 heterocyclic group is a substituted or unsubstituted carbazolyl group, a substituted or unsubstituted benzofuranyl group, a substituted or unsubstituted benzothiophenyl group, a substituted or unsubstituted dibenzofuranyl group, a substituted or unsubstituted dibenzothiophenyl group, or a combination thereof.

7. The organic optoelectric device of claim 1, wherein $R^1$ to $R^3$ of Chemical Formula I are independently a substituted or unsubstituted C6 to C30 aryl group, or a substituted or unsubstituted C2 to C30 heterocyclic group, and the substituted or unsubstituted C6 to C30 aryl group and the substituted or unsubstituted C2 to C30 heterocyclic group are selected from substituted or unsubstituted groups of Group II:

[Group II]

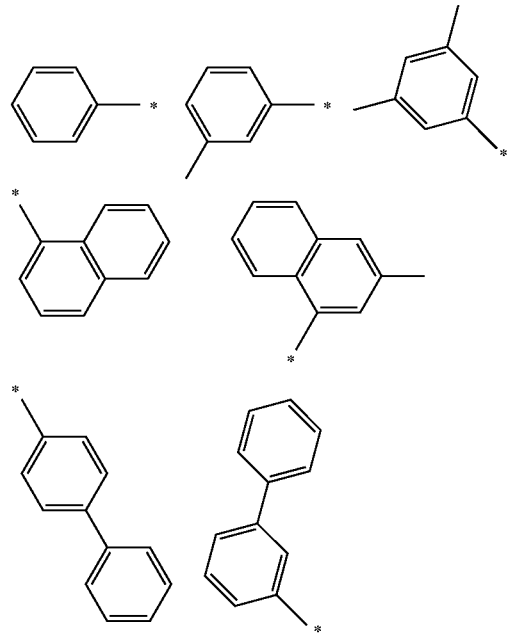

-continued

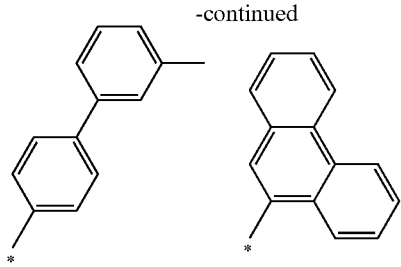

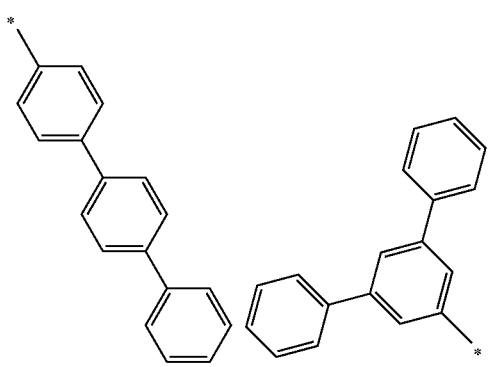

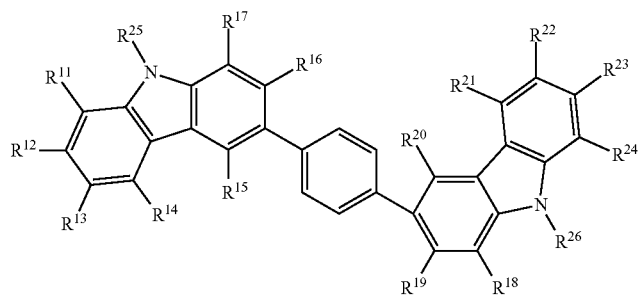

-continued

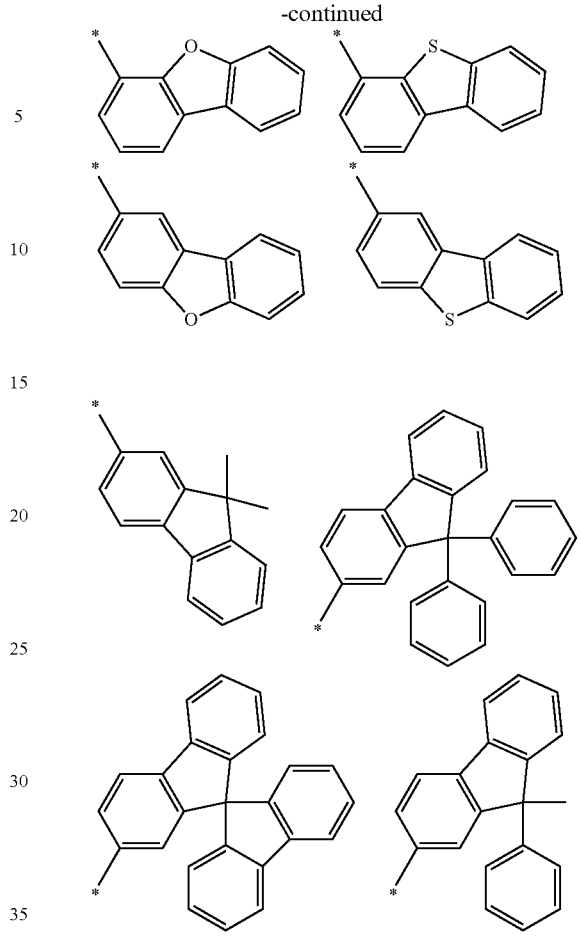

wherein, in Group II,
is a linking point,
wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

8. The organic optoelectric device of claim 1, wherein the compound represented by Chemical Formula II is represented by one of Chemical Formula II-1 to Chemical Formula II-16:

[Chemical Formula II-1]

[Chemical Formula II-2]
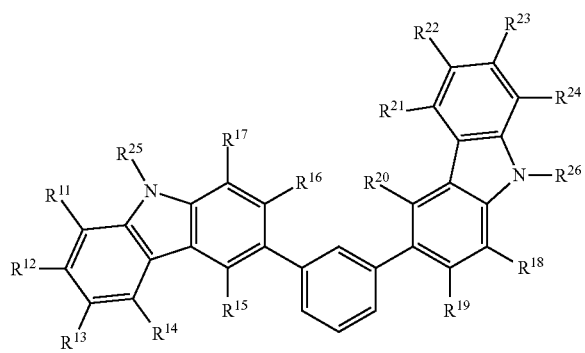
[Chemical Formula II-3]
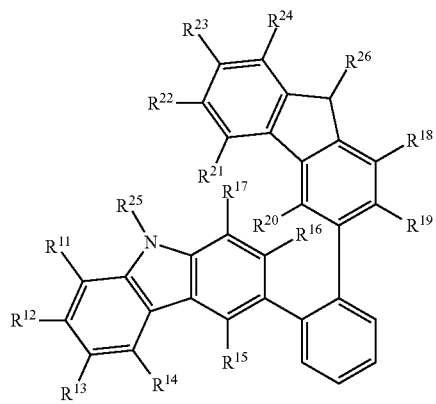
[Chemical Formula II-4]
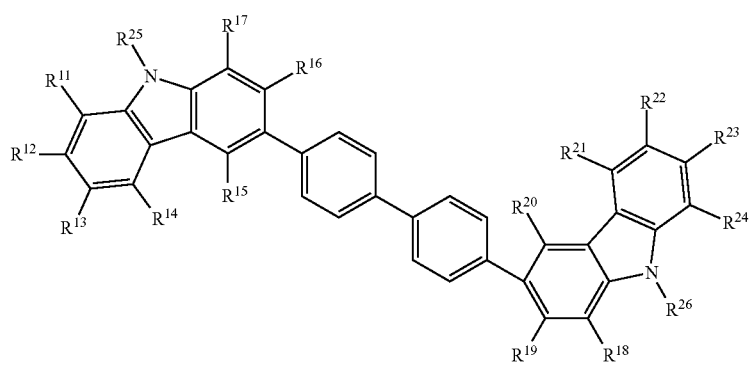
[Chemical Formula II-5]
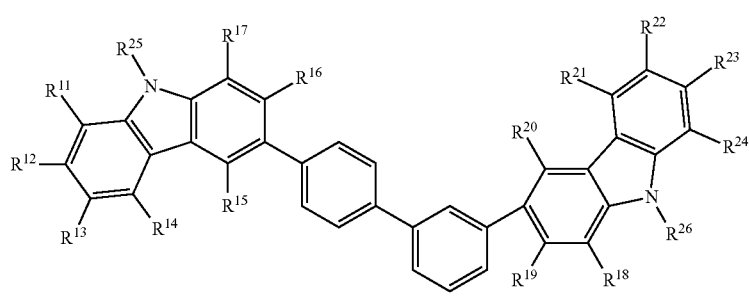

[Chemical Formula II-6]
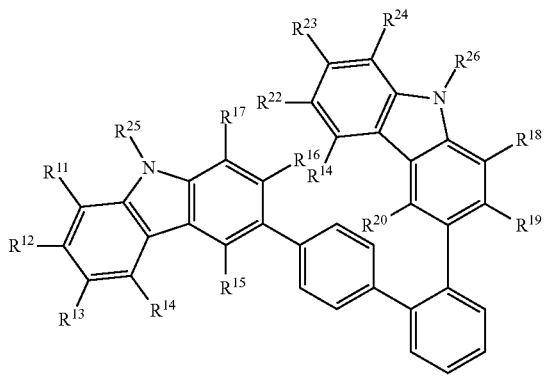
[Chemical Formula II-7]
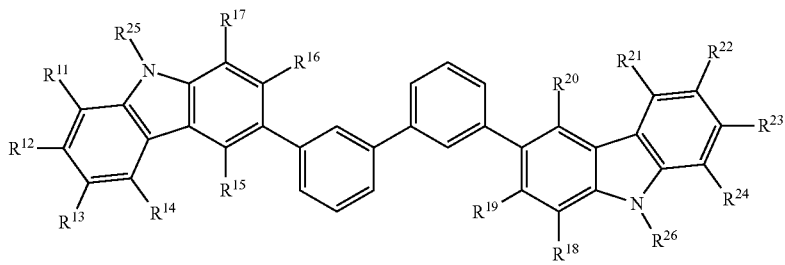
[Chemical Formula II-8]
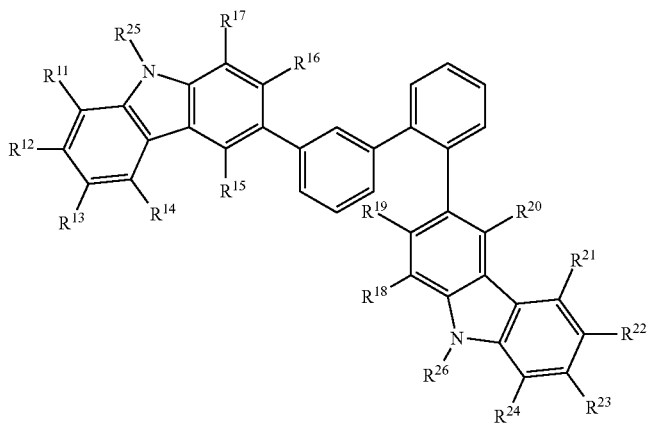
[Chemical Formula II-9]
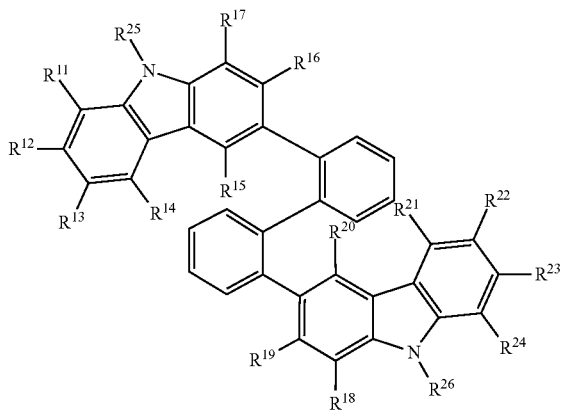

[Chemical Formula II-10]
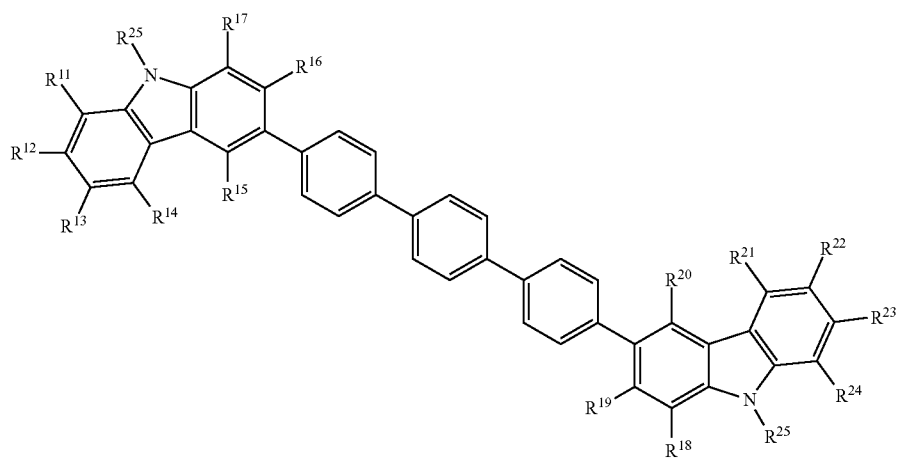
[Chemical Formula II-11]
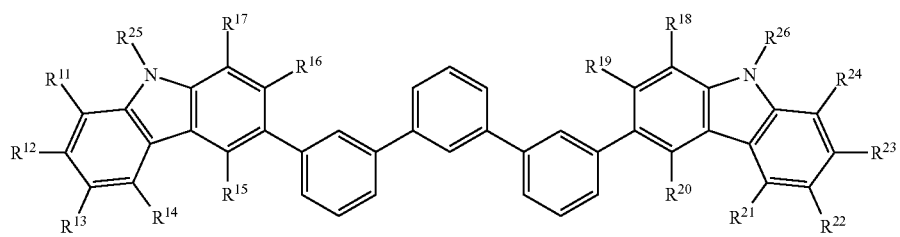
[Chemical Formula II-12]
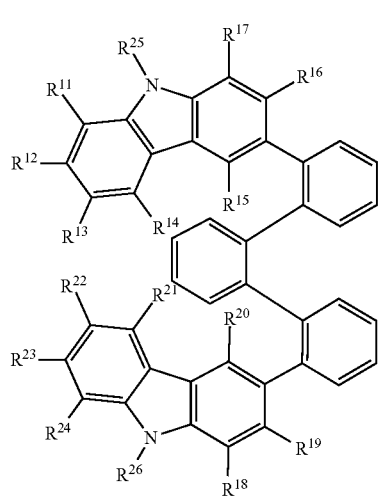

[Chemical Formula II-13]
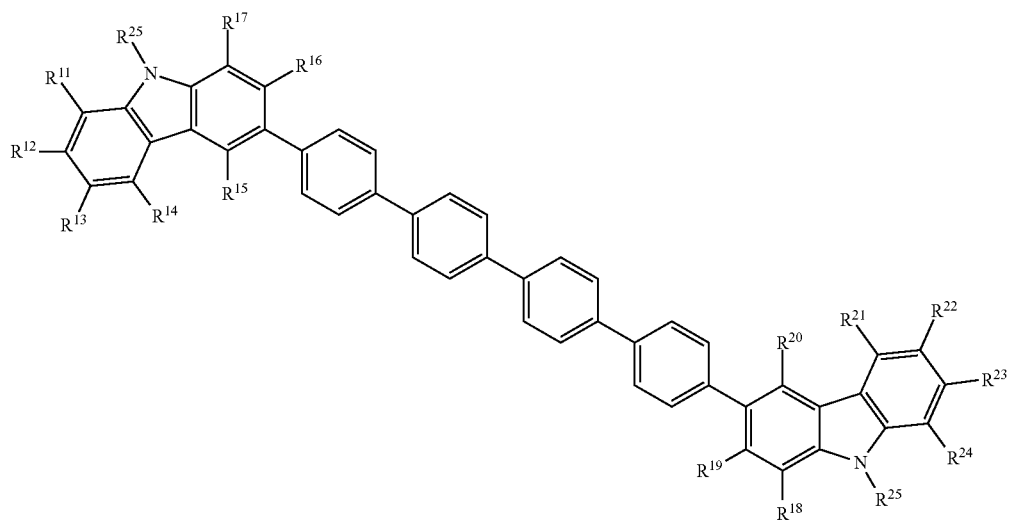
[Chemical Formula II-14]
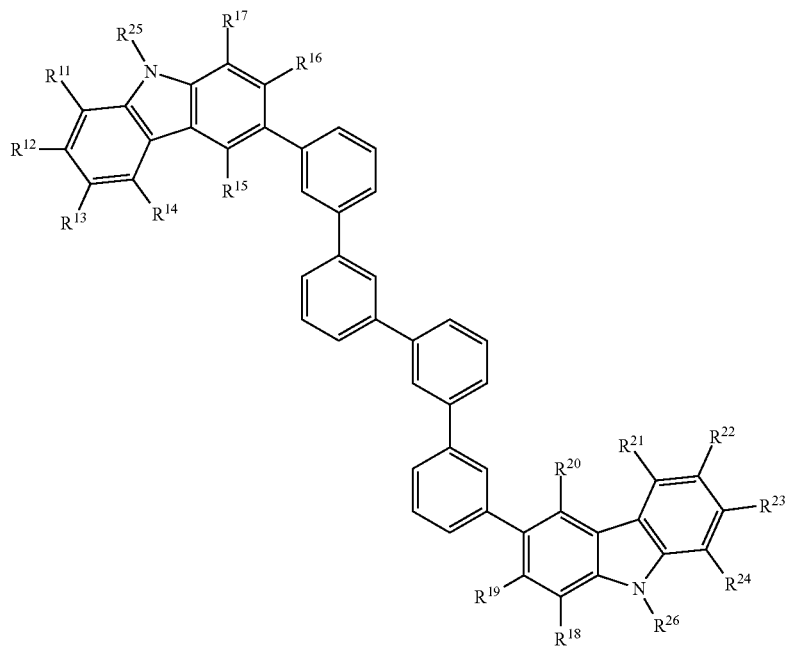

[Chemical Formula II-15]

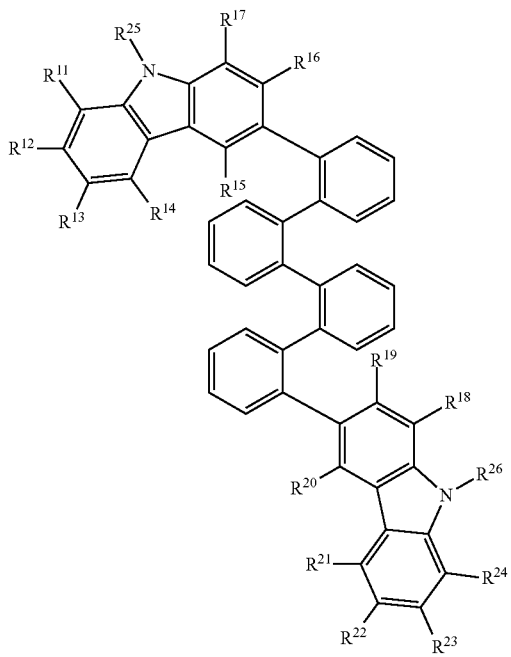

[Chemical Formula II-16]

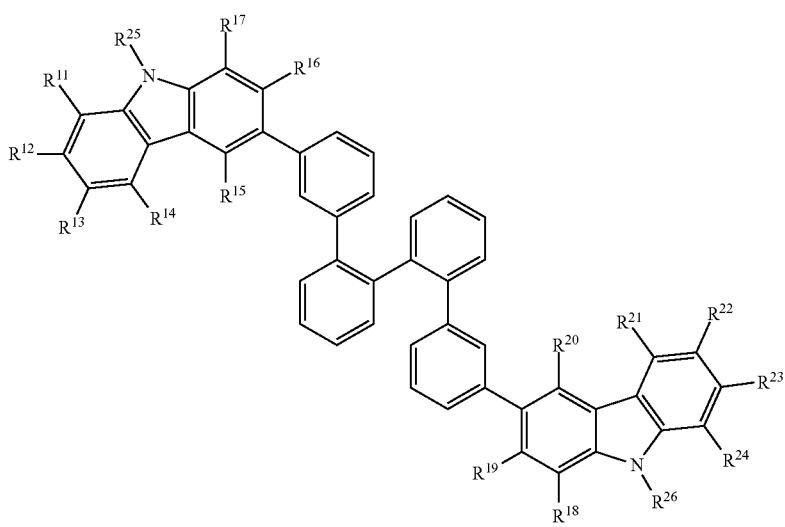

wherein, in Chemical Formula II-1 to Chemical Formula II-16, $R^{11}$ to $R^{24}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, adjacent two of $R^{11}$ to $R^{17}$ and $R^{18}$ to $R^{24}$ are fused to provide a ring, and $R^{25}$ and $R^{26}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

9. The organic optoelectric device of claim 1, wherein $R^{25}$ and $R^{26}$ of Chemical Formula II are independently hydrogen, deuterium, a substituted or unsubstituted C6 to C30 aryl group, or a substituted or unsubstituted C2 to C30 heteroaryl group.

10. The organic optoelectric device of claim 9, wherein:
R$^{25}$ and R$^{26}$ of Chemical Formula II are independently a substituted or unsubstituted C6 to C30 aryl group or a substituted or unsubstituted C2 to C30 heteroaryl group,
the substituted or unsubstituted C6 to C30 aryl group is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted fluorenyl group, a substituted or unsubstituted triphenylene group, or a combination thereof, and
the substituted or unsubstituted C2 to C30 heteroaryl group is a substituted or unsubstituted pyridyl group, a substituted or unsubstituted pyrimidinyl group, a substituted or unsubstituted triazinyl group, or a combination thereof.

11. The organic optoelectric device of claim 9, wherein at least one of R$^{25}$ and R$^{26}$ of Chemical Formula II is a substituted C6 to C30 aryl group or a substituted C2 to C30 heteroaryl group, in which at least one hydrogen of the substituted C6 to C30 aryl group and the substituted C2 to C30 heteroaryl group is replaced by a phenyl group, a biphenyl group, a naphthyl group, a pyridyl group, a pyrimidinyl group, or a triazinyl group.

12. The organic optoelectric device of claim 1, wherein R$^{11}$ to R$^{24}$ of Chemical Formula II are independently hydrogen, deuterium, or a substituted or unsubstituted C6 to C30 aryl group.

13. The organic optoelectric device of claim 1, wherein the compound represented by Chemical Formula I is selected from compounds of Group III:

[Group III]

1

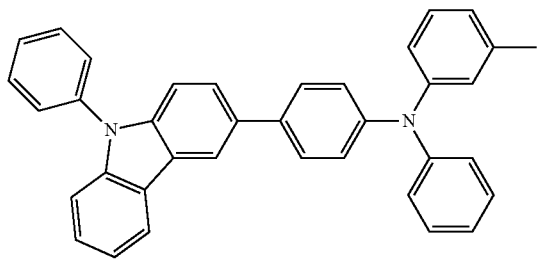

2

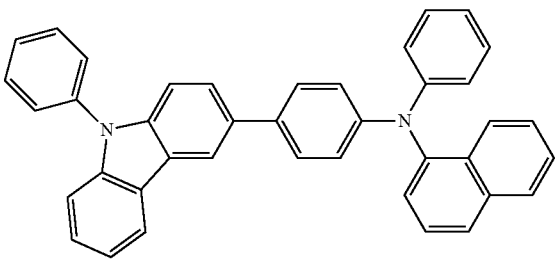

3

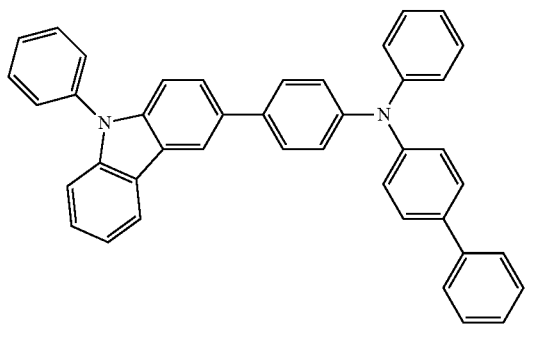

4

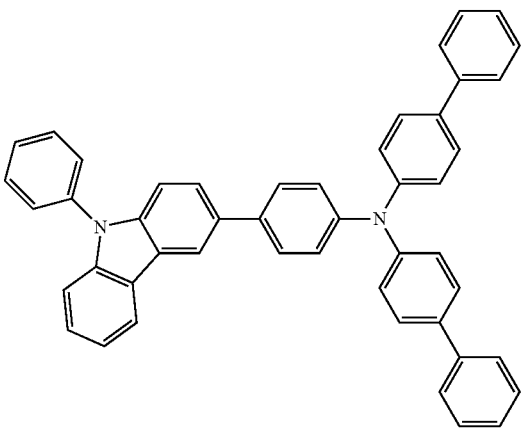

5

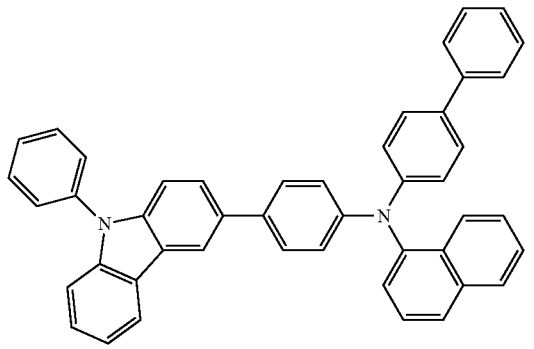

6

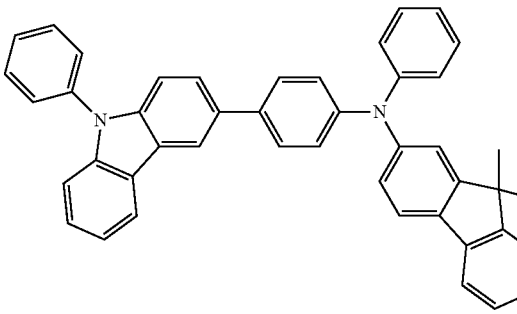

-continued
7
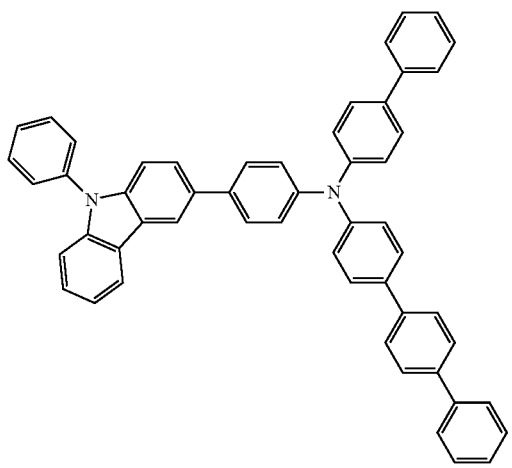
8
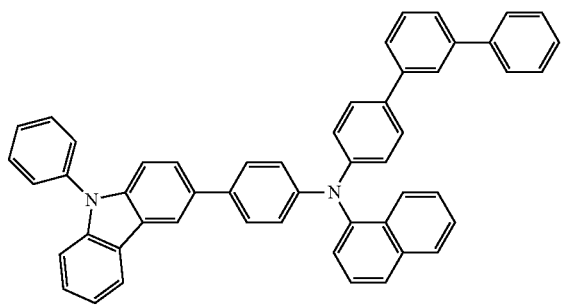
9
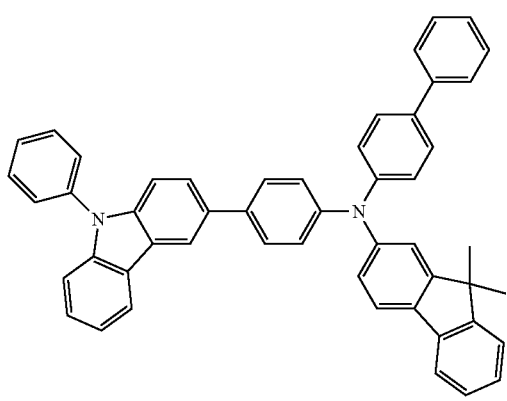
10
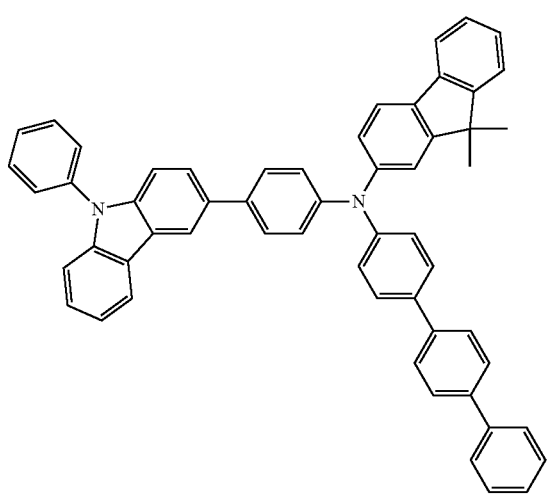
11
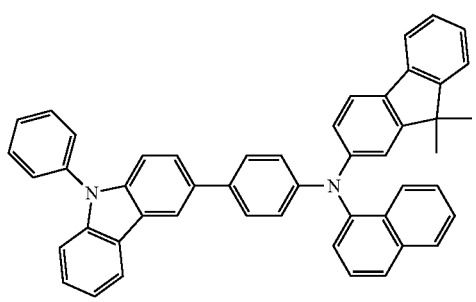
12
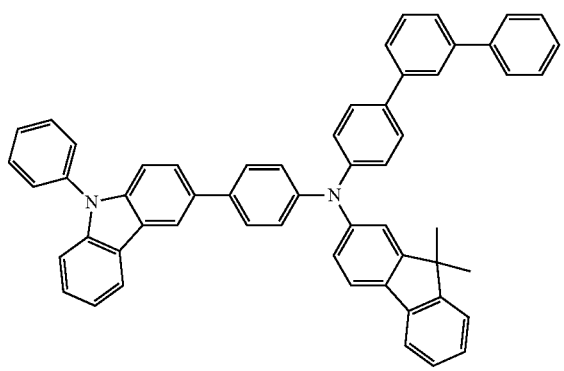

-continued
13
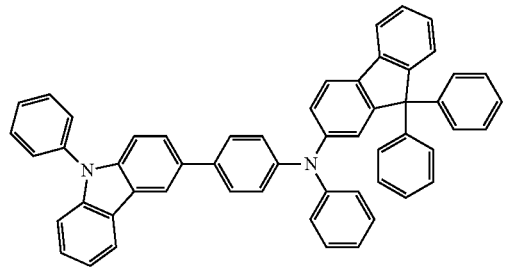
14
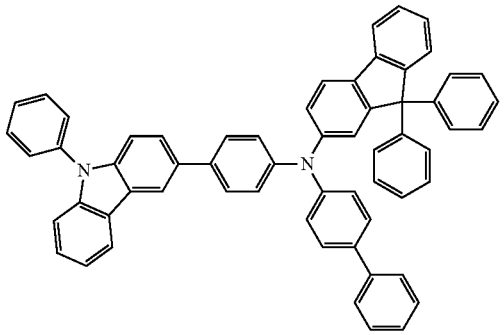
15
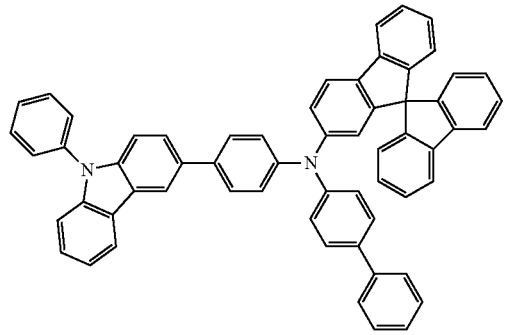
16
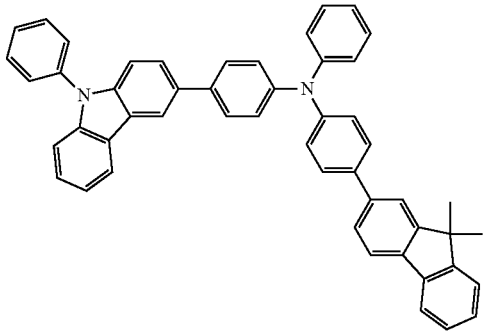
17
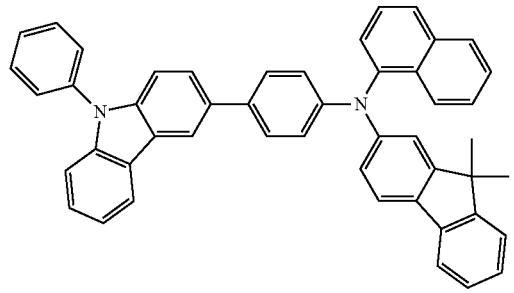
18
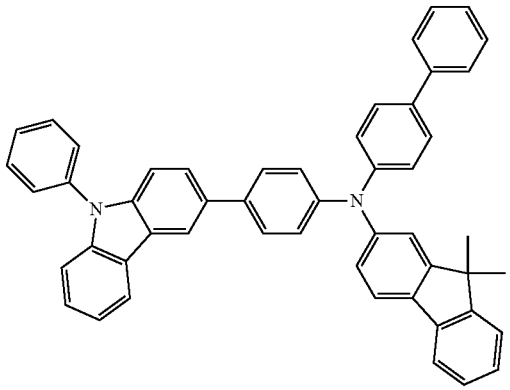
19
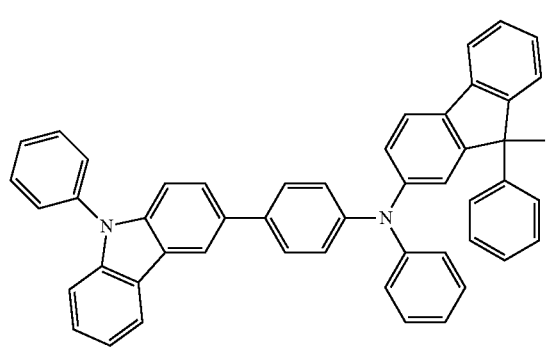
20
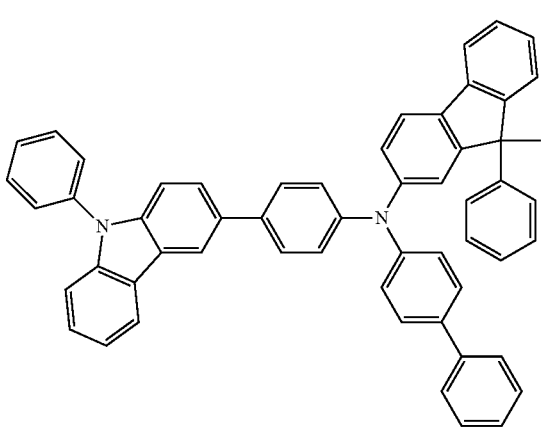

21
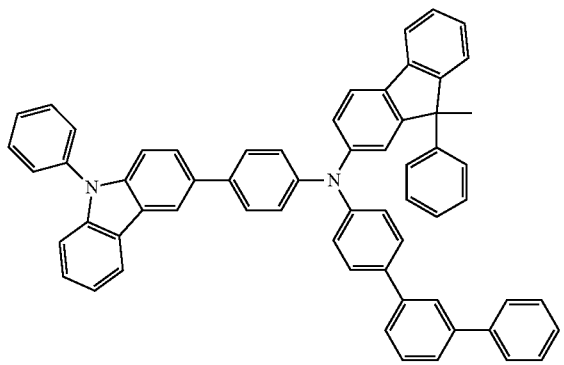
22
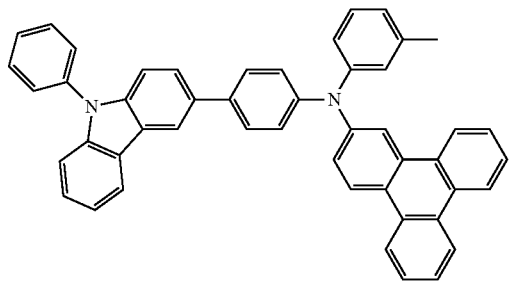
23
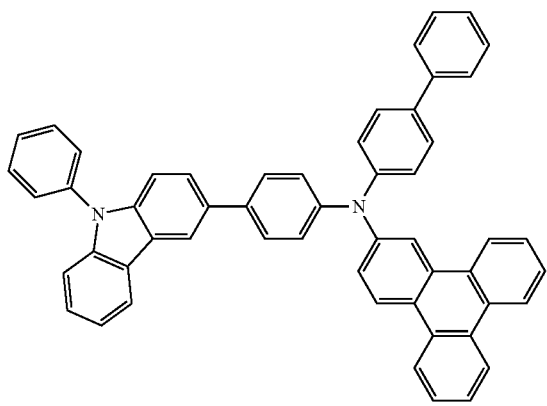
24
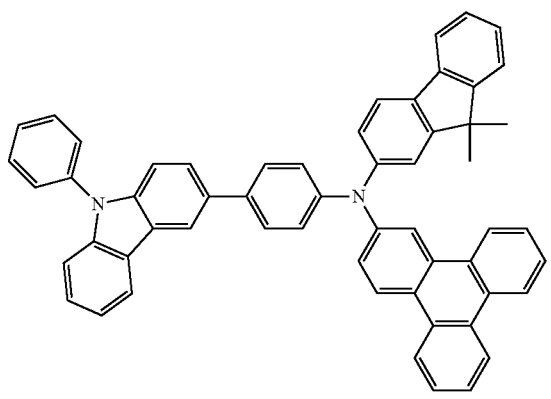
25
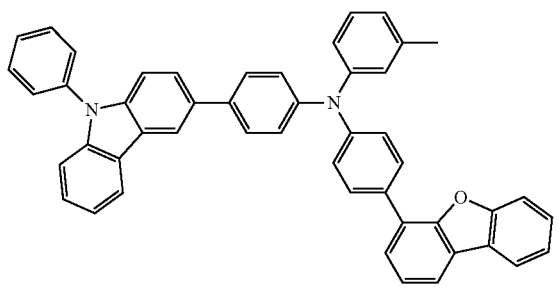
26
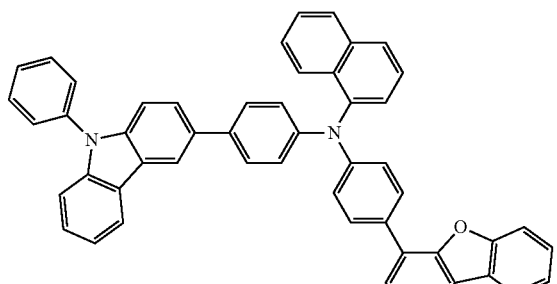
27
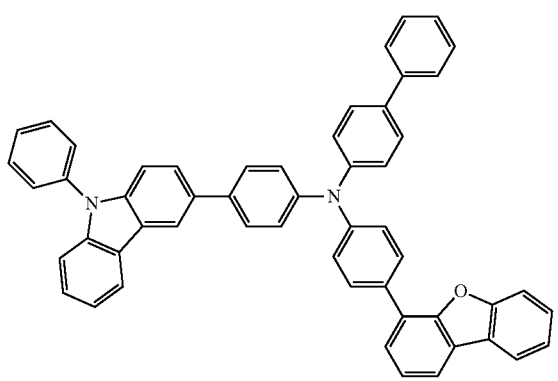
28
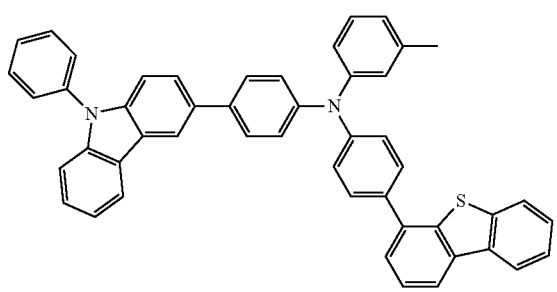

-continued
29
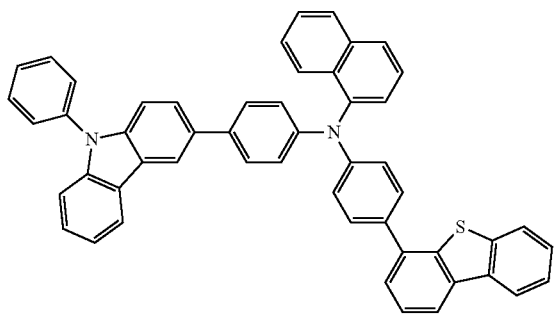
30
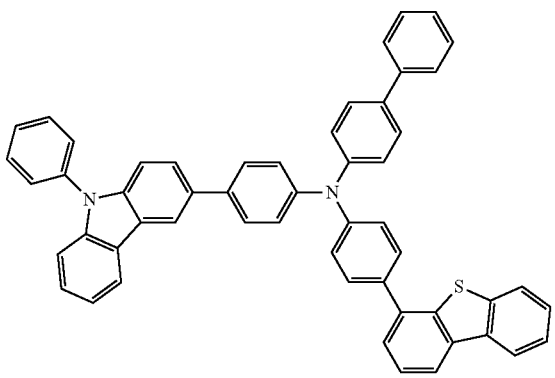
31
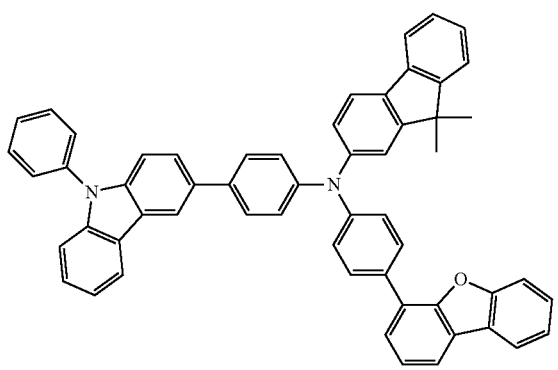
32
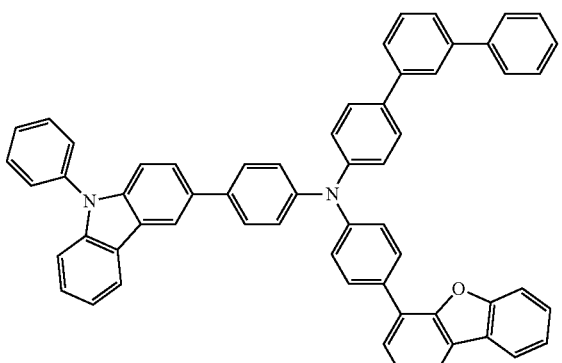
33
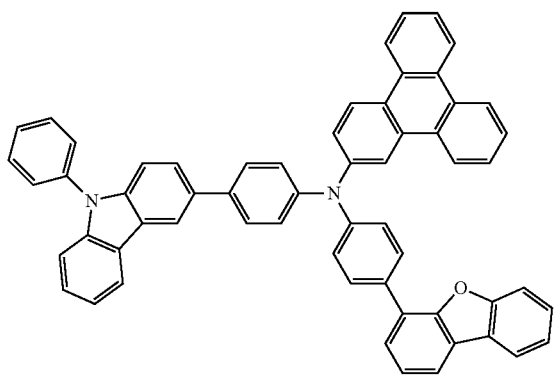
34
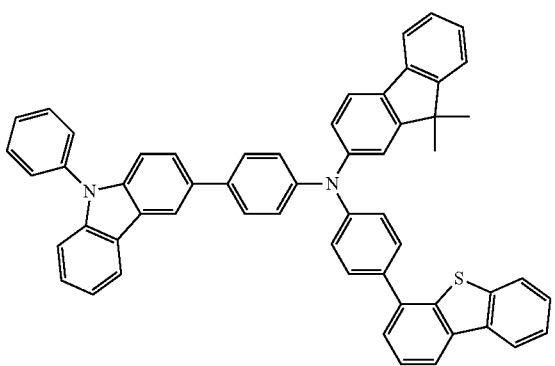
35
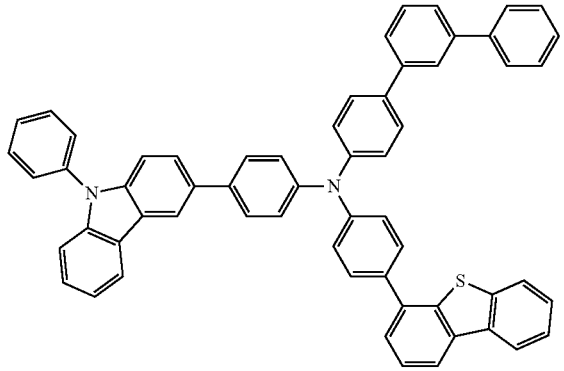
36
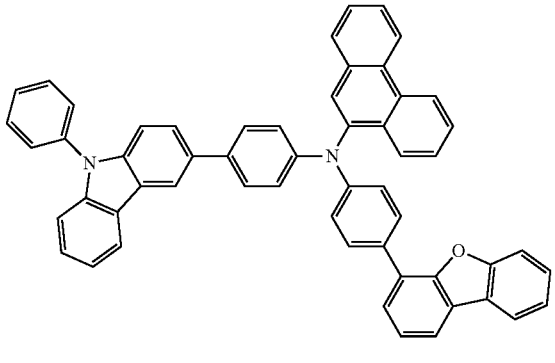

-continued
37
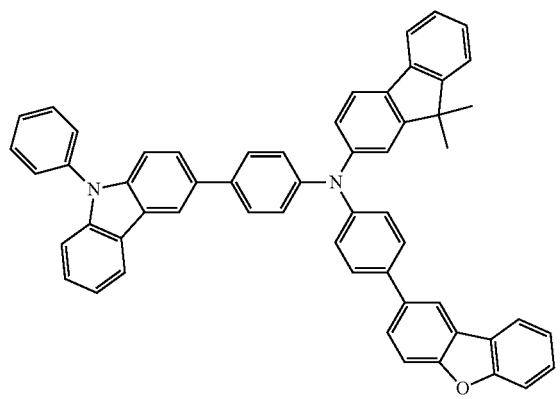
38
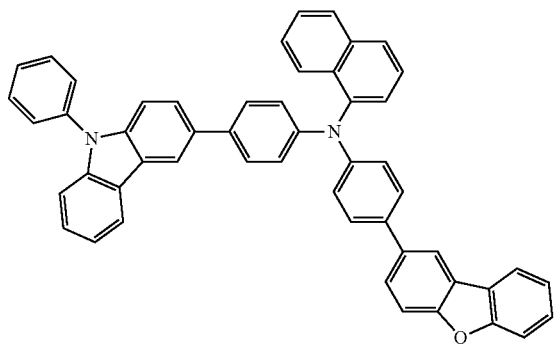
39
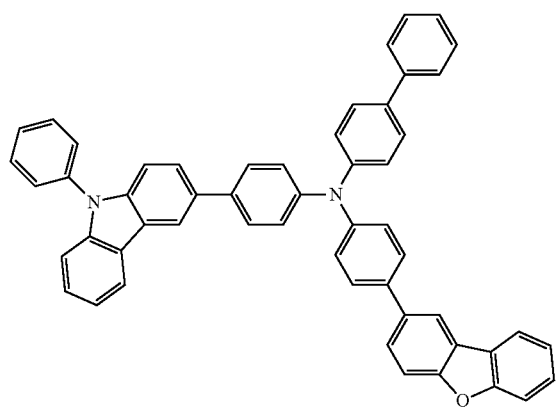
40
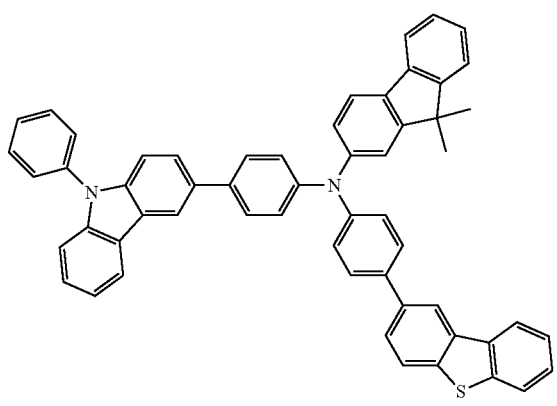
41
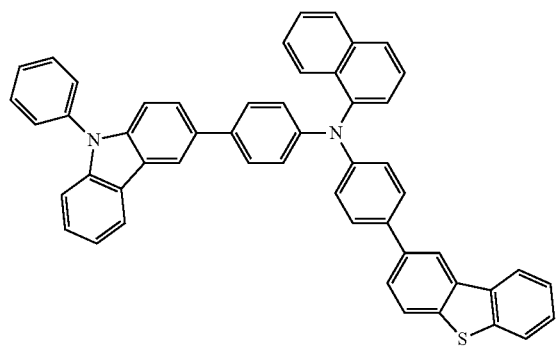
42
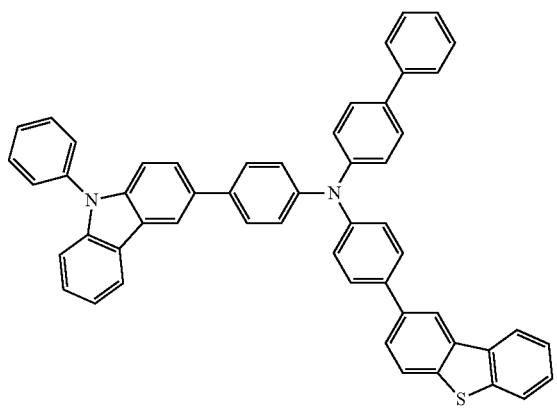

-continued
43
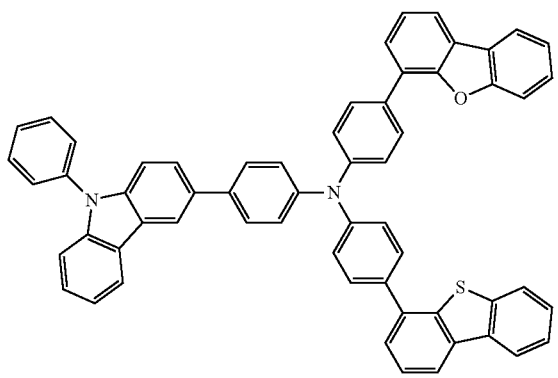
44
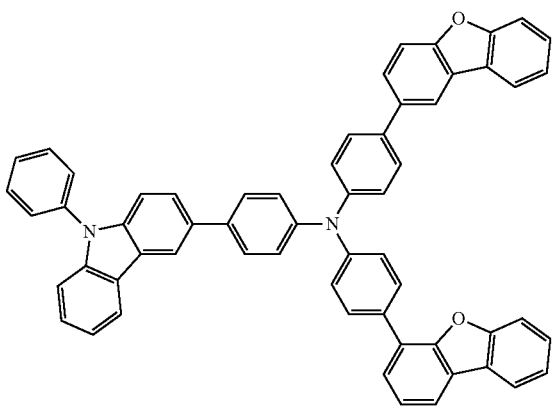
45
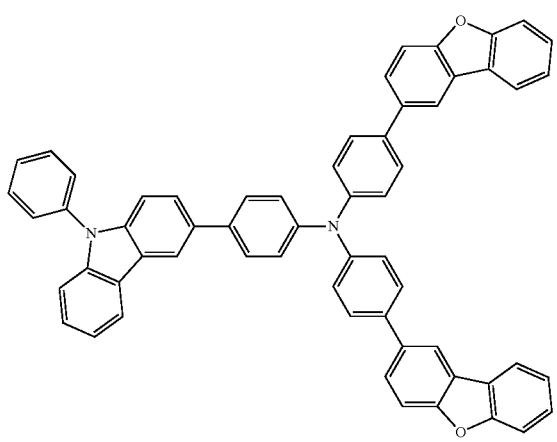
46
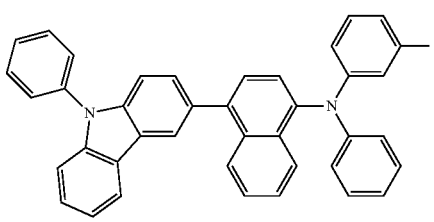
47
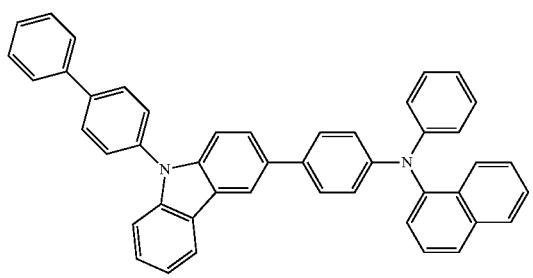
48
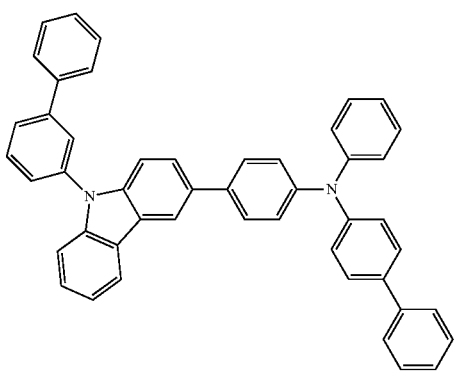
49
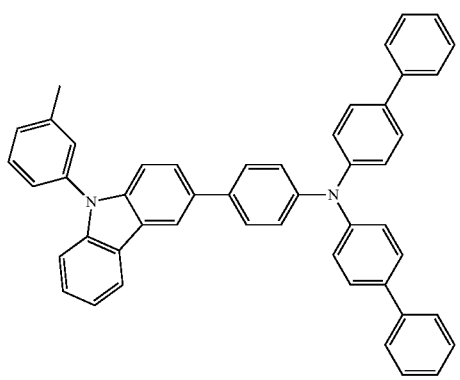
50
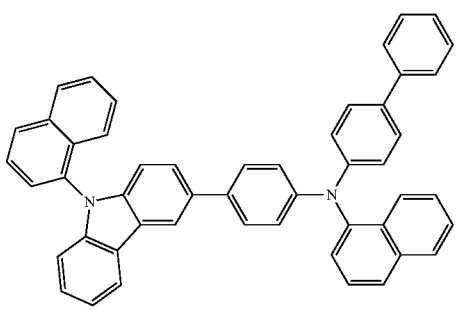

-continued
51
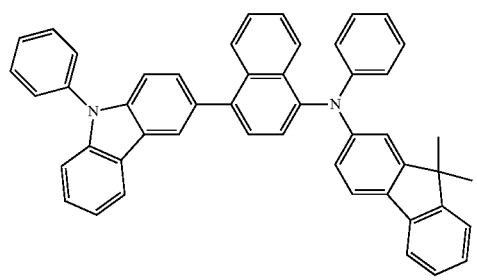
52
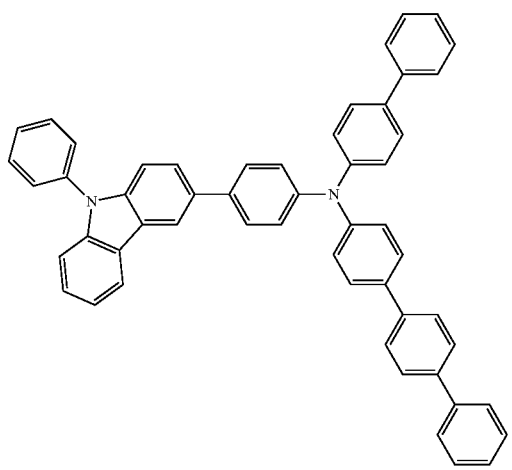
53
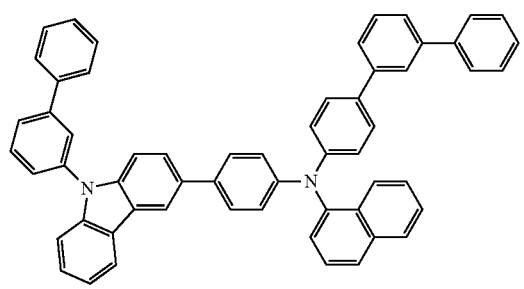
54
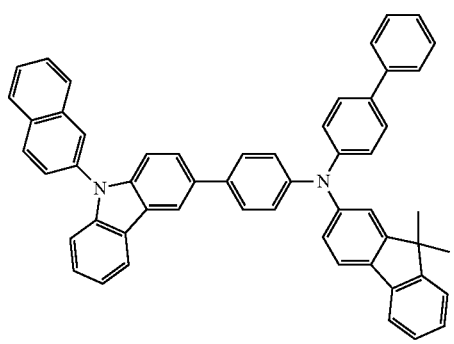
55
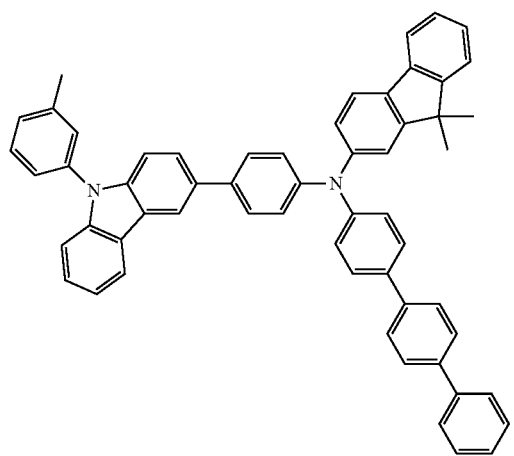
56
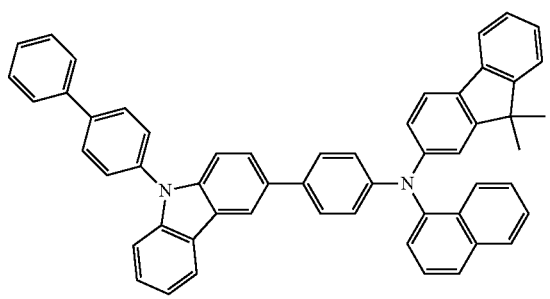

-continued
57
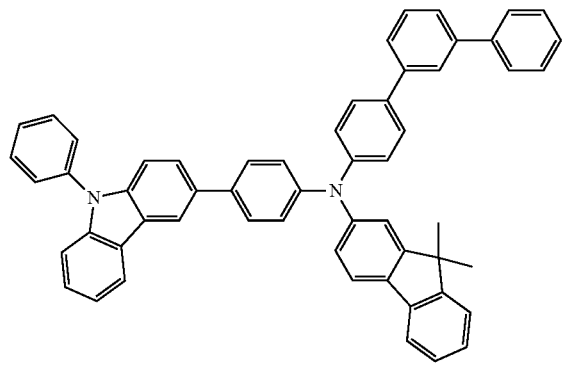
58
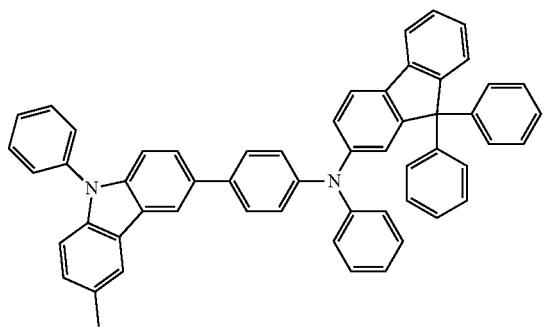
59
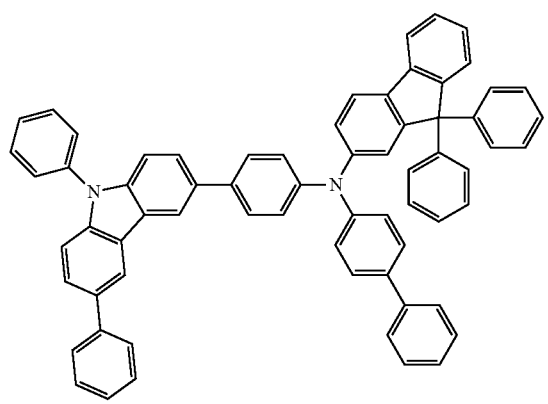
60
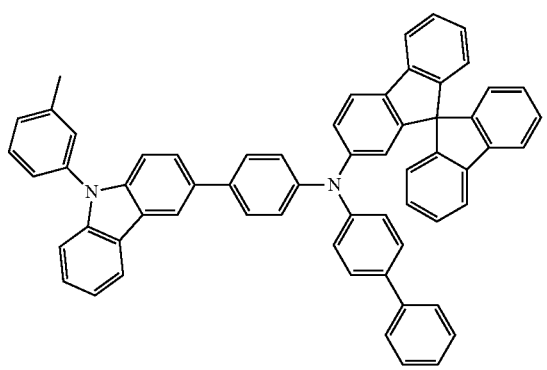
61
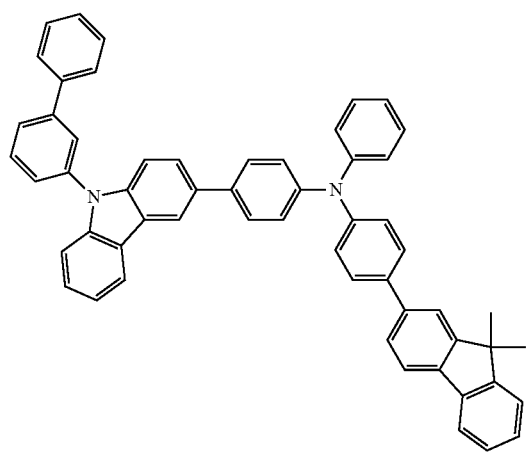
62
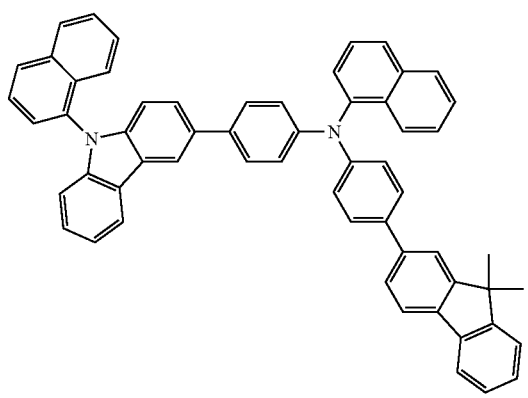

63
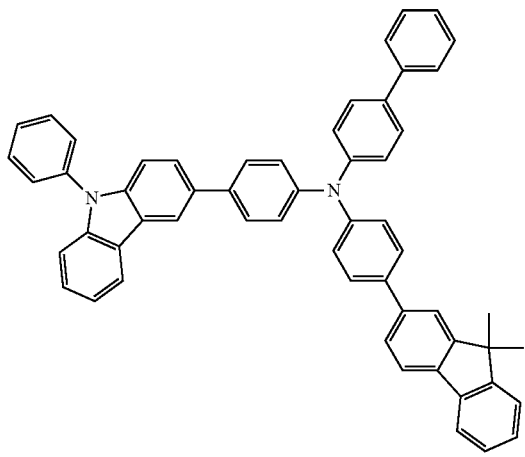
64
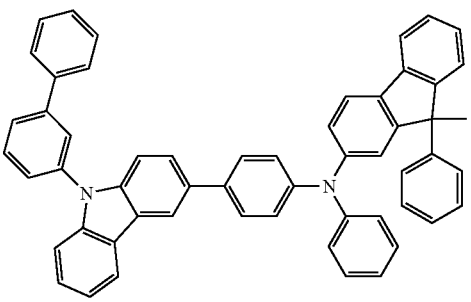
65
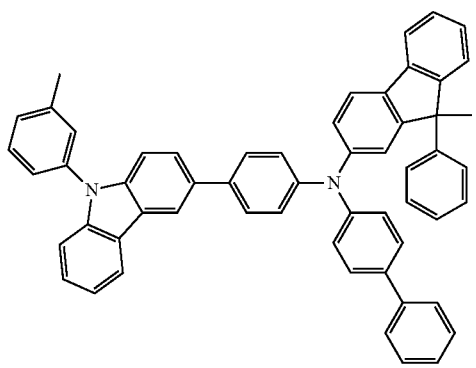
66
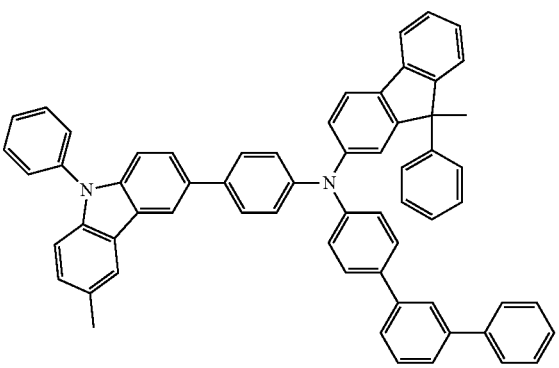
67
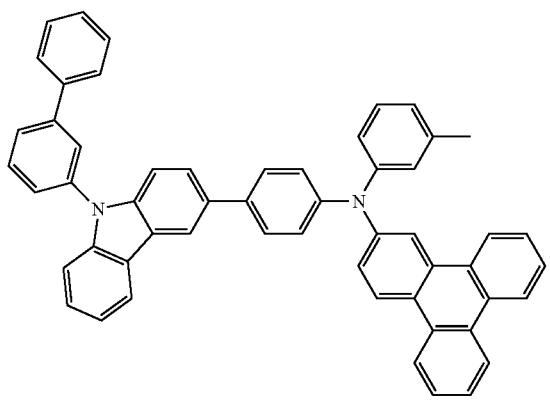
68
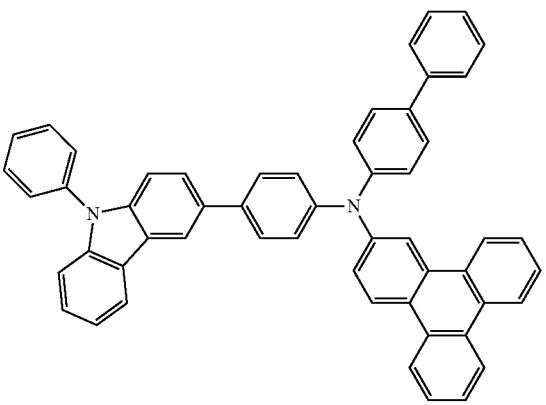
69
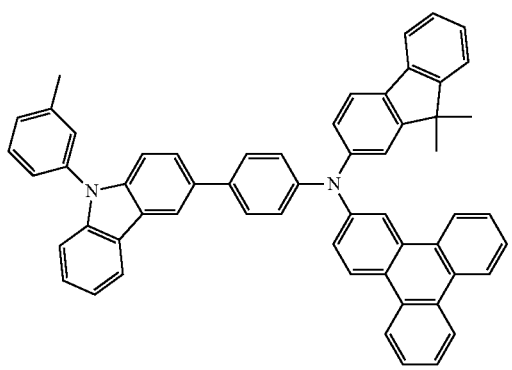
70
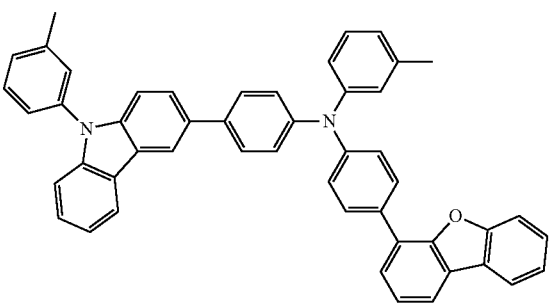

-continued
71
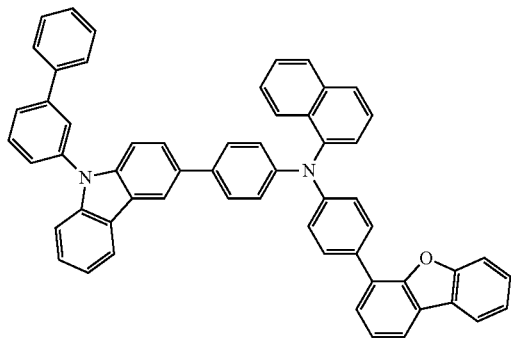
72
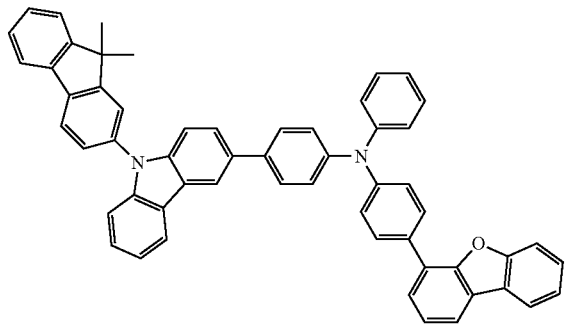
73
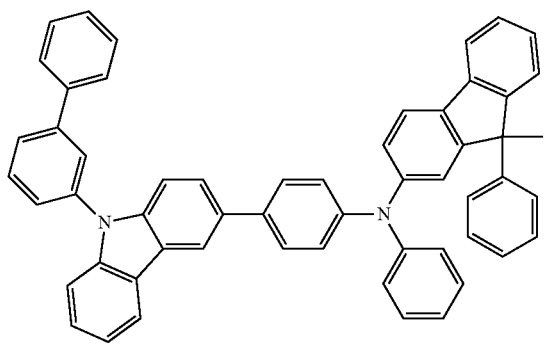
74
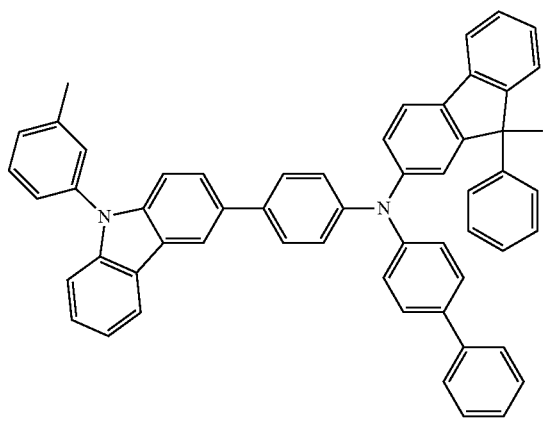
75
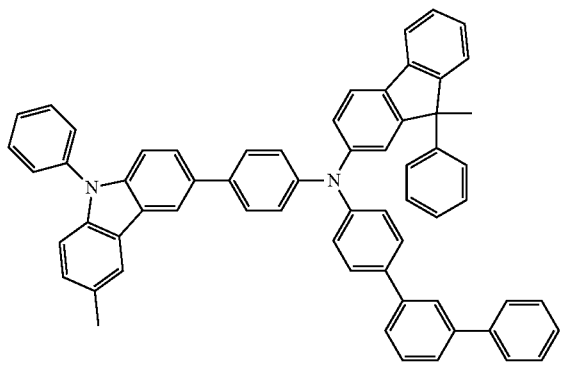
76
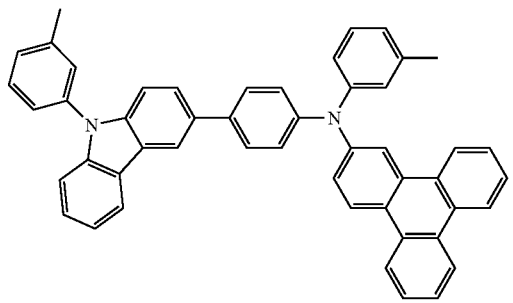
77
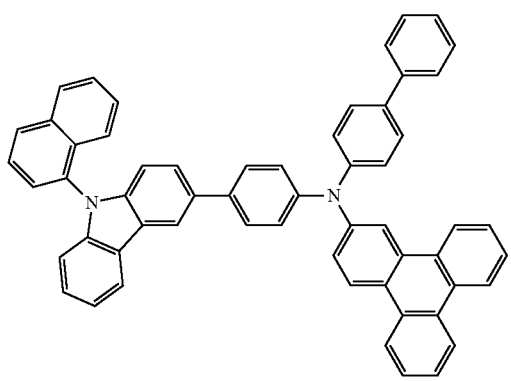
78
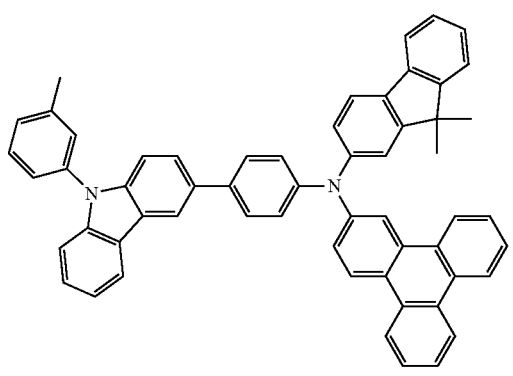

79
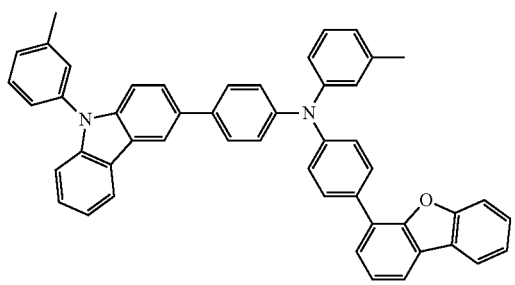
80
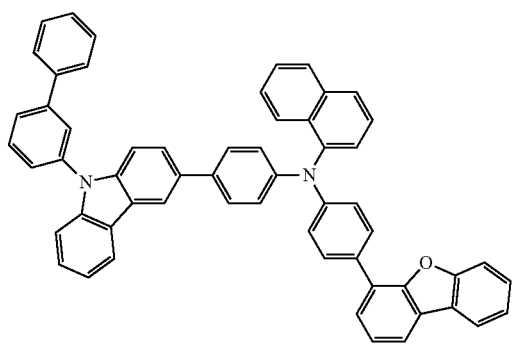
81
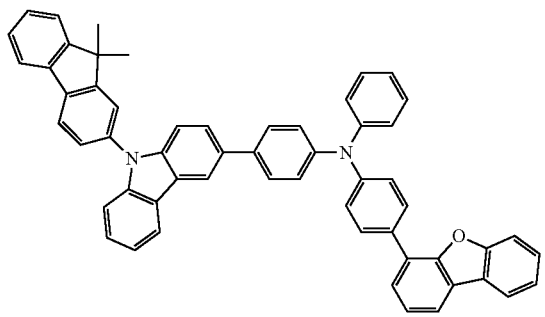
82
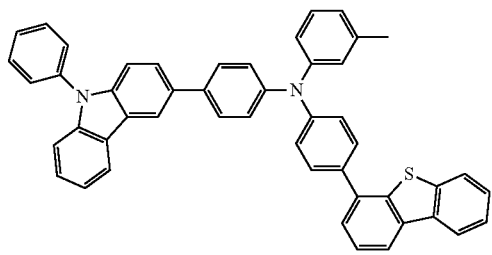
83
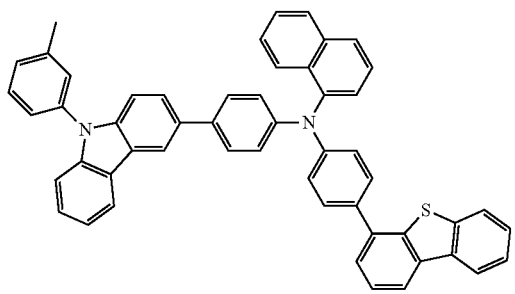
84
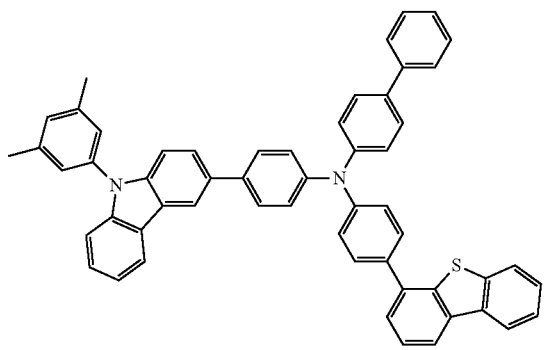
85
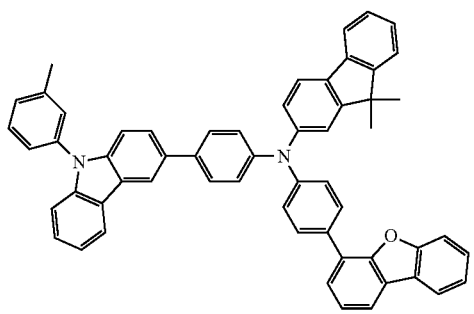
86
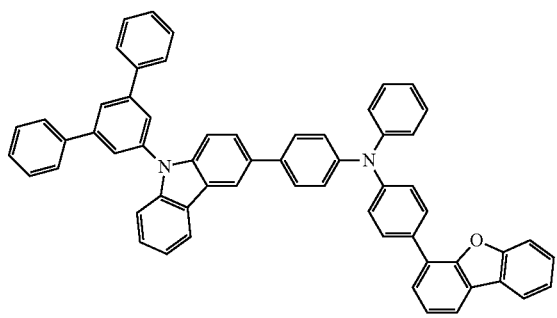

-continued
87
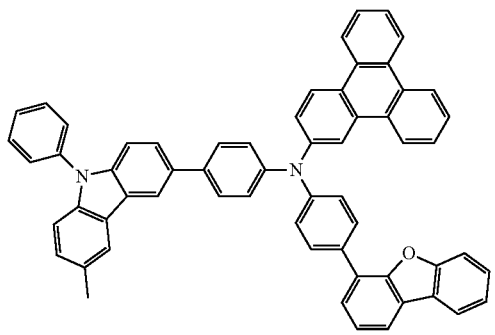
88
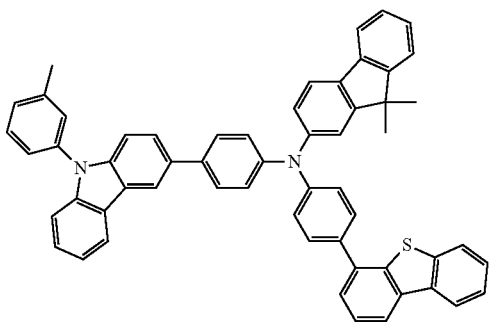
89
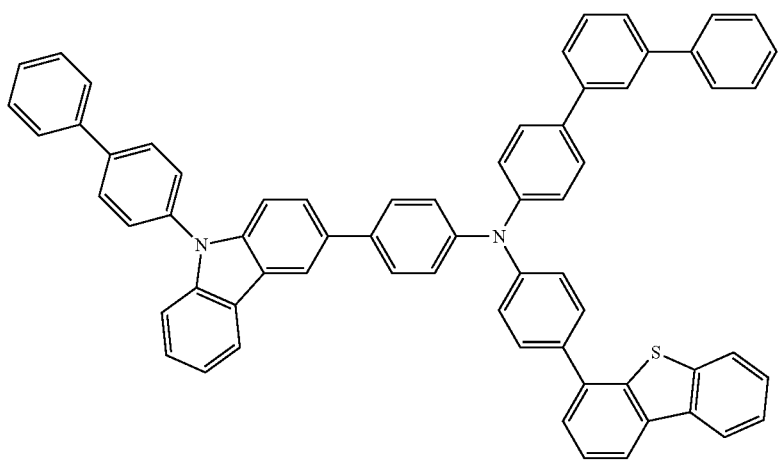
90
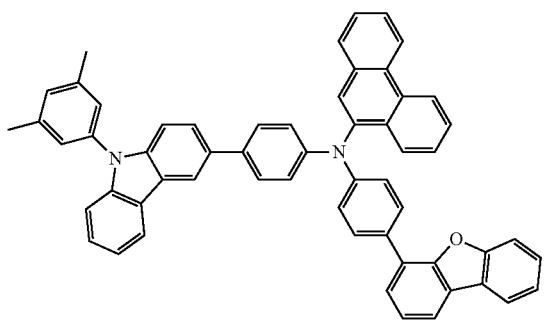
91
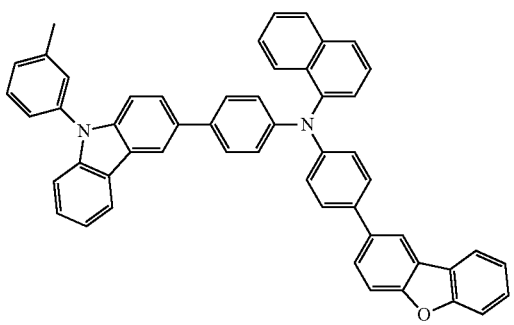
92
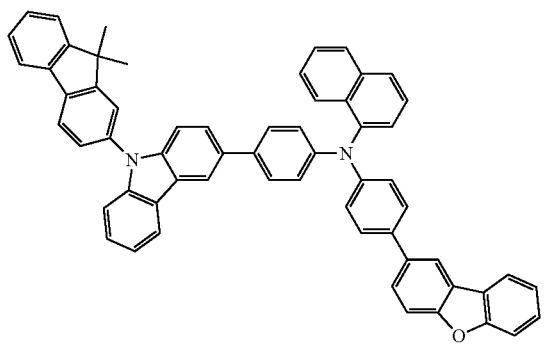
93
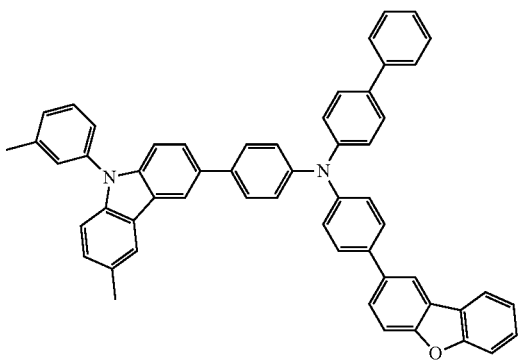

-continued
94
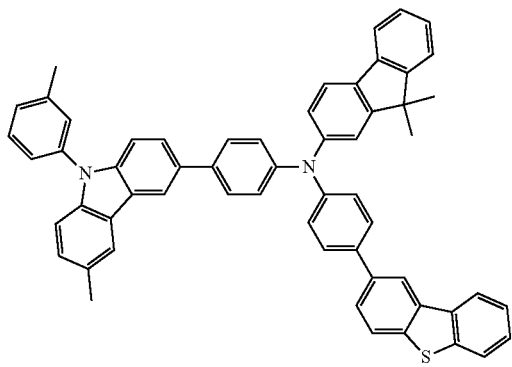
95
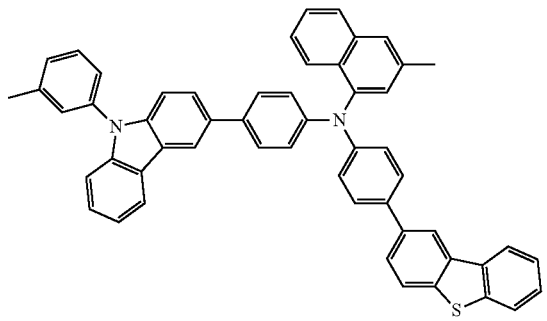
96
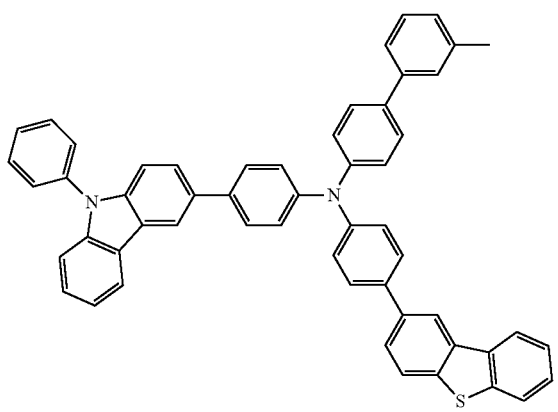
97
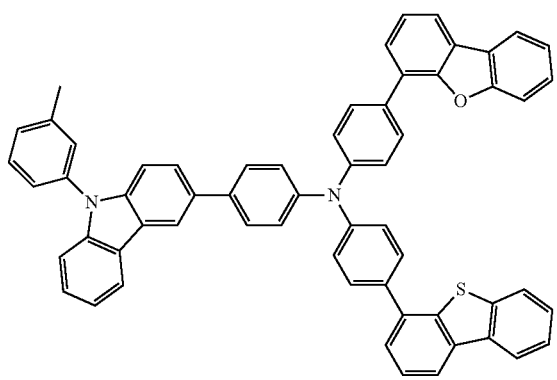
98
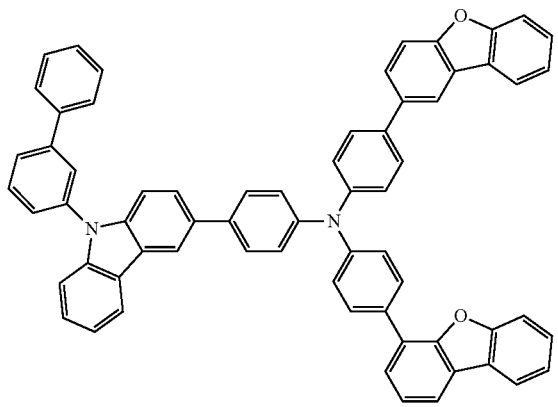
99
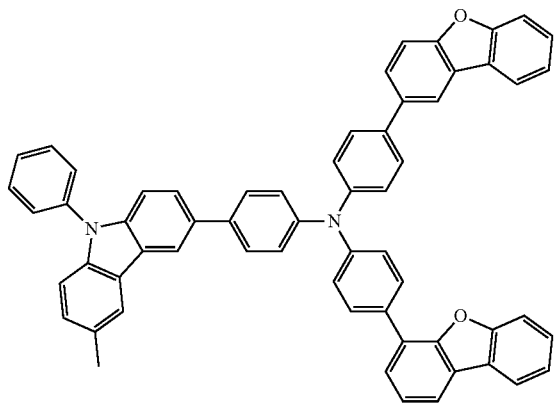
100
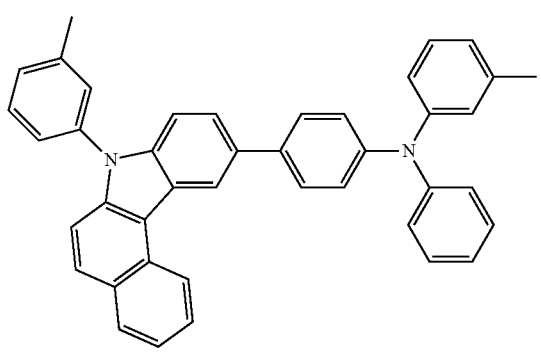
101
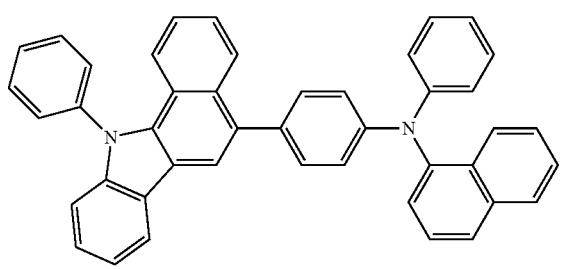

-continued
102
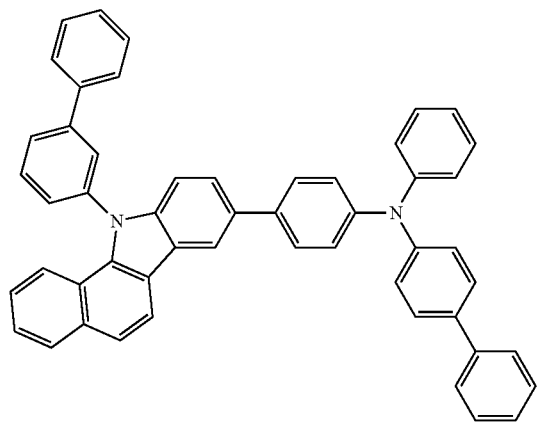
103
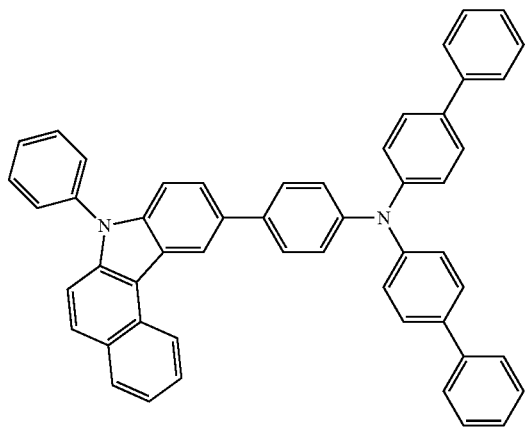
104
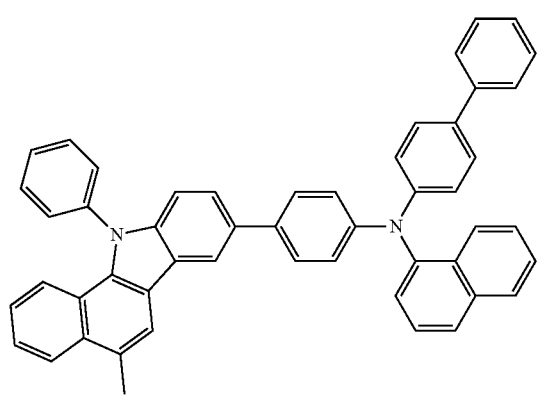
105
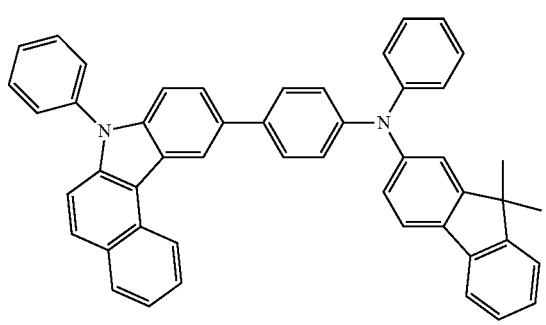
106
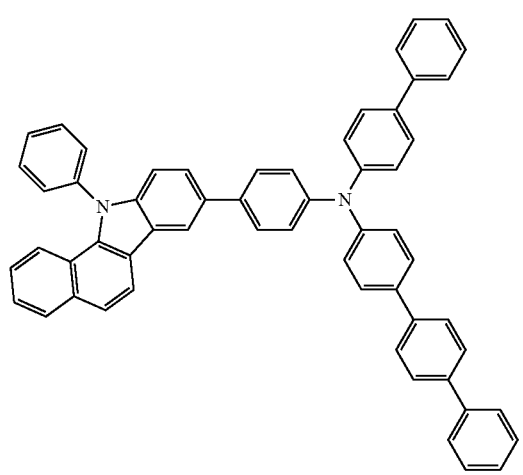
107
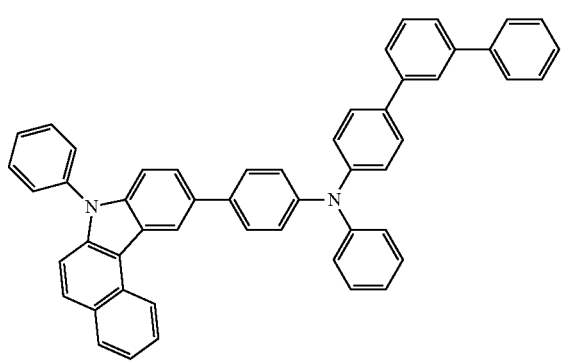

-continued
108
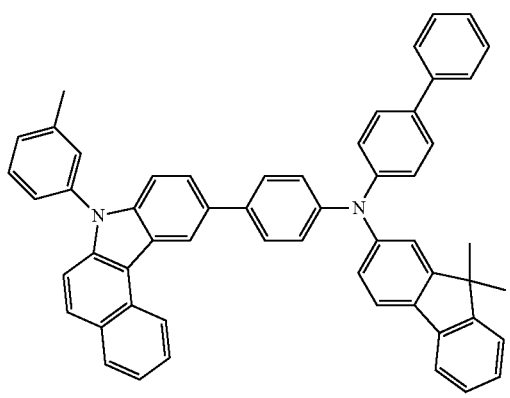
109
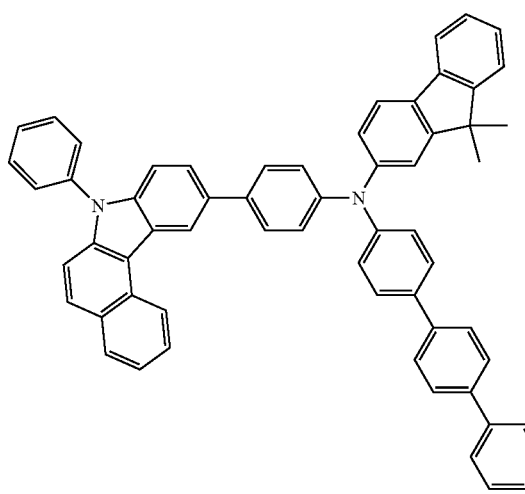
110
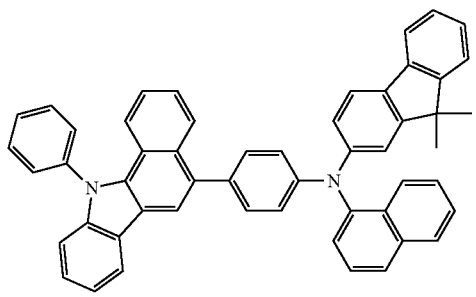
111
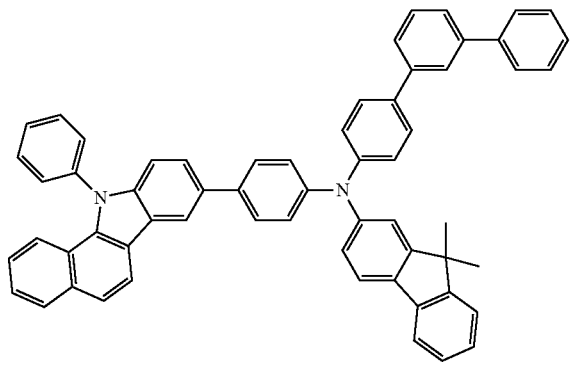
112
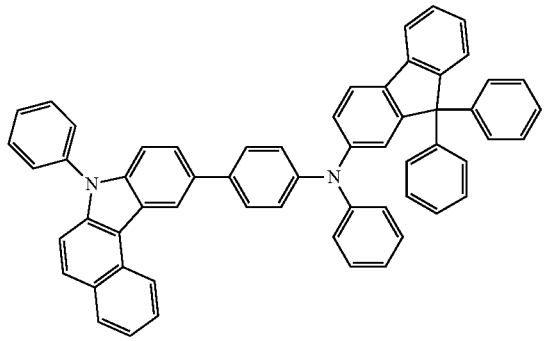
113
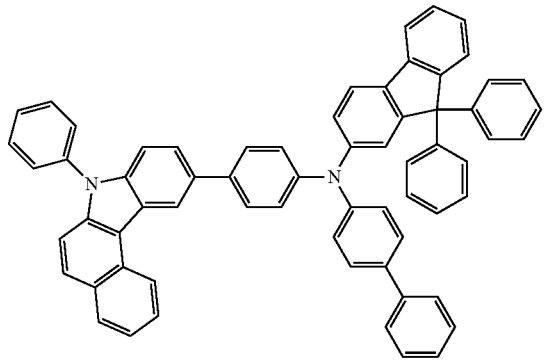
114
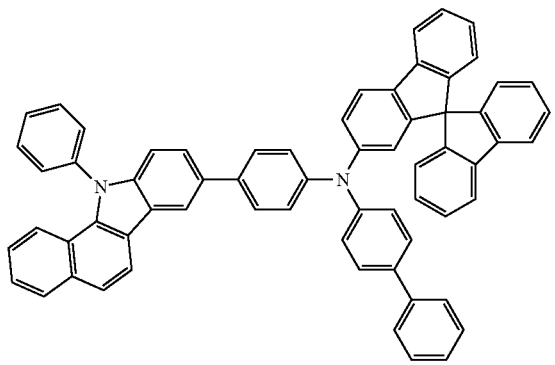
115
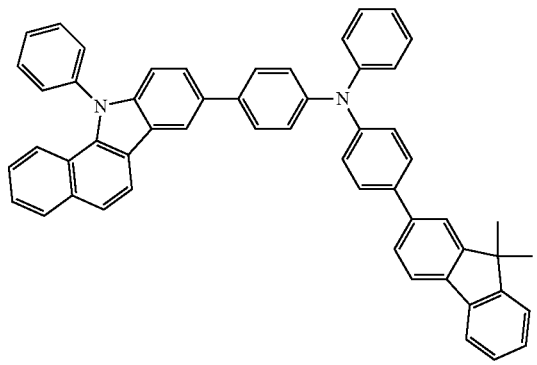

-continued
116
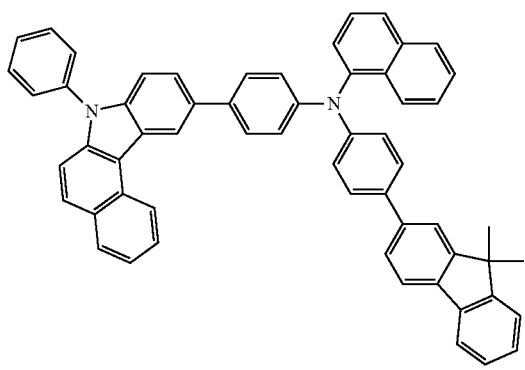
117
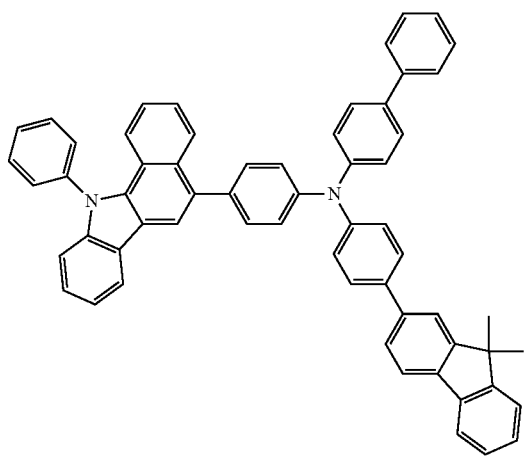
118
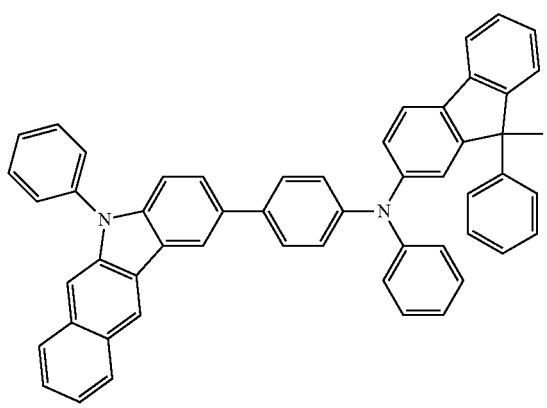
119
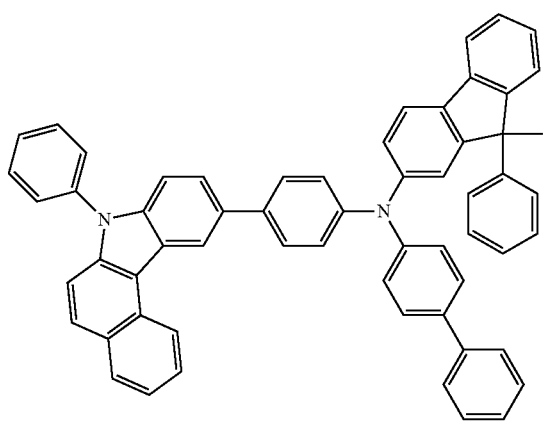
120
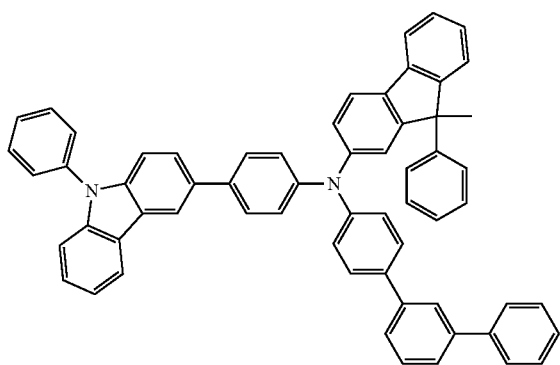
121
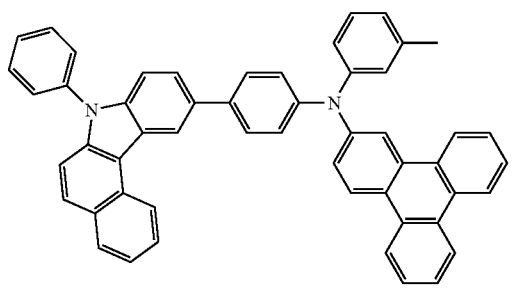

-continued
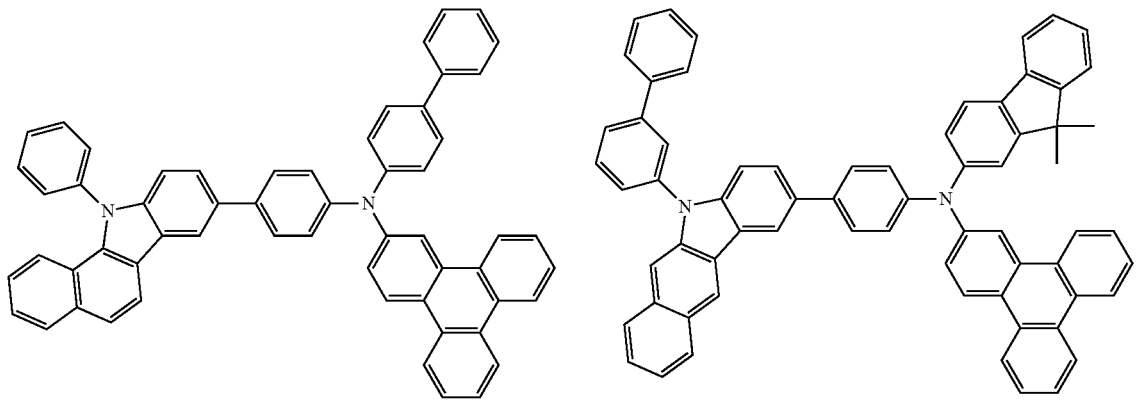
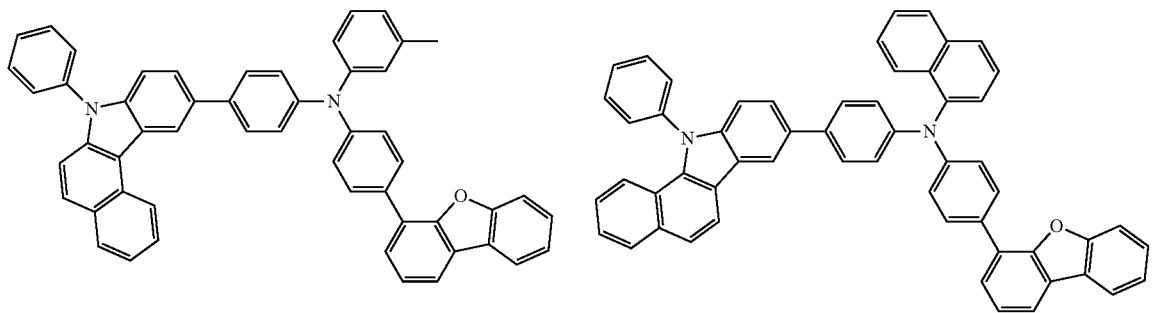
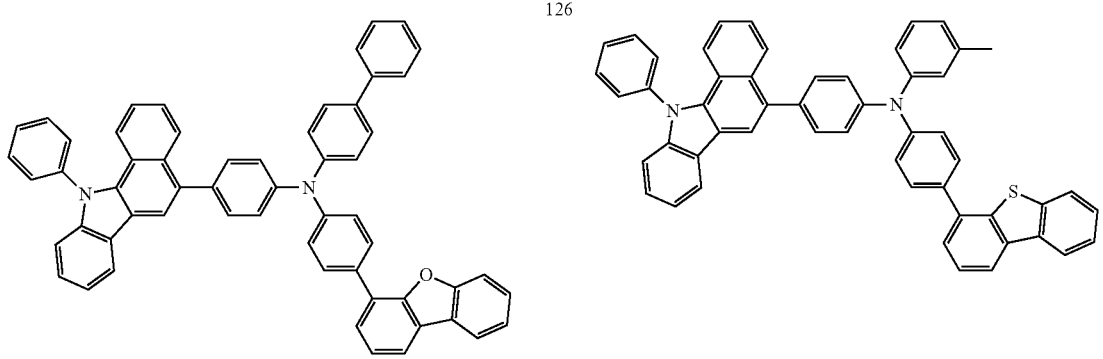
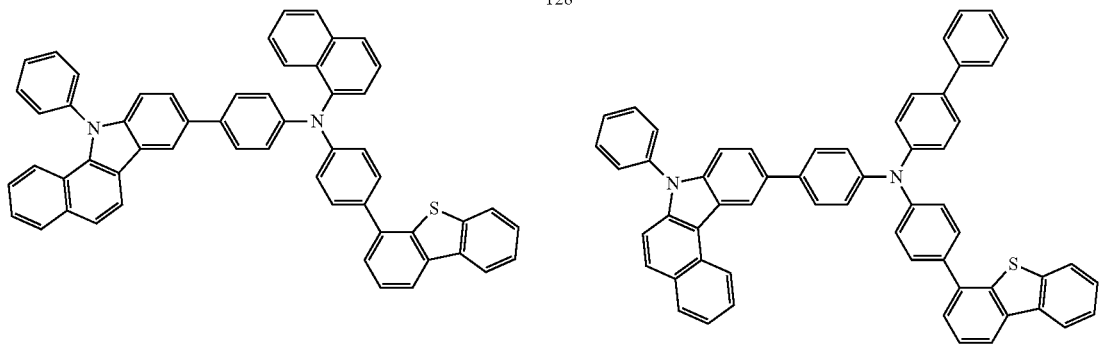

-continued
130
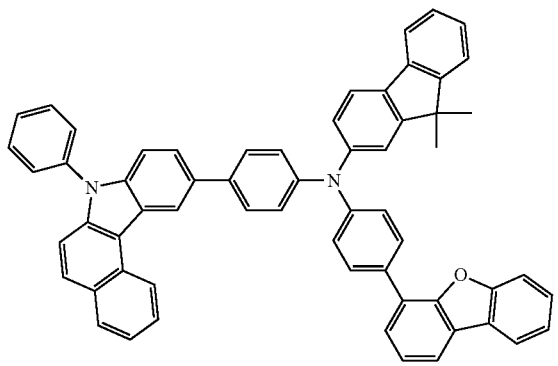
131
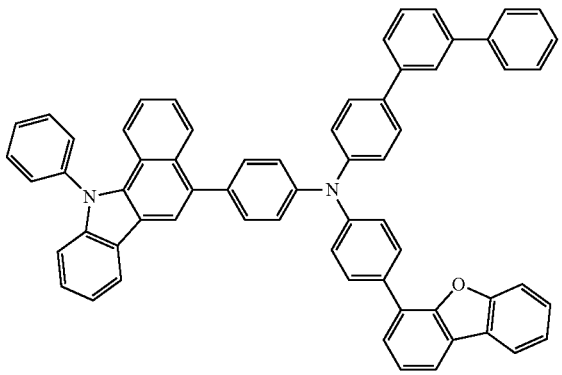
132
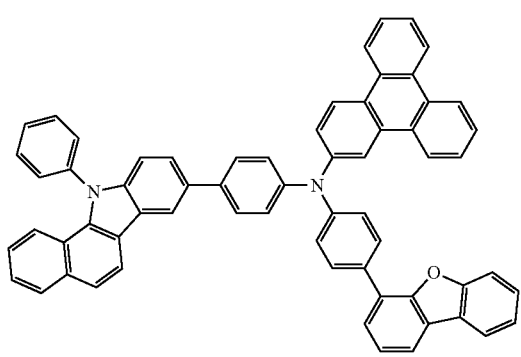
133
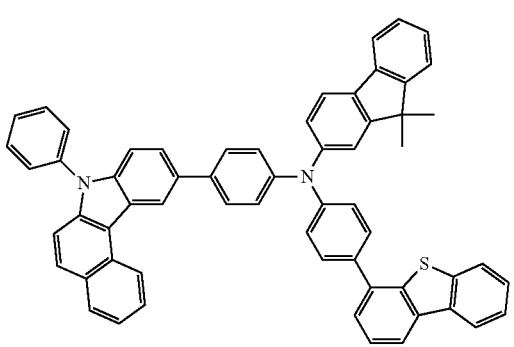
134
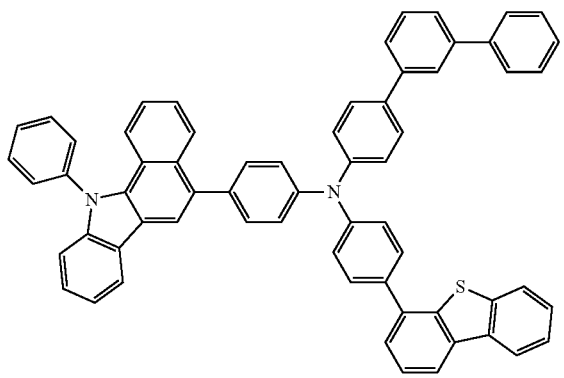
135
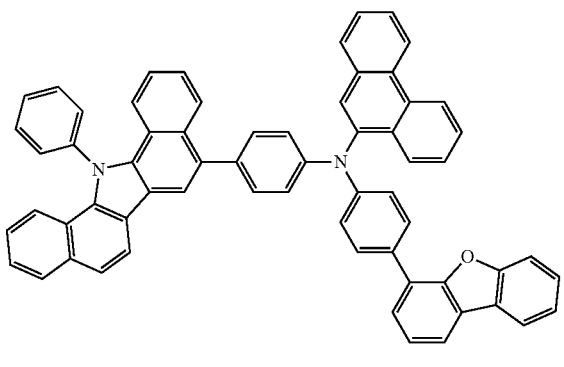
136
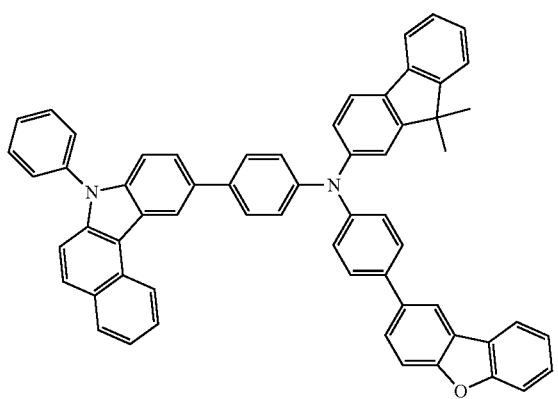
137
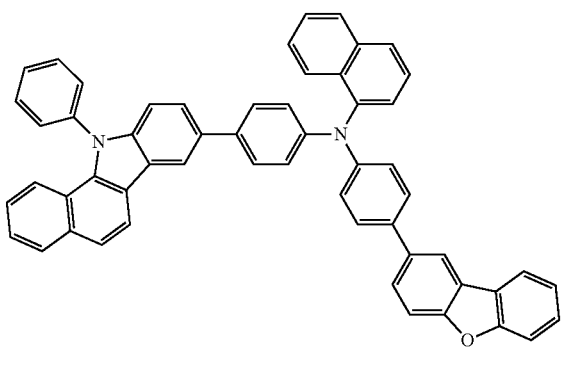

-continued
138
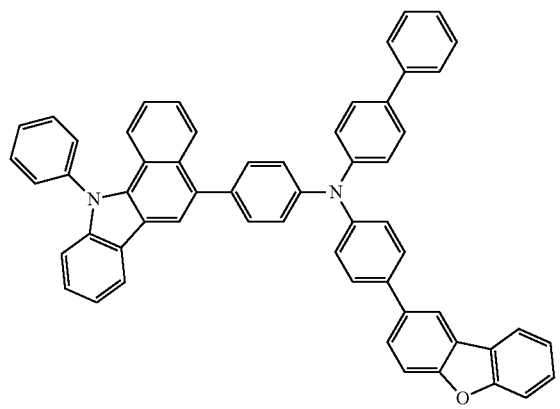
139
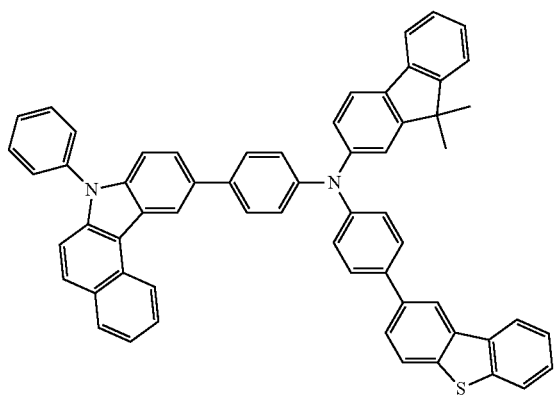
140
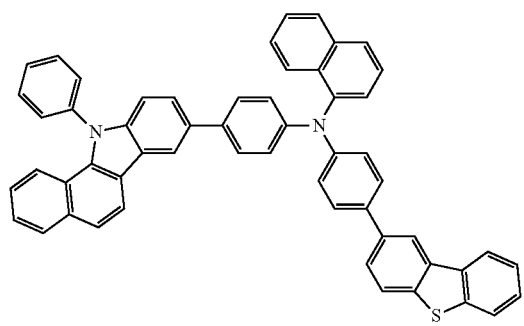
141
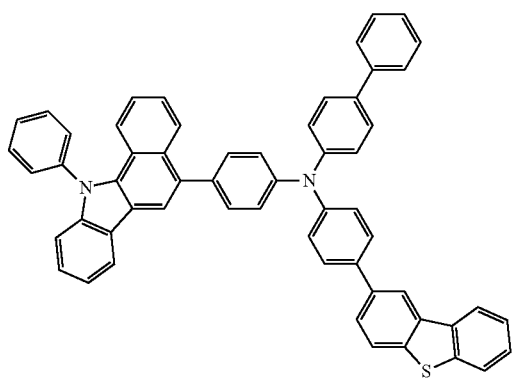
142
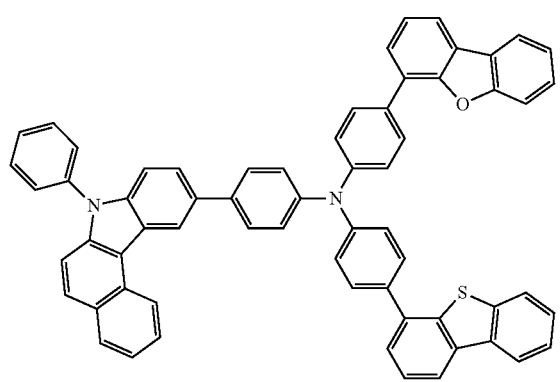
143
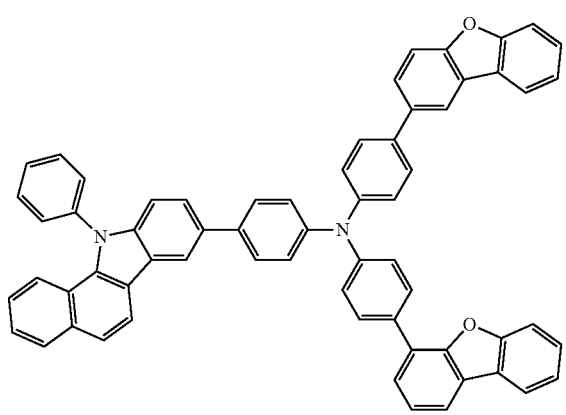

-continued
144
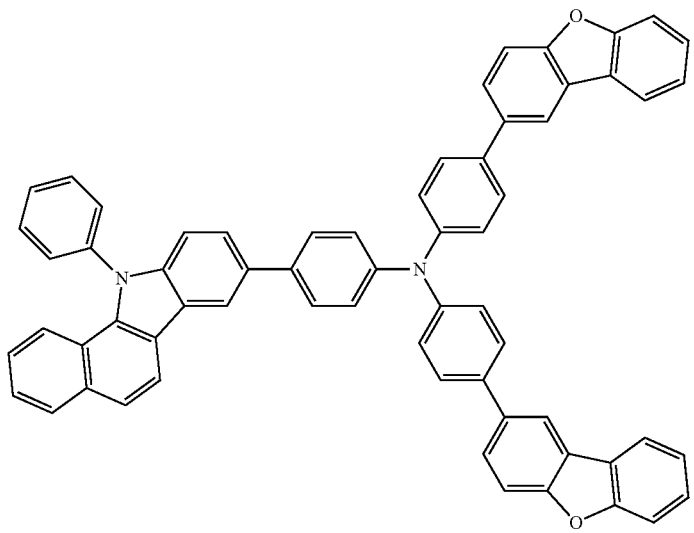
14. The organic optoelectric device of claim 1, wherein the compound represented by Chemical Formula II is one selected from compounds of Group IV:
[Group IV]
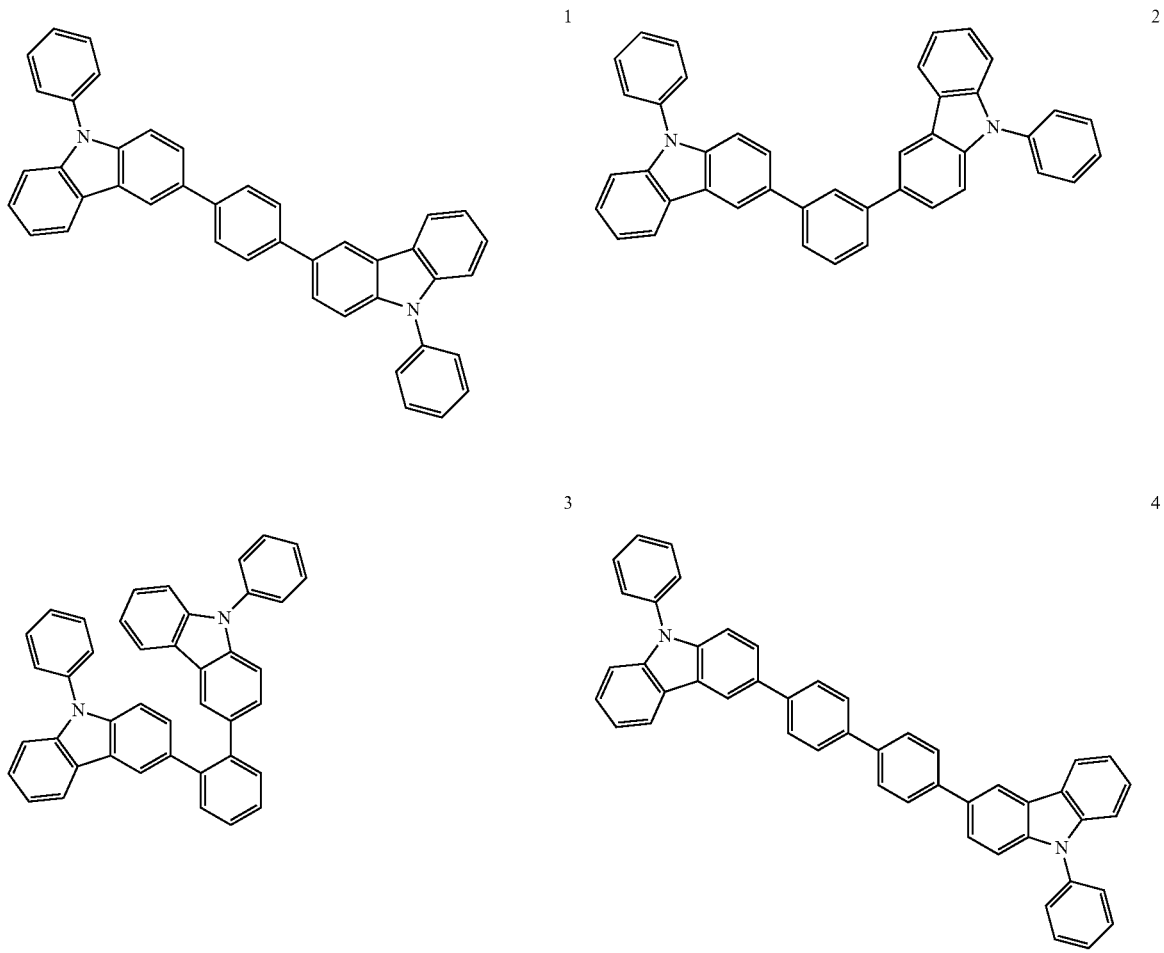

-continued
215
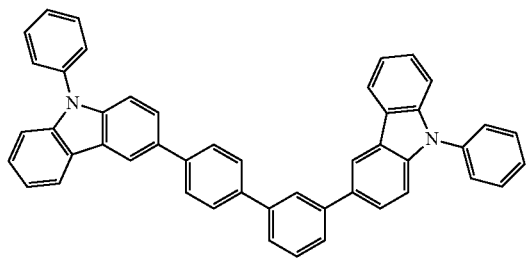
216
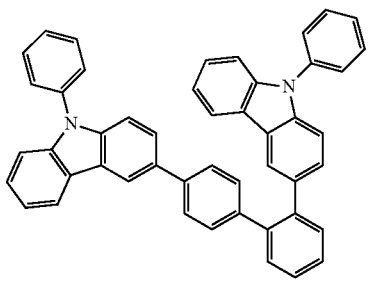
7
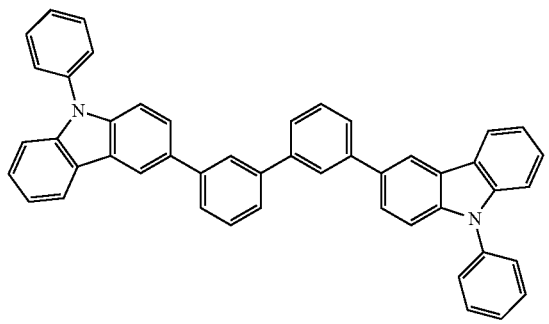
8
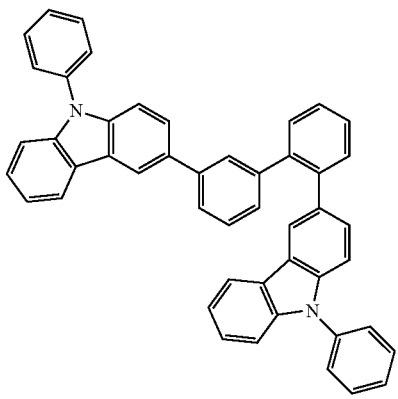
9
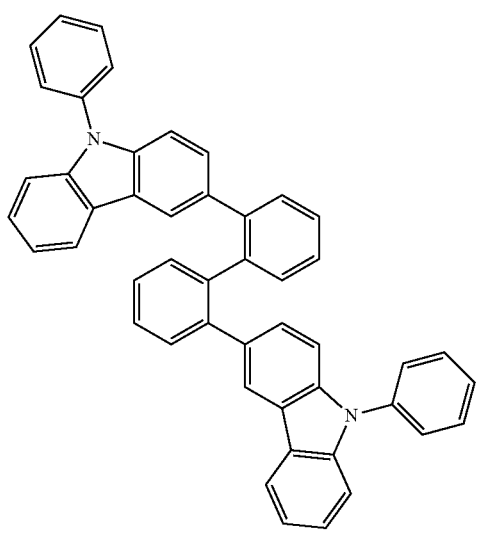

10
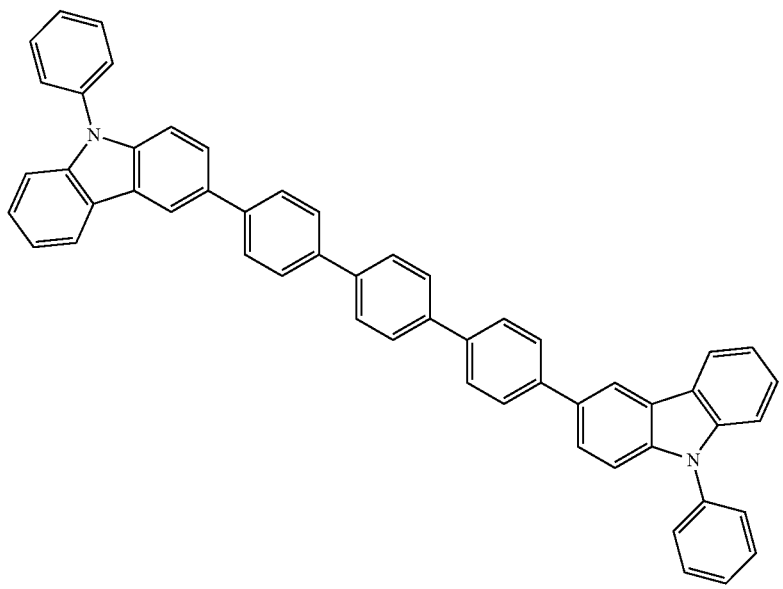
11
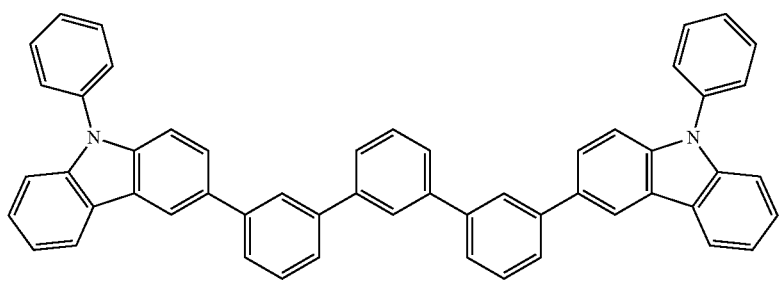
12
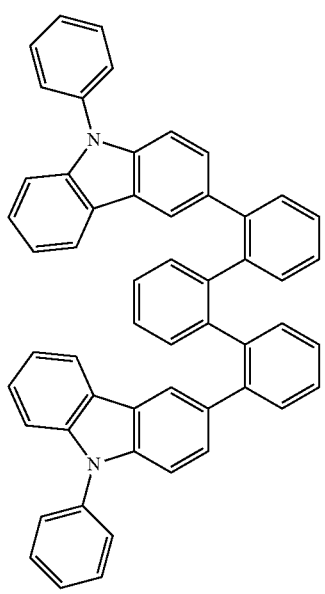

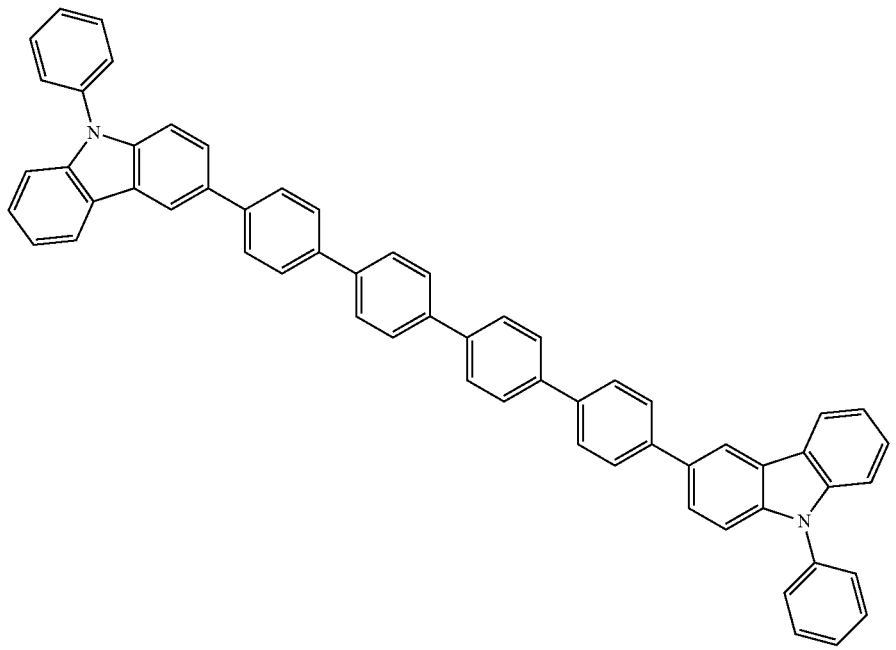
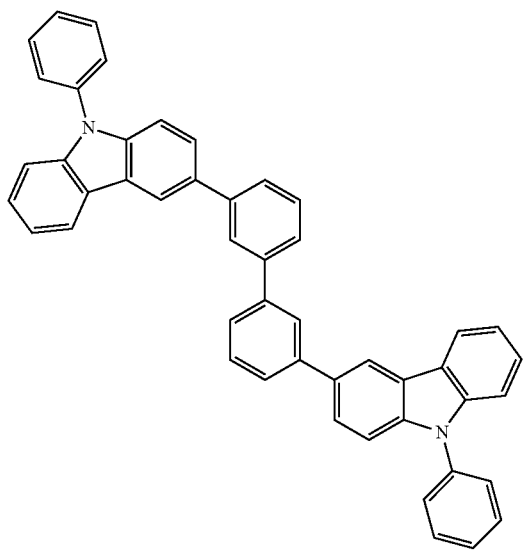
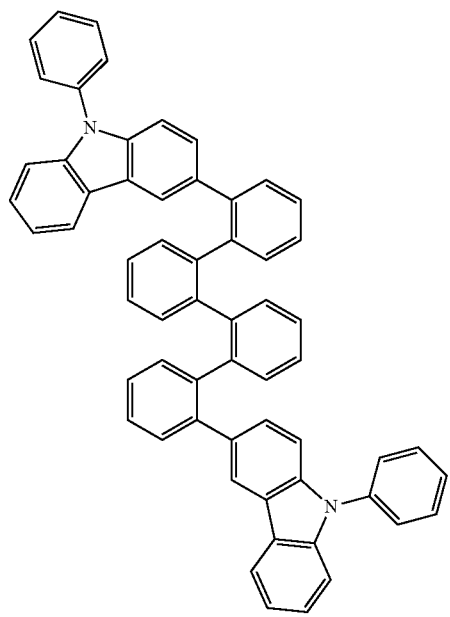

16
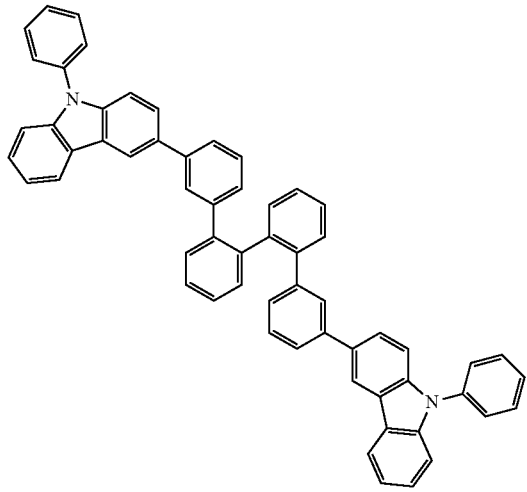
17
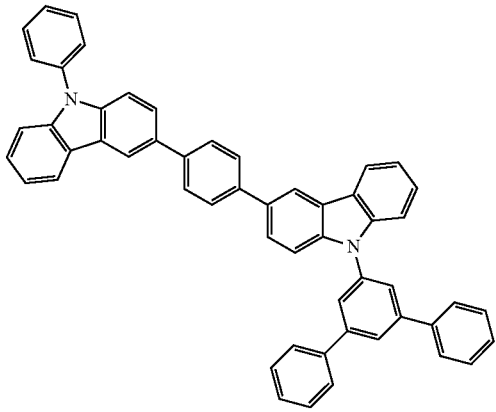
18
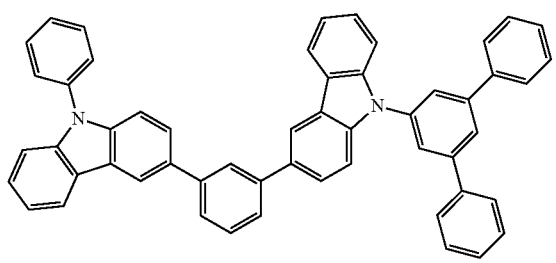
19
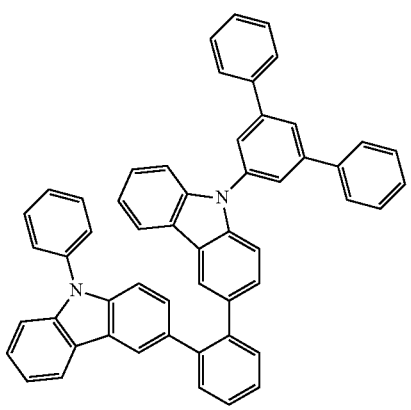
20
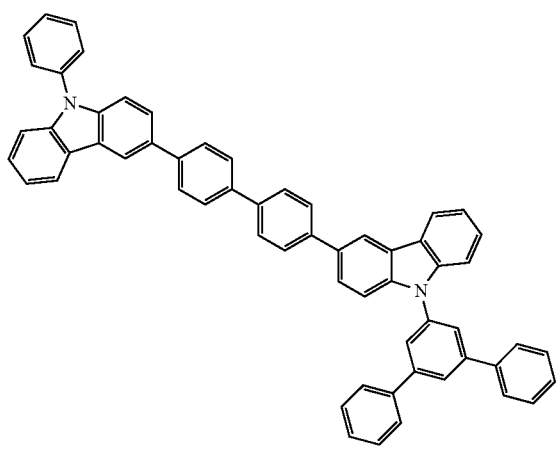
21
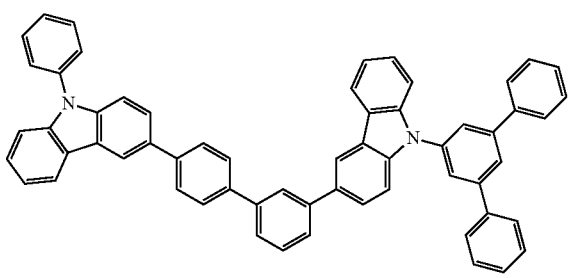

-continued
22
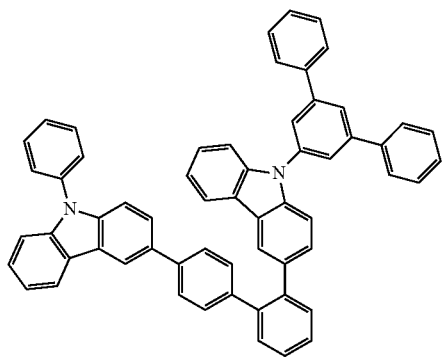
23
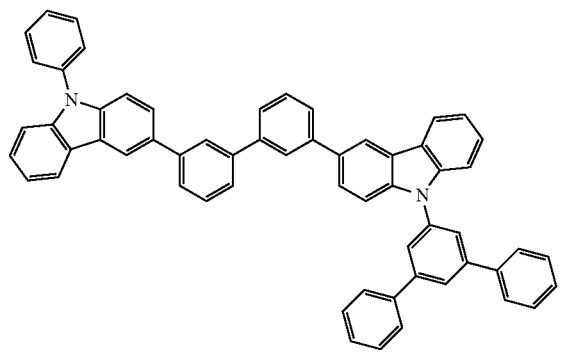
24
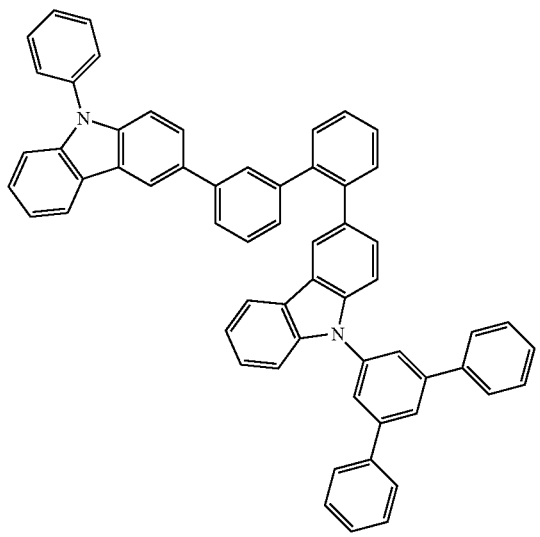
25
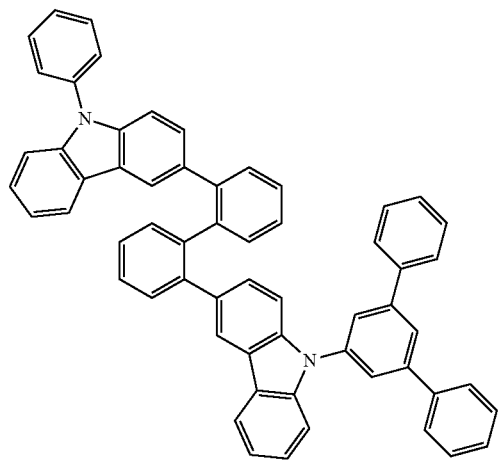
26
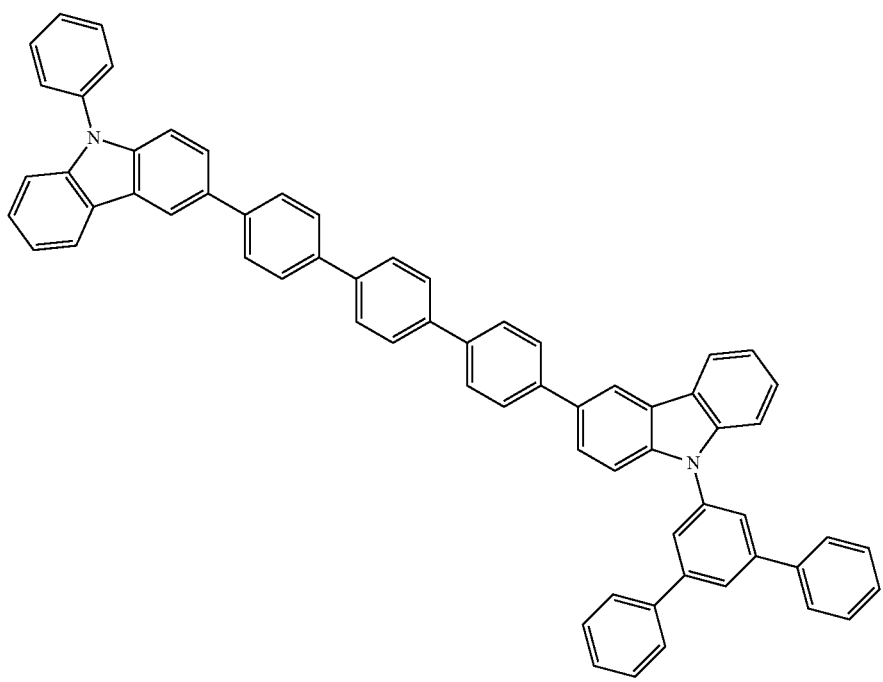

-continued
27
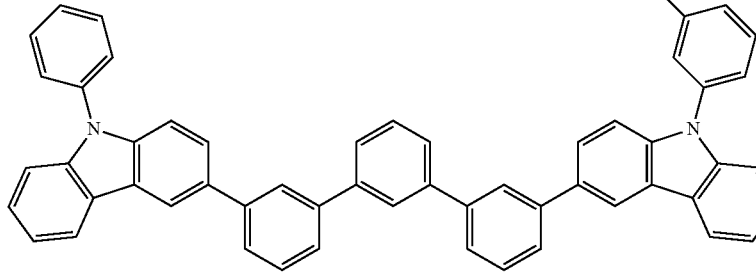
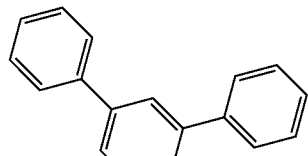
28
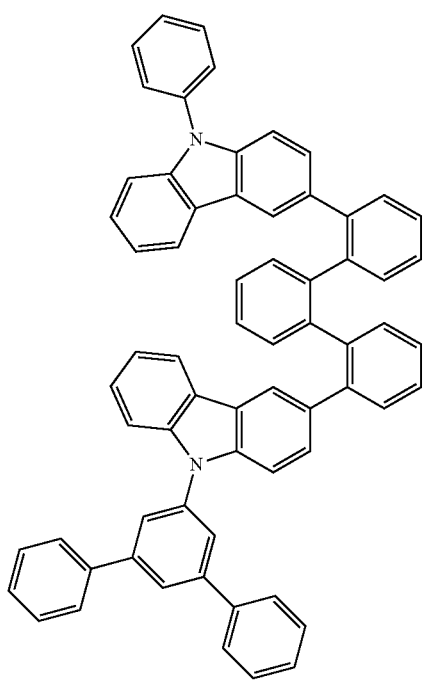

29
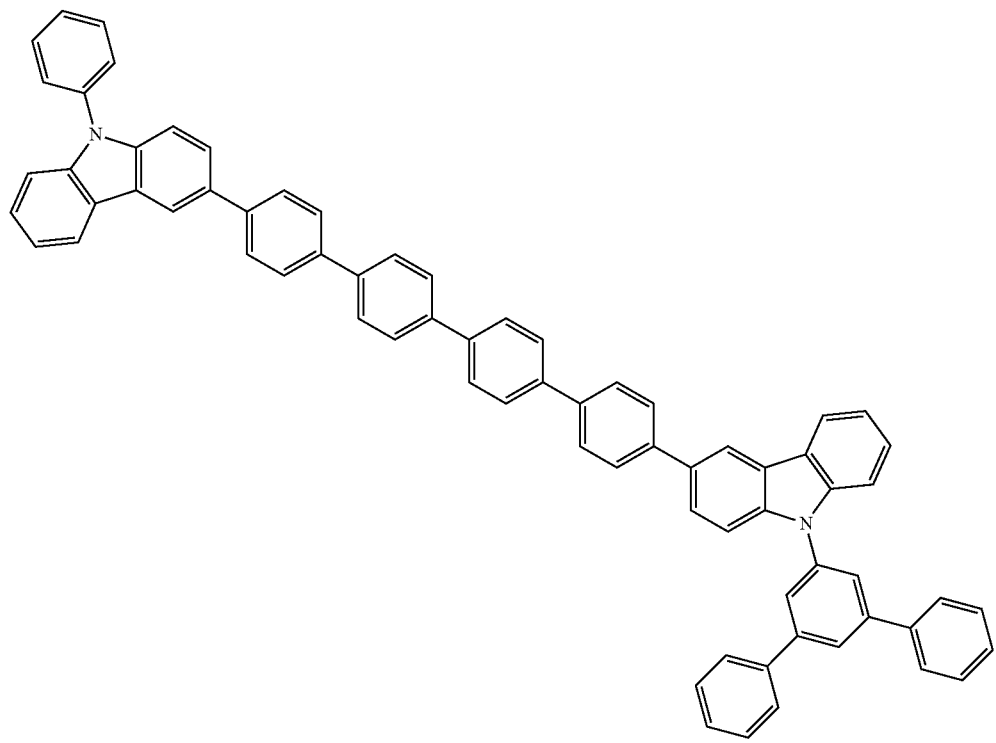
30
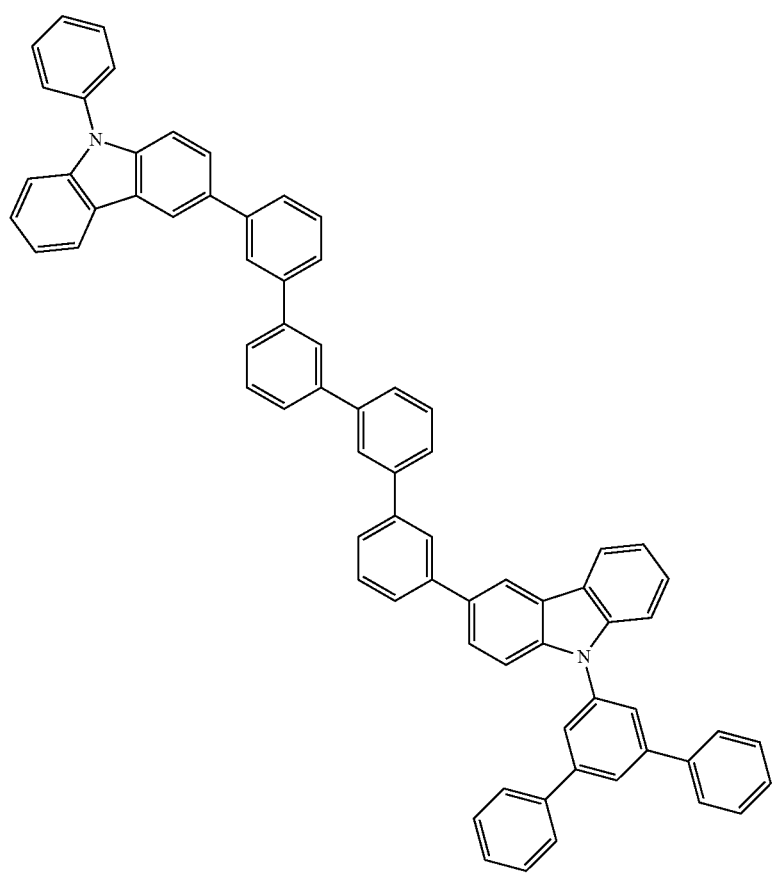

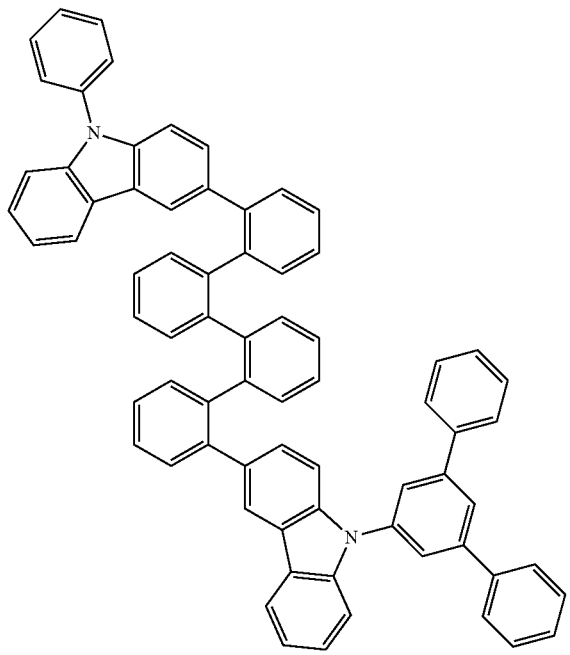
31
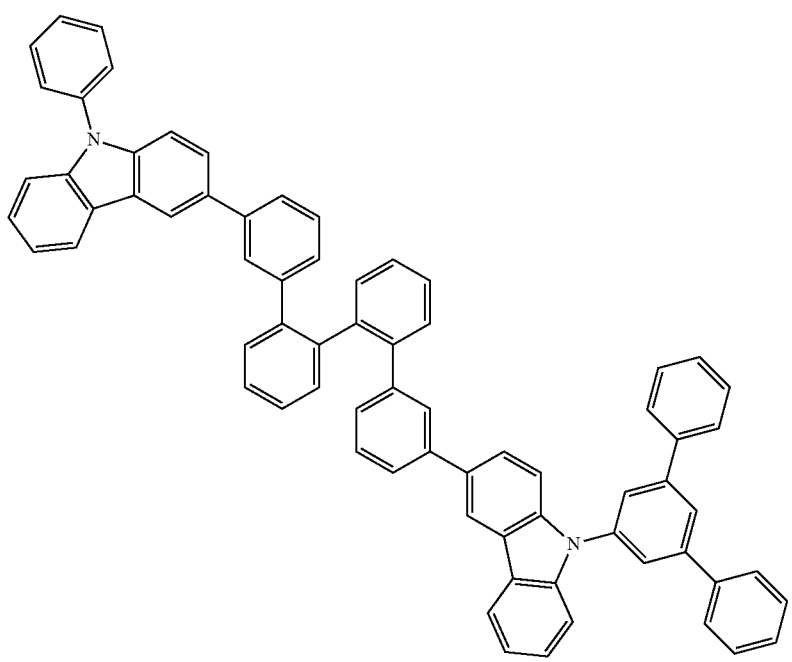
32

33
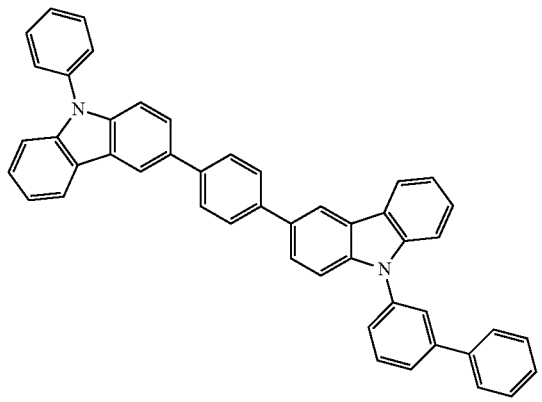
34
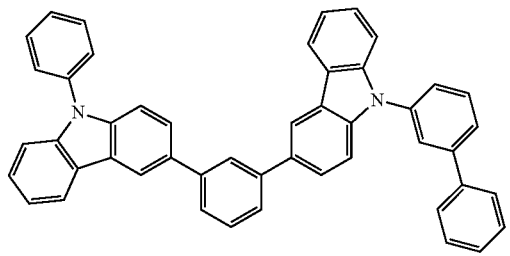
35
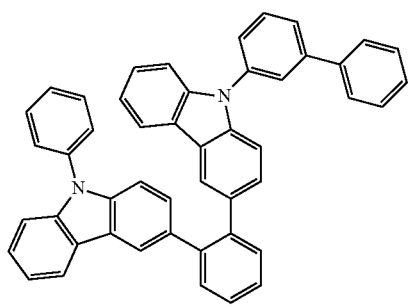
36
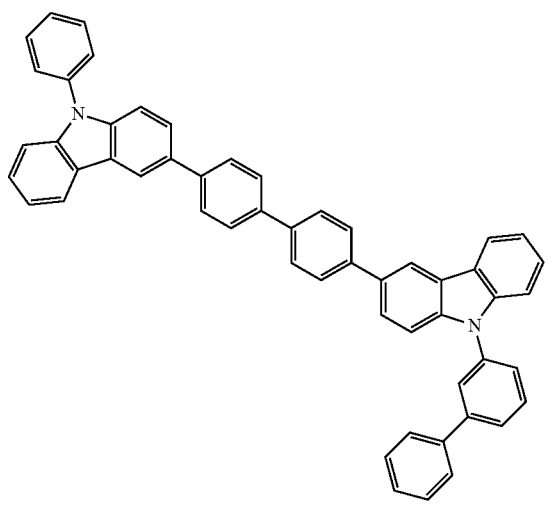
37
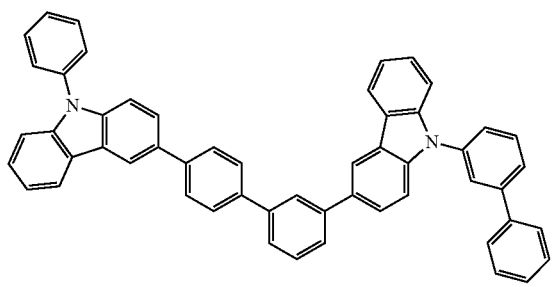
38
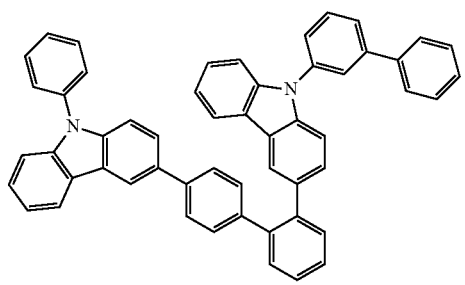

39
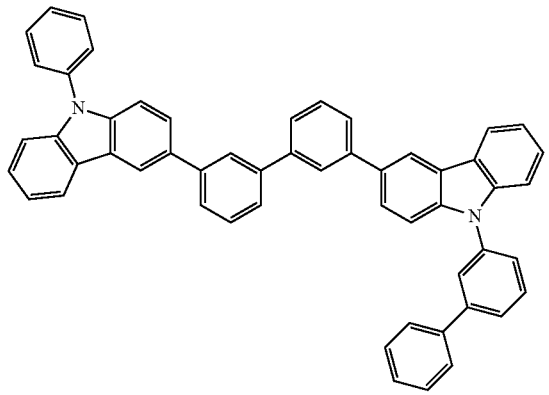
40
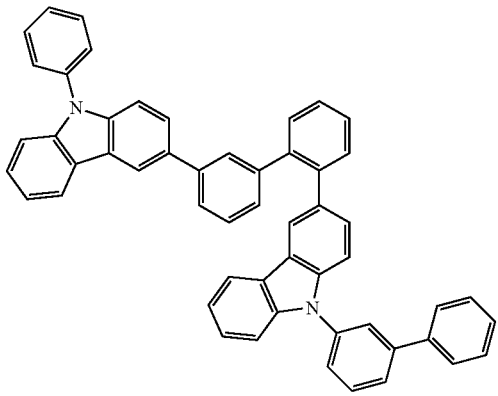
41
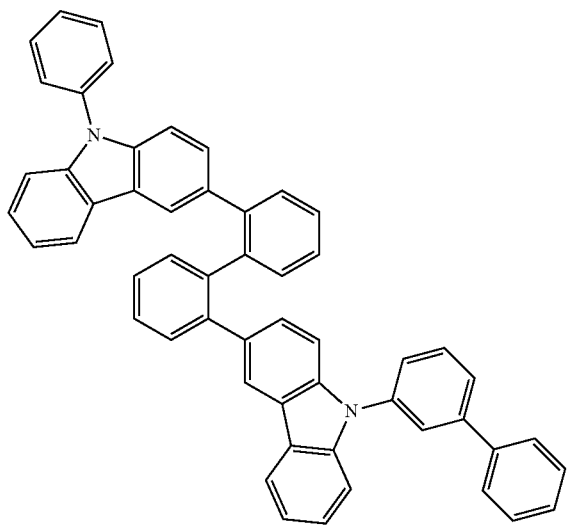
42
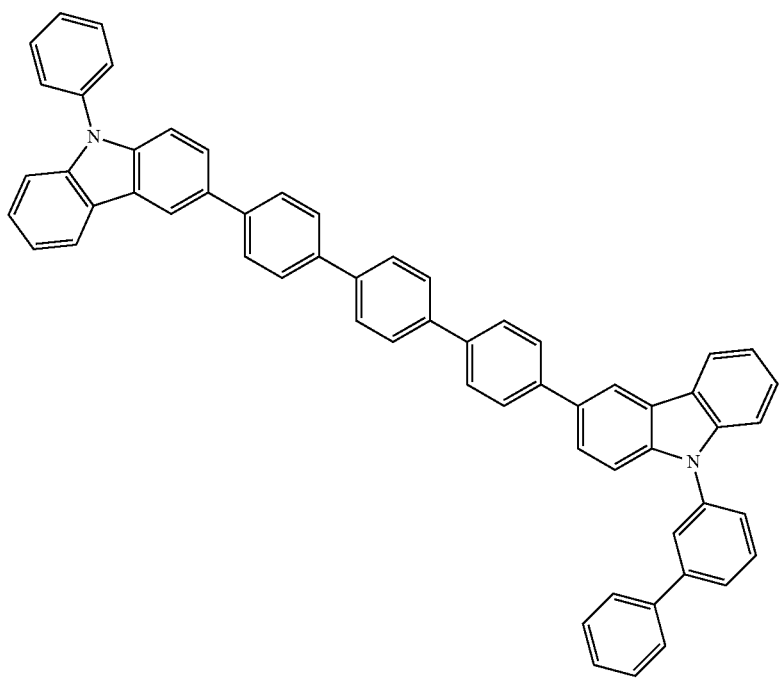

43
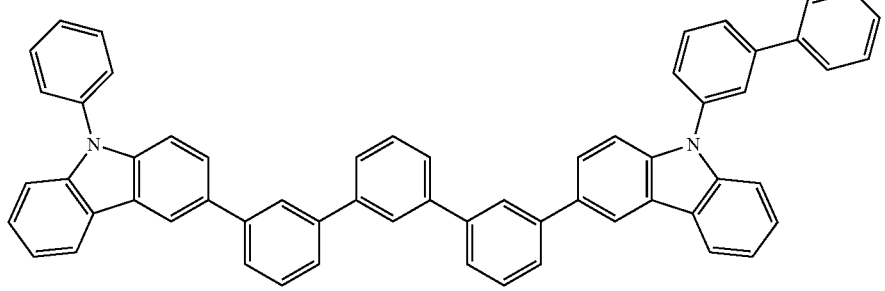
44
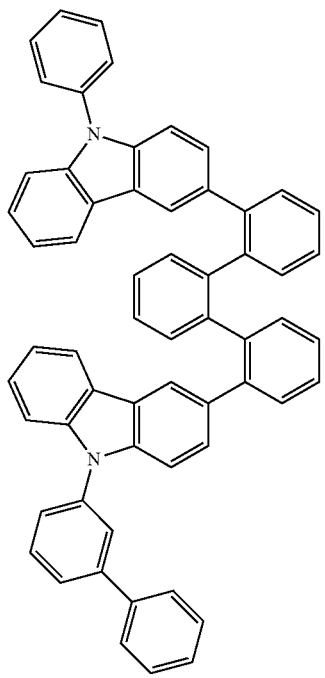
45
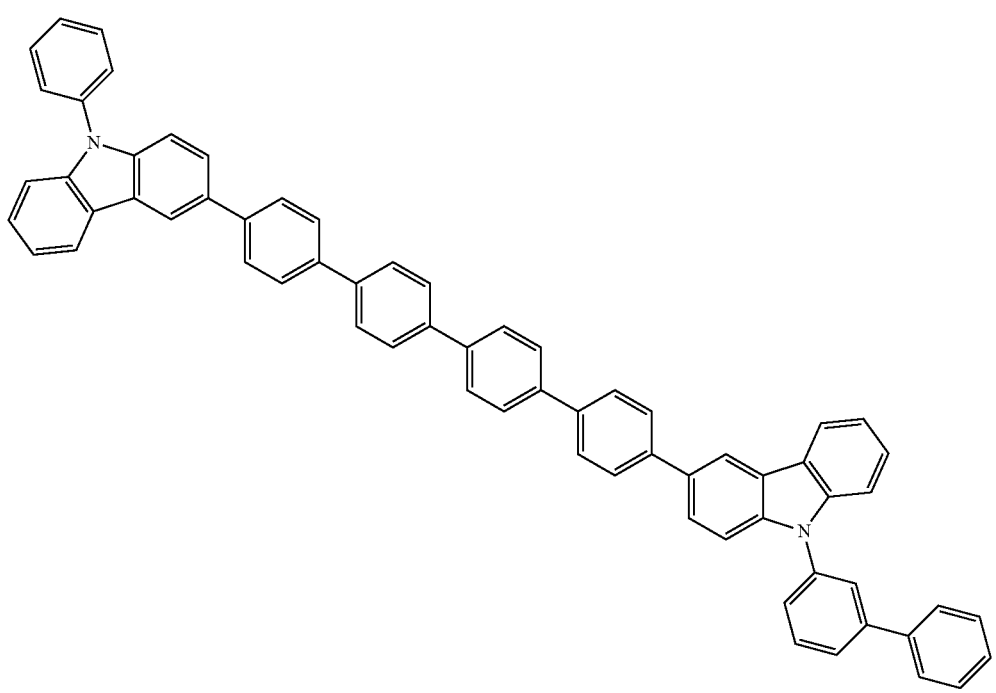

46
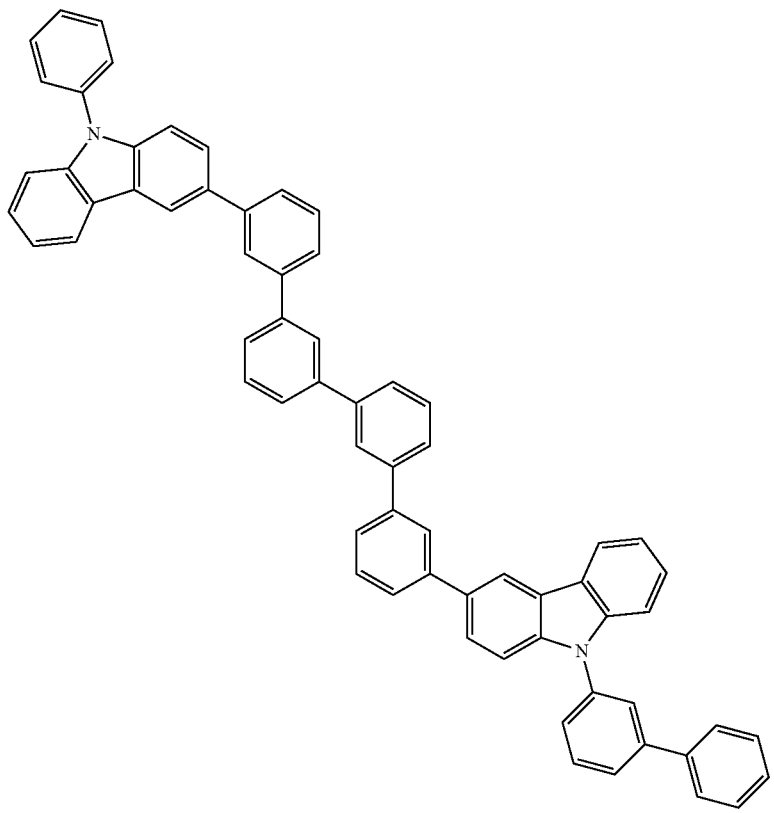
47 48
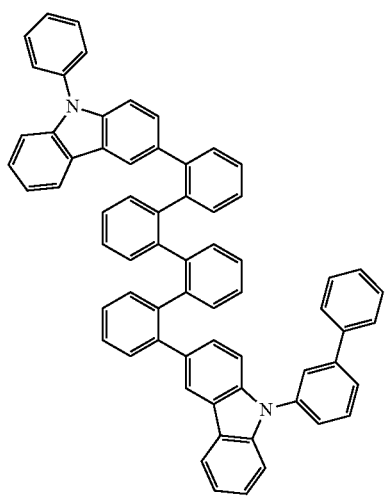

49
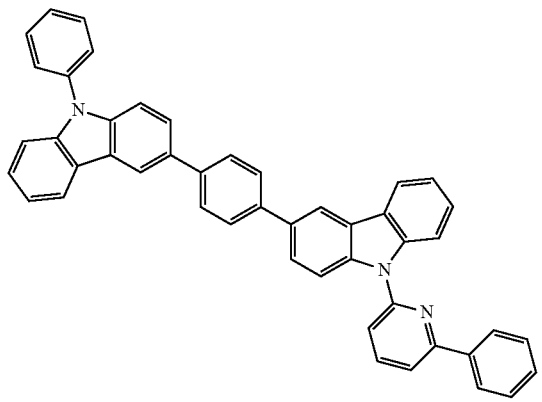
50
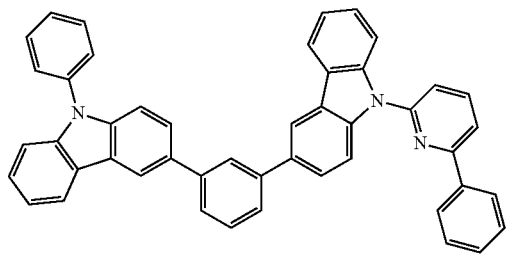
51
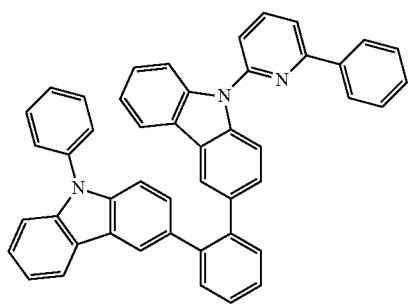
52
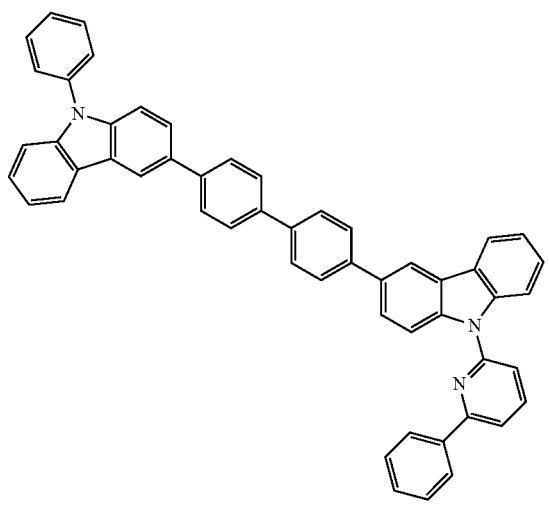
53
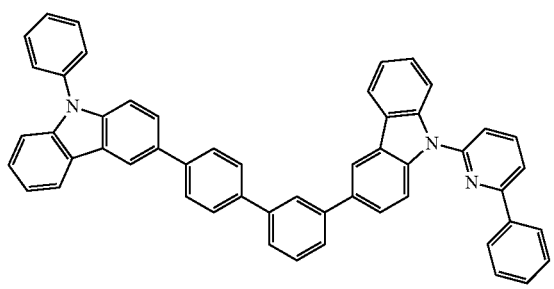
54
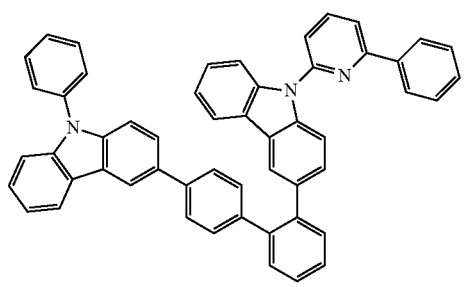

55
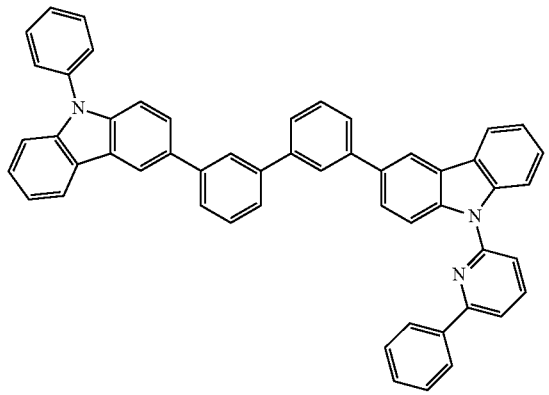
56
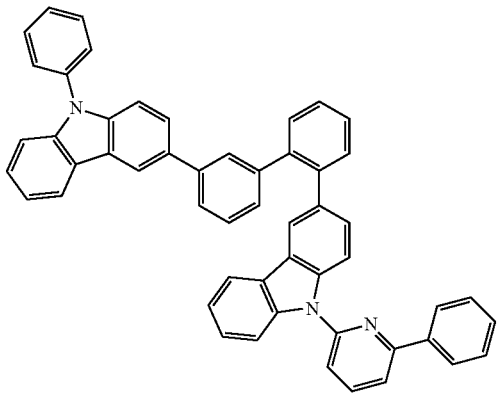
57
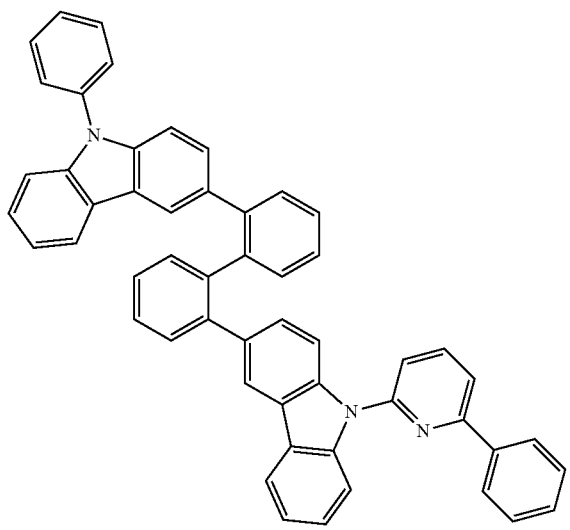
58
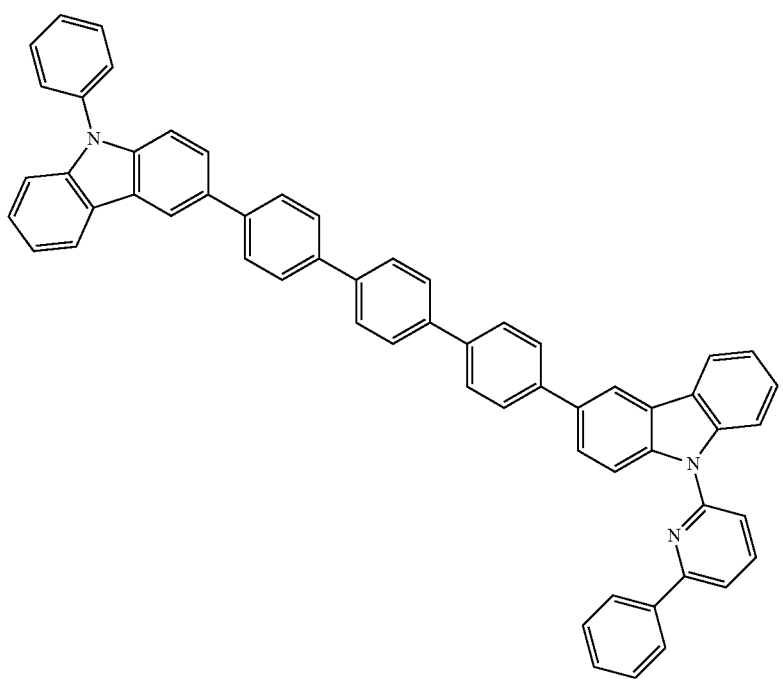

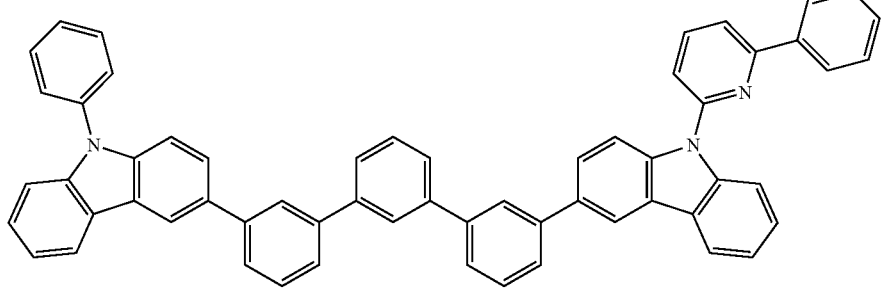
59
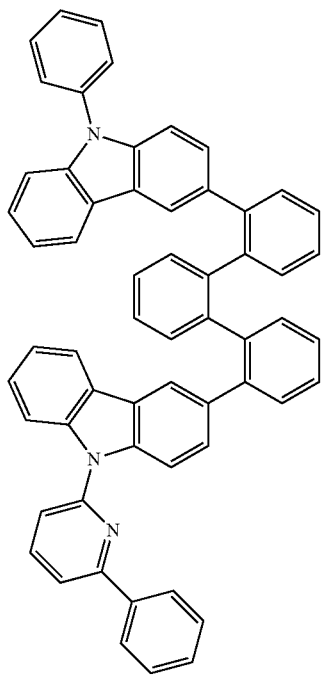
60
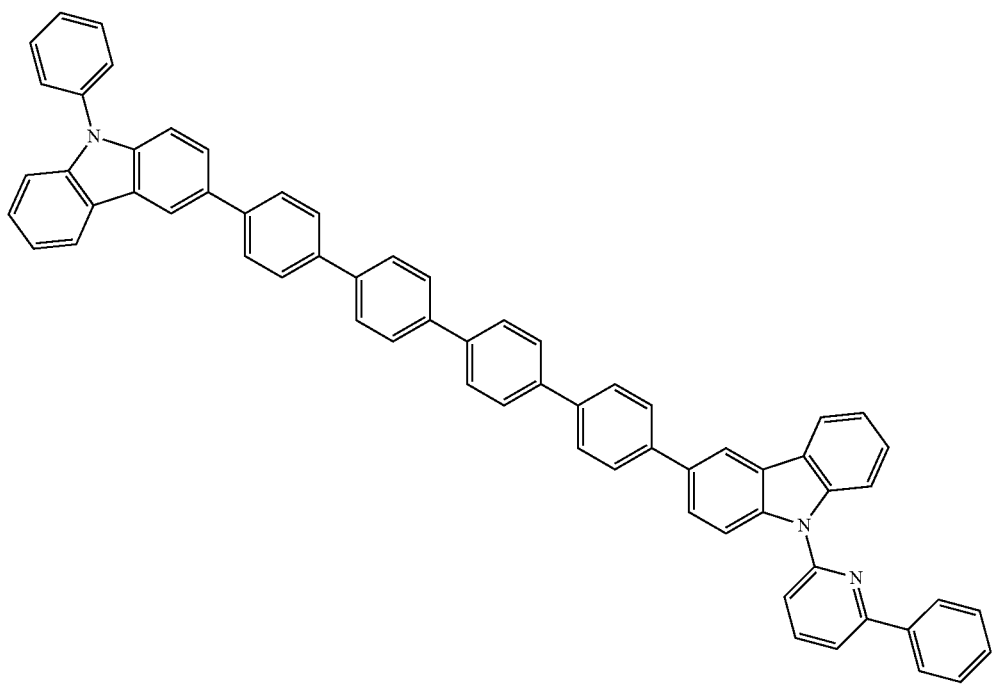
61

-continued
62
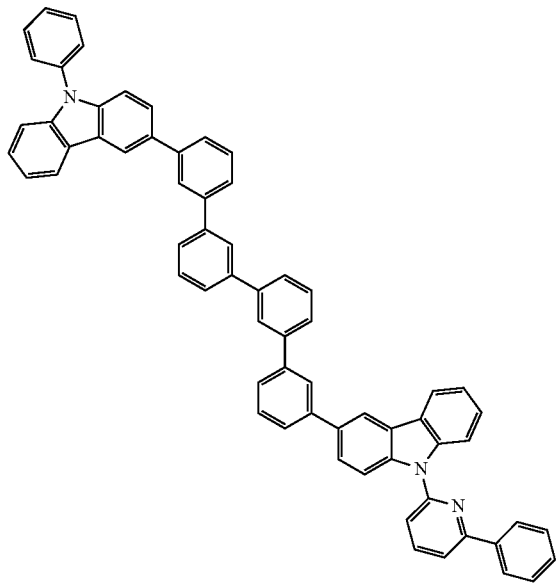
63
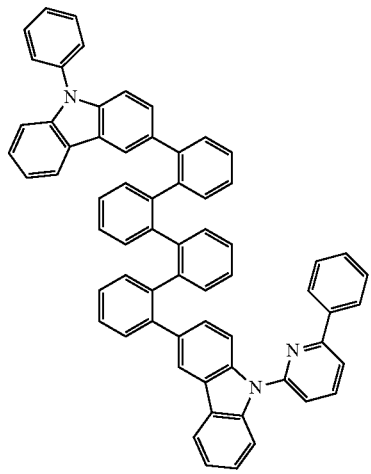
64
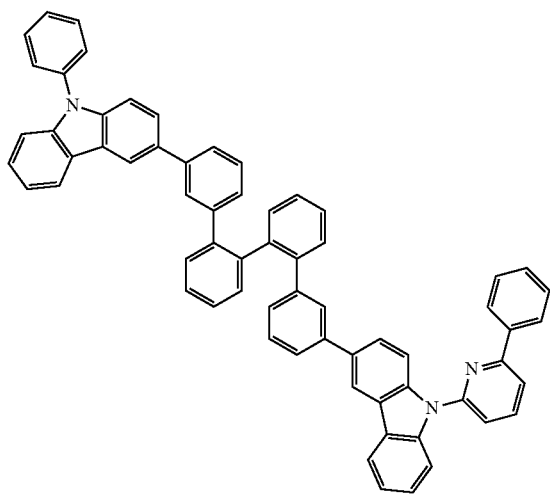
65
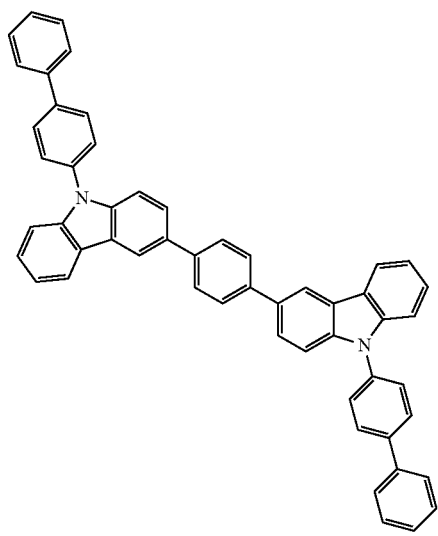
66
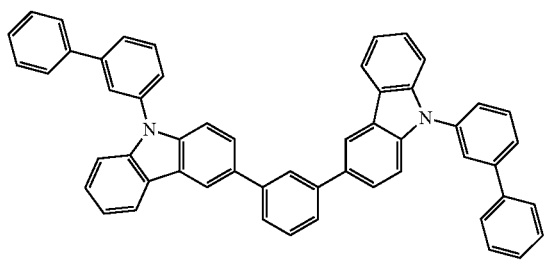
67
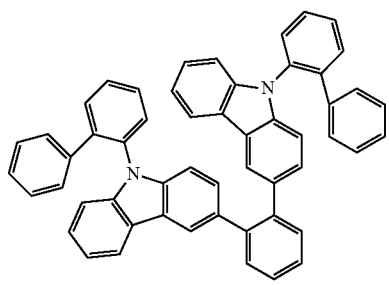

68
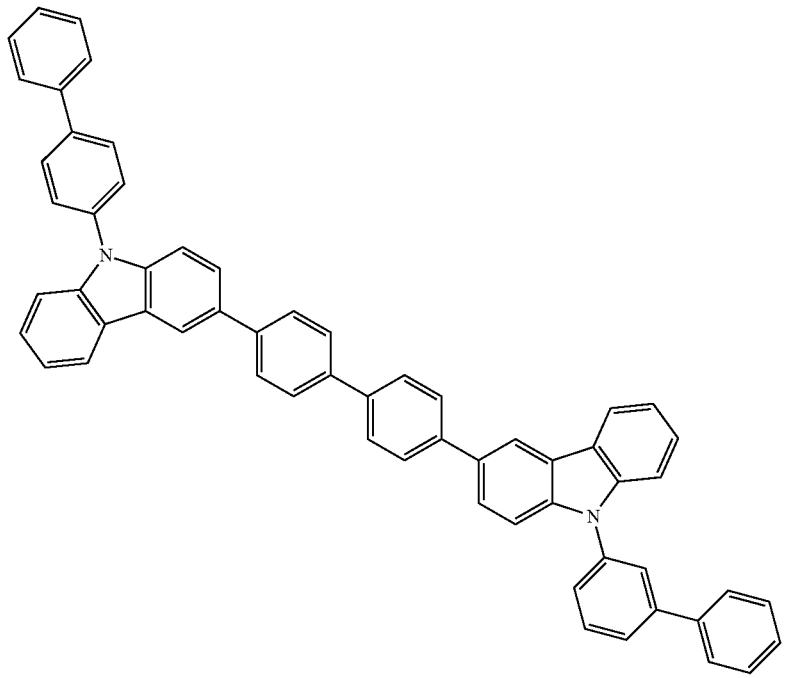
69
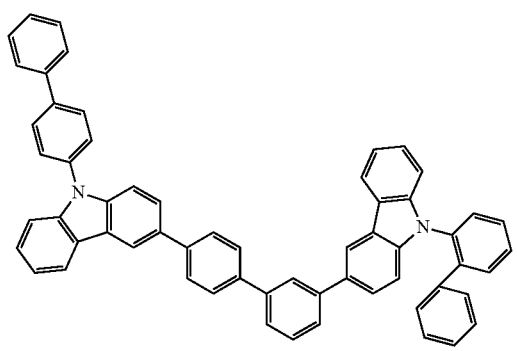
70
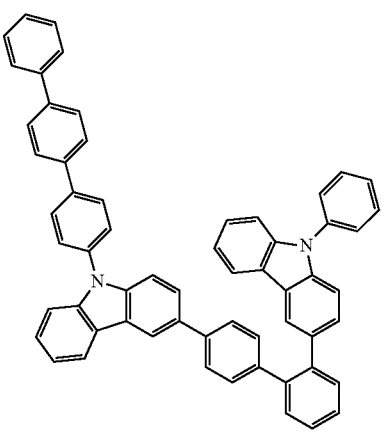
71
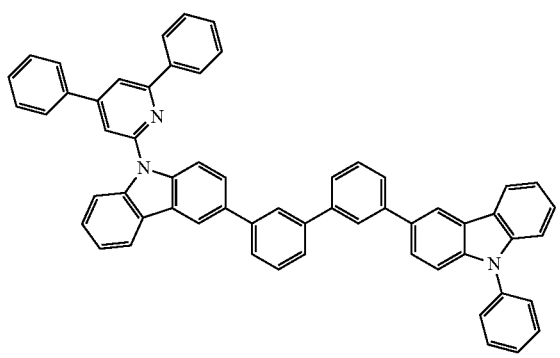
72
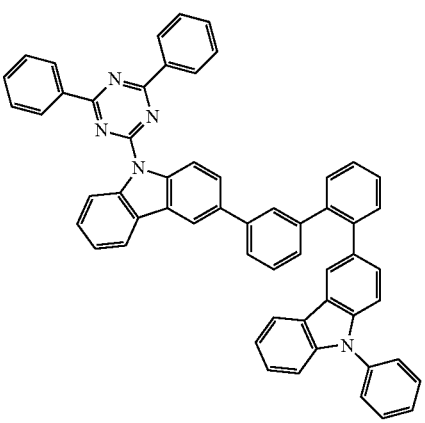

73
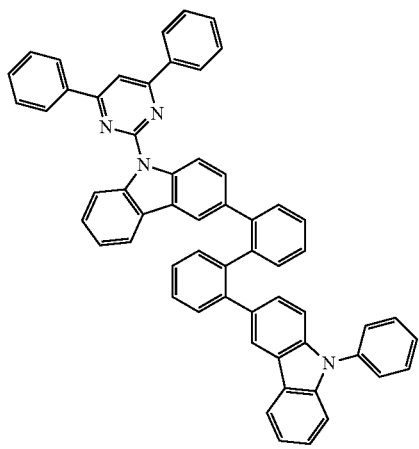
74
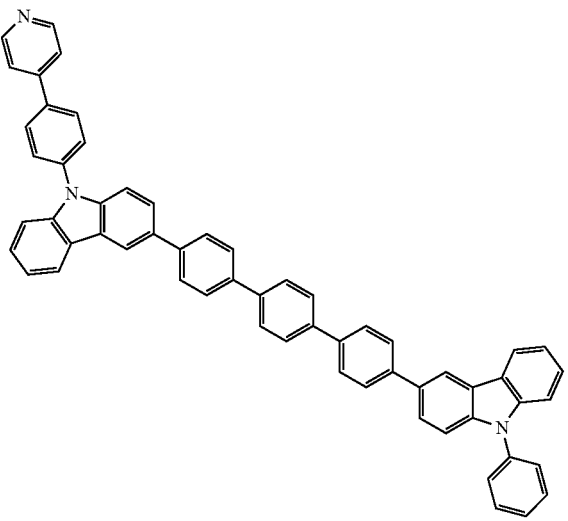
75
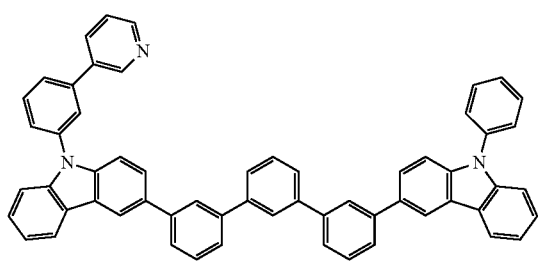
76
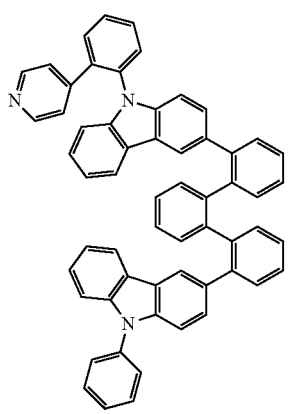

-continued
77
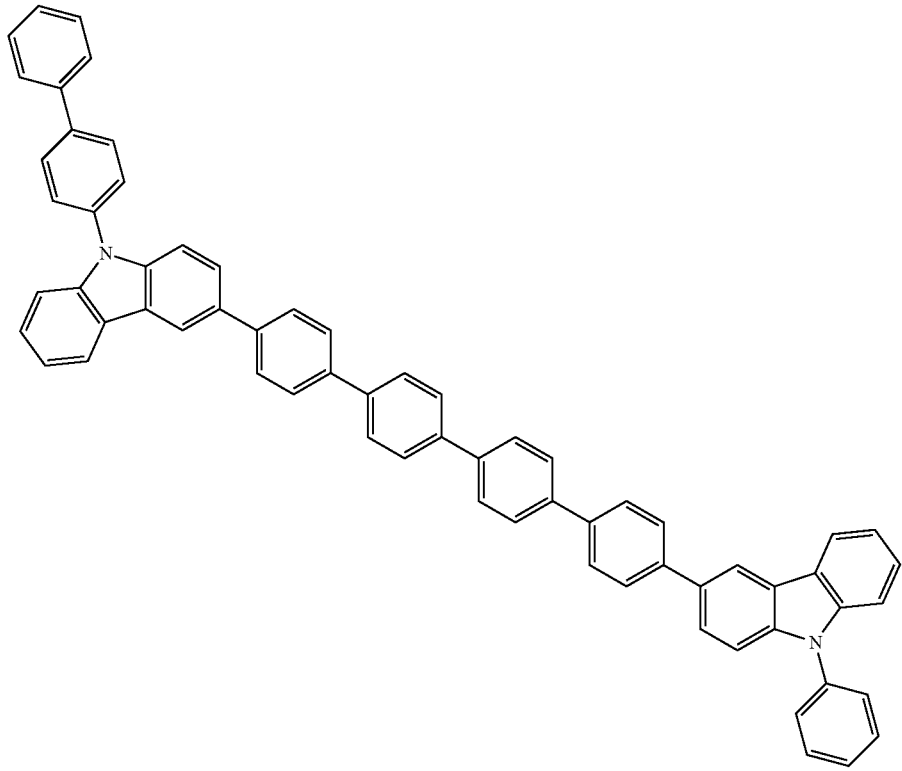
78 79
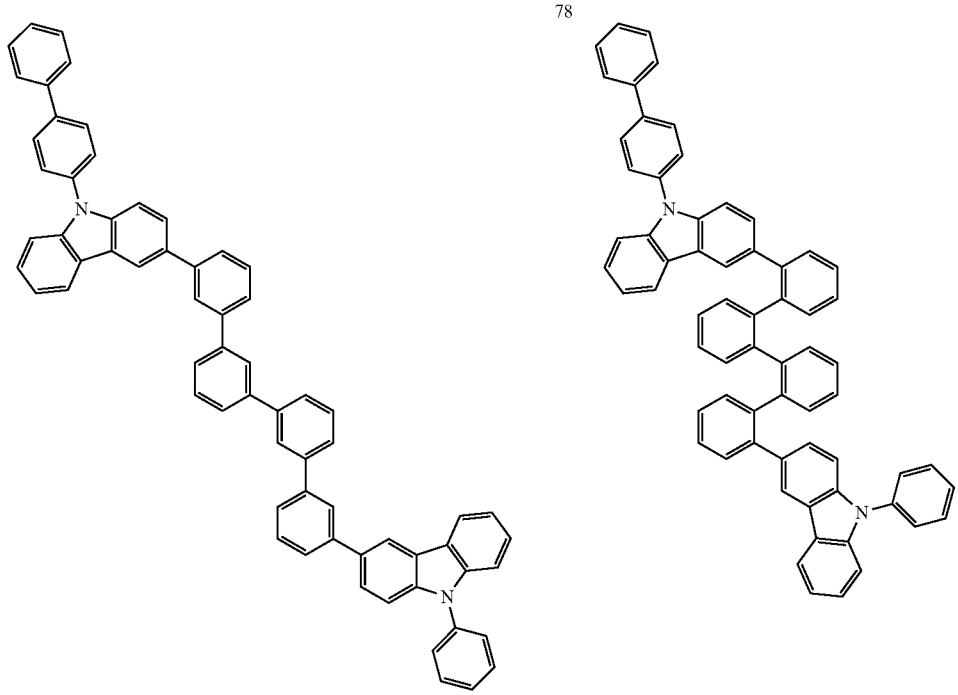

80
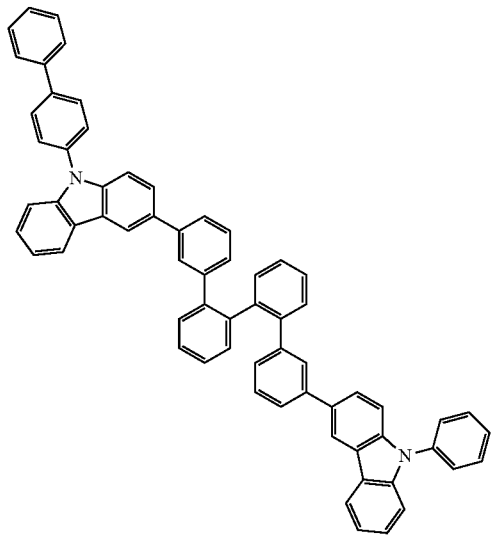
81
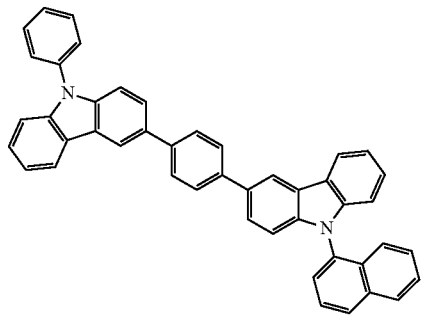
82
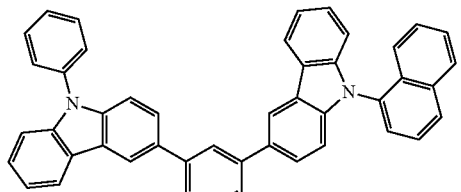
83
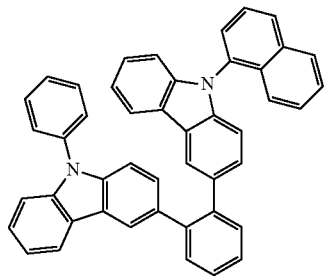
84
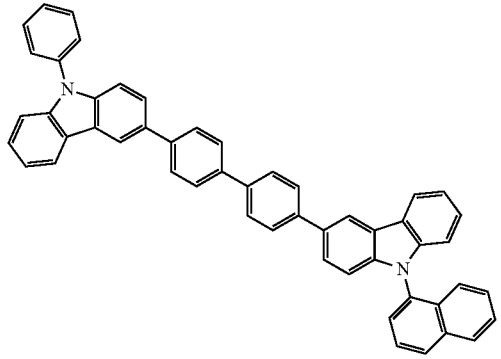
85
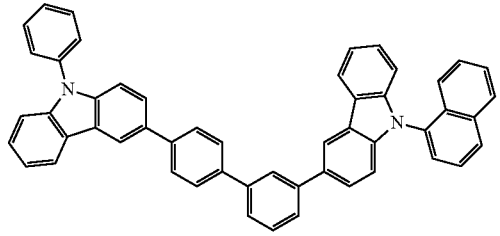
86
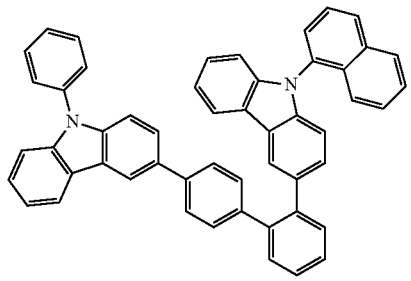
87
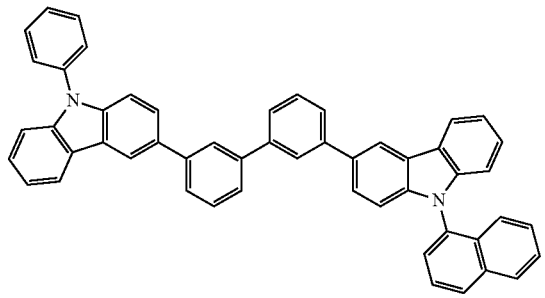

88
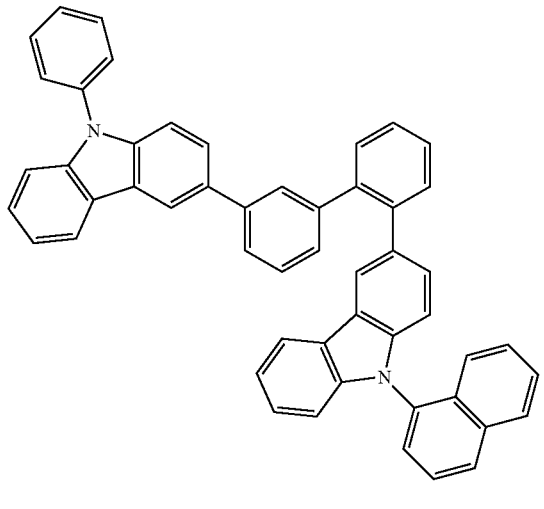
89
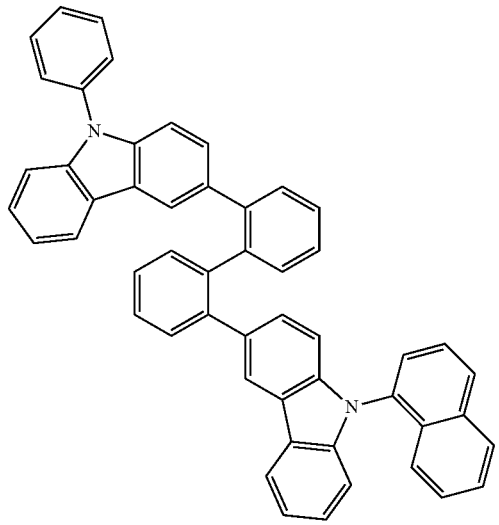
90
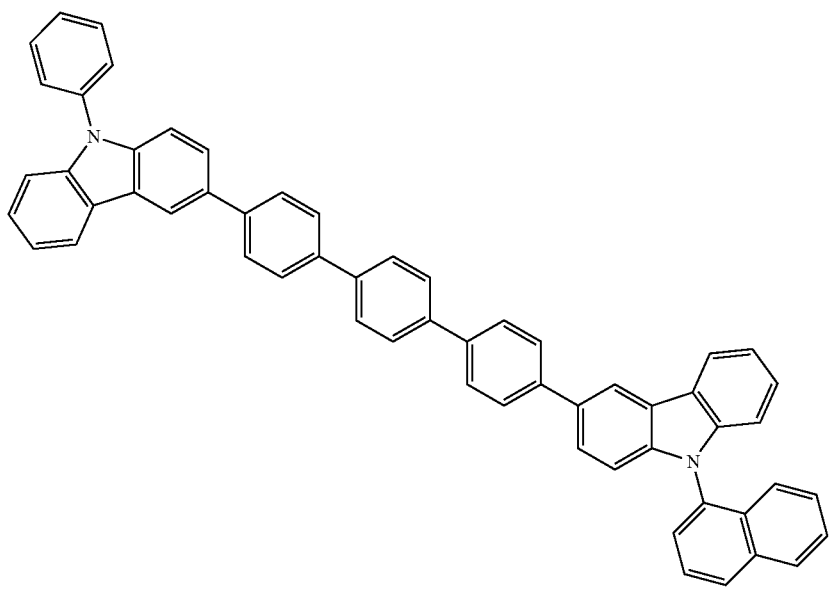
91
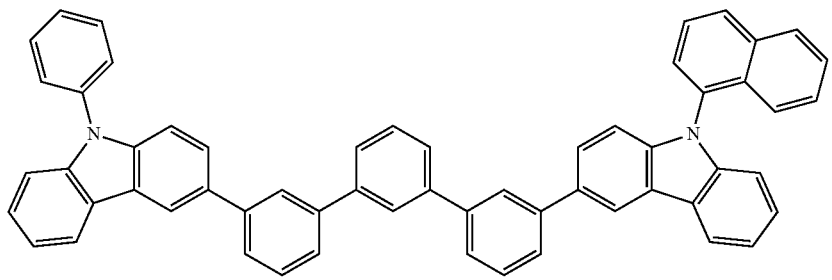

92
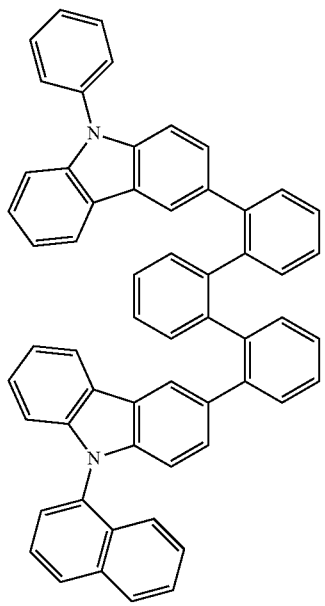
93
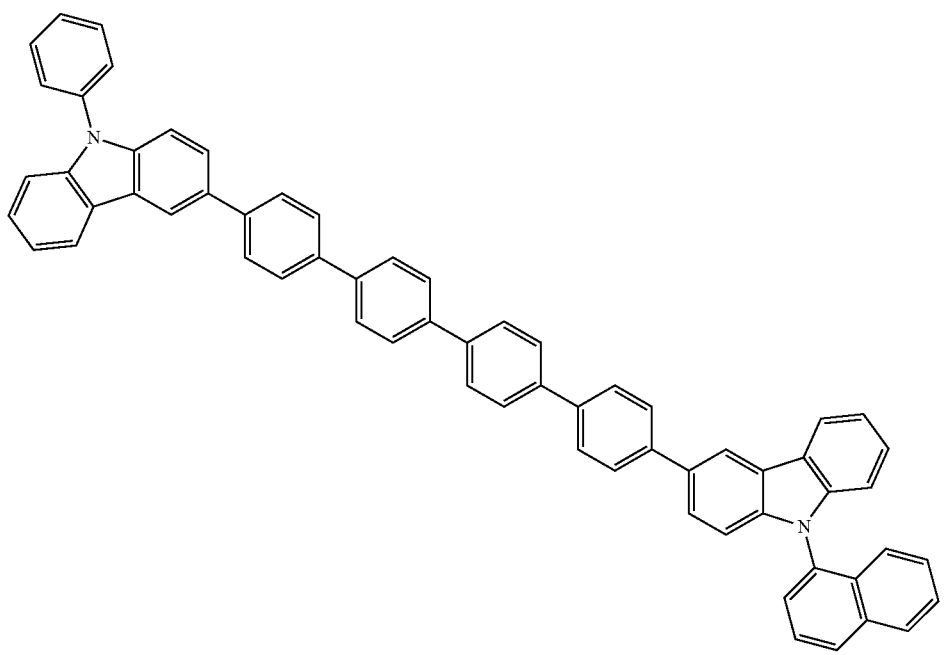

-continued
94
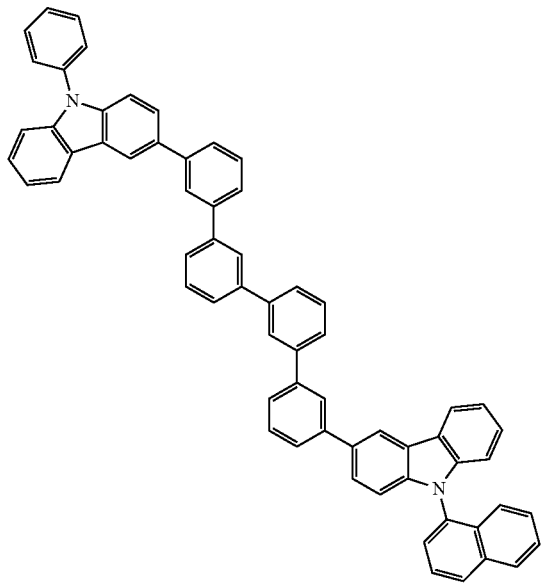
95
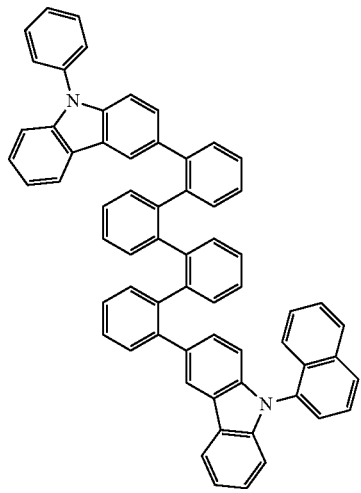
96
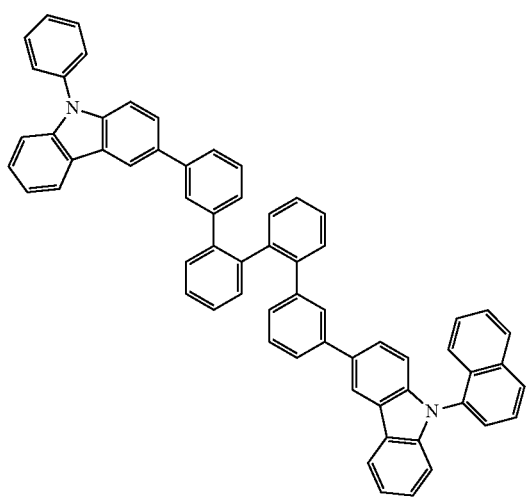
97
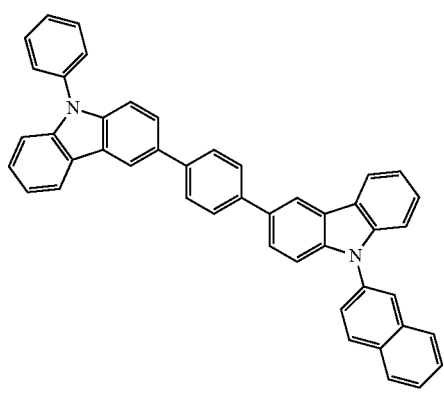
98
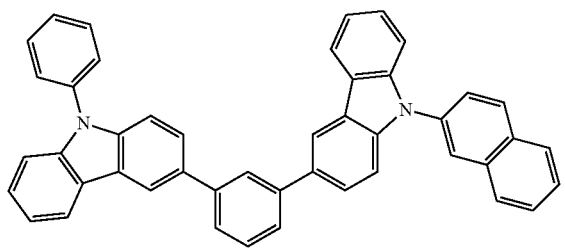
99
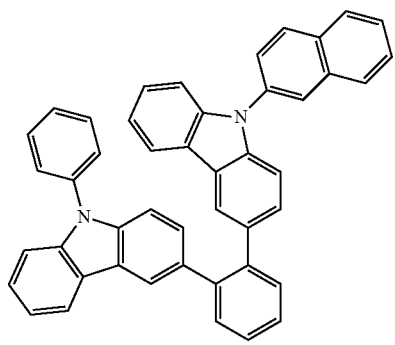

100
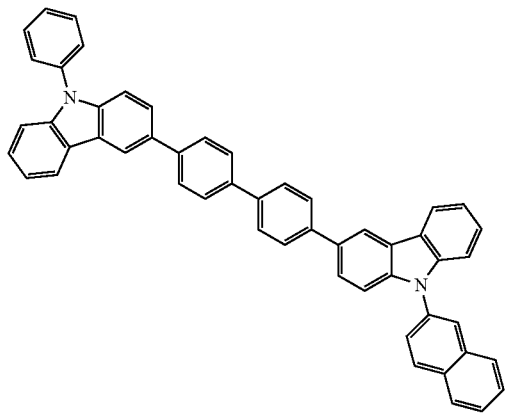
101
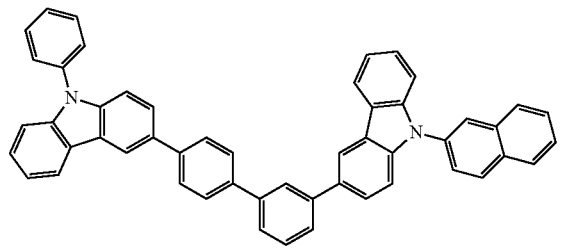
102
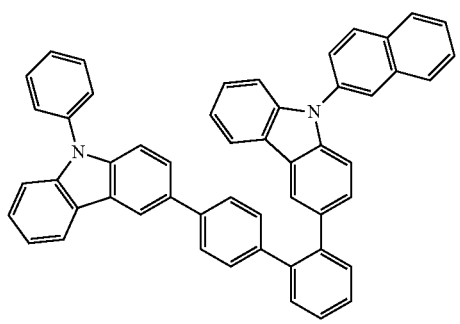
103
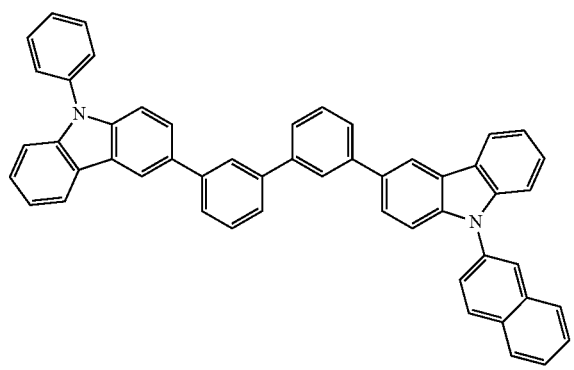
104
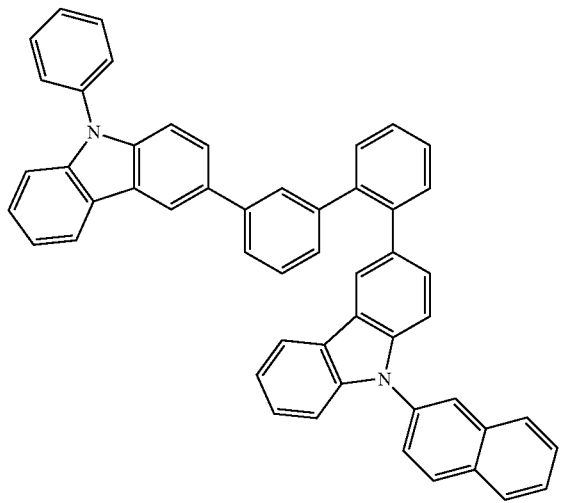
105
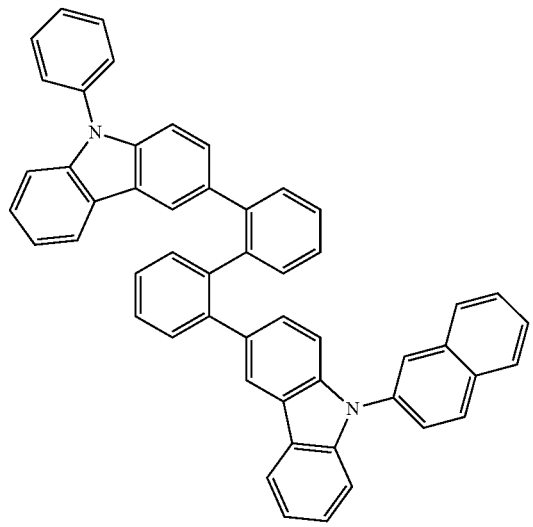

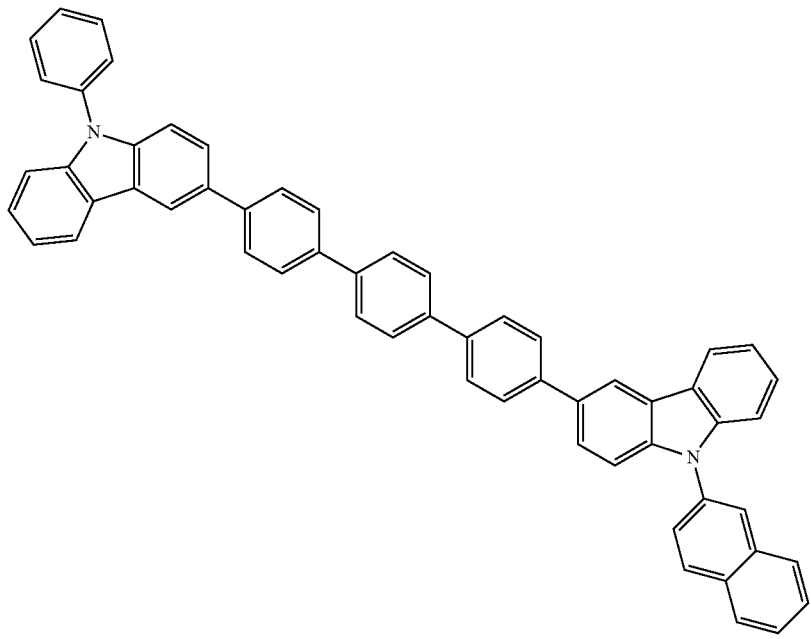
106
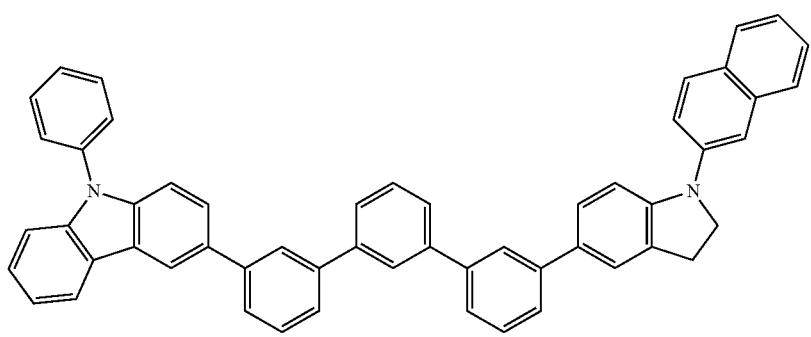
107
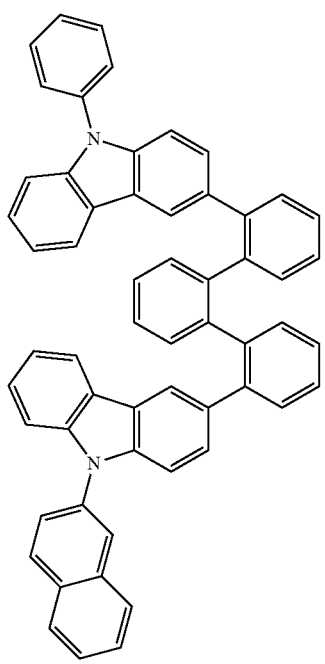
108

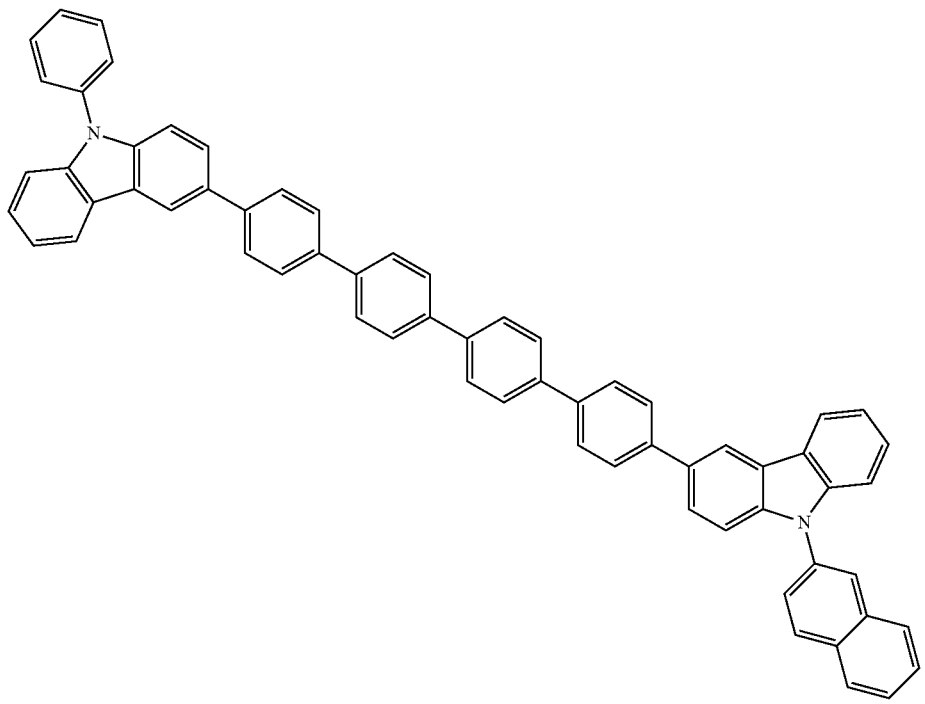
109
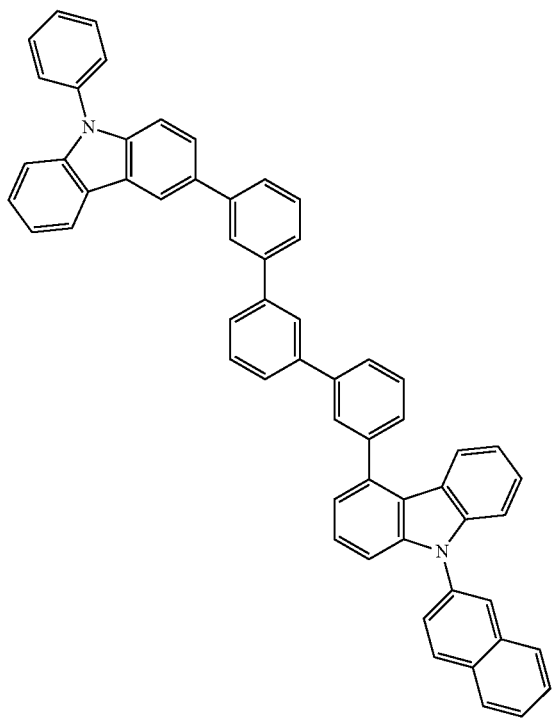
110
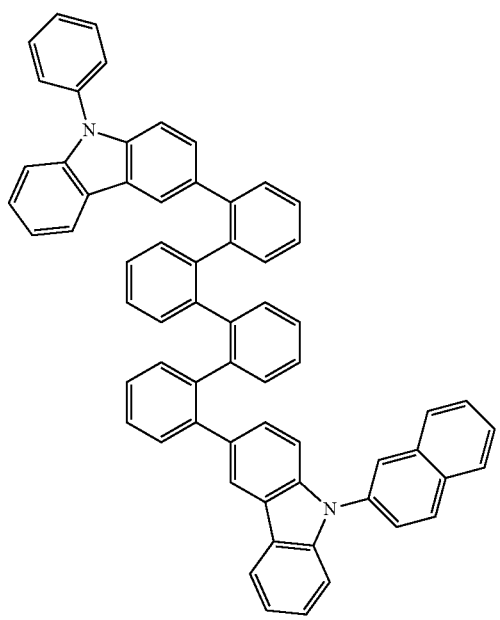
111

-continued
112
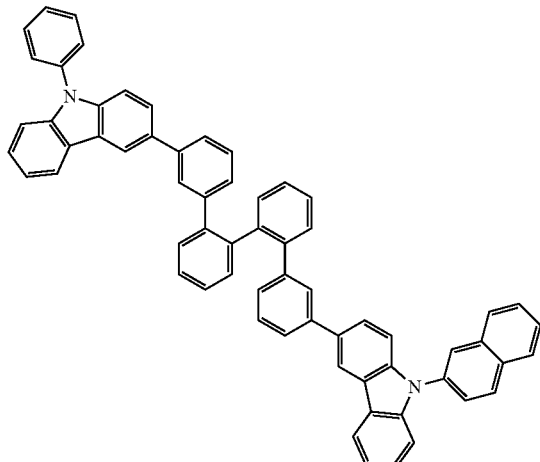
113
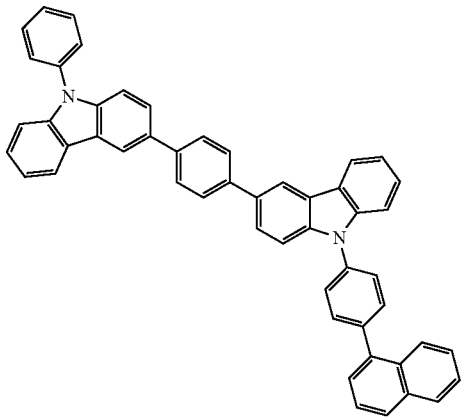
114
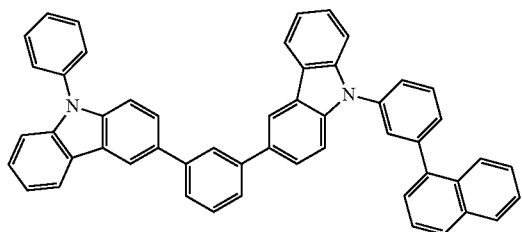
115
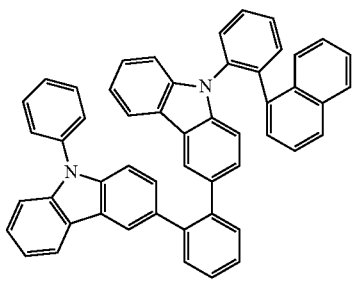
116
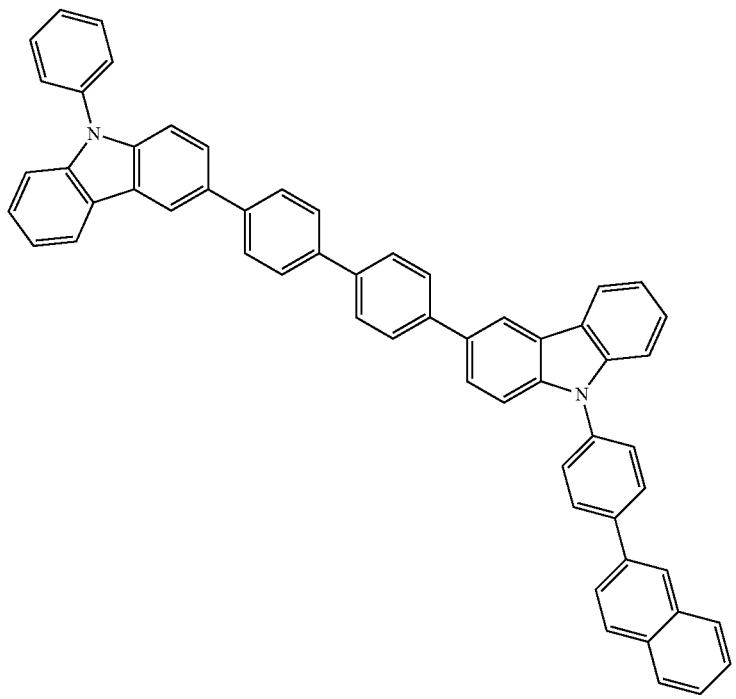

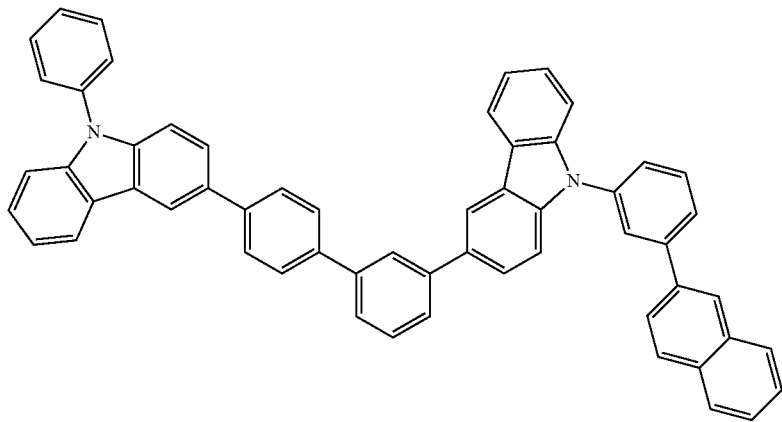
117
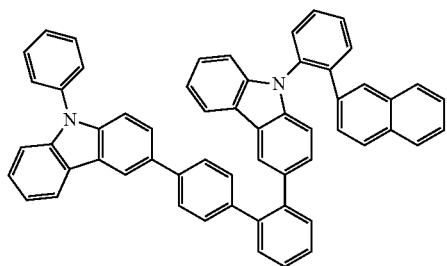
118
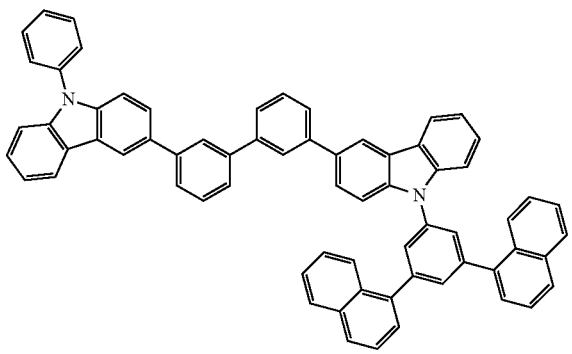
119
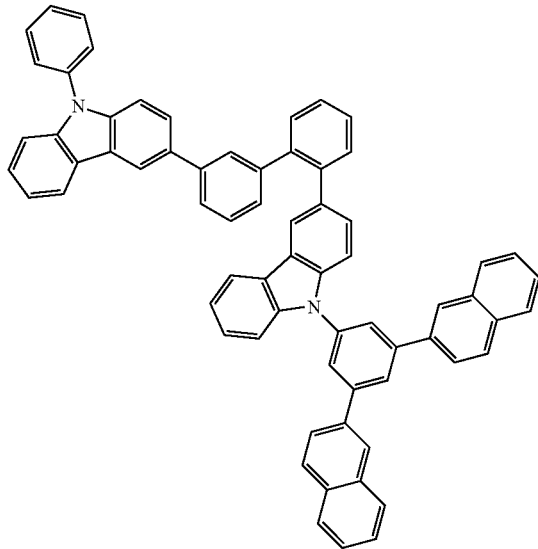
120
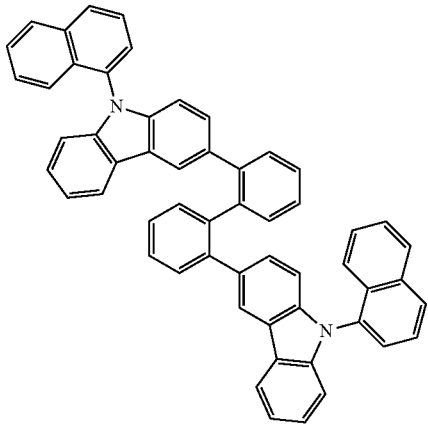
121

-continued
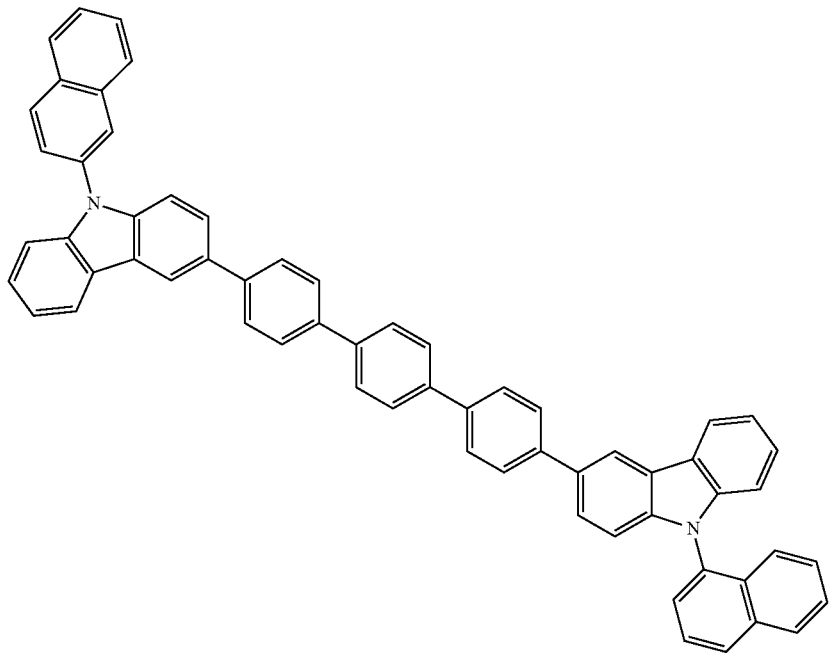
122
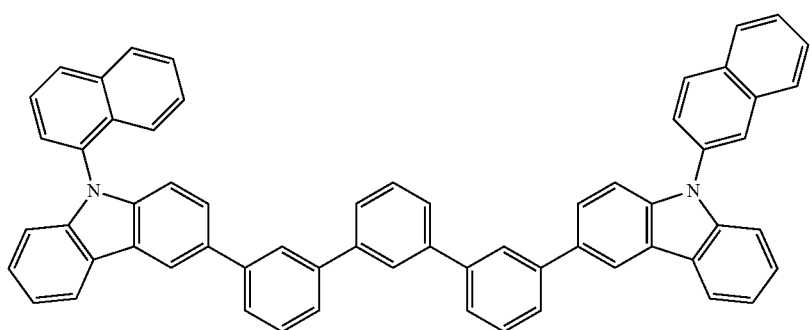
123

124
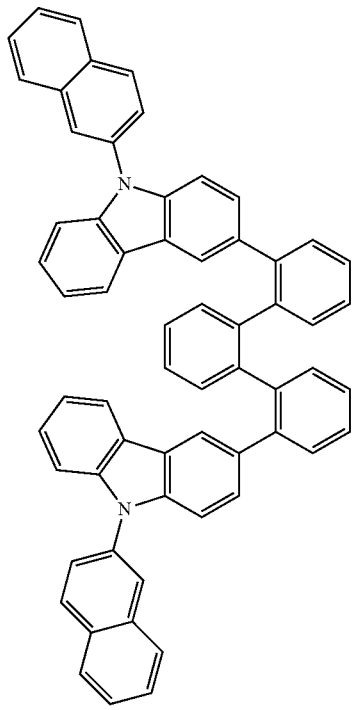
125
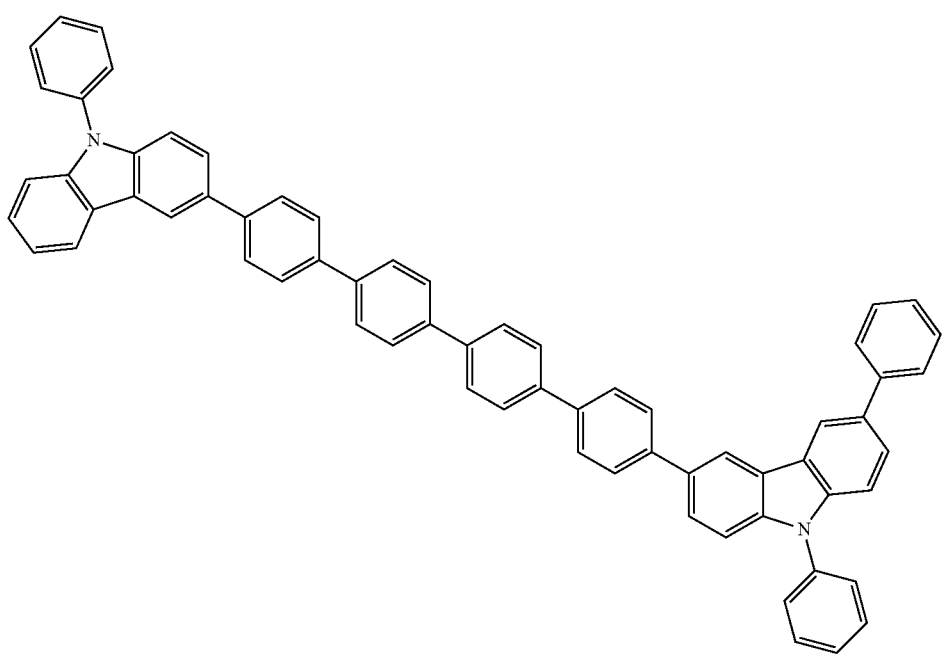

-continued
126
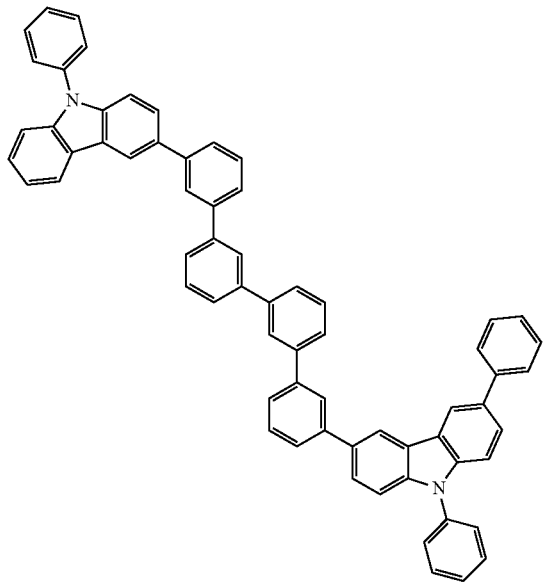
127
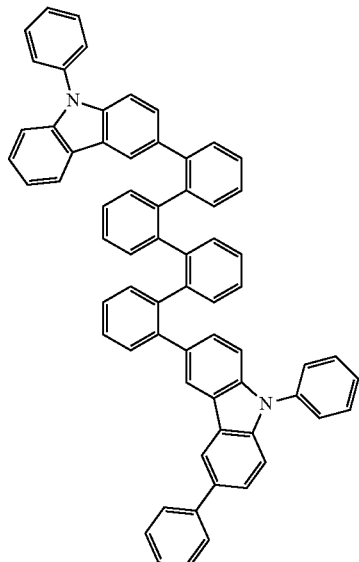
128
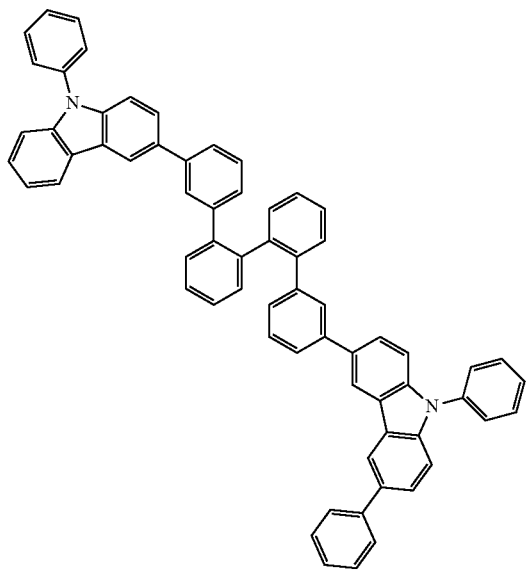
129
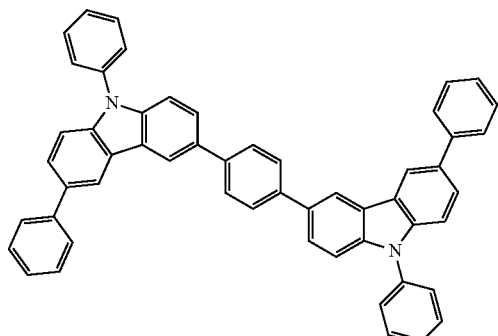
130
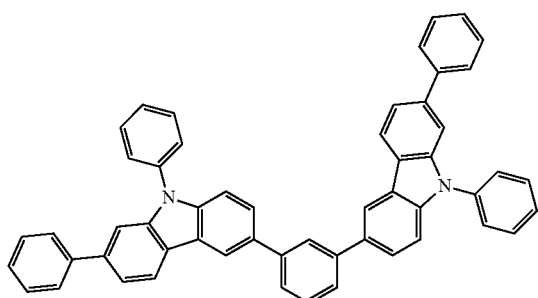
131
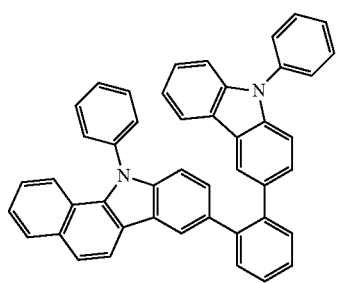

132
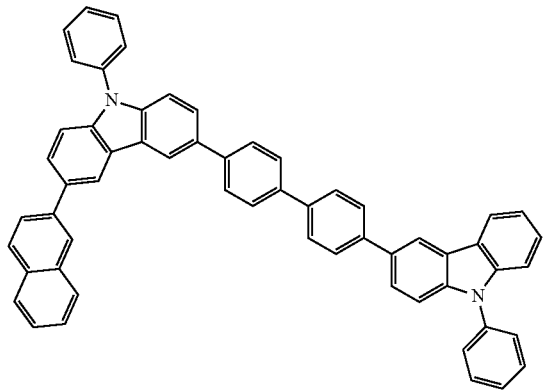
133
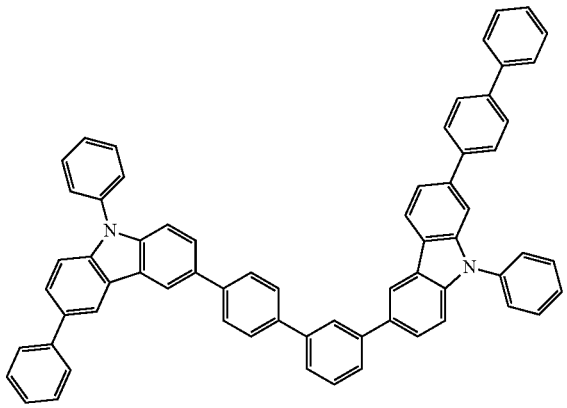
134
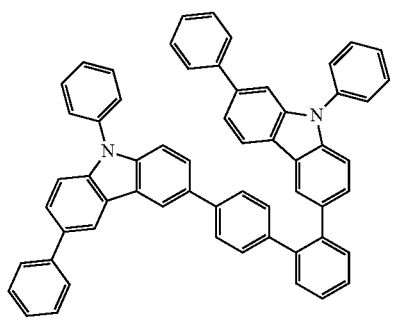
135
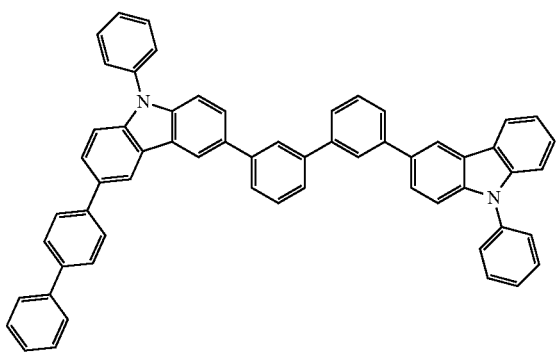
136
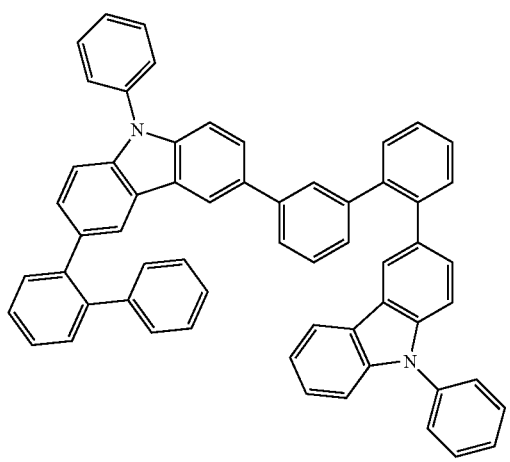
137
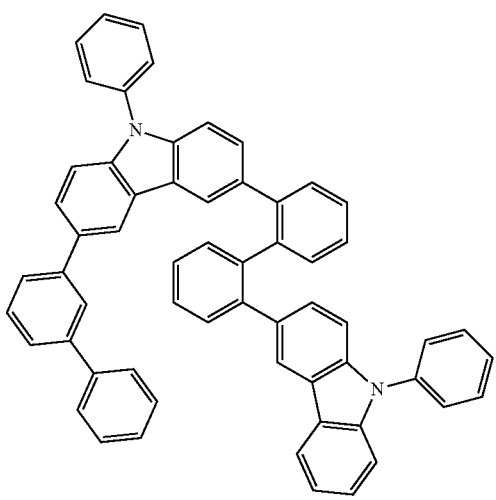

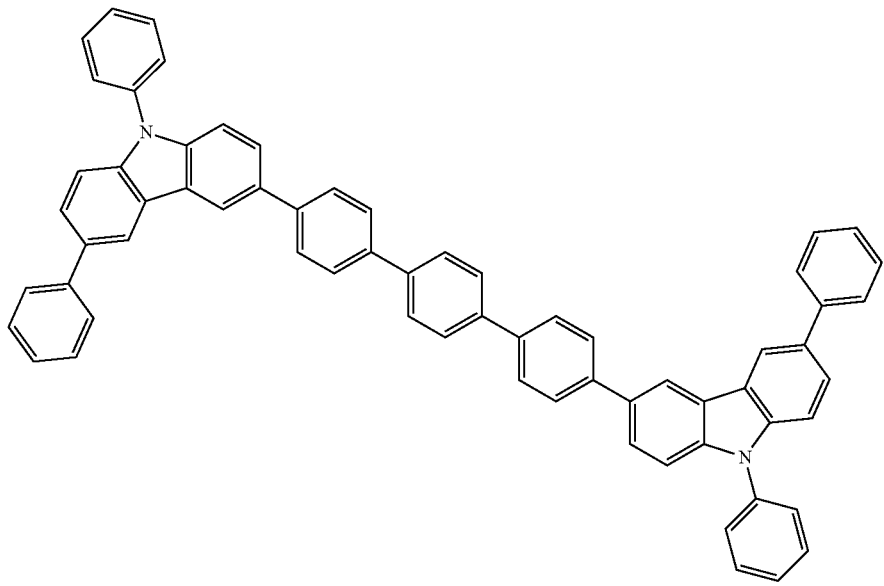
138
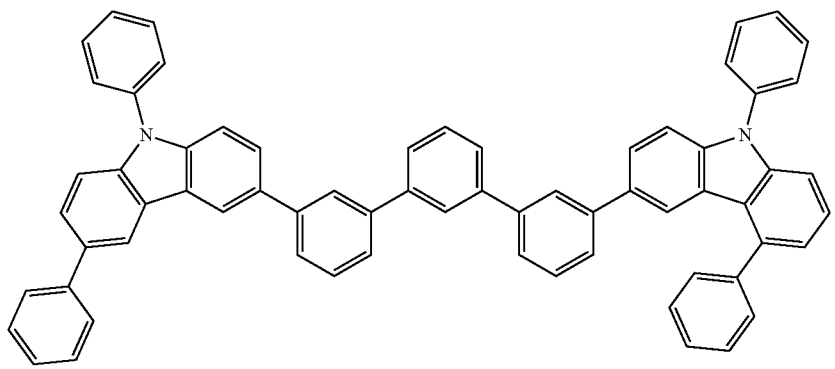
139
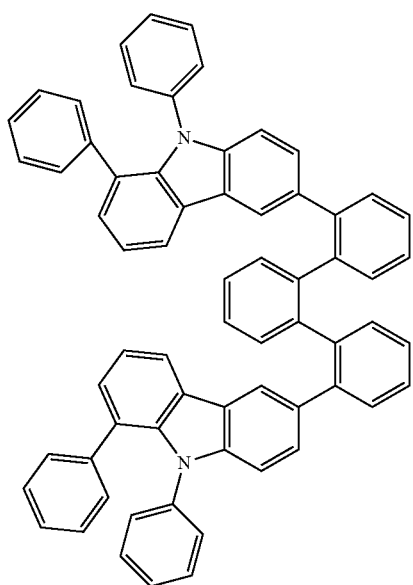
140

15. The organic optoelectric device of claim 1, wherein the hole transport auxiliary layer contacts the hole transport layer and the light-emitting layer respectively.

16. A display device comprising the organic optoelectric device of claim 1.

17. An organic optoelectric device, comprising:
an anode and a cathode facing each other,
a light-emitting layer disposed between the anode and cathode,
a hole transport layer disposed between the anode and the light-emitting layer, and
an auxiliary hole transport layer disposed between the hole transport layer and the light-emitting layer,
wherein the hole transport layer includes a compound represented by Chemical Formula I-a, and
the hole transport auxiliary layer includes a compound represented by Chemical Formula II:

[Chemical Formula I-a]

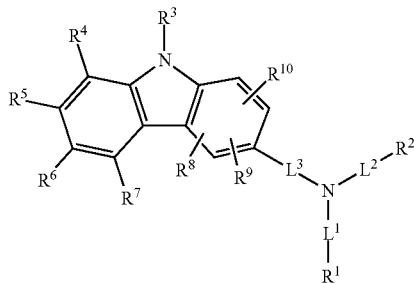

wherein, in Chemical Formula I-a,
$R^1$ to $R^3$ are independently a substituted or unsubstituted C6 to C30 aryl group, a substituted or unsubstituted C2 to C30 heterocyclic group, or a combination thereof,
$R^4$ to $R^{10}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C3 to C40 silyloxy group, a substituted or unsubstituted C1 to C30 alkylthio group, a substituted or unsubstituted C6 to C30 arylthiol group, a halogen, a halogen-containing group, a cyano group, a hydroxyl group, an amino group, a nitro group, or a combination thereof,
adjacent two of $R^4$ to $R^{10}$ are fused to provide a ring, and
$L^1$ to $L^3$ are independently a single bond, a substituted or unsubstituted C1 to C30 alkylene group, a substituted or unsubstituted C3 to C30 cycloalkylene group, a substituted or unsubstituted C6 to C30 arylene group, a substituted or unsubstituted C2 to C30 heteroarylene group, a substituted or unsubstituted C2 to C30 alkenylene group, a substituted or unsubstituted C2 to C30 alkynylene group, or a combination thereof, wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group,

[Chemical Formula II]

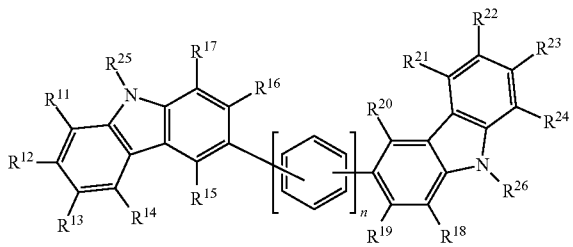

wherein, in Chemical Formula II,
$R^{11}$ to $R^{24}$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof,
adjacent two of $R^{11}$ to $R^{17}$ and $R^{18}$ to $R^{24}$ are fused to provide a ring,
$R^{25}$ and $R^{26}$ are independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, a substituted or unsubstituted C6 to C30 arylamine group, a substituted or unsubstituted C1 to C30 alkoxy group, a substituted or unsubstituted C3 to C40 silyl group, a substituted or unsubstituted C1 to C30 alkylthiol group, a substituted or unsubstituted C6 to C30 arylthiol group, a halogen, a halogen-containing group, a cyano group, a hydroxyl group, an amino group, a nitro group, or a combination thereof, and
n is an integer ranging from 1 to 4,
wherein "substituted" refers to replacement of at least one hydrogen by deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C2 to C30 heterocycloalkyl group, a C6 to C30 aryl group, a C2 to C30 heteroaryl group, a C1 to C20 alkoxy group, a fluoro group, a C1 to C10 trifluoroalkyl group, or a cyano group.

18. The organic optoelectric device of claim 17, wherein, in Chemical Formula I-a, $L^3$ is a substituted or unsubstituted phenyl group or a substituted or unsubstituted naphthyl group.

19. A display device comprising the organic optoelectric device of claim 17.

* * * * *